United States Patent
Zhao et al.

(10) Patent No.: US 12,018,310 B2
(45) Date of Patent: Jun. 25, 2024

(54) METHODS AND MICROORGANISMS FOR MAKING 1,4-BUTANEDIOL AND DERIVATIVES THEREOF FROM C1 CARBONS

(71) Applicant: PRECIGEN, INC., Germantown, MD (US)

(72) Inventors: Xinhua Zhao, Dublin, CA (US); Tina Huynh, Oakland, CA (US); Jeffrey Orth, Alameda, CA (US); Lily Yuin Chao, San Francisco, CA (US); James Kealey, Sebastopol, CA (US)

(73) Assignee: PRECIGEN, INC., Germantown, MD (US)

( * ) Notice: Subject to any disclaimer, the term of this patent is extended or adjusted under 35 U.S.C. 154(b) by 0 days.

(21) Appl. No.: 17/447,568

(22) Filed: Sep. 13, 2021

(65) Prior Publication Data

US 2022/0064677 A1    Mar. 3, 2022

Related U.S. Application Data

(62) Division of application No. 16/492,411, filed as application No. PCT/US2018/022204 on Mar. 13, 2018, now Pat. No. 11,155,837.

(60) Provisional application No. 62/470,953, filed on Mar. 14, 2017.

(51) Int. Cl.
    *C12P 7/04*    (2006.01)
    *C12N 1/20*    (2006.01)
    *C12N 15/74*   (2006.01)

(52) U.S. Cl.
    CPC .................. *C12P 7/04* (2013.01); *C12N 1/20* (2013.01); *C12N 15/74* (2013.01)

(58) Field of Classification Search
    CPC .............. C12N 15/74; C12N 1/20; C12P 7/04
    See application file for complete search history.

(56) References Cited

U.S. PATENT DOCUMENTS

2014/0363847 A1    12/2014    Fujii et al.

FOREIGN PATENT DOCUMENTS

| EP | 2738247 A1 | 6/2014 |
|----|------------|--------|
| WO | 2007136762 A2 | 5/2006 |
| WO | 2009154683 A1 | 12/2009 |
| WO | 2014074886 A1 | 5/2014 |
| WO | 2016165025 A1 | 10/2016 |

OTHER PUBLICATIONS

Whisstock et al. Quaterly Reviews of Biophysics, 2003, "Prediction of protein function from protein sequence and structure", 36(3): 307-340.
Witkowski et al. Conversion of a beta-ketoacyl synthase to a malonyl decarboxylase by replacement of the active-site cysteine with glutamine, Biochemistry. Sep. 7, 1999;38(36): 11643-50.
Kisselev L., Polypeptide release factors in prokaryotes and eukaryotes: same function, different structure. Structure, 2002, vol. 10: 8-9.
Kalyuzhnaya et al., Metab Eng., 29:142-152 (2015).
International Search Report issued in PCT/US2018/022204.
Written Opinion issued in PCT/US2018/022204.
Nguyen et al., Metab Eng (2018), 47:323-333.
Vecherskaya et al., Environmental Microbiology Reports (2009), 1: 442-449.

*Primary Examiner* — Iqbal H Chowdhury
(74) *Attorney, Agent, or Firm* — Gene J. Yao; Barnes & Thornburg LLP

(57) ABSTRACT

Genetically modified microorganisms that have the ability to convert carbon substrates into chemical products such as 1,4-BDO are disclosed. For example, genetically modified methanotrophs that are capable of generating 1,4-BDO at high titers from a methane source are disclosed. Methods of making these genetically modified microorganisms and methods of using them are also disclosed.

20 Claims, 8 Drawing Sheets

Specification includes a Sequence Listing.

METHODS AND MICROORGANISMS FOR MAKING 1,4-BUTANEDIOL AND DERIVATIVES THEREOF FROM C1 CARBONS

CROSS-REFERENCE

This application is a division of U.S. application Ser. No. 16/492,411 (now U.S. Pat. No. 11,155,837), which is a U.S. national stage filing of International Application No. PCT/US2018/022204, filed Mar. 13, 2018, which in turn claims the priority benefit of U.S. Provisional Application No. 62/470,953, filed Mar. 14, 2017. The contents of each of the aforementioned is hereby incorporated by reference in their entireties.

SEQUENCE LISTING

The instant application contains a Sequence Listing which has been submitted electronically in ASCII format and is hereby incorporated by reference in its entirety. The ASCII copy was created on Nov. 16, 2021, is named 17447568SequenceListing.txt, and is 201,202 bytes in size.

BACKGROUND OF THE DISCLOSURE

There has been great interest in generating fuels and chemicals by microbial fermentation in order to curb the use of fossil fuels. One such chemical of interest is 1,4-butanediol (1,4-BDO). 1,4-BDO is currently produced from petrochemical precursors, primarily acetylene, maleic anhydride, and propylene oxide.

1,4-BDO is also known as BD; 1,4-butylene glycol; 1,4-dihydroxybutane; BDO; butanediol; and 1,4-tetramethylene glycol and the IUPAC name is Butane-1,4-diol. Its chemical formula is $C_4H_{10}O_2$. The CAS number is 110-63-4.

1,4-BDO has a large number of industrial applications. For example, 1,4-BDO can be used as a monomer such as an acrylonitrile butadiene styrene (ABS) copolymer and polyurethane (PU), and may be converted into tetrahydrofuran, which may be used as a raw material for spandex fibers such as polytetramethylene ether glycol (PTMEG).

1,4-BDO is not known to be produced by any microorganism. 1,4-BDO is only produced with the aid of novel, engineered metabolic pathways or through chemical synthesis. See e.g., Adkins, J., "Engineering microbial chemical factories to produce renewable 'biomonomers'", *Front. Microbiology* (2012).

The present inventors disclose a way using genetically modified microorganisms, such as methanotrophs, in order to produce 1,4-BDO from C1 carbon feedstock.

INCORPORATION BY REFERENCE

All publications, patents, and patent applications herein are incorporated by reference to the same extent as if each individual publication, patent, or patent application was specifically and individually indicated to be incorporated by reference. In the event of a conflict between a term herein and a term in an incorporated reference, the term herein controls.

SUMMARY

Disclosed herein are various genetically modified microorganisms that are capable of producing a desired organic compound, starting from a single carbon containing hydrocarbon molecule such as methane. Various methods of producing the desired organic compounds, including by using a genetically modified microorganism are disclosed.

For example, disclosed herein is a genetically modified microorganism capable of converting a C1 carbon source to a multicarbon product. The genetically modified microorganism can be genetically altered to produce different multicarbon products such as 1,4-butanediol. In some cases, the genetically modified microorganism can comprise one or more heterologous genes. The one or more heterologous genes can be one or more of pyruvate dehydrogenase (aceEF), citrate synthase (gltA), aconitate hydratase 1 (acnA), or isocitrate dehydrogenase (icdA). In some cases, the genetically modified microorganism will have all the genes above, however, at least one of the genes is endogenous to the microorganism. In some cases, all the genes can be heterologous to the microorganism. In some embodiments, the microorganism can further comprise one or more genes from α-ketoglutarate decarboxylase (kgd), 4-hyrobutyrate dehydrogenase (4hbD), 4-hydroxybutyryl-CoA transferase (Cat2), aldehyde dehydrogenase (Ald), or alcohol dehydrogenase (Adh). These additional genes can be one or more endogenous genes or one or more heterologous genes. In other embodiments, the microorganism can further comprise one or more genes from succinyl-CoA synthetase (SucC), CoA-dependent succinate semialdehyde dehydrogenase (SucD), 4-hyrobutyrate dehydrogenase (4hbD), 4-hydroxybutyryl-CoA transferase (Cat2), aldehyde dehydrogenase (Ald), or alcohol dehydrogenase (Adh). These additional genes can be one or more endogenous genes or one or more heterologous genes. In an additional embodiment, the microorganism can further comprise one or more genes from α-ketoglutarate decarboxylase (kgd), succinyl-CoA synthetase (SucC), CoA-dependent succinate semialdehyde dehydrogenase (SucD), 4-hyrobutyrate dehydrogenase (4hbD), 4-hydroxybutyryl-CoA transferase (Cat2), aldehyde dehydrogenase (Ald), or alcohol dehydrogenase (Adh). These additional genes can be one or more endogenous genes or one or more heterologous genes.

Also disclosed herein is a genetically modified microorganism that has one or more heterologous genes from α-ketoglutarate decarboxylase (kgd), 4-hyrobutyrate dehydrogenase (4hbD), 4-hydroxybutyryl-CoA transferase (Cat2), aldehyde dehydrogenase (Ald), or alcohol dehydrogenase (Adh). In some cases, the genetically modified microorganism will have all the genes, however, at least one of the genes is endogenous to the microorganism. In some cases, all the genes can be heterologous to the microorganism.

Also disclosed herein is a genetically modified microorganism that has one or more heterologous genes from succinyl-CoA synthetase (SucC), CoA-dependent succinate semialdehyde dehydrogenase (SucD), 4-hyrobutyrate dehydrogenase (4hbD), 4-hydroxybutyryl-CoA transferase (Cat2), aldehyde dehydrogenase (Ald), or alcohol dehydrogenase (Adh). In some cases, the genetically modified microorganism will have all the genes, however, at least one of the genes is endogenous to the microorganism. In some cases, all the genes can be heterologous to the microorganism.

Also disclosed herein is a genetically modified microorganism that has one or more heterologous genes from α-ketoglutarate decarboxylase (kgd), succinyl-CoA synthetase (SucC), CoA-dependent succinate semialdehyde dehydrogenase (SucD), 4-hyrobutyrate dehydrogenase (4hbD), 4-hydroxybutyryl-CoA transferase (Cat2), aldehyde dehydrogenase (Ald), or alcohol dehydrogenase (Adh). In some cases, the genetically modified microorganism will have all the genes, however, at least one of the genes is endogenous to the microorganism. In some cases, all the genes can be heterologous to the microorganism.

In some cases, the genetically modified microorganism disclosed throughout can further comprise one or more genes that are fumarate hydratase (fum) and/or fumarate reductase (frd).

The genes disclosed herein can be overexpressed, including both heterologous and endogenous genes.

The genetically modified microorganisms disclosed herein can be capable of converting a C1 carbon to a multicarbon product (e.g., 1,4-BDO) comprising one or more heterologous genes, where the heterologous gene encodes for an enzyme that can increase overall carbon flow from succinate to 1,4-BDO. Also, the genetically modified microorganisms disclosed herein are capable of converting a C1 carbon to a multicarbon product (e.g., 1,4-BDO) comprising one or more heterologous genes, where the heterologous gene encodes for an enzyme that can increase overall carbon flow from α-ketoglutarate to 1,4-BDO. Also disclosed herein is a genetically modified microorganism capable of converting a C1 carbon to a multi-carbon product comprising one or more heterologous genes, where the heterologous gene encodes for an enzyme that can increase overall carbon flow from oxaloacetate to succinate.

The genetically modified microorganism in some cases is a methylotroph, such as a methanotroph. The methanotroph can be from various genera such as *Methylobacter, Methylomicrobium, Methylomonas, Methylocaldum, Methylococcus, Methylosoma, Methylosarcina, Methylothermus, Methylohalobius, Methylogaea, Methylovulum, Crenothrix, Clonothrix, Methylosphaera, Methylocapsa, Methylocella, Methylosinus, Methylocystis, Methyloferula, Methylomarinum,* or *Methylacidiphilum.* A species that can be used is a *Methylococcus capsulatus*.

Also disclosed herein are vectors. The vectors can comprise any two or more genes of: pyruvate dehydrogenase (aceEF) gene, citrate synthase (gltA) gene, aconitate hydratase 1 (acnA) gene, isocitrate dehydrogenase (icdA) gene, α-ketoglutarate decarboxylase (kgd) gene, succinyl-CoA synthetase (sucC) gene, CoA-dependent succinate semialdehyde dehydrogenase (sucD) gene 4-hyrobutyrate dehydrogenase (4hbD) gene, 4-hydroxybutyryl-CoA transferase (cat2) gene, aldehyde dehydrogenase (ald), and/or alcohol dehydrogenase (adh) gene. For example, a vector as disclosed herein can comprise two or more genes of: pyruvate dehydrogenase (aceEF) gene, citrate synthase (gltA) gene, aconitate hydratase 1 (acnA) gene, and isocitrate dehydrogenase (icdA) gene. A vector as disclosed herein can also comprise two or more genes of: α-ketoglutarate decarboxylase (kgd) gene, 4-hyrobutyrate dehydrogenase (4hbD) gene, 4-hydroxybutyryl-CoA transferase (cat2) gene, aldehyde dehydrogenase (ald), and/or alcohol dehydrogenase (adh) gene. A vector as disclosed herein can also comprise two or more genes of: succinyl-CoA synthetase (sucC) gene, CoA-dependent succinate semialdehyde dehydrogenase (sucD) gene, 4-hyrobutyrate dehydrogenase (4hbD) gene, 4-hydroxybutyryl-CoA transferase (cat2) gene, aldehyde dehydrogenase (ald) gene, and/or alcohol dehydrogenase (adh) gene. In some cases, the vectors can comprise fumarate hydratase, and/or fumarate reductase.

Further disclosed herein are isolated polynucleic acids. For example, the isolated polynucleic acid can be a nucleotide sequence that is at least 85% identical to SEQ ID NO. 2. In some cases, the nucleotide sequence can encode for a protein that has 2-oxoglutarate decarboxylase activity. Also disclosed herein is an isolated polynucleic acid comprising a nucleotide sequence that is at least 85% identical to SEQ ID NO. 4 and/or a nucleotide sequence that is at least 87% identical to SEQ ID NO. 6. The nucleotide sequence can encode for a protein that has α-ketoglutarate decarboxylase activity. Disclosed is also an isolated polynucleic acid comprising a nucleotide sequence that is at least 86% identical to SEQ ID NO. 8. The nucleotide sequence can encode for a protein that has 2-oxoglutarate dehydrogenase E1 component activity. Further disclosed herein is an isolated polynucleic acid comprising a nucleotide sequence that is at least 79% identical to SEQ ID NO. 10. The nucleotide sequence can encode for a protein that has oxidoreductase activity. Disclosed also is an isolated polynucleic acid comprising a nucleotide sequence that is at least 60% identical to SEQ ID NO. 12 or 14. The nucleotide sequence can encode for a protein that has 4-hydroxybutyrate dehydrogenase activity. Also disclosed herein is an isolated polynucleic acid comprising a nucleotide sequence that is at least 60% identical to SEQ ID NO. 16; a nucleotide sequence that is at least 80% identical to SEQ ID NO. 18; and/or a nucleotide sequence that is at least 60% identical to SEQ ID NO. 20. The nucleotide sequence can encode for a protein that has 4-hydroxybutyrate CoA-transferase activity. Also disclosed herein is an isolated polynucleic acid comprising a nucleotide sequence that is at least 60% identical to SEQ ID NO. 22; a nucleotide sequence that is at least 84% identical to SEQ ID NO. 24; a nucleotide sequence that is SEQ ID NO. 26; a nucleotide sequence that is at least 60% identical to SEQ ID NO. 28; a nucleotide sequence that is at least 60% identical to SEQ ID NO. 30; a nucleotide sequence that is at least 60% identical to SEQ ID NO. 32; and/or a nucleotide sequence that is at least 82% identical to SEQ ID NO. 36. The nucleotide sequence can encode for a protein that has aldehyde dehydrogenase and/or alcohol dehydrogenase activity. Further disclosed herein is an isolated polynucleic acid comprising a nucleotide sequence that is at least 60% identical to SEQ ID NO. 34. The nucleotide sequence can encode for a protein that has ATP-dependent permease activity. Also disclosed herein is an isolated polynucleic acid comprising a nucleotide sequence that is at least 86% identical to SEQ ID NO. 38. The nucleotide sequence can encode for a protein that has succinyl-CoA synthetase, beta subunit activity. Further disclosed herein is an isolated polynucleic acid comprising a nucleotide sequence that is at least 86% identical to SEQ ID NO. 40; a nucleotide sequence that is at least 60% identical to SEQ ID NO. 42; and/or a nucleotide sequence that is at least 81% identical to SEQ ID NO. 44. The nucleotide sequence can encode for a protein that has succinyl-CoA synthetase, alpha subunit activity. Additionally disclosed herein is an isolated polynucleic acid comprising a nucleotide sequence that is at least 60% identical to SEQ ID NO. 48 and/or a nucleotide sequence that is at least 60% identical to SEQ ID NO. 50. The nucleotide sequence can encode for a protein that has fumarate hydratase activity. Also disclosed herein is an isolated polynucleic acid comprising a nucleotide sequence that is at least 83% identical to SEQ ID NO. 52; a nucleotide sequence that is at least 84% identical to SEQ ID NO. 54; a nucleotide sequence that is at least 60% identical to SEQ ID NO. 56; and/or a nucleotide sequence that is at least 81% identical to SEQ ID NO. 58. The nucleotide sequence can encode for a protein that has fumarate reductase activity.

Further disclosed herein is a method of making a genetically modified microorganism capable of converting a C1 carbon to a multicarbon product (e.g., 1,4-BDO) comprising contacting a microorganism with a nucleic acid that expresses or is capable of expressing at least one heterologous gene from i) aceEF, ii) lpdA, iii) gltA, iv) acnA, v) icdA, vi) kgd, vii) sucC, viii) sucD, ix) 4hbD, x) Cat2, xi) Ald, xii) Adh, xiii) Fum, xiv) Frd, or xv) any combination thereof. In some cases, the microorganism can be transformed with at least two, three, four, or five heterologous genes.

Additionally disclosed here is a method of making 1,4-BDO comprising (a) contacting a C1 carbon with a genetically modified microorganism capable of converting a C1 carbon into a multicarbon product (e.g., 1,4-BDO), where the microorganism comprises at least one heterologous gene encoding for: i) aceEF, ii) lpdA, iii) gltA, iv) acnA, v) icdA, vi) kgd, vii) sucC, viii) sucD, ix) 4hbD, x) Cat2, xi) Ald, xii) Adh, xiii) Fum, xiv) Frd, or xv) any combination thereof; and (b) growing the microorganism to produce the multicarbon product. The multicarbon product can be 1,4-BDO. In some instances, the growing microorganism can be supplemented with exogenous GHB and/or exogenous α-ketoglutarate and/or exogenous succinate. After the multicarbon product (e.g., 1,4-BDO) is created, the multicarbon product can be recovered.

In some cases, the microorganisms described throughout can be fermented or grown for at least 96 hours.

The multicarbon product (e.g., 1,4-BDO) that is created can be further processed into other useful products such as tetrahydrofuran (THF). The 1,4-BDO that is made from the method disclosed throughout, can be converted into THF by contacting the 1,4-BDO from with a catalyst to produce THF. The 1,4-BDO can be isolated prior to contacting it with a catalyst to form THF. The catalyst used can be an acid catalyst, an alumina catalyst, a silica-alumina catalyst, an alumina-supported tungsten oxide catalyst, a heteropolyacid catalyst, or a zirconium sulfate catalyst. The THF produced by this method can be substantially pure and the method can also comprise recovering the THF. The recovered THF can also be further processed.

The multicarbon product (e.g., 1,4-BDO) that is created from the methods described throughout can also be further processed into chemicals such as polyurethanes. The 1,4-BDO that is made from the methods described throughout, can be converted into polyurethanes by condensing the 1,4-BDO with a dicarboxylic acid/anhydride. The 1,4-BDO can be isolated prior to condensing it with a dicarboxylic acid/anhydride. In some cases, dicarboxylic acid/anhydride can be aliphatic or aromatic. The polyurethanes produced can be substantially pure. The polyurethanes produced by this method can be recovered and optionally further processed.

The multicarbon product (e.g., 1,4-BDO) that is created from the methods described throughout can also be further processed into chemicals such as polybutylene terephthalate (PBT). The 1,4-BDO that is made from the methods described throughout, can be converted into PBT by transesterfying the 1,4-BDO. The 1,4-BDO can be isolated prior to transesterification. In some cases, the transesterification can be done by contacting the 1,4-BDO with dimethyl terephthalate (DMT). The PBT produced can be substantially pure. The PBT produced by this method can be recovered and optionally further processed.

Also disclosed herein is a genetically modified microorganism capable of converting a C1 carbon source to multicarbon product (e.g., 1,4-BDO) comprising one or more heterologous genes, where the one or more heterologous genes is a gene from one or more of the following groups: GROUP 1: pyruvate dehydrogenase (aceEF), citrate synthase (gltA), aconitate hydratase 1 (acnA), isocitrate dehydrogenase (icdA); fumarate hydratase (fum); and/or fumarate reductase (frd); GROUP 2: α-ketoglutarate decarboxylase (kgd), 4-hyrobutyrate dehydrogenase (4hbD), 4-hydroxybutyryl-CoA transferase (Cat2), aldehyde dehydrogenase (Ald), and/or alcohol dehydrogenase (Adh); or GROUP 3: succinyl-CoA synthetase (SucC), CoA-dependent succinate semialdehyde dehydrogenase (SucD), 4-hyrobutyrate dehydrogenase (4hbD), 4-hydroxybutyryl-CoA transferase (Cat2), aldehyde dehydrogenase (Ald), and/or alcohol dehydrogenase (Adh). The heterologous gene can be overexpressed. In some cases, one or more of the genes or groups of genes can be endogenous to the microorganism. For example, in one case, one or more of the genes in GROUP 1 can be heterologous, and the microorganism contains endogenous genes belonging to GROUP 2, GROUP 3, or both GROUP 2 and 3. In another instance, one or more genes from GROUP 2 can be heterologous, and the microorganism contains endogenous genes belonging to GROUP 1, GROUP 3, or both GROUP 1 and 3. In another example, one or more genes from GROUP 3 can be heterologous, and the microorganism contains endogenous genes belonging to GROUP 1, GROUP 2, or both GROUP 1 and 2. In another example, one or more genes from GROUP 1 and 2, can be heterologous whereas one or more genes from GROUP 3 can be endogenous. In other case, one or more genes from GROUP 1 and 3 can be heterologous, wherein one or more genes from GROUP 2 can be endogenous. In other cases, one or more genes from GROUP 1, 2, and 3 can be heterologous. Even if there is one or more heterologous genes from any of the GROUPs, this does not mean the microorganism does not contain endogenous genes from that same group. For example, a microorganism can have both a heterologous and endogenous gene from GROUP 1.

Further disclosed herein is a method of making succinate comprising (a) contacting a C1 carbon with a genetically modified microorganism, wherein the genetically modified microorganism comprises a heterologous fumarate hydratase, fumarate reductase, or any combination thereof; and (b) growing the genetically modified microorganism to produce succinate. In some cases, the genetically modified microorganism can comprise a pyruvate dehydrogenase (aceEF), citrate synthase (gltA), aconitate hydratase 1 (acnA), and/or isocitrate dehydrogenase (icdA). In some cases, the succinate from (b) is isolated. In some cases, the succinate is converted into 1,4-BDO.

In some cases, the genetically modified microorganism is grown for at least 96 hours.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE DISCLOSURE

Figure 1:
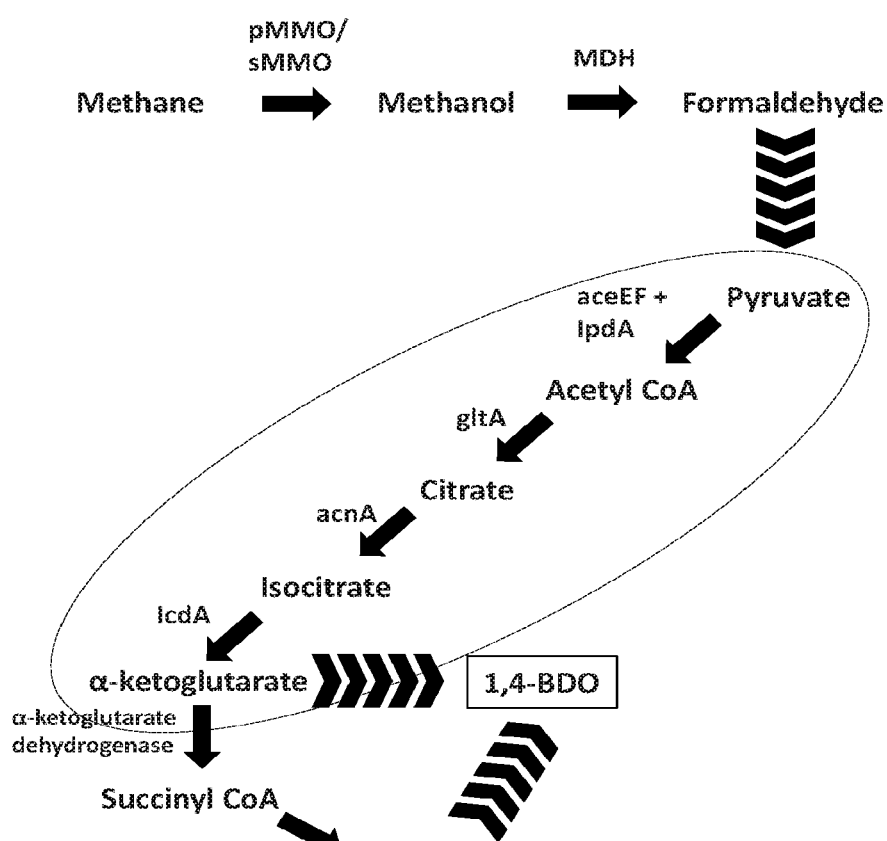
FIG. 1 shows a metabolic pathway from methane ($CH_4$) to 1,4-BDO. The circled part shows the pathway from pyruvate to α-ketoglutarate, which is common to both the α-ketoglutarate to 1,4-BDO pathway and the succinate to 1,4-BDO pathway. The group of enzymes that is responsible for converting pyruvate into α-ketoglutarate is referred to as GROUP 1 throughout. GROUP 1 comprises at least the following enzymes: pyruvate dehydrogenase (aceEF), citrate synthase (gltA), aconitate hydratase 1 (acnA), and isocitrate dehydrogenase (icdA).

The following description and examples illustrate embodiments of the invention in detail. It is to be understood that this invention is not limited to the particular embodiments described herein and as such can vary. Those of skill in the art will recognize that there are numerous variations and modifications of this invention, which are encompassed within its scope.

1,4-BDO is a high value chemical that is currently produced mainly from petroleum sources. There has been some interest in recent years, however, to produce 1,4-BDO by fermentation. Fermentation typically involves taking a carbon source (usually sugar) and fermenting it using a microorganism that is capable of converting the carbon source into a desired product.

Costs to produce chemicals such as 1,4-BDO by fermentation typically depends on the cost of the carbon source used. Sugars are generally higher cost carbon sources that also result in a decrease of food supply. One carbon source is currently extremely cost-effective and abundant is natural gas. The primary source of carbon within natural gas is methane, a C1 carbon. By using cheap carbon sources such as methane, 1,4-BDO can be produced economically. However, the challenge lies engineering fermentation methods and microorganisms to efficiently convert cheap carbon sources, such as methane, into 1,4-BDO using a fermentation process.

As discussed above, 1,4-BDO is not known to be naturally produced by any microorganisms. Thus, intense and extensive genetic engineering is required to produce 1,4-BDO.

Described herein are genetically modified microorganisms, e.g., methylotrophs, for example, methanotrophs, that can convert a C1 carbon substrate, such as methane, into desired products. Some of the genetically modified microorganisms disclosed herein have been designed and altered to efficiently produce 1,4-BDO, multiple folds over what is expected to be produced. For example, methanotrophs, which do not normally produce 1,4-BDO, can be genetically engineered to efficiently produce large quantities of 1,4-BDO. Additionally some of the genetically modified microorganisms disclosed herein can be used to convert a C1 carbon substrate into 1,4-BDO and subsequently into polyurethanes, tetrahydrofurans (THF), polybutylene terephthalates (PBT), or other desired products. These genetically modified microorganisms and the novel methods of fermentation and uses thereof are described herein.

Definitions

The term "about" in relation to a reference numerical value and its grammatical equivalents as used herein can include the numerical value itself and a range of values plus or minus 10% from that numerical value. For example, the amount "about 10" includes 10 and any amounts from 9 to 11. For example, the term "about" in relation to a reference numerical value can also include a range of values plus or minus 10%, 9%, 8%, 7%, 6%, 5%, 4%, 3%, 2%, or 1% from that value. In some cases, the numerical disclosed throughout can be "about" that numerical value even without specifically mentioning the term "about."

The term "genetic modification" or "genetically modified" and their grammatical equivalents as used herein can refer to one or more alterations of a nucleic acid, e.g., the nucleic acid within a microorganism's genome. For example, genetic modification can refer to alterations, additions, and/or deletion of nucleic acid (e.g., whole genes or fragments of genes).

The term "disrupting" and its grammatical equivalents as used herein can refer to a process of altering a gene, e.g., by deletion, insertion, mutation, rearrangement, or any combination thereof. For example, a gene can be disrupted by knockout. Disrupting a gene can be partially reducing or completely suppressing expression (e.g., mRNA and/or protein expression) of the gene. Disrupting can also include inhibitory technology, such as shRNA, siRNA, microRNA, dominant negative, or any other means to inhibit functionality or expression of a gene or protein.

The term "gene editing" and its grammatical equivalents as used herein can refer to genetic engineering in which one or more nucleotides are inserted, replaced, or removed from a genome. For example, gene editing can be performed using a nuclease (e.g., a natural-existing nuclease or an artificially engineered nuclease).

The terms "and/or" and "any combination thereof" and their grammatical equivalents as used herein, can be used interchangeably. These terms can convey that any combination is specifically contemplated. Solely for illustrative purposes, the following phrases "A, B, and/or C" or "A, B, C, or any combination thereof" can mean "A individually; B individually; C individually; A and B; B and C; A and C; and A, B, and C."

The term "substantially pure" and its grammatical equivalents as used herein can mean that a particular substance does not contain a majority of another substance. For example, "substantially pure 1,4-BDO" can mean at least 90% 1,4-BDO. In some instances, "substantially pure 1,4-BDO" can mean at least 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, 99.99%, 99.999%, or 99.9999% 1,4-BDO. For example, substantially pure 1,4-BDO can mean at least 70% 1,4-BDO. In some cases, substantially pure 1,4-BDO can mean at least 75% 1,4-BDO. In some cases, substantially pure 1,4-BDO can mean at least 80% 1,4-BDO. In some cases, substantially pure 1,4-BDO can mean at least 85% 1,4-BDO. In some cases, substantially pure 1,4-BDO can mean at least 90% 1,4-BDO. In some cases, substantially pure 1,4-BDO can mean at least 91% 1,4-BDO. In some cases, substantially pure 1,4-BDO can mean at least 92% 1,4-BDO. In some cases, substantially pure 1,4-BDO can mean at least 93% 1,4-BDO. In some cases, substantially pure 1,4-BDO can mean at least 94% 1,4-BDO. In some cases, substantially pure 1,4-BDO can mean at least 95% 1,4-BDO. In some cases, substantially pure 1,4-BDO can mean at least 96% 1,4-BDO. In some cases, substantially pure 1,4-BDO can mean at least 97% 1,4-BDO. In some cases, substantially pure 1,4-BDO can mean at least 98% 1,4-BDO. In some cases, substantially pure 1,4-BDO can mean at least 99% 1,4-BDO.

The term "heterologous" and its grammatical equivalents as used herein can mean "derived from a different species." For example, a "heterologous gene" can mean a gene that is from a different species. In some instances, as "a methanotroph comprising a heterologous gene" can mean that the methanotroph contains a gene that is not from the same methanotroph. The gene can be from a different microorganism such as yeast or from a different species such as a different methanotroph species.

The term "substantially similar" and its grammatical equivalents in reference to another sequence as used herein can mean at least 50% identical. In some instances, the term substantially similar refers to a sequence that is 55% identical. In some instances, the term substantially similar refers to a sequence that is 60% identical. In some instances, the term substantially similar refers to a sequence that is 65% identical. In some instances, the term substantially similar refers to a sequence that is 70% identical. In some instances, the term substantially similar refers to a sequence that is 75% identical. In some instances, the term substantially similar refers to a sequence that is 80% identical. In other instances, the term substantially similar refers to a sequence that is 81% identical. In other instances, the term substantially similar refers to a sequence that is 82% identical. In other instances, the term substantially similar refers to a sequence that is 83% identical. In other instances, the term substantially similar refers to a sequence that is 84% identical. In other instances, the term substantially similar refers to a sequence that is 85% identical. In other instances, the term substantially similar refers to a sequence that is 86% identical. In other instances, the term substantially similar refers to a sequence that is 87% identical. In other instances, the term substantially similar refers to a sequence that is 88% identical. In other instances, the term substantially similar refers to a sequence that is 89% identical. In some instances, the term substantially similar refers to a sequence that is 90% identical. In some instances, the term substantially similar refers to a sequence that is 91% identical. In some instances, the term substantially similar refers to a sequence that is 92% identical. In some instances, the term substantially similar refers to a sequence that is 93% identical. In some instances, the term substantially similar refers to a sequence that is 94% identical. In some instances, the term substantially similar refers to a sequence that is 95% identical. In some instances, the term substantially similar refers to a sequence that is 96% identical. In some instances, the term substantially similar refers to a sequence that is 97% identical. In some instances, the term substantially similar refers to a sequence that is 98% identical. In some instances, the term substantially similar refers to a sequence that is 99% identical. In some instances, the term substantially similar refers to a sequence that is 100% identical. In order to determine the percentage of identity between two sequences, the two sequences are aligned, using for example the alignment method of Needleman and Wunsch (J. Mol. Biol., 1970, 48: 443), as revised by Smith and Waterman (Adv. Appl. Math., 1981, 2: 482) so that the highest order match is obtained between the two sequences and the number of identical amino acids/nucleotides is determined between the two sequences. For example, methods to calculate the percentage identity between two amino acid sequences are generally art recognized and include, for example, those described by Carillo and Lipton (SIAM J. Applied Math., 1988, 48:1073) and those described in Computational Molecular Biology, Lesk, e.d. Oxford University Press, New York, 1988, Biocomputing: Informatics and Genomics Projects. Generally, computer programs will be employed for such calculations. Computer programs that may be used in this regard include, but are not limited to, GCG (Devereux et al., Nucleic Acids Res., 1984, 12: 387) BLASTP, BLASTN and FASTA (Altschul et al., J. Molec. Biol., 1990:215:403). A particularly preferred method for determining the percentage identity between two polypeptides involves the Clustal W algorithm (Thompson, J D, Higgines, D G and Gibson T J, 1994, Nucleic Acid Res 22(22): 4673-4680 together with the BLOSUM 62 scoring matrix (Henikoff S & Henikoff, J G, 1992, Proc. Natl. Acad. Sci. USA 89: 10915-10919 using a gap opening penalty of 10 and a gap extension penalty of 0.1, so that the highest order match obtained between two sequences wherein at least 50% of the total length of one of the two sequences is involved in the alignment.

The term "C1 carbon" or "C1 carbon substrates" and their grammatical equivalents as used herein can be used interchangeably and can mean any organic compound that contains a single carbon atom. Examples can include, but are not limited to, CO, $CH_4$, and/or $CO_2$.

I. Genetically Modified Microorganisms and Methods of Making the Same 1,4-BDO is not known to be naturally produced by any organism. However, this application discloses genetically modified microorganisms that can produce 1,4-BDO, and can do so at high levels. For example, disclosed herein are microorganisms that do not naturally produce 1,4-BDO but can be genetically modified to synthesize 1,4-BDO, including at commercially feasible levels.

Microorganisms

The microorganisms described herein can produce multicarbon products from a C1 carbon substrate, such as, but not limited to CO, $CO_2$, and $CH_4$. This however does not mean that these microorganisms use solely C1 carbons. Some of the microorganisms disclosed herein can be made to utilize additional carbon substrates, including carbon substrates that the microorganism naturally uses in addition to other carbon substrates.

The microorganisms disclosed herein can be a prokaryote or eukaryote. Additionally, other microorganisms such as bacteria, yeast, or algae can be used.

Some microorganisms can use a C1 carbon to generate a desired product. For example, some of the microorganisms that can convert C1 carbon substrates into desired products can be a microorganism that is capable of using natural gas as a carbon substrate. In some cases, the microorganism can use the methane contained within the natural gas a as a carbon source to make desired products. One type of microorganism that uses C1 carbon substrates to form desired organic compounds are methylotrophs, such as methanotrophs. The methanotrophs that can be particularly useful include methanotrophs from the genera *Methylobacter, Methylomicrobium, Methylomonas, Methylocaldum, Methylococcus, Methylosoma, Methylosarcina, Methylothermus, Methylohalobius, Methylogaea, Methylovulum, Crenothrix, Clonothrix, Methylosphaera, Methylocapsa, Methylocella, Methylosinus, Methylocystis, Methyloferula, Methylomarinum, Methylacidiphilum*, or any combinations thereof. Methanotrophs from the genus *Methylococcus* can be particularly useful. When a methanotroph from the genus *Methylococcus* is used, a methanotroph from the species *Methylococcus capsulatus* can be used.

Some microorganisms are microorganisms that are capable of using $CO_2$ as a carbon substrate. For instance, the microorganisms can be a methanogen. Microorganisms that are capable of using $CO_2$ as a substrate can contain chlorophyll. One type of microorganism that uses $CO_2$ to form desired organic compounds are algae. Another type of microorganism that can use $CO_2$ as a substrate is a cyanobacterium.

Some microorganisms that can convert C1 carbon substrates into desired products can be a microorganism that is capable of using CO as a carbon substrate. Anaerobic microorganism can typically process CO and therefore can be used herein. One type of microorganism that uses CO to form desired organic compounds are bacterium such as *Clostridium*. These microorganism can be genetically modified into making substantial amounts of 1,4-BDO.

Enzymes

In order to genetically engineer certain microorganisms to produce certain useful products such as 1,4-BDO, microorganisms can be transformed with one or more genes that encode for specific enzymes. These genes can be heterologous to the microorganism.

It is also contemplated that any and all genes disclosed herein can be overexpressed. This can lead to an overexpression of the gene but also lead to an increase of the actual polypeptide levels. For example, when a microorganism or vector comprises a gene (e.g., a heterologous gene), the gene can be overexpressed. This is done typically by using a promoter that is highly expressed or inserting multiple copies of the gene.

For example, the genetically modified microorganism can comprise one or more nucleic acids encoding for an enzyme capable of catalyzing one or more of the reactions: i) methane to methanol; ii) methanol to formaldehyde; iii) formaldehyde to pyruvate; iv) pyruvate to acetyl CoA; v) acetyl CoA to citrate; vi) citrate to isocitrate; vii) isocitrate to α-ketoglutarate; viii) α-ketoglutarate to succinyl CoA; ix) succinate CoA to succinate; x) oxaloacetate and/or malyl-CoA to L-malate; xi) L-malate to fumarate; and/or xii) fumarate to succinate. For example, the genetically modified microorganism can comprise one or more genes including but not limited to: pyruvate dehydrogenase (aceEF), citrate synthase (gltA), aconitate hydratase 1 (acnA), and isocitrate dehydrogenase (icdA), α-ketoglutarate dehydrogenase, succinyl-CoA synthetase; fumarate hydratase (fum); fumarate reductase (frd); or any combination thereof. Depending on the substrate used, any of the products of the pathway can be made by increasing or decreasing the expression of the enzymes that promote the formation of the desired product. Some of the nucleic acids can be endogenous to the microorganism and some of the nucleic acids can be heterologous to the microorganism.

Figure 2:
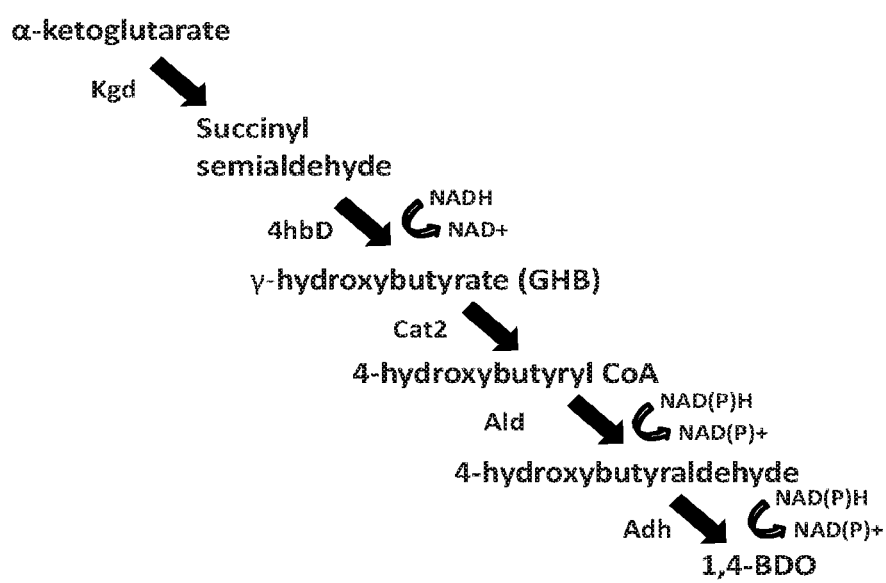
FIG. 2 shows the α-ketoglutarate to 1,4-BDO pathway. α-ketoglutarate is converted to succinate semialdehyde through an α-ketoglutarate decarboxylase (kgd). Succinate semialdehyde is then converted to gamma hydroxybutyrate (GHB) by 4-hydroxybutyrate dehydrogenase (4hbD). GHB is then converted to 4-hydroxybutyryl CoA by 4-hydroxybutyrate CoA transferase (cat2). 4-hydroxybutyryl CoA is then converted to 4-hydroxybutyraldehyde by aldehyde dehydrogenase (Ald) through the use of NAD(P)H. 4-hydroxybutyraldehyde is converted to 1,4-BDO by alcohol dehydrogenase through the use of NAD(P)H. The group of enzymes that is responsible for converting α-ketoglutarate to 1,4-BDO is referred to as GROUP 2 throughout.
Figure 3:
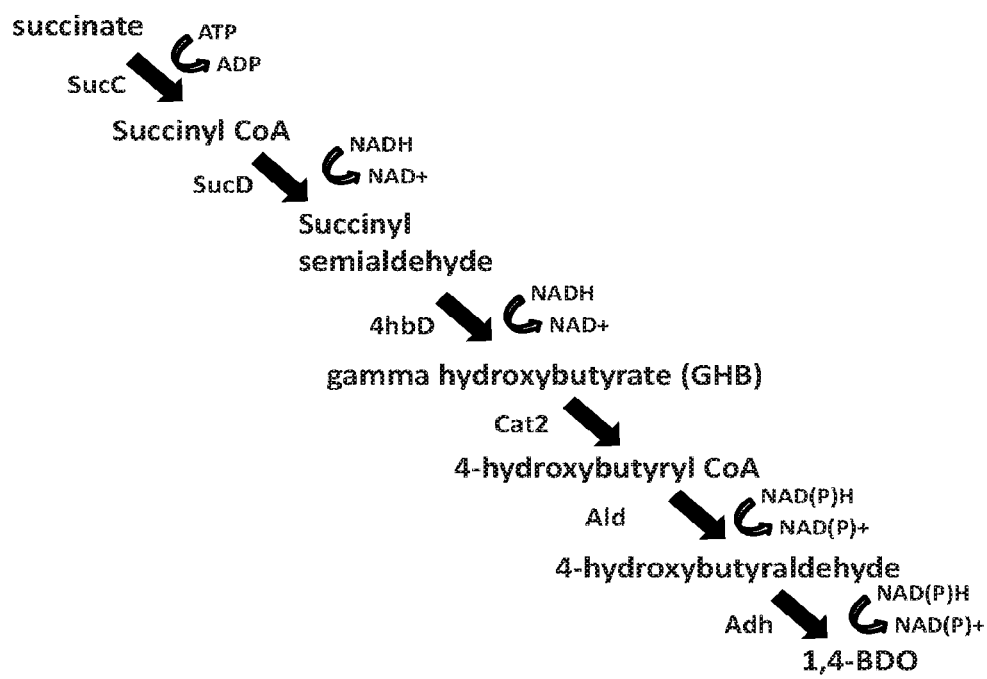
FIG. 3 shows the succinate to 1,4-BDO pathway. Succinate is converted to succinyl CoA by Succinyl CoA synthease beta subunit (sucC). Succinyl CoA is then converted to succinate semialdehyde by succinyl CoA synthease alpha subunit (sucD). Succinate semialdehyde is then converted to 7-hydroxybutyrate (ghb) through the use of 4-hydroxybutyrate dehydrogenase (4hbD). GHB is then converted to 4-hydroxybutyryl CoA by 4-hydroxybutyrate CoA transferase (cat2). 4-hydroxybutyryl CoA is then converted to 4-hydroxybutyraldehyde by aldehyde dehydrogenase (ald) through the use of NAD(P)H. 4-hydroxybutyraldehyde is converted to 1,4-BDO by alcohol dehydrogenase through the use of NAD(P)H. The group of enzymes that is responsible for converting succinate to 1,4-BDO is referred to as GROUP 3 throughout.

Further, in order to create a microorganism that can produce a multicarbon product such as 1,4-BDO, one or more genes (e.g., heterologous genes) can be transformed/transfected (i.e., inserted) into the microorganism (transiently or stably). At least one genes of any of the i) GROUP 2: α-ketoglutarate to 1,4-BDO (see e.g., FIG. 2) and ii) GROUP 3: succinate to 1,4-BDO pathway (see e.g., FIG. 3) can be used to generate a multicarbon substrate such as 1,4-BDO at efficiently levels. A microorganism containing one or more genes from one or both pathway can be placed inside a microorganism in order to produce a multicarbon substrate such as 1,4-BDO. For example, a gene from GROUP 2 (the α-ketoglutarate to 1,4-BDO pathway) can be used in order to produce multicarbon substrate such as 1,4-BDO from a microorganism. Alternatively, a gene from GROUP 3 (the succinate to 1,4-BDO pathway) can be used in order to produce a multicarbon substrate such as 1,4-BDO from a microorganism. Another way to produce multicarbon substrate such as 1,4-BDO from a microorganism can be expressing one or more genes from both GROUP 2 (the α-ketoglutarate to 1,4-BDO pathway) and GROUP 3 (the succinate to 1,4-BDO pathway). In some case, all of the genes from GROUP 2 can be used. In other cases, all of the genes from GROUP 3 can be used. In other instances, all the genes from both GROUPS 2 and 3 can be used. In some cases, the microorganism can comprise a fumarate hydratase (fum) and/or fumarate reductase (frd). In some cases, some of the genes from the groups can be an endogenous gene.

In some cases, when the microorganism utilizes the α-ketoglutarate to 1,4-BDO pathway, the microorganism can comprise α-ketoglutarate decarboxylase (kgd), which is an enzyme that is capable of converting α-ketoglutarate to succinate semialdehyde. In some cases, the microorganism can comprise a 4-hydroxybutyrate dehydrogenase (4hbD), which is an enzyme that converts succinate semialdehyde to 7-hydroxybutyrate (GHB). In some cases, the microorganism can comprise a 4-hydroxybutyrate CoA transferase (cat2), which is an enzyme that converts 7-hydroxybutyrate (GHB) to 4-hydroxybutyryl CoA. In some cases, the microorganism can comprise an aldehyde dehydrogenase (ald), which is an enzyme that converts 4-hydroxybutyryl CoA to 4-hydroxybutyraldehyde. In some cases, the microorganism can comprise an alcohol dehydrogenase (adh), which is an enzyme that converts 4-hydroxybutyraldehyde to 1,4-BDO. In some cases, all the enzymes from the α-ketoglutarate to 1,4-BDO pathway can be used. One or more of these enzymes can be endogenous to the microorganism.

Described here are microorganisms used to make a multicarbon product such as 1,4-BDO from a C1 carbon (e.g., methane). In some cases, the microorganism herein can be transformed with a gene encoding for one or more of the following: i) α-ketoglutarate decarboxylase (kgd); ii) 4-hydroxybutyrate dehydrogenase (4hbD); iii) 4-hydroxybutyrate CoA transferase (cat2); (iv) aldehyde dehydrogenase (ald); (v) alcohol dehydrogenase (adh); or (vi) any combination thereof. These genes can be heterologous to the microorganism. The genes can also encode for an enzyme that can conduct the chemical conversions as described above. For example, the aldehyde dehydrogenase (Ald) can be an enzyme that converts 4-hydroxybutyryl CoA to 4-hydroxybutyraldehyde, whereas the alcohol dehydrogenase (adh) can be an enzyme that converts 4-hydroxybutyraldehyde to 1,4-BDO.

In some cases, the microorganism can comprise a fumarate hydratase (fum), which is an enzyme that converts L-malate to fumarate. In some cases, the microorganism can comprise a fumarate reductase (frd), which is an enzyme that converts fumarate to succinate.

When an α-ketoglutarate decarboxylase (kgd) is used the α-ketoglutarate decarboxylase can be from a bacteria (e.g., a gram positive bacterium or a bacterium that is neither gram positive or gram negative), such as from the genus *Mycobacterium, Corynebacterium* and/or *Rhodococcus*. For example, an α-ketoglutarate decarboxylase (kgd) can be from the species *Mycobacterium bovis, Mycobacterium tuberculosis, Corynebacterium terpenotabidum*, and/or *Rhbodococcus jostii*.

The α-ketoglutarate decarboxylase (kgd) can comprise an amino acid sequence that is substantially similar to any one of SEQ ID NOs. 1, 3, 5, or 7. For example, the α-ketoglutarate decarboxylase can comprise an amino acid sequence that is at least 60% identical to any one of SEQ ID NOs. 1, 3, 5, or 7. For example, the α-ketoglutarate decarboxylase can comprise an amino acid sequence that is at least 65% identical to any one of SEQ ID NOs. 1, 3, 5, or 7. In some cases, the α-ketoglutarate decarboxylase can comprise an amino acid sequence that is at least 70% identical to any one of SEQ ID NOs. 1, 3, 5, or 7. For example, the α-ketoglutarate decarboxylase can comprise an amino acid sequence that is at least 75% identical to any one of SEQ ID NOs. 1, 3, 5, or 7. In some cases, the α-ketoglutarate decarboxylase can comprise an amino acid sequence that is at least 80% identical to any one of SEQ ID NOs. 1, 3, 5, or 7. For example, the α-ketoglutarate decarboxylase can comprise an amino acid sequence that is at least 85% identical to any one of SEQ ID NOs. 1, 3, 5, or 7. In some cases, the α-ketoglutarate decarboxylase can comprise an amino acid sequence that is at least 90% identical to any one of SEQ ID NOs. 1, 3, 5, or 7. In some cases, the α-ketoglutarate decarboxylase can comprise an amino acid sequence that is at least 91% identical to any one of SEQ ID NOs. 1, 3, 5, or 7. In some cases, the α-ketoglutarate decarboxylase can comprise an amino acid sequence that is at least 92% identical to any one of SEQ ID NOs. 1, 3, 5, or 7. In some cases, the α-ketoglutarate decarboxylase can comprise an amino acid sequence that is at least 93% identical to any one of SEQ ID NOs. 1, 3, 5, or 7. In some cases, the α-ketoglutarate decarboxylase can comprise an amino acid sequence that is at least 94% identical to any one of SEQ ID NOs. 1, 3, 5, or 7. In some cases, the α-ketoglutarate decarboxylase can comprise an amino acid sequence that is at least 95% identical to any one of SEQ ID NOs. 1, 3, 5, or 7. In some cases, the α-ketoglutarate decarboxylase can comprise an amino acid sequence that is at least 96% identical to any one of SEQ ID NOs. 1, 3, 5, or 7. In some cases, the α-ketoglutarate decarboxylase can comprise an amino acid sequence that is at least 97% identical to any one of SEQ ID NOs. 1, 3, 5, or 7. In some cases, the α-ketoglutarate decarboxylase can comprise an amino acid sequence that is at least 98% identical to any one of SEQ ID NOs. 1, 3, 5, or 7. In some cases, the α-ketoglutarate decarboxylase can comprise an amino acid sequence that is at least 99% identical to any one of SEQ ID NOs. 1, 3, 5, or 7. In some cases, the α-ketoglutarate decarboxylase can comprise an amino acid sequence that is any one of SEQ ID NOs. 1, 3, 5, or 7.

When a 4-hydroxybutyrate dehydrogenase (4hbD) is desired the 4-hydroxybutyrate dehydrogenase can be from a bacterium (e.g., a gram negative or positive bacterium), such as from the genus *Escherichia, Porphyromonas*, and/or *Clostridium*. For example, a 4-hydroxybutyrate dehydrogenase can be from the species *Escherichia coli, Porphyromonas gingivalis*, and/or *Clostridium kluyveri*.

The 4-hydroxybutyrate dehydrogenase can comprise an amino acid sequence that is substantially similar to SEQ ID NO. 11 or 13. For example, the 4-hydroxybutyrate dehydrogenase can comprise an amino acid sequence that is at least 60% identical to SEQ ID NO. 11 or 13. For example, the 4-hydroxybutyrate dehydrogenase can comprise an amino acid sequence that is at least 65% identical to SEQ ID NO. 11 or 13. In some cases, the 4-hydroxybutyrate dehydrogenase can comprise an amino acid sequence that is at least 70% identical to SEQ ID NO. 11 or 13. For example, the 4-hydroxybutyrate dehydrogenase can comprise an amino acid sequence that is at least 75% identical to SEQ ID NO. 11 or 13. In some cases, the 4-hydroxybutyrate dehydrogenase can comprise an amino acid sequence that is at least 80% identical to SEQ ID NO. 11 or 13. For example, the 4-hydroxybutyrate dehydrogenase can comprise an amino acid sequence that is at least 85% identical to SEQ ID NO. 11 or 13. In some cases, the 4-hydroxybutyrate dehydrogenase can comprise an amino acid sequence that is at least 90% identical to SEQ ID NO. 11 or 13. In some cases, the 4-hydroxybutyrate dehydrogenase can comprise an amino acid sequence that is at least 91% identical to SEQ ID NO. 11 or 13. In some cases, the 4-hydroxybutyrate dehydrogenase can comprise an amino acid sequence that is at least 92% identical to SEQ ID NO. 11 or 13. In some cases, the 4-hydroxybutyrate dehydrogenase can comprise an amino acid sequence that is at least 93% identical to SEQ ID NO. 11 or 13. In some cases, the 4-hydroxybutyrate dehydrogenase can comprise an amino acid sequence that is at least 94% identical to SEQ ID NO. 11 or 13. In some cases, the 4-hydroxybutyrate dehydrogenase can comprise an amino acid sequence that is at least 95% identical to SEQ ID NO. 11 or 13. In some cases, the 4-hydroxybutyrate dehydrogenase can comprise an amino acid sequence that is at least 96% identical to SEQ ID NO. 11 or 13. In some cases, the 4-hydroxybutyrate dehydrogenase can comprise an amino acid sequence that is at least 97% identical to SEQ ID NO. 11 or 13. In some cases, the 4-hydroxybutyrate dehydrogenase can comprise an amino acid sequence that is at least 98% identical to SEQ ID NO. 11 or 13. In some cases, the 4-hydroxybutyrate dehydrogenase can comprise an amino acid sequence that is at least 99% identical to SEQ ID NO. 11 or 13. In some cases, the 4-hydroxybutyrate dehydrogenase can comprise an amino acid sequence that is SEQ ID NO. 11 or 13.

When a 4-hydroxybutyrate CoA transferase (Cat2) is desired the 4-hydroxybutyrate CoA transferase can be from a bacterium (e.g., a gram negative or positive bacterium), such as from the genus *Porphyromonas*, and/or *Clostridium*. For example, a 4-hydroxybutyrate CoA transferase can be from the species *Porphyromonas gingivalis* and/or *Clostridium acetobutylicum*.

The 4-hydroxybutyrate CoA transferase can comprise an amino acid sequence that is substantially similar to any one of SEQ ID NOs. 15, 17, or 19. For example, the 4-hydroxybutyrate CoA transferase can comprise an amino acid sequence that is at least 60% identical to any one of SEQ ID NOs. 15, 17, or 19. For example, the 4-hydroxybutyrate CoA transferase can comprise an amino acid sequence that is at least 65% identical to any one of SEQ ID NOs. 15, 17, or 19. In some cases, the 4-hydroxybutyrate CoA transferase can comprise an amino acid sequence that is at least 70% identical to any one of SEQ ID NOs. 15, 17, or 19. For example, the 4-hydroxybutyrate CoA transferase can comprise an amino acid sequence that is at least 75% identical to any one of SEQ ID NOs. 15, 17, or 19. In some cases, the 4-hydroxybutyrate CoA transferase can comprise an amino acid sequence that is at least 80% identical to any one of SEQ ID NOs. 15, 17, or 19. For example, the 4-hydroxybutyrate CoA transferase can comprise an amino acid sequence that is at least 85% identical to any one of SEQ ID NOs. 15, 17, or 19. In some cases, the 4-hydroxybutyrate CoA transferase can comprise an amino acid sequence that is at least 90% identical to any one of SEQ ID NOs. 15, 17, or 19. In some cases, the 4-hydroxybutyrate CoA transferase can comprise an amino acid sequence that is at least 91% identical to any one of SEQ ID NOs. 15, 17, or 19. In some cases, the 4-hydroxybutyrate CoA transferase can comprise an amino acid sequence that is at least 92% identical to any one of SEQ ID NOs. 15, 17, or 19. In some cases, the 4-hydroxybutyrate CoA transferase can comprise an amino acid sequence that is at least 93% identical to any one of SEQ ID NOs. 15, 17, or 19. In some cases, the 4-hydroxybutyrate CoA transferase can comprise an amino acid sequence that is at least 94% identical to any one of SEQ ID NOs. 15, 17, or 19. In some cases, the 4-hydroxybutyrate CoA transferase can comprise an amino acid sequence that is at least 95% identical to any one of SEQ ID NOs. 15, 17, or 19. In some cases, the 4-hydroxybutyrate CoA transferase can comprise an amino acid sequence that is at least 96% identical to any one of SEQ ID NOs. 15, 17, or 19. In some cases, the 4-hydroxybutyrate CoA transferase can comprise an amino acid sequence that is at least 97% identical to any one of SEQ ID NOs. 15, 17, or 19. In some cases, the 4-hydroxybutyrate CoA transferase can comprise an amino acid sequence that is at least 98% identical to any one of SEQ ID NOs. 15, 17, or 19. In some cases, the 4-hydroxybutyrate CoA transferase can comprise an amino acid sequence that is at least 99% identical to any one of SEQ ID NOs. 15, 17, or 19. In some cases, the 4-hydroxybutyrate CoA transferase can comprise an amino acid sequence that is any one of SEQ ID NOs. 15, 17, or 19.

When an aldehyde dehydrogenase (Ald) and/or an alcohol dehydrogenase (Adh) is desired the aldehyde dehydrogenase and/or alcohol dehydrogenase can be from a bacterium (e.g., a gram negative or positive bacterium), such as from the genus *Escherichia, Acinetobacter, Porphyromonas*, and/or *Clostridium*, or from a yeast such as from the genus *Saccharomyces*. For example, a 4-hydroxybutyrate CoA transferase can be from the species *Escherichia coli, Acinetobacter baylyi, Porphyromonas gingivalis, Clostridium acetobutylicum* and/or *Saccharomyces cerevisiae*. In some cases, more than one aldehyde dehydrogenase and/or alcohol dehydrogenase can be used.

The aldehyde dehydrogenase and/or alcohol dehydrogenase can comprise an amino acid sequence that is substantially similar to any one of SEQ ID NOs. 21, 23, 25, 27, 29, 31, 33, or 35. For example, the aldehyde dehydrogenase and/or alcohol dehydrogenase can comprise an amino acid sequence that is at least 60% identical to any one of SEQ ID NOs. 21, 23, 25, 27, 29, 31, 33, or 35. For example, the aldehyde dehydrogenase and/or alcohol dehydrogenase can comprise an amino acid sequence that is at least 65% identical to any one of SEQ ID NOs. 21, 23, 25, 27, 29, 31, 33, or 35. In some cases, the aldehyde dehydrogenase and/or alcohol dehydrogenase can comprise an amino acid sequence that is at least 70% identical to any one of SEQ ID NOs. 21, 23, 25, 27, 29, 31, 33, or 35. For example, the aldehyde dehydrogenase and/or alcohol dehydrogenase can comprise an amino acid sequence that is at least 75% identical to any one of SEQ ID NOs. 21, 23, 25, 27, 29, 31, 33, or 35. In some cases, the aldehyde dehydrogenase and/or alcohol dehydrogenase can comprise an amino acid sequence that is at least 80% identical to any one of SEQ ID NOs. 21, 23, 25, 27, 29, 31, 33, or 35. For example, the aldehyde dehydrogenase and/or alcohol dehydrogenase can comprise an amino acid sequence that is at least 85% identical to any one of SEQ ID NOs. 21, 23, 25, 27, 29, 31, 33, or 35. In some cases, the aldehyde dehydrogenase and/or alcohol dehydrogenase can comprise an amino acid sequence that is at least 90% identical to any one of SEQ ID NOs. 21, 23, 25, 27, 29, 31, 33, or 35. In some cases, the aldehyde dehydrogenase and/or alcohol dehydrogenase can comprise an amino acid sequence that is at least 91% identical to any one of SEQ ID NOs. 21, 23, 25, 27, 29, 31, 33, or 35. In some cases, the aldehyde dehydrogenase and/or alcohol dehydrogenase can comprise an amino acid sequence that is at least 92% identical to any one of SEQ ID NOs. 21, 23, 25, 27, 29, 31, 33, or 35. In some cases, the aldehyde dehydrogenase and/or alcohol dehydrogenase can comprise an amino acid sequence that is at least 93% identical to any one of SEQ ID NOs. 21, 23, 25, 27, 29, 31, 33, or 35. In some cases, the aldehyde dehydrogenase and/or alcohol dehydrogenase can comprise an amino acid sequence that is at least 94% identical to any one of SEQ ID NOs. 21, 23, 25, 27, 29, 31, 33, or 35. In some cases, the aldehyde dehydrogenase and/or alcohol dehydrogenase can comprise an amino acid sequence that is at least 95% identical to any one of SEQ ID NOs. 21, 23, 25, 27, 29, 31, 33, or 35. In some cases, the aldehyde dehydrogenase and/or alcohol dehydrogenase can comprise an amino acid sequence that is at least 96% identical to any one of SEQ ID NOs. 21, 23, 25, 27, 29, 31, 33, or 35. In some cases, the aldehyde dehydrogenase and/or alcohol dehydrogenase can comprise an amino acid sequence that is at least 97% identical to any one of SEQ ID NOs. 21, 23, 25, 27, 29, 31, 33, or 35. In some cases, the aldehyde dehydrogenase and/or alcohol dehydrogenase can comprise an amino acid sequence that is at least 98% identical to any one of SEQ ID NOs. 21, 23, 25, 27, 29, 31, 33, or 35. In some cases, the aldehyde dehydrogenase and/or alcohol dehydrogenase can comprise an amino acid sequence that is at least 99% identical to any one of SEQ ID NOs. 21, 23, 25, 27, 29, 31, 33, or 35. In some cases, the aldehyde dehydrogenase and/or alcohol dehydrogenase can comprise an amino acid sequence that is any one of SEQ ID NOs. 21, 23, 25, 27, 29, 31, 33, or 35.

Alternatively, α-ketoglutarate can be pushed towards the succinate pathway. α-ketoglutarate can be converted to succinyl CoA through the use of α-ketoglutarate dehydrogenase complex. Succinyl CoA can be converted to succinate through the use of succinyl-CoA synthase. Once succinate is formed, the succinate can be lead towards the 1,4-BDO pathway.

Succinate can be converted into a multicarbon product such as 1,4-BDO. In some cases, when the microorganism utilizes the succinate to 1,4-BDO pathway, the microorganism can comprise succinyl CoA synthase beta subunit (SucC), which is an enzyme that is capable of converting succinate to succinyl CoA. In some cases, the microorganism can comprise a succinyl CoA synthase alpha subunit (SucD), which is an enzyme that converts succinyl CoA to succinate semialdehyde. In some cases, the microorganism can comprise a 4-hydroxybutyrate dehydrogenase (4hbD), which is an enzyme that converts succinate semialdehyde to 7-hydroxybutyrate (GHB). In some cases, the microorganism can comprise a 4-hydroxybutyrate CoA transferase (cat2), which is an enzyme that converts 7-hydroxybutyrate (GHB) to 4-hydroxybutyryl CoA. In some cases, the microorganism can comprise an aldehyde dehydrogenase (ald), which is an enzyme that converts 4-hydroxybutyryl CoA to 4-hydroxybutyraldehyde. In some cases, the microorganism can comprise an alcohol dehydrogenase (adh), which is an enzyme that converts 4-hydroxybutyraldehyde to 1,4-BDO. One or more of these enzymes can be heterologous to the microorganism. Additionally, one or more of these enzymes can be endogenous to the microorganism.

Described here are microorganisms used to make 1,4-BDO from a C1 carbon (e.g., methane). In some cases, the microorganism herein can be transformed with a gene encoding for one or more of the following: i) succinyl CoA synthase beta subunit (sucC); ii) succinyl CoA synthase alpha subunit (sucD); iii) 4-hydroxybutyrate dehydrogenase (4hbD); iv) 4-hydroxybutyrate CoA transferase (Cat2); (v) aldehyde dehydrogenase (Ald); (vi) alcohol dehydrogenase (adh); or (vii) any combination thereof. These genes can be heterologous to the microorganism. The genes can also encode for an enzyme that can conduct the chemical conversions as described above. For example, the aldehyde dehydrogenase (ald) can be an enzyme that converts 4-hydroxybutyryl CoA to 4-hydroxybutyraldehyde, whereas the alcohol dehydrogenase (adh) can be an enzyme that converts 4-hydroxybutyraldehyde to 1,4-BDO.

When a succinyl CoA synthase beta subunit (SucC) is used the succinyl CoA synthase beta subunit can be from a bacteria (e.g., a gram negative bacterium), such as from the genus *Escherichia*. For example, the succinyl CoA synthease beta subunit can be from the species *Escherichia coli*.

The succinyl CoA synthease beta subunit can comprise an amino acid sequence that is substantially similar to SEQ ID NO. 37. For example, the succinyl CoA synthase beta subunit can comprise an amino acid sequence that is at least 60% identical to SEQ ID NO. 37. For example, the succinyl CoA synthease beta subunit can comprise an amino acid sequence that is at least 65% identical to SEQ ID NO. 37. In some cases, the succinyl CoA synthease beta subunit can comprise an amino acid sequence that is at least 70% identical to SEQ ID NO. 37. For example, the succinyl CoA synthase beta subunit can comprise an amino acid sequence that is at least 75% identical to SEQ ID NO. 37. In some cases, the succinyl CoA synthease beta subunit can comprise an amino acid sequence that is at least 80% identical to SEQ ID NO. 37. For example, the succinyl CoA synthease beta subunit can comprise an amino acid sequence that is at least 85% identical to SEQ ID NO. 37. In some cases, the succinyl CoA synthease beta subunit can comprise an amino acid sequence that is at least 90% identical to SEQ ID NO. 37. In some cases, the succinyl CoA synthease beta subunit can comprise an amino acid sequence that is at least 91% identical to SEQ ID NO. 37. In some cases, the succinyl CoA synthease beta subunit can comprise an amino acid sequence that is at least 92% identical to SEQ ID NO. 37. In some cases, the succinyl CoA synthease beta subunit can comprise an amino acid sequence that is at least 93% identical to SEQ ID NO. 37. In some cases, the succinyl CoA synthease beta subunit can comprise an amino acid sequence that is at least 94% identical to SEQ ID NO. 37. In some cases, the succinyl CoA synthease beta subunit can comprise an amino acid sequence that is at least 95% identical to SEQ ID NO. 37. In some cases, the succinyl CoA synthease beta subunit can comprise an amino acid sequence that is at least 96% identical to SEQ ID NO. 37. In some cases, the succinyl CoA synthease beta subunit can comprise an amino acid sequence that is at least 97% identical to SEQ ID NO. 37. In some cases, the succinyl CoA synthease beta subunit can comprise an amino acid sequence that is at least 98% identical to SEQ ID NO. 37. In some cases, the succinyl CoA synthease beta subunit can comprise an amino acid sequence that is at least 99% identical to SEQ ID NO. 37. In some cases, the succinyl CoA synthease beta subunit can comprise an amino acid sequence that is SEQ ID NO. 37.

When a succinyl CoA synthase alpha subunit (SucD) is used the succinyl CoA synthase alpha subunit can be from a bacteria (e.g., a gram negative or gram positive bacterium), such as from the genus *Escherichia*, *Clostridium*, or *Porphyromonas*. For example, the succinyl CoA synthase alpha subunit can be from the species *Escherichia coli*, *Clostridium kluyveri*, *Porphyromonas gingivalis*.

The succinyl CoA synthase alpha subunit (sucD) can comprise an amino acid sequence that is substantially similar to any one of SEQ ID NOs. 39, 41, or 43. For example, the succinyl CoA synthase alpha subunit can comprise an amino acid sequence that is at least 60% identical to any one of SEQ ID NOs. 39, 41, or 43. In some cases, the succinyl CoA synthase alpha subunit can comprise an amino acid sequence that is at least 65% identical to any one of SEQ ID NOs. 39, 41, or 43. In some cases, the succinyl CoA synthase alpha subunit can comprise an amino acid sequence that is at least 70% identical to any one of SEQ ID NOs. 39, 41, or 43. For example, the succinyl CoA synthase alpha subunit can comprise an amino acid sequence that is at least 75% identical to any one of SEQ ID NOs. 39, 41, or 43. In some cases, the succinyl CoA synthase alpha subunit can comprise an amino acid sequence that is at least 80% identical to any one of SEQ ID NOs. 39, 41, or 43. In some cases, the succinyl CoA synthase alpha subunit can comprise an amino acid sequence that is at least 85% identical to any one of SEQ ID NOs. 39, 41, or 43. In some cases, the succinyl CoA synthase alpha subunit can comprise an amino acid sequence that is at least 90% identical to any one of SEQ ID NOs. 39, 41, or 43. In some cases, the succinyl CoA synthease alpha subunit can comprise an amino acid sequence that is at least 91% identical to any one of SEQ ID NOs. 39, 41, or 43. In some cases, the succinyl CoA synthease alpha subunit can comprise an amino acid sequence that is at least 92% identical to any one of SEQ ID NOs. 39, 41, or 43. In some cases, the succinyl CoA synthease alpha subunit can comprise an amino acid sequence that is at least 93% identical to any one of SEQ ID NOs. 39, 41, or 43. In some cases, the succinyl CoA synthease alpha subunit can comprise an amino acid sequence that is at least 94% identical to any one of SEQ ID NOs. 39, 41, or 43. In some cases, the succinyl CoA synthease alpha subunit can comprise an amino acid sequence that is at least 95% identical to any one of SEQ ID NOs. 39, 41, or 43. In some cases, the succinyl CoA synthease alpha subunit can comprise an amino acid sequence that is at least 96% identical to any one of SEQ ID NOs. 39, 41, or 43. In some cases, the succinyl CoA synthease alpha subunit can comprise an amino acid sequence that is at least 97% identical to any one of SEQ ID NOs. 39, 41, or 43. In some cases, the succinyl CoA synthease alpha subunit can comprise an amino acid sequence that is at least 98% identical to any one of SEQ ID NOs. 39, 41, or 43. In some cases, the succinyl CoA synthease alpha subunit can comprise an amino acid sequence that is at least 99% identical to any one of SEQ ID NOs. 39, 41, or 43. In some cases, the succinyl CoA synthease alpha subunit can comprise an amino acid sequence that is any one of SEQ ID NOs. 39, 41, or 43.

The remaining four enzymes of the succinate to 1,4-BDO pathway are the same enzymes as the final four α-ketoglutarate to 1,4-BDO pathway enzymes. Therefore, when 4-hydroxybutyrate dehydrogenase (4hbD), 4-hydroxybutyrate CoA transferase (cat2), aldehyde dehydrogenase (ald), and/or alcohol dehydrogenase (adh) are desired, the respective enzymes disclosed for the α-ketoglutarate to 1,4-BDO pathway can be used.

Additionally, in some cases, the pathway to 1,4-BDO can be pushed from oxaloacetate/malyl-CoA to succinate, and then succinate to 1,4-BDO. In these cases, a fumarate hydratase (fum) and/or a fumarate reductase (frd) can be used.

When a fumarate hydratase (fum) is used the fumarate hydratase can be from a bacteria (e.g., a bacterium that is gram positive or gram negative), such as from the genus *Methylococcus, Escherichia* and/or *Mycobacterium*. For example, a fumarate hydratase (fum) can be from the species *Methylococcus capsulatus, Escherichia coli*, and/or *Mycobacterium tuberculosis*.

The fumarate hydratase (fum) can comprise an amino acid sequence that is substantially similar to any one of SEQ ID NOs. 45, 47, or 49. For example, the fumarate hydratase can comprise an amino acid sequence that is at least 60% identical to any one of SEQ ID NOs. 45, 47, or 49. For example, the fumarate hydratase can comprise an amino acid sequence that is at least 65% identical to any one of SEQ ID NOs. 45, 47, or 49. In some cases, the fumarate hydratase can comprise an amino acid sequence that is at least 70% identical to any one of SEQ ID NOs. 45, 47, or 49. For example, the fumarate hydratase can comprise an amino acid sequence that is at least 75% identical to any one of SEQ ID NOs. 45, 47, or 49. In some cases, the fumarate hydratase can comprise an amino acid sequence that is at least 80% identical to any one of SEQ ID NOs. 45, 47, or 49. For example, the fumarate hydratase can comprise an amino acid sequence that is at least 85% identical to any one of SEQ ID NOs. 45, 47, or 49. In some cases, the fumarate hydratase can comprise an amino acid sequence that is at least 90% identical to any one of SEQ ID NOs. 45, 47, or 49. In some cases, the fumarate hydratase can comprise an amino acid sequence that is at least 91% identical to any one of SEQ ID NOs. 45, 47, or 49. In some cases, the fumarate hydratase can comprise an amino acid sequence that is at least 92% identical to any one of SEQ ID NOs. 45, 47, or 49. In some cases, the fumarate hydratase can comprise an amino acid sequence that is at least 93% identical to any one of SEQ ID NOs. 45, 47, or 49. In some cases, the fumarate hydratase can comprise an amino acid sequence that is at least 94% identical to any one of SEQ ID NOs. 45, 47, or 49. In some cases, the fumarate hydratase can comprise an amino acid sequence that is at least 95% identical to any one of SEQ ID NOs. 45, 47, or 49. In some cases, the fumarate hydratase can comprise an amino acid sequence that is at least 96% identical to any one of SEQ ID NOs. 45, 47, or 49. In some cases, the fumarate hydratase can comprise an amino acid sequence that is at least 97% identical to any one of SEQ ID NOs. 45, 47, or 49. In some cases, the fumarate hydratase can comprise an amino acid sequence that is at least 98% identical to any one of SEQ ID NOs. 45, 47, or 49. In some cases, the fumarate hydratase can comprise an amino acid sequence that is at least 99% identical to any one of SEQ ID NOs. 45, 47, or 49. In some cases, the fumarate hydratase can comprise an amino acid sequence that is any one of SEQ ID NOs. 45, 47, or 49.

When a fumarate reductase (frd) is used the fumarate reductase can be from a bacteria (e.g., a bacterium that is gram negative), such as from the genus *Escherichia*. For example, a fumarate reductase (frd) can be from the species *Escherichia coli*.

The fumarate reductase (frd) can comprise an amino acid sequence that is substantially similar to any one of SEQ ID NOs. 51, 53, 55, or 57. For example, the fumarate reductase can comprise an amino acid sequence that is at least 60% identical to any one of SEQ ID NOs. 51, 53, 55, or 57. For example, the fumarate reductase can comprise an amino acid sequence that is at least 65% identical to any one of SEQ ID NOs. 51, 53, 55, or 57. In some cases, the fumarate reductase can comprise an amino acid sequence that is at least 70% identical to any one of SEQ ID NOs. 51, 53, 55, or 57. For example, the fumarate reductase can comprise an amino acid sequence that is at least 75% identical to any one of SEQ ID NOs. 51, 53, 55, or 57. In some cases, the fumarate reductase can comprise an amino acid sequence that is at least 80% identical to any one of SEQ ID NOs. 51, 53, 55, or 57. For example, the fumarate reductase can comprise an amino acid sequence that is at least 85% identical to any one of SEQ ID NOs. 51, 53, 55, or 57. In some cases, the fumarate reductase can comprise an amino acid sequence that is at least 90% identical to any one of SEQ ID NOs. 51, 53, 55, or 57. In some cases, the fumarate reductase can comprise an amino acid sequence that is at least 91% identical to any one of SEQ ID NOs. 51, 53, 55, or 57. In some cases, the fumarate reductase can comprise an amino acid sequence that is at least 92% identical to any one of SEQ ID NOs. 51, 53, 55, or 57. In some cases, the fumarate reductase can comprise an amino acid sequence that is at least 93% identical to any one of SEQ ID NOs. 51, 53, 55, or 57. In some cases, the fumarate reductase can comprise an amino acid sequence that is at least 94% identical to any one of SEQ ID NOs. 51, 53, 55, or 57. In some cases, the fumarate reductase can comprise an amino acid sequence that is at least 95% identical to any one of SEQ ID NOs. 51, 53, 55, or 57. In some cases, the fumarate reductase can comprise an amino acid sequence that is at least 96% identical to any one of SEQ ID NOs. 51, 53, 55, or 57. In some cases, the fumarate reductase can comprise an amino acid sequence that is at least 97% identical to any one of SEQ ID NOs. 51, 53, 55, or 57. In some cases, the fumarate reductase can comprise an amino acid sequence that is at least 98% identical to any one of SEQ ID NOs. 51, 53, 55, or 57. In some cases, the fumarate reductase can comprise an amino acid sequence that is at least 99% identical to any one of SEQ ID NOs. 51, 53, 55, or 57. In some cases, the fumarate reductase can comprise an amino acid sequence that is any one of SEQ ID NOs. 51, 53, 55, or 57.

Additional enzymes can be placed inside the microorganism in order to make other desired end products by fermentation.

The amino acid sequence can also be optimized based on the microorganism in which the enzymes will be expressed. In other words, conservative amino acids substitutions can be made based on whether the respective microorganism typically uses a specific amino acid or how much of that particular amino acid is available for use within the microorganism.

Additionally, in some cases, two or more enzymes that catalyze consecutive reactions can be used within the microorganism. For example, the two enzymes that catalyze consecution reactions can be α-ketoglutarate dehydrogenase and 4-hyrobutyrate dehydrogenase. Any combination of consecutive enzymes can be used and can be found in FIGS. 1, 2, 3, and 7. In some cases, three or more enzymes that catalyze consecutive reactions can be used within the microorganism. In some cases, four or more enzymes that catalyze consecutive reactions can be used within the microorganism. In some cases, five or more enzymes that catalyze consecutive reactions can be used within the microorganism. In some cases, six or more enzymes that catalyze consecutive reactions can be used within the microorganism. In some cases, seven or more enzymes that catalyze consecutive reactions can be used within the microorganism. In some cases, eight or more enzymes that catalyze consecutive reactions can be used within the microorganism. In some cases, nine or more enzymes that catalyze consecutive reactions can be used within the microorganism. In some cases, ten or more enzymes that catalyze consecutive reactions can be used within the microorganism.

Vectors

Polynucleotide constructs prepared for introduction into a prokaryotic or eukaryotic host may typically, but not always, comprise a replication system (i.e. vector) recognized by the host, including the intended polynucleotide fragment encoding the desired polypeptide, and can, but not necessarily, also include transcription and translational initiation regulatory sequences operably linked to the polypeptide-encoding segment. Expression systems (such as expression vectors) may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, mRNA stabilizing sequences, nucleotide sequences homologous to host chromosomal DNA, and/or a multiple cloning site. Signal peptides may also be included where appropriate, preferably from secreted polypeptides of the same or related species, which allow the protein to cross and/or lodge in cell membranes or be secreted from the cell.

The vectors can be constructed using standard methods (see, e.g., Sambrook et al., Molecular Biology: A Laboratory Manual, Cold Spring Harbor, N.Y. 1989; and Ausubel, et al., Current Protocols in Molecular Biology, Greene Publishing, Co. N.Y, 1995).

The manipulation of polynucleotides that encode the enzymes disclosed herein is typically carried out in recombinant vectors. Numerous vectors are publicly available, including bacterial plasmids, bacteriophage, artificial chromosomes, episomal vectors and gene expression vectors, which can all be employed. A vector may be selected to accommodate a polynucleotide encoding a protein of a desired size. Following recombinant modification of a selected vector, a suitable host cell (e.g., the microorganisms described herein) is transfected or transformed with the vector. Each vector contains various functional components, which generally include a cloning site, an origin of replication and at least one selectable marker gene. A vector may additionally possess one or more of the following elements: an enhancer, promoter, and transcription termination and/or other signal sequences. Such sequence elements may be optimized for the selected host species. Such sequence elements may be positioned in the vicinity of the cloning site, such that they are operatively linked to the gene encoding a preselected enzyme.

Vectors, including cloning and expression vectors, may contain nucleic acid sequences that enable the vector to replicate in one or more selected microorganisms. For example, the sequence may be one that enables the vector to replicate independently of the host chromosomal DNA and may include origins of replication or autonomously replicating sequences. Such sequences are well known for a variety of bacteria, yeast and viruses. For example, the origin of replication from the plasmid pBR322 is suitable for most Gram-negative bacteria, the 2 micron plasmid origin is suitable for yeast, and various viral origins (e.g.SV40, adenovirus) are useful for cloning vectors.

A cloning or expression vector may contain a selection gene (also referred to as a selectable marker). This gene encodes a protein necessary for the survival or growth of transformed microorganisms in a selective culture medium. Microorganisms not transformed with the vector containing the selection gene will therefore not survive in the culture medium. Typical selection genes encode proteins that confer resistance to antibiotics and other toxins, e.g. ampicillin, neomycin, methotrexate, hygromycin, thiostrepton, apramycin or tetracycline, complement auxotrophic deficiencies, or supply critical nutrients not available in the growth media.

The replication of vectors may be performed in E. coli. An E. coli-selectable marker, for example, the β-lactamase gene that confers resistance to the antibiotic ampicillin, may be of use. These selectable markers can be obtained from E. coli plasmids, such as pBR322 or a pUC plasmid such as pUC18 or pUC19, or pUC119.

Promoters

Vectors may contain a promoter that is recognized by the host microorganism. The promoter may be operably linked to a coding sequence of interest. Such a promoter may be inducible or constitutive. Polynucleotides are operably linked when the polynucleotides are in a relationship permitting them to function in their intended manner.

Different promoters can be used to drive the expression of the genes. For example, if temporary gene expression (i.e., non-constitutively expressed) is desired, expression can be driven by inducible promoters.

In some cases, some of the genes disclosed can be expressed temporarily. In other words, the genes are not constitutively expressed. The expression of the genes can be driven by inducible or repressible promoters. For example, the inducible or repressible promoters that can be used include but are not limited to: (a) sugars such as arabinose and lactose (or non metabolizable analogs, e.g., isopropyl β-D-1-thiogalactopyranoside (IPTG)); (b) metals such as lanthanum (or other rare earth metals), copper, calcium; (c) temperature; (d) Nitrogen-source; (e) oxygen; (f) cell state (growth or stationary); (g) metabolites such as phosphate; (h) CRISPRi; (i) jun; (j) fos, (k) metallothionein and/or (1) heat shock. These promoters can be used in a methanotroph systems. For example, one example of an inducible promoter that can be used within the methanotrophs is a pBAD or a pMxaF promoter.

Constitutively expressed promoters can also be used in the vector systems herein. For example, the expression of some of the genes disclosed throughout can be controlled by constitutively active promoters. For examples, the promoters that can be used include but are not limited to p.Bba.J23111, J23111, and J23100.

Promoters suitable for use with prokaryotic hosts may include, for example, the a-lactamase and lactose promoter systems, alkaline phosphatase, the tryptophan (trp) promoter system, the erythromycin promoter, apramycin promoter, hygromycin promoter, methylenomycin promoter and hybrid promoters such as the tac promoter. Promoters for use in bacterial systems will also generally contain a Shine-Dalgarno sequence operably linked to the coding sequence.

Generally, a strong promoter may be employed to provide for high level transcription and expression of the desired product.

One or more promoters of a transcription unit can be an inducible promoter. For example, a GFP can be expressed from a constitutive promoter while an inducible promoter drives transcription of a gene coding for one or more enzymes as disclosed herein and/or the amplifiable selectable marker.

Some vectors may contain prokaryotic sequences that facilitate the propagation of the vector in bacteria. Thus, the vectors may have other components such as an origin of replication (e.g., a nucleic acid sequence that enables the vector to replicate in one or more selected microorganisms), antibiotic resistance genes for selection in bacteria, and/or an amber stop codon which can permit translation to read through the codon. Additional selectable gene(s) may also be incorporated. Generally, in cloning vectors the origin of replication is one that enables the vector to replicate independently of the host chromosomal DNA, and includes origins of replication or autonomously replicating sequences. Such sequences can include the ColEl origin of replication in bacteria or other known sequences.

Genes

The vectors can comprise a nucleic acid sequence of one or more enzymes that are capable of catalyzing one or more of the following reactions: i) methane to methanol; ii) methanol to formaldehyde; iii) formaldehyde to pyruvate; iv) pyruvate to acetyl CoA; v) acetyl CoA to citrate; vi) citrate to isocitrate; vii) isocitrate to α-ketoglutarate; viii) α-ketoglutarate to succinate CoA; ix) succinate CoA to succinate; x) oxaloacetate and/or malyl-CoA to L-malate; xi) L-malate to fumarate; and/or xii) fumarate to succinate.

In some instances, the vector can comprise one or more of the following genes from the α-ketoglutarate to 1,4-BDO pathway: i) α-ketoglutarate decarboxylase (kgd); ii) 4-hydroxybutyrate dehydrogenase (4hbD); iii) 4-hydroxybutyrate CoA transferase (Cat2); (iv) aldehyde dehydrogenase (Ald); (v) alcohol dehydrogenase (adh); or (vi) any combination thereof.

In some cases, the vector can comprise one or more of the following genes from the succinate to 1,4-BDO pathway: i) succinyl CoA synthease beta subunit (sucC); ii) succinyl CoA synthease alpha subunit (sucD); iii) 4-hydroxybutyrate dehydrogenase (4hbD); iv) 4-hydroxybutyrate CoA transferase (Cat2); (v) aldehyde dehydrogenase (Ald); (vi) alcohol dehydrogenase (adh); or (vii) any combination thereof.

The vector in some cases can comprise a fumarate hydratase and/or fumarate reductase.

One or more of the genes can be heterologous to the microorganism in which the vector is contacted with (and eventually transformed with).

It is also contemplated that any and all genes disclosed herein can be overexpressed. For example, when a microorganism or vector comprises a gene (e.g., a heterologous gene), the gene can be overexpressed. This is done typically but using a promoter that is highly expressed or inserting multiple copies of the gene.

When an α-ketoglutarate decarboxylase (kgd) gene is used the α-ketoglutarate decarboxylase gene can be from a bacteria (e.g., a gram positive bacterium or a bacterium that is neither gram positive or gram negative), such as from the genus *Mycobacterium, Corynebacterium* and/or *Rhodococcus*. For example, an α-ketoglutarate decarboxylase (kgd) gene can be from the species *Mycobacterium bovis, Mycobacterium tuberculosis, Corynebacterium terpenotabidum*, and/or *Rhodococcus jostii*.

The α-ketoglutarate decarboxylase (kgd) can comprise a nucleic acid sequence that is substantially similar to any one of SEQ ID NOs. 2, 4, 6, or 8. For example, the α-ketoglutarate decarboxylase can comprise a nucleic acid sequence that is at least 60% identical to any one of SEQ ID NOs. 2, 4, 6, or 8. In some cases, the α-ketoglutarate decarboxylase can comprise a nucleic acid sequence that is at least 65% identical to any one of SEQ ID NOs. 2, 4, 6, or 8. In some cases, the α-ketoglutarate decarboxylase can comprise a nucleic acid sequence that is at least 70% identical to any one of SEQ ID NOs. 2, 4, 6, or 8. In some cases, the α-ketoglutarate decarboxylase can comprise a nucleic acid sequence that is at least 75% identical to any one of SEQ ID NOs. 2, 4, 6, or 8. In some cases, the α-ketoglutarate decarboxylase can comprise a nucleic acid sequence that is at least 80% identical to any one of SEQ ID NOs. 2, 4, 6, or 8. In some cases, the α-ketoglutarate decarboxylase can comprise a nucleic acid sequence that is at least 85% identical to any one of SEQ ID NOs. 2, 4, 6, or 8. In some cases, the α-ketoglutarate decarboxylase can comprise a nucleic acid sequence that is at least 90% identical to any one of SEQ ID NOs. 2, 4, 6, or 8. In some cases, the α-ketoglutarate decarboxylase can comprise a nucleic acid sequence that is at least 91% identical to any one of SEQ ID NOs. 2, 4, 6, or 8. In some cases, the α-ketoglutarate decarboxylase can comprise a nucleic acid sequence that is at least 92% identical to any one of SEQ ID NOs. 2, 4, 6, or 8. In some cases, the α-ketoglutarate decarboxylase can comprise a nucleic acid sequence that is at least 93% identical to any one of SEQ ID NOs. 2, 4, 6, or 8. In some cases, the α-ketoglutarate decarboxylase can comprise a nucleic acid sequence that is at least 94% identical to any one of SEQ ID NOs. 2, 4, 6, or 8. In some cases, the α-ketoglutarate decarboxylase can comprise a nucleic acid sequence that is at least 95% identical to any one of SEQ ID NOs. 2, 4, 6, or 8. In some cases, the α-ketoglutarate decarboxylase can comprise a nucleic acid sequence that is at least 96% identical to any one of SEQ ID NOs. 2, 4, 6, or 8. In some cases, the α-ketoglutarate decarboxylase can comprise a nucleic acid sequence that is at least 97% identical to any one of SEQ ID NOs. 2, 4, 6, or 8. In some cases, the α-ketoglutarate decarboxylase can comprise a nucleic acid sequence that is at least 98% identical to any one of SEQ ID NOs. 2, 4, 6, or 8. In some cases, the α-ketoglutarate decarboxylase can comprise a nucleic acid sequence that is at least 99% identical to any one of SEQ ID NOs. 2, 4, 6, or 8. In some cases, the α-ketoglutarate decarboxylase can comprise a nucleic acid sequence that is any one of SEQ ID NOs. 2, 4, 6, or 8.

When a 4-hydroxybutyrate dehydrogenase (4hbD) gene is desired the 4-hydroxybutyrate dehydrogenase gene can be from a bacterium (e.g., a gram negative or positive bacterium), such as from the genus *Escherichia, Porphyromonas*, and/or *Clostridium*. For example, a 4-hydroxybutyrate dehydrogenase gene can be from the species *Escherichia coli, Porphyromonas gingivalis*, and/or *Clostridium kluyveri*.

The 4-hydroxybutyrate dehydrogenase gene can comprise a nucleic acid sequence that is substantially similar to SEQ ID NO. 12 or 14. For example, the 4-hydroxybutyrate dehydrogenase gene can comprise a nucleic acid sequence that is at least 60% identical to SEQ ID NO. 12 or 14. For example, the 4-hydroxybutyrate dehydrogenase gene can comprise a nucleic acid sequence that is at least 65% identical to SEQ ID NO. 12 or 14. In some cases, the 4-hydroxybutyrate dehydrogenase gene can comprise a nucleic acid sequence that is at least 70% identical to SEQ ID NO. 12 or 14. For example, the 4-hydroxybutyrate dehydrogenase gene can comprise a nucleic acid sequence that is at least 75% identical to SEQ ID NO. 12 or 14. In some cases, the 4-hydroxybutyrate dehydrogenase gene can comprise a nucleic acid sequence that is at least 80% identical to SEQ ID NO. 12 or 14. For example, the 4-hydroxybutyrate dehydrogenase gene can comprise a nucleic acid sequence that is at least 85% identical to SEQ ID NO. 12 or 14. In some cases, the 4-hydroxybutyrate dehydrogenase gene can comprise a nucleic acid sequence that is at least 90% identical to SEQ ID NO. 12 or 14. In some cases, the 4-hydroxybutyrate dehydrogenase gene can comprise a nucleic acid sequence that is at least 91% identical to SEQ ID NO. 12 or 14. In some cases, the 4-hydroxybutyrate dehydrogenase gene can comprise a nucleic acid sequence that is at least 92% identical to SEQ ID NO. 12 or 14. In some cases, the 4-hydroxybutyrate dehydrogenase gene can comprise a nucleic acid sequence that is at least 93% identical to SEQ ID NO. 12 or 14. In some cases, the 4-hydroxybutyrate dehydrogenase gene can comprise a nucleic acid sequence that is at least 94% identical to SEQ ID NO. 12 or 14. In some cases, the 4-hydroxybutyrate dehydrogenase gene can comprise a nucleic acid sequence that is at least 95% identical to SEQ ID NO. 12 or 14. In some cases, the 4-hydroxybutyrate dehydrogenase gene can comprise a nucleic acid sequence that is at least 96% identical to SEQ ID NO. 12 or 14. In some cases, the 4-hydroxybutyrate dehydrogenase gene can comprise a nucleic acid sequence that is at least 97% identical to SEQ ID NO. 12 or 14. In some cases, the 4-hydroxybutyrate dehydrogenase gene can comprise a nucleic acid sequence that is at least 98% identical to SEQ ID NO. 12 or 14. In some cases, the 4-hydroxybutyrate dehydrogenase gene can comprise a nucleic acid sequence that is at least 99% identical to SEQ ID NO. 12 or 14. In some cases, the 4-hydroxybutyrate dehydrogenase gene can comprise a nucleic acid sequence that is SEQ ID NO. 12 or 14.

When a 4-hydroxybutyrate CoA transferase (cat2) gene is desired the 4-hydroxybutyrate CoA transferase gene can be from a bacterium (e.g., a gram negative or positive bacterium), such as from the genus *Porphyromonas*, and/or *Clostridium*. For example, a 4-hydroxybutyrate CoA transferase gene can be from the species *Porphyromonas gingivalis* and/or *Clostridium acetobutylicum*.

The 4-hydroxybutyrate CoA transferase gene can comprise a nucleic acid sequence that is substantially similar to any one of SEQ ID NOs. 16, 18, or 20. For example, the 4-hydroxybutyrate CoA transferase gene can comprise a nucleic acid sequence that is at least 60% identical to any one of SEQ ID NOs. 16, 18, or 20. For example, the 4-hydroxybutyrate CoA transferase gene can comprise a nucleic acid sequence that is at least 65% identical to any one of SEQ ID NOs. 16, 18, or 20. In some cases, the 4-hydroxybutyrate CoA transferase gene can comprise a nucleic acid sequence that is at least 70% identical to any one of SEQ ID NOs. 16, 18, or 20. For example, the 4-hydroxybutyrate CoA transferase gene can comprise a nucleic acid sequence that is at least 75% identical to any one of SEQ ID NOs. 16, 18, or 20. In some cases, the 4-hydroxybutyrate CoA transferase gene can comprise a nucleic acid sequence that is at least 80% identical to any one of SEQ ID NOs. 16, 18, or 20. For example, the 4-hydroxybutyrate CoA transferase gene can comprise a nucleic acid sequence that is at least 85% identical to any one of SEQ ID NOs. 16, 18, or 20. In some cases, the 4-hydroxybutyrate CoA transferase gene can comprise a nucleic acid sequence that is at least 90% identical to any one of SEQ ID NOs. 16, 18, or 20. In some cases, the 4-hydroxybutyrate CoA transferase gene can comprise a nucleic acid sequence that is at least 91% identical to any one of SEQ ID NOs. 16, 18, or 20. In some cases, the 4-hydroxybutyrate CoA transferase gene can comprise a nucleic acid sequence that is at least 92% identical to any one of SEQ ID NOs. 16, 18, or 20. In some cases, the 4-hydroxybutyrate CoA transferase gene can comprise a nucleic acid sequence that is at least 93% identical to any one of SEQ ID NOs. 16, 18, or 20. In some cases, the 4-hydroxybutyrate CoA transferase gene can comprise a nucleic acid sequence that is at least 94% identical to any one of SEQ ID NOs. 16, 18, or 20. In some cases, the 4-hydroxybutyrate CoA transferase gene can comprise a nucleic acid sequence that is at least 95% identical to any one of SEQ ID NOs. 16, 18, or 20. In some cases, the 4-hydroxybutyrate CoA transferase gene can comprise a nucleic acid sequence that is at least 96% identical to any one of SEQ ID NOs. 16, 18, or 20. In some cases, the 4-hydroxybutyrate CoA transferase gene can comprise a nucleic acid sequence that is at least 97% identical to any one of SEQ ID NOs. 16, 18, or 20. In some cases, the 4-hydroxybutyrate CoA transferase gene can comprise a nucleic acid sequence that is at least 98% identical to any one of SEQ ID NOs. 16, 18, or 20. In some cases, the 4-hydroxybutyrate CoA transferase gene can comprise a nucleic acid sequence that is at least 99% identical to any one of SEQ ID NOs. 16, 18, or 20. In some cases, the 4-hydroxybutyrate CoA transferase gene can comprise a nucleic acid sequence that is any one of SEQ ID NOs. 16, 18, or 20.

When an aldehyde dehydrogenase (ald) gene and/or an alcohol dehydrogenase (adh) gene is desired the aldehyde dehydrogenase gene and/or alcohol dehydrogenase gene can be from a bacterium (e.g., a gram negative or positive bacterium), such as from the genus *Escherichia, Acinetobacter, Porphyromonas*, and/or *Clostridium*, or from a yeast such as from the genus *Saccharomyces*. For example, an aldehyde dehydrogenase gene and/or alcohol dehydrogenase gene can be from the species *Escherichia coli, Acinetobacter baylyi, Porphyromonas gingivalis, Clostridium acetobutylicum* and/or *Saccharomyces cerevisiae*. In some cases, more than one aldehyde dehydrogenase gene and/or alcohol dehydrogenase gene can be used.

The aldehyde dehydrogenase gene and/or alcohol dehydrogenase gene can comprise a nucleic acid sequence that is substantially similar to any one of SEQ ID NOs. 22, 24, 26, 28, 30, 32, 34, or 36. For example, the aldehyde dehydrogenase gene and/or alcohol dehydrogenase gene can comprise a nucleic acid sequence that is at least 60% identical to any one of SEQ ID NOs. 22, 24, 26, 28, 30, 32, 34, or 36. For example, the aldehyde dehydrogenase gene and/or alcohol dehydrogenase gene can comprise a nucleic acid sequence that is at least 65% identical to any one of SEQ ID NOs. 22, 24, 26, 28, 30, 32, 34, or 36. In some cases, the aldehyde dehydrogenase gene and/or alcohol dehydrogenase gene can comprise a nucleic acid sequence that is at least 70% identical to any one of SEQ ID NOs. 22, 24, 26, 28, 30, 32, 34, or 36. For example, the aldehyde dehydrogenase gene and/or alcohol dehydrogenase gene can comprise a nucleic acid sequence that is at least 75% identical to any one of SEQ ID NOs. 22, 24, 26, 28, 30, 32, 34, or 36. In some cases, the aldehyde dehydrogenase gene and/or alcohol dehydrogenase gene can comprise a nucleic acid sequence that is at least 80% identical to any one of SEQ ID NOs. 22, 24, 26, 28, 30, 32, 34, or 36. For example, the aldehyde dehydrogenase gene and/or alcohol dehydrogenase gene can comprise a nucleic acid sequence that is at least 85% identical to any one of SEQ ID NOs. 22, 24, 26, 28, 30, 32, 34, or 36. In some cases, the aldehyde dehydrogenase gene and/or alcohol dehydrogenase gene can comprise a nucleic acid sequence that is at least 90% identical to any one of SEQ ID NOs. 22, 24, 26, 28, 30, 32, 34, or 36. In some cases, the aldehyde dehydrogenase gene and/or alcohol dehydrogenase gene can comprise a nucleic acid sequence that is at least 91% identical to any one of SEQ ID NOs. 22, 24, 26, 28, 30, 32, 34, or 36. In some cases, the aldehyde dehydrogenase gene and/or alcohol dehydrogenase gene can comprise a nucleic acid sequence that is at least 92% identical to any one of SEQ ID NOs. 22, 24, 26, 28, 30, 32, 34, or 36. In some cases, the aldehyde dehydrogenase gene and/or alcohol dehydrogenase gene can comprise a nucleic acid sequence that is at least 93% identical to any one of SEQ ID NOs. 22, 24, 26, 28, 30, 32, 34, or 36. In some cases, the aldehyde dehydrogenase gene and/or alcohol dehydrogenase gene can comprise a nucleic acid sequence that is at least 94% identical to any one of SEQ ID NOs. 22, 24, 26, 28, 30, 32, 34, or 36. In some cases, the aldehyde dehydrogenase gene and/or alcohol dehydrogenase gene can comprise a nucleic acid sequence that is at least 95% identical to any one of SEQ ID NOs. 22, 24, 26, 28, 30, 32, 34, or 36. In some cases, the aldehyde dehydrogenase gene and/or alcohol dehydrogenase gene can comprise a nucleic acid sequence that is at least 96% identical to any one of SEQ ID NOs. 22, 24, 26, 28, 30, 32, 34, or 36. In some cases, the aldehyde dehydrogenase gene and/or alcohol dehydrogenase gene can comprise a nucleic acid sequence that is at least 97% identical to any one of SEQ ID NOs. 22, 24, 26, 28, 30, 32, 34, or 36. In some cases, the aldehyde dehydrogenase gene and/or alcohol dehydrogenase gene can comprise a nucleic acid sequence that is at least 98% identical to any one of SEQ ID NOs. 22, 24, 26, 28, 30, 32, 34, or 36. In some cases, the aldehyde dehydrogenase gene and/or alcohol dehydrogenase gene can comprise a nucleic acid sequence that is at least 99% identical to any one of SEQ ID NOs. 22, 24, 26, 28, 30, 32, 34, or 36. In some cases, the aldehyde dehydrogenase gene and/or alcohol dehydrogenase gene can comprise a nucleic acid sequence that is any one of SEQ ID NOs. 22, 24, 26, 28, 30, 32, 34, or 36.

When a succinyl CoA synthease beta subunit (sucC) gene is used the succinyl CoA synthease beta subunit gene can be from a bacteria (e.g., a gram negative bacterium), such as from the genus *Escherichia*. For example, the succinyl CoA synthease beta subunit gene can be from the species *Escherichia coli*.

The succinyl CoA synthease beta subunit gene can comprise a nucleic acid sequence that is substantially similar to SEQ ID NO. 38. For example, the succinyl CoA synthease beta subunit gene can comprise a nucleic acid sequence that is at least 60% identical to SEQ ID NO. 38. For example, the succinyl CoA synthease beta subunit gene can comprise a nucleic acid sequence that is at least 65% identical to SEQ ID NO. 38. In some cases, the succinyl CoA synthease beta subunit gene can comprise a nucleic acid sequence that is at least 70% identical to SEQ ID NO. 38. For example, the succinyl CoA synthease beta subunit gene can comprise a nucleic acid sequence that is at least 75% identical to SEQ ID NO. 38. In some cases, the succinyl CoA synthease beta subunit gene can comprise a nucleic acid sequence that is at least 80% identical to SEQ ID NO. 38. For example, the succinyl CoA synthease beta subunit gene can comprise a nucleic acid sequence that is at least 85% identical to SEQ ID NO. 38. In some cases, the succinyl CoA synthease beta subunit gene can comprise a nucleic acid sequence that is at least 90% identical to SEQ ID NO. 38. In some cases, the succinyl CoA synthease beta subunit gene can comprise a nucleic acid sequence that is at least 91% identical to SEQ ID NO. 38. In some cases, the succinyl CoA synthease beta subunit gene can comprise a nucleic acid sequence that is at least 92% identical to SEQ ID NO. 38. In some cases, the succinyl CoA synthease beta subunit gene can comprise a nucleic acid sequence that is at least 93% identical to SEQ ID NO. 38. In some cases, the succinyl CoA synthease beta subunit gene can comprise a nucleic acid sequence that is at least 94% identical to SEQ ID NO. 38. In some cases, the succinyl CoA synthease beta subunit gene can comprise a nucleic acid sequence that is at least 95% identical to SEQ ID NO. 38. In some cases, the succinyl CoA synthease beta subunit gene can comprise a nucleic acid sequence that is at least 96% identical to SEQ ID NO. 38. In some cases, the succinyl CoA synthease beta subunit gene can comprise a nucleic acid sequence that is at least 97% identical to SEQ ID NO. 38. In some cases, the succinyl CoA synthease beta subunit gene can comprise a nucleic acid sequence that is at least 98% identical to SEQ ID NO. 38. In some cases, the succinyl CoA synthease beta subunit gene can comprise a nucleic acid sequence that is at least 99% identical to SEQ ID NO. 38. In some cases, the succinyl CoA synthease beta subunit gene can comprise a nucleic acid sequence that is SEQ ID NO. 38.

When a succinyl CoA synthease alpha subunit (sucD) gene is used the succinyl CoA synthease alpha subunit gene can be from a bacteria (e.g., a gram negative or gram positive bacterium), such as from the genus *Escherichia, Clostridium*, or *Porphyromonas*. For example, the succinyl CoA synthease alpha subunit gene can be from the species *Escherichia coli, Clostridium kluyveri, Porphyromonas gingivalis*.

The succinyl CoA synthease alpha subunit gene can comprise a nucleic acid sequence that is substantially similar to any one of SEQ ID NOs. 40, 43, or 44. For example, the succinyl CoA synthease alpha subunit gene can comprise a nucleic acid sequence that is at least 60% identical to any one of SEQ ID NOs. 40, 43, or 44. For example, the succinyl CoA synthease alpha subunit gene can comprise a nucleic acid sequence that is at least 65% identical to any one of SEQ ID NOs. 40, 43, or 44. In some cases, the succinyl CoA synthease alpha subunit gene can comprise a nucleic acid sequence that is at least 70% identical to any one of SEQ ID NOs. 40, 43, or 44. For example, the succinyl CoA synthease alpha subunit gene can comprise a nucleic acid sequence that is at least 75% identical to any one of SEQ ID NOs. 40, 43, or 44. In some cases, the succinyl CoA synthease alpha subunit gene can comprise a nucleic acid sequence that is at least 80% identical to any one of SEQ ID NOs. 40, 43, or 44. For example, the succinyl CoA synthease alpha subunit gene can comprise a nucleic acid sequence that is at least 85% identical to any one of SEQ ID NOs. 40, 43, or 44. In some cases, the succinyl CoA synthease alpha subunit gene can comprise a nucleic acid sequence that is at least 90% identical to any one of SEQ ID NOs. 40, 43, or 44. In some cases, the succinyl CoA synthease alpha subunit gene can comprise a nucleic acid sequence that is at least 91% identical to any one of SEQ ID NOs. 40, 43, or 44. In some cases, the succinyl CoA synthease alpha subunit gene can comprise a nucleic acid sequence that is at least 92% identical to any one of SEQ ID NOs. 40, 43, or 44. In some cases, the succinyl CoA synthease alpha subunit gene can comprise a nucleic acid sequence that is at least 93% identical to any one of SEQ ID NOs. 40, 43, or 44. In some cases, the succinyl CoA synthease alpha subunit gene can comprise a nucleic acid sequence that is at least 94% identical to any one of SEQ ID NOs. 40, 43, or 44. In some cases, the succinyl CoA synthease alpha subunit gene can comprise a nucleic acid sequence that is at least 95% identical to any one of SEQ ID NOs. 40, 43, or 44. In some cases, the succinyl CoA synthease alpha subunit gene can comprise a nucleic acid sequence that is at least 96% identical to any one of SEQ ID NOs. 40, 43, or 44. In some cases, the succinyl CoA synthease alpha subunit gene can comprise a nucleic acid sequence that is at least 97% identical to any one of SEQ ID NOs. 40, 43, or 44. In some cases, the succinyl CoA synthease alpha subunit gene can comprise a nucleic acid sequence that is at least 98% identical to any one of SEQ ID NOs. 40, 43, or 44. In some cases, the succinyl CoA synthease alpha subunit gene can comprise a nucleic acid sequence that is at least 99% identical to any one of SEQ ID NOs. 40, 43, or 44. In some cases, the succinyl CoA synthease alpha subunit gene can comprise a nucleic acid sequence that is any one of SEQ ID NOs. 40, 43, or 44.

The remaining four enzymes of the succinate to 1,4-BDO pathway are the same enzymes as the final four α-ketoglutarate to 1,4-BDO pathway enzymes. Therefore, when 4-hydroxybutyrate dehydrogenase gene, 4-hydroxybutyrate CoA transferase gene, aldehyde dehydrogenase gene, and/or alcohol dehydrogenase gene are desired, the respective genes disclosed for the α-ketoglutarate to 1,4-BDO pathway can be used.

Additionally, in some cases, the pathway to 1,4-BDO can be pushed from oxaloacetate/malyl-CoA to succinate, and then succinate to 1,4-BDO. In these cases, a fumarate hydratase (fum) and/or a fumarate reductase (frd) can be used.

When a fumarate hydratase (fum) gene is used the fumarate hydratase gene can be from a bacteria (e.g., a bacterium that is gram positive or gram negative), such as from the genus *Methylococcus*, *Escherichia* and/or *Mycobacterium*. For example, a fumarate hydratase (fum) gene can be from the species *Methylococcus capsulatus*, *Escherichia coli*, and/or *Mycobacterium tuberculosis*.

The fumarate hydratase (fum) gene can comprise a nucleic acid sequence that is substantially similar to any one of SEQ ID NOs. 46, 48, or 50. For example, the fumarate hydratase gene can comprise a nucleic acid sequence that is at least 60% identical to any one of SEQ ID NOs. 46, 48, or 50. For example, the fumarate hydratase gene can comprise a nucleic acid sequence that is at least 65% identical to any one of SEQ ID NOs. 46, 48, or 50. In some cases, the fumarate hydratase gene can comprise a nucleic acid sequence that is at least 70% identical to any one of SEQ ID NOs. 46, 48, or 50. For example, the fumarate hydratase gene can comprise a nucleic acid sequence that is at least 75% identical to any one of SEQ ID NOs. 46, 48, or 50. In some cases, the fumarate hydratase gene can comprise a nucleic acid sequence that is at least 80% identical to any one of SEQ ID NOs. 46, 48, or 50. For example, the fumarate hydratase gene can comprise a nucleic acid sequence that is at least 85% identical to any one of SEQ ID NOs. 46, 48, or 50. In some cases, the fumarate hydratase gene can comprise a nucleic acid sequence that is at least 90% identical to any one of SEQ ID NOs. 46, 48, or 50. In some cases, the fumarate hydratase gene can comprise a nucleic acid sequence that is at least 91% identical to any one of SEQ ID NOs. 46, 48, or 50. In some cases, the fumarate hydratase gene can comprise a nucleic acid sequence that is at least 92% identical to any one of SEQ ID NOs. 46, 48, or 50. In some cases, the fumarate hydratase gene can comprise a nucleic acid sequence that is at least 93% identical to any one of SEQ ID NOs. 46, 48, or 50. In some cases, the fumarate hydratase gene can comprise a nucleic acid sequence that is at least 94% identical to any one of SEQ ID NOs. 46, 48, or 50. In some cases, the fumarate hydratase gene can comprise a nucleic acid sequence that is at least 95% identical to any one of SEQ ID NOs. 46, 48, or 50. In some cases, the fumarate hydratase gene can comprise a nucleic acid sequence that is at least 96% identical to any one of SEQ ID NOs. 46, 48, or 50. In some cases, the fumarate hydratase gene can comprise a nucleic acid sequence that is at least 97% identical to any one of SEQ ID NOs. 46, 48, or 50. In some cases, the fumarate hydratase gene can comprise a nucleic acid sequence that is at least 98% identical to any one of SEQ ID NOs. 46, 48, or 50. In some cases, the fumarate hydratase gene can comprise a nucleic acid sequence that is at least 99% identical to any one of SEQ ID NOs. 46, 48, or 50. In some cases, the fumarate hydratase gene can comprise a nucleic acid sequence that is any one of SEQ ID NOs. 46, 48, or 50.

When a fumarate reductase (frd) gene is used the fumarate reductase gene can be from a bacteria (e.g., a bacterium that is gram negative), such as from the genus *Escherichia*. For example, a fumarate reductase (frd) gene can be from the species *Escherichia coli*.

The fumarate reductase (frd) gene can comprise a nucleic acid sequence that is substantially similar to any one of SEQ ID NOs. 52, 54, 56, or 58. For example, the fumarate reductase gene can comprise a nucleic acid sequence that is at least 60% identical to any one of SEQ ID NOs. 52, 54, 56, or 58. For example, the fumarate reductase gene can comprise a nucleic acid sequence that is at least 65% identical to any one of SEQ ID NOs. 52, 54, 56, or 58. In some cases, the fumarate reductase gene can comprise a nucleic acid sequence that is at least 70% identical to any one of SEQ ID NOs. 52, 54, 56, or 58. For example, the fumarate reductase gene can comprise a nucleic acid sequence that is at least 75% identical to any one of SEQ ID NOs. 52, 54, 56, or 58. In some cases, the fumarate reductase gene can comprise a nucleic acid sequence that is at least 80% identical to any one of SEQ ID NOs. 52, 54, 56, or 58. For example, the fumarate reductase gene can comprise a nucleic acid sequence that is at least 85% identical to any one of SEQ ID NOs. 52, 54, 56, or 58. In some cases, the fumarate reductase gene can comprise a nucleic acid sequence that is at least 90% identical to any one of SEQ ID NOs. 52, 54, 56, or 58. In some cases, the fumarate reductase gene can comprise a nucleic acid sequence that is at least 91% identical to any one of SEQ ID NOs. 52, 54, 56, or 58. In some cases, the fumarate reductase gene can comprise a nucleic acid sequence that is at least 92% identical to any one of SEQ ID NOs. 52, 54, 56, or 58. In some cases, the fumarate reductase gene can comprise a nucleic acid sequence that is at least 93% identical to any one of SEQ ID NOs. 52, 54, 56, or 58. In some cases, the fumarate reductase gene can comprise a nucleic acid sequence that is at least 94% identical to any one of SEQ ID NOs. 52, 54, 56, or 58. In some cases, the fumarate reductase gene can comprise a nucleic acid sequence that is at least 95% identical to any one of SEQ ID NOs. 52, 54, 56, or 58. In some cases, the fumarate reductase gene can comprise a nucleic acid sequence that is at least 96% identical to any one of SEQ ID NOs. 52, 54, 56, or 58. In some cases, the fumarate reductase gene can comprise a nucleic acid sequence that is at least 97% identical to any one of SEQ ID NOs. 52, 54, 56, or 58. In some cases, the fumarate reductase gene can comprise a nucleic acid sequence that is at least 98% identical to any one of SEQ ID NOs. 52, 54, 56, or 58. In some cases, the fumarate reductase gene can comprise a nucleic acid sequence that is at least 99% identical to any one of SEQ ID NOs. 52, 54, 56, or 58. In some cases, the fumarate reductase gene can comprise a nucleic acid sequence that is any one of SEQ ID NOs. 52, 54, 56, or 58.

Additional genes can be placed inside the microorganism in order to make other desired end products by fermentation. The nucleotide sequence (or more specifically the codons that are encoded by the nucleotide sequences) can be optimized based on the microorganism in which the nucleotide sequences will be expressed. The nucleotide sequences can be codon optimized based on the amount of tRNA available within each individual microorganism. In other words, conservative codon substitutions can be made based on whether the respective microorganism typically uses a specific codon or how much of a particular tRNA is available within the microorganism.

Additionally, in some cases, genes encoding for two or more enzymes that catalyze consecutive reactions can be expressed within the microorganism. For example, two or more genes encoding for enzymes that catalyze consecution reactions can be an α-ketoglutarate dehydrogenase gene and a 4-hyrobutyrate dehydrogenase gene. Any combination of consecutive enzymes can be expressed and can be found in FIGS. 1, 2, 3, and 7. In some cases, genes encoding for three or more enzymes that catalyze consecutive reactions can be expressed within the microorganism. In some cases, genes encoding for four or more enzymes that catalyze consecutive reactions can be expressed within the microorganism. In some cases, genes encoding for five or more enzymes that catalyze consecutive reactions can be expressed within the microorganism. In some cases, genes encoding for six or more enzymes that catalyze consecutive reactions can be expressed within the microorganism. In some cases, genes encoding for seven or more enzymes that catalyze consecutive reactions can be expressed within the microorganism. In some cases, genes encoding for eight or more enzymes that catalyze consecutive reactions can be expressed within the microorganism. In some cases, genes encoding for nine or more enzymes that catalyze consecutive reactions can be expressed within the microorganism. In some cases, genes encoding for ten or more enzymes that catalyze consecutive reactions can be expressed within the microorganism.

Isolated Nucleic Acids

The genes described herein can be in the form of an isolated polynucleic acid. In other words, the genes can be in forms that do not exist in nature, isolated from a chromosome. The isolated polynucleic acids can comprise a nucleic acid sequence of one or more of the following genes: i) α-ketoglutarate decarboxylase (kgd); ii) 4-hydroxybutyrate dehydrogenase (4hbD); iii) succinyl CoA synthease beta subunit (sucC); iv) succinyl CoA synthease alpha subunit (sucD); v) 4-hydroxybutyrate CoA transferase (cat2); (vi) aldehyde dehydrogenase (ald); (vii) alcohol dehydrogenase (adh); (viii) fumarate hydratase; and/or (ix) fumarate reductase. For example, the isolated polynucleic acid can comprise an α-ketoglutarate decarboxylase gene. The isolated polynucleic acid can comprise a 4-hydroxybutyrate dehydrogenase gene. The isolated polynucleic acid can comprise a succinyl CoA synthease beta subunit gene. The isolated polynucleic acid can comprise a succinyl CoA synthease alpha subunit gene. In some cases, the isolated polynucleic acid can comprise a 4-hydroxybutyrate CoA transferase gene. In other instances, the isolated polynucleic acid can comprise an aldehyde dehydrogenase gene. In some cases, the isolated polynucleic acid can comprise an alcohol dehydrogenase gene.

In some cases, the isolated polynucleic acid can encode for an α-ketoglutarate decarboxylase gene. For example, the isolated polynucleic acid can comprise a nucleotide sequence that is substantially similar to any one of SEQ ID NOs. 2, 4, 6, or 8. In some cases, the isolated polynucleic acid can comprise a nucleotide sequence that is at least 60% identical to any one of SEQ ID NOs. 2, 4, 6, or 8. In some cases, the isolated polynucleic acid can comprise a nucleotide sequence that is at least 65% identical to any one of SEQ ID NOs. 2, 4, 6, or 8. In some cases, the isolated polynucleic acid can comprise a nucleotide sequence that is at least 70% identical to any one of SEQ ID NOs. 2, 4, 6, or 8. In some cases, the isolated polynucleic acid can comprise a nucleotide sequence that is at least 75% identical to any one of SEQ ID NOs. 2, 4, 6, or 8. In some cases, the isolated polynucleic acid can comprise a nucleotide sequence that is at least 80% identical to any one of SEQ ID NOs. 2, 4, 6, or 8. In some cases, the isolated polynucleic acid can comprise a nucleotide sequence that is at least 81% identical to any one of SEQ ID NOs. 2, 4, 6, or 8. In some cases, the isolated polynucleic acid can comprise a nucleotide sequence that is at least 82% identical to any one of SEQ ID NOs. 2, 4, 6, or 8. In some cases, the isolated polynucleic acid can comprise a nucleotide sequence that is at least 83% identical to any one of SEQ ID NOs. 2, 4, 6, or 8. In some cases, the isolated polynucleic acid can comprise a nucleotide sequence that is at least 84% identical to any one of SEQ ID NOs. 2, 4, 6, or 8. In some cases, the isolated polynucleic acid can comprise a nucleotide sequence that is at least 85% identical to any one of SEQ ID NOs. 2, 4, 6, or 8. In some cases, the isolated polynucleic acid can comprise a nucleotide sequence that is at least 86% identical to any one of SEQ ID NOs. 2, 4, 6, or 8. In some cases, the isolated polynucleic acid can comprise a nucleotide sequence that is at least 87% identical to any one of SEQ ID NOs. 2, 4, 6, or 8. In some cases, the isolated polynucleic acid can comprise a nucleotide sequence that is at least 88% identical to any one of SEQ ID NOs. 2, 4, 6, or 8. In some cases, the isolated polynucleic acid can comprise a nucleotide sequence that is at least 89% identical to any one of SEQ ID NOs. 2, 4, 6, or 8. In some cases, the isolated polynucleic acid can comprise a nucleotide sequence that is at least 90% identical to any one of SEQ ID NOs. 2, 4, 6, or 8. In some cases, the isolated polynucleic acid can comprise a nucleotide sequence that is at least 91% identical to any one of SEQ ID NOs. 2, 4, 6, or 8. In some cases, the isolated polynucleic acid can comprise a nucleotide sequence that is at least 92% identical to any one of SEQ ID NOs. 2, 4, 6, or 8. In some cases, the isolated polynucleic acid can comprise a nucleotide sequence that is at least 93% identical to any one of SEQ ID NOs. 2, 4, 6, or 8. In some cases, the isolated polynucleic acid can comprise a nucleotide sequence that is at least 94% identical to any one of SEQ ID NOs. 2, 4, 6, or 8. In some cases, the isolated polynucleic acid can comprise a nucleotide sequence that is at least 95% identical to any one of SEQ ID NOs. 2, 4, 6, or 8. In some cases, the isolated polynucleic acid can comprise a nucleotide sequence that is at least 96% identical to any one of SEQ ID NOs. 2, 4, 6, or 8. In some cases, the isolated polynucleic acid can comprise a nucleotide sequence that is at least 97% identical to any one of SEQ ID NOs. 2, 4, 6, or 8. In some cases, the isolated polynucleic acid can comprise a nucleotide sequence that is at least 98% identical to any one of SEQ ID NOs. 2, 4, 6, or 8. In some cases, the isolated polynucleic acid can comprise a nucleotide sequence that is at least 99% identical to any one of SEQ ID NOs. 2, 4, 6, or 8. In some cases, the isolated polynucleic acid can comprise a nucleotide sequence that is any one of SEQ ID NOs. 2, 4, 6, or 8.

In some cases, the isolated polynucleic acid can encode for a 4-hydroxybutyrate dehydrogenase. For example, the isolated polynucleic acid can comprise a nucleotide sequence that is substantially similar to SEQ ID NO. 12 or 14. In some cases, the isolated polynucleic acid can comprise a nucleotide sequence that is at least 60% identical to SEQ ID NO. 12 or 14. In some cases, the isolated polynucleic acid can comprise a nucleotide sequence that is at least 65% identical to SEQ ID NO. 12 or 14. In some cases, the isolated polynucleic acid can comprise a nucleotide sequence that is at least 70% identical to SEQ ID NO. 12 or 14. In some cases, the isolated polynucleic acid can comprise a nucleotide sequence that is at least 75% identical to SEQ ID NO. 12 or 14. In some cases, the isolated polynucleic acid can comprise a nucleotide sequence that is at least 80% identical to SEQ ID NO. 12 or 14. In some cases, the isolated polynucleic acid can comprise a nucleotide sequence that is at least 81% identical to SEQ ID NO. 12 or 14. In some cases, the isolated polynucleic acid can comprise a nucleotide sequence that is at least 82% identical to SEQ ID NO. 12 or 14. In some cases, the isolated polynucleic acid can comprise a nucleotide sequence that is at least 83% identical to SEQ ID NO. 12 or 14. In some cases, the isolated polynucleic acid can comprise a nucleotide sequence that is at least 84% identical to SEQ ID NO. 12 or 14. In some cases, the isolated polynucleic acid can comprise a nucleotide sequence that is at least 85% identical to SEQ ID NO. 12 or 14. In some cases, the isolated polynucleic acid can comprise a nucleotide sequence that is at least 86% identical to SEQ ID NO. 12 or 14. In some cases, the isolated polynucleic acid can comprise a nucleotide sequence that is at least 87% identical to SEQ ID NO. 12 or 14. In some cases, the isolated polynucleic acid can comprise a nucleotide sequence that is at least 88% identical to SEQ ID NO. 12 or 14. In some cases, the isolated polynucleic acid can comprise a nucleotide sequence that is at least 89% identical to SEQ ID NO. 12 or 14. In some cases, the isolated polynucleic acid can comprise a nucleotide sequence that is at least 90% identical to SEQ ID NO. 12 or 14. In some cases, the isolated polynucleic acid can comprise a nucleotide sequence that is at least 91% identical to SEQ ID NO. 12 or 14. In some cases, the isolated polynucleic acid can comprise a nucleotide sequence that is at least 92% identical to SEQ ID NO. 12 or 14. In some cases, the isolated polynucleic acid can comprise a nucleotide sequence that is at least 93% identical to SEQ ID NO. 12 or 14. In some cases, the isolated polynucleic acid can comprise a nucleotide sequence that is at least 94% identical to SEQ ID NO. 12 or 14. In some cases, the isolated polynucleic acid can comprise a nucleotide sequence that is at least 95% identical to SEQ ID NO. 12 or 14. In some cases, the isolated polynucleic acid can comprise a nucleotide sequence that is at least 96% identical to SEQ ID NO. 12 or 14. In some cases, the isolated polynucleic acid can comprise a nucleotide sequence that is at least 97% identical to SEQ ID NO. 12 or 14. In some cases, the isolated polynucleic acid can comprise a nucleotide sequence that is at least 98% identical to SEQ ID NO. 12 or 14. In some cases, the isolated polynucleic acid can comprise a nucleotide sequence that is at least 99% identical to SEQ ID NO. 12 or 14. In some cases, the isolated polynucleic acid can comprise a nucleotide sequence that is identical to SEQ ID NO. 12 or 14.

In some cases, the isolated polynucleic acid can comprise a nucleotide sequence that encodes for a 4-hydroxybutyrate CoA transferase. In some cases, the isolated polynucleic acid can comprise a nucleotide sequence that is substantially similar to any one of SEQ ID NOs. 16, 18, or 20. For example, the isolated polynucleic acid can comprise a nucleotide sequence that is at least 60% identical to any one of SEQ ID NOs. 16, 18, or 20. In some cases, the isolated polynucleic acid can comprise a nucleotide sequence that is at least 65% identical to any one of SEQ ID NOs. 16, 18, or 20. In some cases, the isolated polynucleic acid can comprise a nucleotide sequence that is at least 70% identical to any one of SEQ ID NOs. 16, 18, or 20. In some cases, the isolated polynucleic acid can comprise a nucleotide sequence that is at least 75% identical to any one of SEQ ID NOs. 16, 18, or 20. In some cases, the isolated polynucleic acid can comprise a nucleotide sequence that is at least 80% identical to any one of SEQ ID NOs. 16, 18, or 20. In some cases, the isolated polynucleic acid can comprise a nucleotide sequence that is at least 81% identical to any one of SEQ ID NOs. 16, 18, or 20. In some cases, the isolated polynucleic acid can comprise a nucleotide sequence that is at least 82% identical to any one of SEQ ID NOs. 16, 18, or 20. In some cases, the isolated polynucleic acid can comprise a nucleotide sequence that is at least 83% identical to any one of SEQ ID NOs. 16, 18, or 20. In some cases, the isolated polynucleic acid can comprise a nucleotide sequence that is at least 84% identical to any one of SEQ ID NOs. 16, 18, or 20. In some cases, the isolated polynucleic acid can comprise a nucleotide sequence that is at least 85% identical to any one of SEQ ID NOs. 16, 18, or 20. In some cases, the isolated polynucleic acid can comprise a nucleotide sequence that is at least 86% identical to any one of SEQ ID NOs. 16, 18, or 20. In some cases, the isolated polynucleic acid can comprise a nucleotide sequence that is at least 87% identical to any one of SEQ ID NOs. 16, 18, or 20. In some cases, the isolated polynucleic acid can comprise a nucleotide sequence that is at least 88% identical to any one of SEQ ID NOs. 16, 18, or 20. In some cases, the isolated polynucleic acid can comprise a nucleotide sequence that is at least 89% identical to any one of SEQ ID NOs. 16, 18, or 20. In some cases, the isolated polynucleic acid can comprise a nucleotide sequence that is at least 90% identical to any one of SEQ ID NOs. 16, 18, or 20. In some cases, the isolated polynucleic acid can comprise a nucleotide sequence that is at least 91% identical to any one of SEQ ID NOs. 16, 18, or 20. In some cases, the isolated polynucleic acid can comprise a nucleotide sequence that is at least 92% identical to any one of SEQ ID NOs. 16, 18, or 20. In some cases, the isolated polynucleic acid can comprise a nucleotide sequence that is at least 93% identical to any one of SEQ ID NOs. 16, 18, or 20. In some cases, the isolated polynucleic acid can comprise a nucleotide sequence that is at least 94% identical to any one of SEQ ID NOs. 16, 18, or 20. In some cases, the isolated polynucleic acid can comprise a nucleotide sequence that is at least 95% identical to any one of SEQ ID NOs. 16, 18, or 20. In some cases, the isolated polynucleic acid can comprise a nucleotide sequence that is at least 96% identical to any one of SEQ ID NOs. 16, 18, or 20. In some cases, the isolated polynucleic acid can comprise a nucleotide sequence that is at least 97% identical to any one of SEQ ID NOs. 16, 18, or 20. In some cases, the isolated polynucleic acid can comprise a nucleotide sequence that is at least 98% identical to any one of SEQ ID NOs. 16, 18, or 20. In some cases, the isolated polynucleic acid can comprise a nucleotide sequence that is at least 99% identical to any one of SEQ ID NOs. 16, 18, or 20. In some cases, the isolated polynucleic acid can comprise a nucleotide sequence that is identical to any one of SEQ ID NOs. 16, 18, or 20.

In some cases, the isolated polynucleic acid can comprise a nucleotide sequence that encodes for an aldehyde dehydrogenase and/or alcohol dehydrogenase. In some cases, the isolated polynucleic acid can comprise a nucleotide sequence that is substantially similar to any one of SEQ ID NOs. 22, 24, 26, 28, 30, 32, 34, or 36. For example, the isolated polynucleic acid can comprise a nucleotide sequence that is at least 60% identical to any one of SEQ ID NOs. 22, 24, 26, 28, 30, 32, 34, or 36. In some cases, the isolated polynucleic acid can comprise a nucleotide sequence that is at least 65% identical to any one of SEQ ID NOs. 22, 24, 26, 28, 30, 32, 34, or 36. In some cases, the isolated polynucleic acid can comprise a nucleotide sequence that is at least 70% identical to any one of SEQ ID NOs. 22, 24, 26, 28, 30, 32, 34, or 36. In some cases, the isolated polynucleic acid can comprise a nucleotide sequence that is at least 75% identical to any one of SEQ ID NOs. 22, 24, 26, 28, 30, 32, 34, or 36. In some cases, the isolated polynucleic acid can comprise a nucleotide sequence that is at least 80% identical to any one of SEQ ID NOs. 22, 24, 26, 28, 30, 32, 34, or 36. In some cases, the isolated polynucleic acid can comprise a nucleotide sequence that is at least 81% identical to any one of SEQ ID NOs. 22, 24, 26, 28, 30, 32, 34, or 36. In some cases, the isolated polynucleic acid can comprise a nucleotide sequence that is at least 82% identical to any one of SEQ ID NOs. 22, 24, 26, 28, 30, 32, 34, or 36. In some cases, the isolated polynucleic acid can comprise a nucleotide sequence that is at least 83% identical to any one of SEQ ID NOs. 22, 24, 26, 28, 30, 32, 34, or 36. In some cases, the isolated polynucleic acid can comprise a nucleotide sequence that is at least 84% identical to any one of SEQ ID NOs. 22, 24, 26, 28, 30, 32, 34, or 36. In some cases, the isolated polynucleic acid can comprise a nucleotide sequence that is at least 85% identical to any one of SEQ ID NOs. 22, 24, 26, 28, 30, 32, 34, or 36. In some cases, the isolated polynucleic acid can comprise a nucleotide sequence that is at least 86% identical to any one of SEQ ID NOs. 22, 24, 26, 28, 30, 32, 34, or 36. In some cases, the isolated polynucleic acid can comprise a nucleotide sequence that is at least 87% identical to any one of SEQ ID NOs. 22, 24, 26, 28, 30, 32, 34, or 36. In some cases, the isolated polynucleic acid can comprise a nucleotide sequence that is at least 88% identical to any one of SEQ ID NOs. 22, 24, 26, 28, 30, 32, 34, or 36. In some cases, the isolated polynucleic acid can comprise a nucleotide sequence that is at least 89% identical to any one of SEQ ID NOs. 22, 24, 26, 28, 30, 32, 34, or 36. In some cases, the isolated polynucleic acid can comprise a nucleotide sequence that is at least 90% identical to any one of SEQ ID NOs. 22, 24, 26, 28, 30, 32, 34, or 36. In some cases, the isolated polynucleic acid can comprise a nucleotide sequence that is at least 91% identical to any one of SEQ ID NOs. 22, 24, 26, 28, 30, 32, 34, or 36. In some cases, the isolated polynucleic acid can comprise a nucleotide sequence that is at least 92% identical to any one of SEQ ID NOs. 22, 24, 26, 28, 30, 32, 34, or 36. In some cases, the isolated polynucleic acid can comprise a nucleotide sequence that is at least 93% identical to any one of SEQ ID NOs. 22, 24, 26, 28, 30, 32, 34, or 36. In some cases, the isolated polynucleic acid can comprise a nucleotide sequence that is at least 94% identical to any one of SEQ ID NOs. 22, 24, 26, 28, 30, 32, 34, or 36. In some cases, the isolated polynucleic acid can comprise a nucleotide sequence that is at least 95% identical to any one of SEQ ID NOs. 22, 24, 26, 28, 30, 32, 34, or 36. In some cases, the isolated polynucleic acid can comprise a nucleotide sequence that is at least 96% identical to any one of SEQ ID NOs. 22, 24, 26, 28, 30, 32, 34, or 36. In some cases, the isolated polynucleic acid can comprise a nucleotide sequence that is at least 97% identical to any one of SEQ ID NOs. 22, 24, 26, 28, 30, 32, 34, or 36. In some cases, the isolated polynucleic acid can comprise a nucleotide sequence that is at least 98% identical to any one of SEQ ID NOs. 22, 24, 26, 28, 30, 32, 34, or 36. In some cases, the isolated polynucleic acid can comprise a nucleotide sequence that is at least 99% identical to any one of SEQ ID NOs. 22, 24, 26, 28, 30, 32, 34, or 36. In some cases, the isolated polynucleic acid can comprise a nucleotide sequence that is identical to any one of SEQ ID NOs. 22, 24, 26, 28, 30, 32, 34, or 36.

In some cases, the isolated polynucleic acid can comprise a nucleotide sequence that encodes for a succinyl CoA synthease beta subunit. In some cases, the isolated polynucleic acid can comprise a nucleotide sequence that is substantially similar to SEQ ID NO. 38. For example, the isolated polynucleic acid can comprise a nucleotide sequence that is at least 60% identical to SEQ ID NO. 38. In some cases, the isolated polynucleic acid can comprise a nucleotide sequence that is at least 65% identical to SEQ ID NO. 38. In some cases, the isolated polynucleic acid can comprise a nucleotide sequence that is at least 70% identical to SEQ ID NO. 38. In some cases, the isolated polynucleic acid can comprise a nucleotide sequence that is at least 75% identical to SEQ ID NO. 38. In some cases, the isolated polynucleic acid can comprise a nucleotide sequence that is at least 80% identical to SEQ ID NO. 38. In some cases, the isolated polynucleic acid can comprise a nucleotide sequence that is at least 81% identical to SEQ ID NO. 38. In some cases, the isolated polynucleic acid can comprise a nucleotide sequence that is at least 82% identical to SEQ ID NO. 38. In some cases, the isolated polynucleic acid can comprise a nucleotide sequence that is at least 83% identical to SEQ ID NO. 38. In some cases, the isolated polynucleic acid can comprise a nucleotide sequence that is at least 84% identical to SEQ ID NO. 38. In some cases, the isolated polynucleic acid can comprise a nucleotide sequence that is at least 85% identical to SEQ ID NO. 38. In some cases, the isolated polynucleic acid can comprise a nucleotide sequence that is at least 86% identical to SEQ ID NO. 38. In some cases, the isolated polynucleic acid can comprise a nucleotide sequence that is at least 87% identical to SEQ ID NO. 38. In some cases, the isolated polynucleic acid can comprise a nucleotide sequence that is at least 88% identical to SEQ ID NO. 38. In some cases, the isolated polynucleic acid can comprise a nucleotide sequence that is at least 89% identical to SEQ ID NO. 38. In some cases, the isolated polynucleic acid can comprise a nucleotide sequence that is at least 90% identical to SEQ ID NO. 38. In some cases, the isolated polynucleic acid can comprise a nucleotide sequence that is at least 91% identical to SEQ ID NO. 38. In some cases, the isolated polynucleic acid can comprise a nucleotide sequence that is at least 92% identical to SEQ ID NO. 38. In some cases, the isolated polynucleic acid can comprise a nucleotide sequence that is at least 93% identical to SEQ ID NO. 38. In some cases, the isolated polynucleic acid can comprise a nucleotide sequence that is at least 94% identical to SEQ ID NO. 38. In some cases, the isolated polynucleic acid can comprise a nucleotide sequence that is at least 95% identical to SEQ ID NO. 38. In some cases, the isolated polynucleic acid can comprise a nucleotide sequence that is at least 96% identical to SEQ ID NO. 38. In some cases, the isolated polynucleic acid can comprise a nucleotide sequence that is at least 97% identical to SEQ ID NO. 38. In some cases, the isolated polynucleic acid can comprise a nucleotide sequence that is at least 98% identical to SEQ ID NO. 38. In some cases, the isolated polynucleic acid can comprise a nucleotide sequence that is at least 99% identical to SEQ ID NO. 38. In some cases, the isolated polynucleic acid can comprise a nucleotide sequence that is identical to SEQ ID NO. 38.

In some cases, the isolated polynucleic acid can comprise a nucleotide sequence that encodes for a succinyl CoA synthease alpha subunit. In some cases, the isolated polynucleic acid can comprise a nucleotide sequence that is substantially similar to any one of SEQ ID NOs. 40, 43, or 44. For example, the isolated polynucleic acid can comprise a nucleotide sequence that is at least 60% identical to any one of SEQ ID NOs. 40, 43, or 44. In some cases, the isolated polynucleic acid can comprise a nucleotide sequence that is at least 65% identical to any one of SEQ ID NOs. 40, 43, or 44. In some cases, the isolated polynucleic acid can comprise a nucleotide sequence that is at least 70% identical to any one of SEQ ID NOs. 40, 43, or 44. In some cases, the isolated polynucleic acid can comprise a nucleotide sequence that is at least 75% identical to any one of SEQ ID NOs. 40, 43, or 44. In some cases, the isolated polynucleic acid can comprise a nucleotide sequence that is at least 80% identical to any one of SEQ ID NOs. 40, 43, or 44. In some cases, the isolated polynucleic acid can comprise a nucleotide sequence that is at least 81% identical to any one of SEQ ID NOs. 40, 43, or 44. In some cases, the isolated polynucleic acid can comprise a nucleotide sequence that is at least 82% identical to any one of SEQ ID NOs. 40, 43, or 44. In some cases, the isolated polynucleic acid can comprise a nucleotide sequence that is at least 83% identical to any one of SEQ ID NOs. 40, 43, or 44. In some cases, the isolated polynucleic acid can comprise a nucleotide sequence that is at least 84% identical to any one of SEQ ID NOs. 40, 43, or 44. In some cases, the isolated polynucleic acid can comprise a nucleotide sequence that is at least 85% identical to any one of SEQ ID NOs. 40, 43, or 44. In some cases, the isolated polynucleic acid can comprise a nucleotide sequence that is at least 86% identical to any one of SEQ ID NOs. 40, 43, or 44. In some cases, the isolated polynucleic acid can comprise a nucleotide sequence that is at least 87% identical to any one of SEQ ID NOs. 40, 43, or 44. In some cases, the isolated polynucleic acid can comprise a nucleotide sequence that is at least 88% identical to any one of SEQ ID NOs. 40, 43, or 44. In some cases, the isolated polynucleic acid can comprise a nucleotide sequence that is at least 89% identical to any one of SEQ ID NOs. 40, 43, or 44. In some cases, the isolated polynucleic acid can comprise a nucleotide sequence that is at least 90% identical to any one of SEQ ID NOs. 40, 43, or 44. In some cases, the isolated polynucleic acid can comprise a nucleotide sequence that is at least 91% identical to any one of SEQ ID NOs. 40, 43, or 44. In some cases, the isolated polynucleic acid can comprise a nucleotide sequence that is at least 92% identical to any one of SEQ ID NOs. 40, 43, or 44. In some cases, the isolated polynucleic acid can comprise a nucleotide sequence that is at least 93% identical to any one of SEQ ID NOs. 40, 43, or 44. In some cases, the isolated polynucleic acid can comprise a nucleotide sequence that is at least 94% identical to any one of SEQ ID NOs. 40, 43, or 44. In some cases, the isolated polynucleic acid can comprise a nucleotide sequence that is at least 95% identical to any one of SEQ ID NOs. 40, 43, or 44. In some cases, the isolated polynucleic acid can comprise a nucleotide sequence that is at least 96% identical to any one of SEQ ID NOs. 40, 43, or 44. In some cases, the isolated polynucleic acid can comprise a nucleotide sequence that is at least 97% identical to any one of SEQ ID NOs. 40, 43, or 44. In some cases, the isolated polynucleic acid can comprise a nucleotide sequence that is at least 98% identical to any one of SEQ ID NOs. 40, 43, or 44. In some cases, the isolated polynucleic acid can comprise a nucleotide sequence that is at least 99% identical to any one of SEQ ID NOs. 40, 43, or 44. In some cases, the isolated polynucleic acid can comprise a nucleotide sequence that is identical to any one of SEQ ID NOs. 40, 43, or 44.

In some cases, the isolated polynucleic acid can comprise a nucleotide sequence that encodes for a fumarate hydratase. In some cases, the isolated polynucleic acid can comprise a nucleotide sequence that is substantially similar to any one of SEQ ID NOs. 46, 48, or 50. For example, the isolated polynucleic acid can comprise a nucleotide sequence that is at least 60% identical to any one of SEQ ID NOs. 46, 48, or 50. In some cases, the isolated polynucleic acid can comprise a nucleotide sequence that is at least 65% identical to any one of SEQ ID NOs. 46, 48, or 50. In some cases, the isolated polynucleic acid can comprise a nucleotide sequence that is at least 70% identical to any one of SEQ ID NOs. 46, 48, or 50. For example, the isolated polynucleic acid can comprise a nucleotide sequence that is at least 75% identical to any one of SEQ ID NOs. 46, 48, or 50. In some cases, the isolated polynucleic acid can comprise a nucleotide sequence that is at least 80% identical to any one of SEQ ID NOs. 46, 48, or 50. For example, the isolated polynucleic acid can comprise a nucleotide sequence that is at least 85% identical to any one of SEQ ID NOs. 46, 48, or 50. In some cases, the isolated polynucleic acid can comprise a nucleotide sequence that is at least 90% identical to any one of SEQ ID NOs. 46, 48, or 50. In some cases, the isolated polynucleic acid can comprise a nucleotide sequence that is at least 91% identical to any one of SEQ ID NOs. 46, 48, or 50.

In some cases, the isolated polynucleic acid can comprise a nucleotide sequence that is at least 92% identical to any one of SEQ ID NOs. 46, 48, or 50. In some cases, the isolated polynucleic acid can comprise a nucleotide sequence that is at least 93% identical to any one of SEQ ID NOs. 46, 48, or 50. In some cases, the isolated polynucleic acid can comprise a nucleotide sequence that is at least 94% identical to any one of SEQ ID NOs. 46, 48, or 50. In some cases, the isolated polynucleic acid can comprise a nucleotide sequence that is at least 95% identical to any one of SEQ ID NOs. 46, 48, or 50. In some cases, the isolated polynucleic acid can comprise a nucleotide sequence that is at least 96% identical to any one of SEQ ID NOs. 46, 48, or 50. In some cases, the isolated polynucleic acid can comprise a nucleotide sequence that is at least 97% identical to any one of SEQ ID NOs. 46, 48, or 50. In some cases, the isolated polynucleic acid can comprise a nucleotide sequence that is at least 98% identical to any one of SEQ ID NOs. 46, 48, or 50. In some cases, the isolated polynucleic acid can comprise a nucleotide sequence that is at least 99% identical to any one of SEQ ID NOs. 46, 48, or 50. In some cases, the isolated polynucleic acid can comprise a nucleotide sequence that is any one of SEQ ID NOs. 46, 48, or 50.

In some cases, the isolated polynucleic acid can comprise a nucleotide sequence that encodes for a fumarate reductase. In some cases, the isolated polynucleic acid can comprise a nucleotide sequence that is substantially similar to any one of SEQ ID NOs. 52, 54, 56, or 58. For example, the isolated polynucleic acid can comprise a nucleotide sequence that is at least 60% identical to any one of SEQ ID NOs. 52, 54, 56, or 58. For example, the isolated polynucleic acid can comprise a nucleotide sequence that is at least 65% identical to any one of SEQ ID NOs. 52, 54, 56, or 58. In some cases, the isolated polynucleic acid can comprise a nucleotide sequence that is at least 70% identical to any one of SEQ ID NOs. 52, 54, 56, or 58. For example, the isolated polynucleic acid can comprise a nucleotide sequence that is at least 75% identical to any one of SEQ ID NOs. 52, 54, 56, or 58. In some cases, the isolated polynucleic acid can comprise a nucleotide sequence that is at least 80% identical to any one of SEQ ID NOs. 52, 54, 56, or 58. For example, the isolated polynucleic acid can comprise a nucleotide sequence that is at least 85% identical to any one of SEQ ID NOs. 52, 54, 56, or 58. In some cases, the isolated polynucleic acid can comprise a nucleotide sequence that is at least 90% identical to any one of SEQ ID NOs. 52, 54, 56, or 58. In some cases, the isolated polynucleic acid can comprise a nucleotide sequence that is at least 91% identical to any one of SEQ ID NOs. 52, 54, 56, or 58. In some cases, the isolated polynucleic acid can comprise a nucleotide sequence that is at least 92% identical to any one of SEQ ID NOs. 52, 54, 56, or 58. In some cases, the isolated polynucleic acid can comprise a nucleotide sequence that is at least 93% identical to any one of SEQ ID NOs. 52, 54, 56, or 58. In some cases, the isolated polynucleic acid can comprise a nucleotide sequence that is at least 94% identical to any one of SEQ ID NOs. 52, 54, 56, or 58. In some cases, the isolated polynucleic acid can comprise a nucleotide sequence that is at least 95% identical to any one of SEQ ID NOs. 52, 54, 56, or 58. In some cases, the isolated polynucleic acid can comprise a nucleotide sequence that is at least 96% identical to any one of SEQ ID NOs. 52, 54, 56, or 58. In some cases, the isolated polynucleic acid can comprise a nucleotide sequence that is at least 97% identical to any one of SEQ ID NOs. 52, 54, 56, or 58. In some cases, the isolated polynucleic acid can comprise a nucleotide sequence that is at least 98% identical to any one of SEQ ID NOs. 52, 54, 56, or 58. In some cases, the isolated polynucleic acid can comprise a nucleotide sequence that is at least 99% identical to any one of SEQ ID NOs. 52, 54, 56, or 58. In some cases, In some cases, the isolated polynucleic acid can comprise a nucleotide sequence that encodes for a fumarate hydratase. In some cases, the isolated polynucleic acid can comprise a nucleotide sequence that is any one of SEQ ID NOs. 52, 54, 56, or 58.

II. Method of Making the Genetically Modified Microorganisms

The genetically modified microorganisms above can be made by a variety of ways. A microorganism may be modified (e.g., genetically engineered) by any method to comprise and/or express one or more polynucleotides encoding for enzymes in a pathway that catalyze a conversion of a fermentable carbon source (e.g., a C1 carbon) to one or more intermediates in a pathway for the production of a multicarbon product such as 1,4-BDO. Such enzymes may include any or all of those enzymes as set forth in FIG. 1, 2, 3, or 7. For example, one or more of any of the genes above can be inserted into a microorganism. The genes can be inserted by an expression vector. The one or more genes can also be stably integrated into the genome of the microorganism.

The microorganism used in this method can be any described above, including but not limited to a prokaryote. Other microorganisms such as bacteria, yeast, or algae can be used. One microorganism of particular interest is a methanotroph, such as a methanotroph from the genera *Methylobacter, Methylomicrobium, Methylomonas, Methylocaldum, Methylococcus, Methylosoma, Methylosarcina, Methylothermus, Methylohalobius, Methylogaea, Methylovulum, Crenothrix, Clonothrix, Methylosphaera, Methylocapsa, Methylocella, Methylosinus, Methylocystis, Methyloferula, Methylomarinum,* or *Methylacidiphilum*. One desired species can include a *Methylococcus capsulatus*.

An exemplary method of making a genetically modified microorganism disclosed herein is contacting (or transforming) a microorganism with a nucleic acid that expresses at least one heterologous genes from: GROUP 1, GROUP 2, and/or GROUP 3. For example, the genes can include: i) α-ketoglutarate decarboxylase (kgd); ii) 4-hydroxybutyrate dehydrogenase (4hbD); iii) 4-hydroxybutyrate CoA transferase (cat2); (iv) aldehyde dehydrogenase (ald); (v) alcohol dehydrogenase (adh); (vi) succinyl CoA synthease beta subunit (sucC); (vii) succinyl CoA synthease alpha subunit (sucD); or (viii) any combination thereof. The genes can also include a fumarate hydratase or a fumarate reductase. The microorganism can be any microorganism that is capable of converting a C1 carbon to a multicarbon product. In some cases, the multicarbon product is 1,4-BDO. The microorganism can be any one of the microorganism described throughout the patent application.

The one or more genes that are inserted into a microorganism can be heterologous to the microorganism itself. For example, if the microorganism is a methanotroph, the one or more genes that are inserted can be from yeast, a bacterium, or a different species of methanotroph. Further, the one or more genes can be endogenously part of the genome of the microorganism.

Techniques for Genetic Modification

The microorganisms disclosed herein may be genetically engineered by using classic microbiological techniques. Some of such techniques are generally disclosed, for example, in Sambrook et al., 1989, Molecular Cloning: A Laboratory Manual, Cold Spring Harbor Labs Press.

The genetically modified microorganisms disclosed herein may include a polynucleotide that has been inserted, deleted or modified (i.e., mutated; e.g., by insertion, deletion, substitution, and/or inversion of nucleotides), in such a manner that such modifications provide the desired effect of expression (e.g., over-expression) of one or more enzymes as provided herein within the microorganism. Genetic modifications which result in an increase in gene expression or function can be referred to as amplification, overproduction, overexpression, activation, enhancement, addition, or up-regulation of a gene. Addition of a gene to increase gene expression can include maintaining the gene(s) on replicating plasmids or integrating the cloned gene(s) into the genome of the production microorganism. Furthermore, increasing the expression of desired genes can include operatively linking the cloned gene(s) to native or heterologous transcriptional control elements.

Where desired, the expression of one or more of the enzymes provided herein is under the control of a regulatory sequence that controls directly or indirectly the enzyme expression in a time-dependent fashion during the fermentation. Inducible promoters can be used to achieve this.

In some cases, a microorganism is transformed or transfected with a genetic vehicle, such as an expression vector comprising a heterologous polynucleotide sequence coding for the enzymes are provided herein.

To facilitate insertion and expression of different genes coding for the enzymes as disclosed herein from the constructs and expression vectors, the constructs may be designed with at least one cloning site for insertion of any gene coding for any enzyme disclosed herein. The cloning site may be a multiple cloning site, e.g., containing multiple restriction sites.

Transfection

Standard transfection techniques can be used to insert genes into a microorganism. As used herein, the term "transfection" or "transformation" can refer to the insertion of an exogenous nucleic acid or polynucleotide into a host cell. The exogenous nucleic acid or polynucleotide may be maintained as a non-integrated vector, for example, a plasmid, or alternatively, may be integrated into the host cell genome. The term transfecting or transfection is intended to encompass all conventional techniques for introducing nucleic acid or polynucleotide into microorganisms. Examples of transfection techniques include, but are not limited to, calcium phosphate precipitation, DEAE-dextran-mediated transfection, lipofection, electroporation, microinjection, rubidium chloride or polycation mediated transfection, protoplast fusion, and sonication. The transfection method that provides optimal transfection frequency and expression of the construct in the particular host cell line and type is favored. For stable transfectants, the constructs are integrated so as to be stably maintained within the host chromosome. In some cases, the preferred transfection is a stable transfection.

Transformation

Expression vectors or other nucleic acids may be introduced to selected microorganisms by any of a number of suitable methods. For example, vector constructs may be introduced to appropriate cells by any of a number of transformation methods for plasmid vectors. Standard calcium-chloride-mediated bacterial transformation is still commonly used to introduce naked DNA to bacteria (see, e.g., Sambrook et al., 1989, Molecular Cloning, A Laboratory Manual, Cold Spring Harbor Laboratory Press, Cold Spring Harbor, N.Y.), but electroporation and conjugation may also be used (see, e.g., Ausubel et al., 1988, Current Protocols in Molecular Biology, John Wiley & Sons, Inc., NY, N.Y.).

For the introduction of vector constructs to yeast or other fungal cells, chemical transformation methods may be used (e.g., Rose et al., 1990, Methods in Yeast Genetics, Cold Spring Harbor Laboratory Press, Cold Spring Harbor, N.Y.). Transformed cells may be isolated on selective media appropriate to the selectable marker used. Alternatively, or in addition, plates or filters lifted from plates may be scanned for GFP fluorescence to identify transformed clones.

For the introduction of vectors comprising differentially expressed sequences to certain types of cells, the method used may depend upon the form of the vector. Plasmid vectors may be introduced by any of a number of transfection methods, including, for example, lipid-mediated transfection ("lipofection"), DEAE-dextran-mediated transfection, electroporation or calcium phosphate precipitation (see, e.g., Ausubel et al., 1988, Current Protocols in Molecular Biology, John Wiley & Sons, Inc., NY, N.Y.).

Lipofection reagents and methods suitable for transient transfection of a wide variety of transformed and non-transformed or primary cells are widely available, making lipofection an attractive method of introducing constructs to eukaryotic, and particularly mammalian cells in culture. Many companies offer kits and ways for this type of transfection.

The host cell may be capable of expressing the construct encoding the desired protein, processing the protein and transporting a secreted protein to the cell surface for secretion. Processing includes co- and post-translational modification such as leader peptide cleavage, GPI attachment, glycosylation, ubiquitination, and disulfide bond formation.

Microorganisms can be transformed or transfected with the above-described expression or vectors for production of one or more enzymes as disclosed herein or with polynucleotides coding for one or more enzymes as disclosed herein and cultured in nutrient media modified as appropriate for the specific microorganism, inducing promoters, selecting transformants, or amplifying the genes encoding the desired sequences.

For example, within the context of a methanotroph, electroporation methods can be used to deliver an expression vector.

Expression of a vector (and the gene contained in the vector) can be verified by an expression assay, for example, qPCR or by measuring levels of RNA. Expression level can be indicative also of copy number. For example, if expression levels are extremely high, this can indicate that more than one copy of a gene was integrated in a genome. Alternatively, high expression can indicate that a gene was integrated in a highly transcribed area, for example, near a highly expressed promoter. Expression can also be verified by measuring protein levels, such as through Western blotting.

CRISPR/Cas System

Methods that require any of the genes described herein can take advantage of pinpoint insertion of genes or the deletion of genes (or parts of genes). Methods described herein can take advantage of a CRISPR/cas system. For example, double-strand breaks (DSBs) can be generated using a CRISPR/cas system, e.g., a type II CRISPR/cas system. A Cas enzyme used in the methods disclosed herein can be Cas9, which catalyzes DNA cleavage. Enzymatic action by Cas9 derived from *Streptococcus pyogenes* or any closely related Cas9 can generate double stranded breaks at target site sequences which hybridize to 20 nucleotides of a guide sequence and that have a protospacer-adjacent motif (PAM) following the 20 nucleotides of the target sequence.

A vector can be operably linked to an enzyme-coding sequence encoding a CRISPR enzyme, such as a Cas protein. Cas proteins that can be used include class 1 and class 2. Non-limiting examples of Cas proteins include Cas1, Cas1B, Cas2, Cas3, Cas4, Cas5, Cas5d, Cas5t, Cas5h, Cas5a, Cas6, Cas7, Cas8, Cas9 (also known as Csn1 or Csx12), Cas10, Csy1, Csy2, Csy3, Csy4, Cse1, Cse2, Cse3, Cse4, Cse5e, Csc1, Csc2, Csa5, Csn1, Csn2, Csm1, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx1S, Csf1, Csf2, CsO, Csf4, Csd1, Csd2, Cst1, Cst2, Csh1, Csh2, Csa1, Csa2, Csa3, Csa4, Csa5, C2c1, C2c2, C2c3, Cpf1, CARF, DinG, homologues thereof, or modified versions thereof. An unmodified CRISPR enzyme can have DNA cleavage activity, such as Cas9. A CRISPR enzyme can direct cleavage of one or both strands at a target sequence, such as within a target sequence and/or within a complement of a target sequence. For example, a CRISPR enzyme can direct cleavage of one or both strands within about 1, 2, 3, 4, 5, 6, 7, 8, 9, 10, 15, 20, 25, 50, 100, 200, 500, or more base pairs from the first or last nucleotide of a target sequence. A vector that encodes a CRISPR enzyme that is mutated to with respect, to a corresponding wild-type enzyme such that the mutated CRISPR enzyme lacks the ability to cleave one or both strands of a target polynucleotide containing a target sequence can be used.

A vector that encodes a CRISPR enzyme comprising one or more nuclear localization sequences (NLSs) can be used. For example, there can be or be about 1, 2, 3, 4, 5, 6, 7, 8, 9, 10 NLSs used. A CRISPR enzyme can comprise the NLSs at or near the ammo-terminus, about or more than about 1, 2, 3, 4, 5, 6, 7, 8, 9, 10 NLSs at or near the carboxy-terminus, or any combination of these (e.g., one or more NLS at the ammo-terminus and one or more NLS at the carboxy terminus). When more than one NLS is present, each can be selected independently of others, such that a single NLS can be present in more than one copy and/or in combination with one or more other NLSs present in one or more copies.

CRISPR enzymes used in the methods can comprise at most 6 NLSs. An NLS is considered near the N- or C-terminus when the nearest amino acid to the NLS is within about 50 amino acids along a polypeptide chain from the N- or C-terminus, e.g., within 1, 2, 3, 4, 5, 10, 15, 20, 25, 30, 40, or 50 amino acids.

Guide RNA

As used herein, the term "guide RNA" and its grammatical equivalents can refer to an RNA which can be specific for a target DNA and can form a complex with Cas protein. An RNA/Cas complex can assist in "guiding" Cas protein to a target DNA.

A method disclosed herein also can comprise introducing into a cell or embryo at least one guide RNA or nucleic acid, e.g., DNA encoding at least one guide RNA. A guide RNA can interact with a RNA-guided endonuclease to direct the endonuclease to a specific target site, at which site the 5' end of the guide RNA base pairs with a specific protospacer sequence in a chromosomal sequence.

A guide RNA can comprise two RNAs, e.g., CRISPR RNA (crRNA) and transactivating crRNA (tracrRNA). A guide RNA can sometimes comprise a single-chain RNA, or single guide RNA (sgRNA) formed by fusion of a portion (e.g., a functional portion) of crRNA and tracrRNA. A guide RNA can also be a dualRNA comprising a crRNA and a tracrRNA. Furthermore, a crRNA can hybridize with a target DNA.

As discussed above, a guide RNA can be an expression product. For example, a DNA that encodes a guide RNA can be a vector comprising a sequence coding for the guide RNA. A guide RNA can be transferred into a cell or microorganism by transfecting the cell or microorganism with an isolated guide RNA or plasmid DNA comprising a sequence coding for the guide RNA and a promoter. A guide RNA can also be transferred into a cell or microorganism in other way, such as using virus-mediated gene delivery.

A guide RNA can be isolated. For example, a guide RNA can be transfected in the form of an isolated RNA into a cell or microorganism. A guide RNA can be prepared by in vitro transcription using any in vitro transcription system known in the art. A guide RNA can be transferred to a cell in the form of isolated RNA rather than in the form of plasmid comprising encoding sequence for a guide RNA.

A guide RNA can comprise three regions: a first region at the 5' end that can be complementary to a target site in a chromosomal sequence, a second internal region that can form a stem loop structure, and a third 3' region that can be single-stranded. A first region of each guide RNA can also be different such that each guide RNA guides a fusion protein to a specific target site. Further, second and third regions of each guide RNA can be identical in all guide RNAs.

A first region of a guide RNA can be complementary to sequence at a target site in a chromosomal sequence such that the first region of the guide RNA can base pair with the target site. In some cases, a first region of a guide RNA can comprise from or from about 10 nucleotides to 25 nucleotides (i.e., from 10 nts to 25 nts; or from about 10 nts to about 25 nts; or from 10 nts to about 25 nts; or from about 10 nts to 25 nts) or more. For example, a region of base pairing between a first region of a guide RNA and a target site in a chromosomal sequence can be or can be about 10, 11, 12, 13, 14, 15, 16, 17, 18, 19, 20, 22, 23, 24, 25, or more nucleotides in length. Sometimes, a first region of a guide RNA can be or can be about 19, 20, or 21 nucleotides in length.

A guide RNA can also comprises a second region that forms a secondary structure. For example, a secondary structure formed by a guide RNA can comprise a stem (or hairpin) and a loop. A length of a loop and a stem can vary. For example, a loop can range from or from about 3 to 10 nucleotides in length, and a stem can range from or from about 6 to 20 base pairs in length. A stem can comprise one or more bulges of 1 to 10 or about 10 nucleotides. The overall length of a second region can range from or from about 16 to 60 nucleotides in length. For example, a loop can be or can be about 4 nucleotides in length and a stem can be or can be about 12 base pairs.

A guide RNA can also comprise a third region at the 3' end that can be essentially single-stranded. For example, a third region is sometimes not complementarity to any chromosomal sequence in a cell of interest and is sometimes not complementarity to the rest of a guide RNA. Further, the length of a third region can vary. A third region can be more than or more than about 4 nucleotides in length. For example, the length of a third region can range from or from about 5 to 60 nucleotides in length.

A guide RNA can be introduced into a cell or embryo as an RNA molecule. For example, a RNA molecule can be transcribed in vitro and/or can be chemically synthesized. An RNA can be transcribed from a synthetic DNA molecule, e.g., a gBlocks® gene fragment. A guide RNA can then be introduced into a cell or embryo as an RNA molecule. A guide RNA can also be introduced into a cell or embryo in the form of a non-RNA nucleic acid molecule, e.g., DNA molecule. For example, a DNA encoding a guide RNA can be operably linked to promoter control sequence for expression of the guide RNA in a cell or embryo of interest. A RNA coding sequence can be operably linked to a promoter sequence that is recognized by RNA polymerase III (Pol III). Plasmid vectors that can be used to express guide RNA include, but are not limited to, px330 vectors and px333 vectors. In some cases, a plasmid vector (e.g., px333 vector) can comprise two guide RNA-encoding DNA sequences.

A DNA sequence encoding a guide RNA can also be part of a vector. Further, a vector can comprise additional expression control sequences (e.g., enhancer sequences, Kozak sequences, polyadenylation sequences, transcriptional termination sequences, etc.), selectable marker sequences (e.g., antibiotic resistance genes), origins of replication, and the like. A DNA molecule encoding a guide RNA can also be linear. A DNA molecule encoding a guide RNA can also be circular.

When DNA sequences encoding an RNA-guided endonuclease and a guide RNA are introduced into a cell, each DNA sequence can be part of a separate molecule (e.g., one vector containing an RNA-guided endonuclease coding sequence and a second vector containing a guide RNA coding sequence) or both can be part of a same molecule (e.g., one vector containing coding (and regulatory) sequence for both an RNA-guided endonuclease and a guide RNA).

Site Specific Insertion

Inserting one or more genes in any of the methods disclosed herein can be site-specific. For example, one or more genes can be inserted adjacent to a promoter.

Modification of a targeted locus of a microorganism can be produced by introducing DNA into microorganisms, where the DNA has homology to the target locus. DNA can include a marker gene, allowing for selection of cells comprising the integrated construct. Homologous DNA in a target vector can recombine with DNA at a target locus. A marker gene can be flanked on both sides by homologous DNA sequences, a 3' recombination arm, and a 5' recombination arm.

A variety of enzymes can catalyze insertion of foreign DNA into a microorganism genome. For example, site-specific recombinases can be clustered into two protein families with distinct biochemical properties, namely tyrosine recombinases (in which DNA is covalently attached to a tyrosine residue) and serine recombinases (where covalent attachment occurs at a serine residue). In some cases, recombinases can comprise Cre, Φ31 integrase (a serine recombinase derived from *Streptomyces* phage (D31), or bacteriophage derived site-specific recombinases (including Flp, lambda integrase, bacteriophage HK022 recombinase, bacteriophage R4 integrase and phage TP901-1 integrase).

The CRISPR/Cas system can be used to perform site specific insertion. For example, a nick on an insertion site in the genome can be made by CRISPR/cas to facilitate the insertion of a transgene at the insertion site.

The methods described herein, can utilize techniques which can be used to allow a DNA or RNA construct entry into a host cell include, but are not limited to, calcium phosphate/DNA co-precipitation, microinjection of DNA into a nucleus, electroporation, bacterial protoplast fusion with intact cells, transfection, lipofection, infection, particle bombardment, sperm mediated gene transfer, or any other technique.

Certain aspects disclosed herein can utilize vectors (including the ones described above). Any plasmids and vectors can be used as long as they are replicable and viable in a selected host microorganism. Vectors known in the art and those commercially available (and variants or derivatives thereof) can be engineered to include one or more recombination sites for use in the methods. Vectors that can be used include, but not limited to eukaryotic expression vectors such as pFastBac, pFastBacHT, pFastBacDUAL, pSFV, and pTet-Splice (Invitrogen), pEUK-C1, pPUR, pMAM, pMAMneo, pBI101, pBI121, pDR2, pCMVEBNA, and pYACneo (Clontech), pSVK3, pSVL, pMSG, pCH110, and pKK232-8 (Pharmacia, Inc.), pXT1, pSG5, pPbac, pMbac, pMClneo, and pOG44 (Stratagene, Inc.), and pYES2, pAC360, pBlueBa-cHis A, B, and C, pVL1392, pBlue-Bac111, pCDM8, pcDNA1, pZeoSV, pcDNA3, pREP4, pCEP4, and pEBVHis (Invitrogen, Corp.), and variants or derivatives thereof.

These vectors can be used to express a gene or portion of a gene of interest. A gene of portion or a gene can be inserted by using known methods, such as restriction enzyme-based techniques.

III. Other Methods

Making Useful Chemicals

The genetically modified microorganisms described herein can be used to make chemicals and other products that are useful, including but not limited to α-ketoglutarate, succinate, citrate and isocitrate, γ-hydroxybutyrate, 4-hydroxybutyraldehyde, 1,4-BDO, tetrahydrofuran (THF), polybutylene terephthalate (PBT), and polyurethanes.

The microorganism can be any of the microorganisms discussed throughout including but not limited to a prokaryote, such as a methanotroph.

The carbon substrate can be any carbon substrate discussed throughout including but not limited to a C1 carbon substrate, such as methane.

α-ketoglutarate

With regards to α-ketoglutarate, one method that is disclosed herein is a method of making α-ketoglutarate comprising: (a) contacting a genetically modified microorganism with a carbon substrate (e.g., a C1 carbon substrate), where the microorganism comprises at least one heterologous gene encoding for an isocitrate dehydrogenase (icdA); and (b) growing the microorganism to produce α-ketoglutarate. The microorganism can be a microorganism that is capable of converted a C1 carbon into a multicarbon product. For example, a methanotroph can be used. Further any of the genetically modified microorganisms described throughout can be used. The α-ketoglutarate produced can be substantially pure. The α-ketoglutarate that is produced can be recovered. Additionally, non-α-ketoglutarate products (i.e., by-products) can also be recovered.

The α-ketoglutarate can be further processed by the same microorganism, a different microorganism, or outside a microorganism (i.e., in vitro) through an α-ketoglutarate decarboxylase (kgd) and/or α-ketoglutarate dehydrogenase. The same microorganism can comprise an α-ketoglutarate decarboxylase (kgd) and/or α-ketoglutarate dehydrogenase. In other instances, a different microorganism can comprise an α-ketoglutarate decarboxylase (kgd) and/or α-ketoglutarate dehydrogenase or the α-ketoglutarate decarboxylase (kgd) and/or α-ketoglutarate dehydrogenase are isolated from a cell. If the α-ketoglutarate decarboxylase (kgd) and/or α-ketoglutarate dehydrogenase is in a different microorganism or is isolated from a cell, the microorganism/ isolated enzyme can convert α-ketoglutarate that is in the culture media (either by supplemental addition or by secretion by a α-ketoglutarate producing microorganism). The conversion of α-ketoglutarate by an α-ketoglutarate decarboxylase (kgd) can produce succinate semialdehyde. The conversion of α-ketoglutarate by an α-ketoglutarate dehydrogenase can produce succinate CoA.

Further conversion of succinate semialdehyde or succinate CoA into various products, such as γ-hydroxybutyrate or succinate semialdehyde can occur through different fermentation processes or by different catalytic conversions.

Succinate

With regards to succinate, one method that is disclosed herein is a method of making succinate comprising: (a) contacting a genetically modified microorganism with a carbon substrate (e.g., a C1 carbon substrate), where the microorganism comprises a heterologous gene encoding for succinyl-CoA synthetase; and (b) growing the microorganism to produce succinate. Another method that is disclosed herein is a method of making succinate comprising: (a) contacting a genetically modified microorganism with a carbon substrate (e.g., a C1 carbon substrate), where the microorganism comprises a heterologous gene encoding for fumarate reductase; and (b) growing the microorganism to produce succinate. The microorganism can be a microorganism that is capable of converting a C1 carbon into a multicarbon product. For example, a methanotroph can be used. Further any of the genetically modified microorganisms described throughout can be used. The succinate produced can be substantially pure. The succinate that is produced can be recovered. Additionally, non-succinate products (i.e., by-products) can also be recovered.

The succinate can be further processed by the same microorganism, a different microorganism, or outside a microorganism (i.e., in vitro) through a succinyl CoA synthease beta subunit (SucC). The same microorganism can comprise a succinyl CoA synthease beta subunit. In other instances, a different microorganism can comprise a succinyl CoA synthease beta subunit or the succinyl CoA synthease beta subunit is isolated from a cell. If the succinyl CoA synthease beta subunit is in a different microorganism or is isolated from a cell, the microorganism/isolated enzyme can convert succinate that is in the culture media (either by supplemental addition or by secretion by a succinate producing microorganism). The conversion of succinate by a succinyl CoA synthease beta subunit can produce succinyl CoA.

Further conversion of succinyl CoA into various products can occur through different fermentation processes or by different catalytic conversions.

Fumarate

With regards to fumarate, one method that is disclosed herein is a method of making fumarate comprising: (a) contacting a genetically modified microorganism with a carbon substrate (e.g., a C1 carbon substrate), where the microorganism comprises a heterologous gene encoding for fumarate hydratase; and (b) growing the microorganism to produce fumarate. The microorganism can be a microorganism that is capable of converting a C1 carbon into a multicarbon product. For example, a methanotroph can be used. Further any of the genetically modified microorganisms described throughout can be used. The fumarate produced can be substantially pure. The fumarate that is produced can be recovered. Additionally, non-fumarate products (i.e., by-products) can also be recovered.

The fumarate can be further processed by the same microorganism, a different microorganism, or outside a microorganism (i.e., in vitro) through a fumarate reductase. The same microorganism can comprise a fumarate reductase. In other instances, a different microorganism can comprise a fumarate reductase or the fumarate reductase is isolated from a cell. If the fumarate reductase is in a different microorganism or is isolated from a cell, the microorganism/isolated enzyme can convert fumarate that is in the culture media (either by supplemental addition or by secretion by a fumarate producing microorganism). The conversion of fumarate by a fumarate reductase can produce succinate.

Further conversion of succinate into various products can occur through different fermentation processes or by different catalytic conversions.

Citrate

With regards to citrate, one method that is disclosed herein is a method of making citrate comprising: (a) contacting a genetically modified microorganism with a carbon substrate (e.g., a C1 carbon substrate), where the microorganism comprises a heterologous gene encoding for citrate synthase; and (b) growing the microorganism to produce citrate. The microorganism can be a microorganism that is capable of converting a C1 carbon into a multicarbon product. For example, a methanotroph can be used. Further any of the genetically modified microorganisms described throughout can be used. The citrate produced can be substantially pure. The citrate that is produced can be recovered. Additionally, non-citrate products (i.e., by-products) can also be recovered.

The citrate can be further processed by the same microorganism, a different microorganism, or outside a microorganism (i.e., in vitro) through an aconitate hydratase 1. The same microorganism can comprise an aconitate hydratase 1. In other instances, a different microorganism can comprise an aconitate hydratase 1 or the aconitate hydratase 1 is isolated from a cell. If the an aconitate hydratase 1 is in a different microorganism or is isolated from a cell, the microorganism/isolated enzyme can convert citrate that is in the culture media (either by supplemental addition or by secretion by a citrate producing microorganism). The conversion of citrate by an aconitate hydratase 1 can produce isocitrate.

Further conversion of isocitrate into various products can occur through different fermentation processes or by different catalytic conversions.

Isocitrate

With regards to isocitrate, one method that is disclosed herein is a method of making isocitrate comprising: (a) contacting a genetically modified microorganism with a carbon substrate (e.g., a C1 carbon substrate), where the microorganism comprises a heterologous gene encoding for aconitate hydratase 1; and (b) growing the microorganism to produce isocitrate. The microorganism can be a microorganism that is capable of converting a C1 carbon into a multicarbon product. For example, a methanotroph can be used. Further any of the genetically modified microorganisms described throughout can be used. The isocitrate produced can be substantially pure. The isocitrate that is produced can be recovered. Additionally, non-isocitrate products (i.e., by-products) can also be recovered.

The isocitrate can be further processed by the same microorganism, a different microorganism, or outside a microorganism (i.e., in vitro) through an isocitrate dehydrogenase. The same microorganism can comprise an isocitrate dehydrogenase. In other instances, a different microorganism can comprise an isocitrate dehydrogenase or the isocitrate dehydrogenase is isolated from a cell. If the isocitrate dehydrogenase is in a different microorganism or is isolated from a cell, the microorganism/isolated enzyme can convert isocitrate that is in the culture media (either by supplemental addition or by secretion by an isocitrate producing microorganism). The conversion of isocitrate by an isocitrate dehydrogenase can produce α-ketoglutarate.

Further conversion of α-ketoglutarate into various products can occur through different fermentation processes or by different catalytic conversions.

γ-hydroxybutyrate

With regards to γ-hydroxybutyrate, one method that is disclosed herein is a method of making γ-hydroxybutyrate comprising: (a) contacting a genetically modified microorganism with a carbon substrate (e.g., a C1 carbon substrate), where the microorganism comprises a heterologous gene encoding for 4-hydroxybutyrate dehydrogenase (4hbD); and (b) growing the microorganism to produce γ-hydroxybutyrate. The microorganism can be a microorganism that is capable of converting a C1 carbon into a multicarbon product. For example, a methanotroph can be used. Further any of the genetically modified microorganisms described throughout can be used. The γ-hydroxybutyrate produced can be substantially pure. The γ-hydroxybutyrate that is produced can be recovered. Additionally, non- γ-hydroxybutyrate products (i.e., by-products) can also be recovered.

The γ-hydroxybutyrate can be further processed by the same microorganism, a different microorganism, or outside a microorganism (i.e., in vitro) through a 4-hydroxybutyrate CoA transferase (Cat2). The same microorganism can comprise a 4-hydroxybutyrate CoA transferase. In other instances, a different microorganism can comprise a 4-hydroxybutyrate CoA transferase or the 4-hydroxybutyrate CoA transferase is isolated from a cell. If the 4-hydroxybutyrate CoA transferase is in a different microorganism or is isolated from a cell, the microorganism/isolated enzyme can convert γ-hydroxybutyrate that is in the culture media (either by supplemental addition or by secretion by a γ-hydroxybutyrate producing microorganism). The conversion of γ-hydroxybutyrate by 4-hydroxybutyrate CoA transferase can produce 4-hydroxybutyryl CoA.

Further conversion of 4-hydroxybutyryl CoA into various products can occur through different fermentation processes or by different catalytic conversions.

4-Hydroxybutyraldehyde

With regards to 4-hydroxybutyraldehyde, one method that is disclosed herein is a method of making 4-hydroxybutyraldehyde comprising: (a) contacting a genetically modified microorganism with a carbon substrate (e.g., a C1 carbon substrate), where the microorganism comprises a heterologous gene encoding for an aldehyde dehydrogenase; and (b) growing the microorganism to produce 4-hydroxybutyraldehyde. The microorganism can be a microorganism that is capable of converting a C1 carbon into a multicarbon product. For example, a methanotroph can be used. Further any of the genetically modified microorganisms described throughout can be used. The 4-hydroxybutyraldehyde produced can be substantially pure. The 4-hydroxybutyraldehyde that is produced can be recovered. Additionally, non-4-hydroxybutyraldehyde products (i.e., by-products) can also be recovered.

The 4-hydroxybutyraldehyde can be further processed by the same microorganism, a different microorganism, or outside a microorganism (i.e., in vitro) through an alcohol dehydrogenase. The same microorganism can comprise an alcohol dehydrogenase. In other instances, a different microorganism can comprise an alcohol dehydrogenase or the alcohol dehydrogenase is isolated from a cell. If the alcohol dehydrogenase is in a different microorganism or is isolated from a cell, the microorganism/isolated enzyme can convert 4-hydroxybutyraldehyde that is in the culture media (either by supplemental addition or by secretion by a 4-hydroxybutyraldehyde producing microorganism). The conversion of 4-hydroxybutyraldehyde by an alcohol dehydrogenase can produce 4-hydroxybutyryl CoA.

Further conversion of 4-hydroxybutyryl CoA into various products can occur through different fermentation processes or by different catalytic conversions.

1,4-BDO

With regards to 1,4-BDO, one method disclosed herein is a method of making 1,4-BDO comprising (a) contacting a genetically modified microorganism with a carbon substrate (e.g., a C1 carbon substrate), where the microorganism comprises at least one heterologous gene encoding for: (i) pyruvate dehydrogenase (aceEF); (ii) dihydrolipoyl dehydrogenase (lpdA); (iii) citrate synthase (gltA); (iv) aconitate hydratase 1 (acnA); (v) isocitrate dehydrogenase (icdA); (vi) kgd; (vii) 4-hydroxybutyrate dehydrogenase (4hbD); (viii) 4-hydroxybutyrate CoA transferase (cat2); (ix) aldehyde dehydrogenase (ald); (x) alcohol dehydrogenase (adh); (xi) succinyl CoA synthease beta subunit (sucC); (xii) succinyl CoA synthease alpha subunit (sucD); (xiii) fumarate hydratase (fum); (xiv) fumarate reductase (frd); or (xv) any combination thereof; and (b) growing the microorganism to produce 1,4-BDO.

The microorganism can be a microorganism that is capable of converting a C1 carbon into a multicarbon product. For example, a methanotroph can be used. Further any of the genetically modified microorganisms described throughout can be used.

The 1,4-BDO that is produced from this method can be substantially pure. The 1,4-BDO produced can be recovered. Additionally, non-1,4-BDO products (i.e., by-products) can also be recovered.

Tetrahydrofuran (THF)

THF can be prepared by using a catalyst. For example, another method for making THF is a method comprising (a) contacting a genetically modified microorganism with a carbon substrate (e.g., a C1 carbon substrate), wherein the microorganism comprises at least one heterologous gene encoding for: (i) pyruvate dehydrogenase (aceEF); (ii) dihydrolipoyl dehydrogenase (lpdA); (iii) citrate synthase (gltA); (iv) aconitate hydratase 1 (acnA); (v) isocitrate dehydrogenase (icdA);
(vi) kgd; (vii) 4-hydroxybutyrate dehydrogenase (4hbD); (viii) 4-hydroxybutyrate CoA transferase (Cat2); (ix) aldehyde dehydrogenase (Ald); (x) alcohol dehydrogenase (Adh); (xi) succinyl CoA synthease beta subunit (SucC); (xii) succinyl CoA synthease alpha subunit (SucD); (xiii) fumarate hydratase (fum); (xiv) fumarate reductase (frd); or (xv) any combination thereof; and (b) growing the microorganism to produce 1,4-BDO, (c) contacting the 1,4-BDO from (b) with a catalyst to produce THF. In some instances, the 1,4-BDO can be isolated or purified before proceeding to (c).

The microorganism can be a microorganism that is capable of converting a C1 carbon into a multicarbon product. For example, a methanotroph can be used. Further any of the genetically modified microorganisms described throughout can be used.

The catalyst can be an enzymatic catalyst or a non-enzymatic catalyst. The catalyst can include any catalyst that is capable of producing THF. For example, THF can be obtained by the dehydration of 1,4-BDO in the presence of an acid catalyst such as sulfuric acid (see e.g., U.S. Pat. No. 7,465,816). Other catalysts (such as an alumina catalyst, a silica-alumina catalyst, an alumina-supported tungsten oxide catalyst, a heteropolyacid catalyst, or an zirconium sulfate catalyst) have been used to dehydrate 1,4-BDO to form THF.

Once converted, the THF can be isolated and/or purified. The THF can be substantially pure.

Polybutylene Terephthalate (PBT)

PBT can be prepared by using a catalyst. For example, another method for making PBT is a method comprising (a) contacting a genetically modified microorganism with a carbon substrate (e.g., a C1 carbon substrate), wherein the microorganism comprises at least one heterologous gene encoding for: (i) pyruvate dehydrogenase (aceEF); (ii) dihydrolipoyl dehydrogenase (lpdA); (iii) citrate synthase (gltA); (iv) aconitate hydratase 1 (acnA); (v) isocitrate dehydrogenase (icdA); (vi) kgd; (vii) 4-hydroxybutyrate dehydrogenase (4hbD); (viii) 4-hydroxybutyrate CoA transferase (Cat2); (ix) aldehyde dehydrogenase (Ald); (x) alcohol dehydrogenase (Adh); (xi) succinyl CoA synthease beta subunit (SucC); (xii) succinyl CoA synthease alpha subunit (SucD); (xiii) fumarate hydratase (fum); (xiv) fumarate reductase (frd); or (xv) any combination thereof; and (b) growing the microorganism to produce 1,4-BDO, (c) transesterfying the 1,4-BDO from (b) to produce PBT. The transesterification can be done using a dimethyl terephthalate (DMT). In some cases, the method can further comprise (d) polycondensation of the transesterfied product when 1,4-BDO is in contact with DMT (e.g., the product of (c)).

The microorganism can be a microorganism that is capable of converting a C1 carbon into a multicarbon product. For example, a methanotroph can be used. Further any of the genetically modified microorganisms described throughout can be used.

Other methods can include a continuous production process of PBT wherein after transesterification of 1,4-BDO with DMT, a pre-polymerization process is implemented. This is followed by polycondensation.

In some instances, the 1,4-BDO can be isolated or purified before proceeding to the transesterification processes.

Once made, the PBT can be isolated and/or purified. The PBT can be substantially pure.

Polyurethanes

Polyurethanes can be prepared by condensing 1,4-BDO with dicarboxylic acid/anhydride. For example, another method for making polyurethanes is a method comprising (a) contacting a genetically modified microorganism with a carbon substrate (e.g., a C1 carbon substrate), wherein the microorganism comprises at least one heterologous gene encoding for: (i) pyruvate dehydrogenase (aceEF); (ii) dihydrolipoyl dehydrogenase (lpdA); (iii) citrate synthase (gltA); (iv) aconitate hydratase 1 (acnA); (v) isocitrate dehydrogenase (icdA); (vi) kgd; (vii) 4-hydroxybutyrate dehydrogenase (4hbD); (viii) 4-hydroxybutyrate CoA transferase (Cat2); (ix) aldehyde dehydrogenase (Ald); (x) alcohol dehydrogenase (Adh); (xi) succinyl CoA synthease beta subunit (SucC); (xii) succinyl CoA synthease alpha subunit (SucD); (xiii) fumarate hydratase (fum); (xiv) fumarate reductase (frd); or (xv) any combination thereof; and (b) growing the microorganism to produce 1,4-BDO, (c) condensing the 1,4-BDO from (b) with a dicarboxylic acid/anhydride to produce a polyurethane. In some cases the dicarboxylic acid/anhydride can be aliphatic or aromatic.

The microorganism can be a microorganism that is capable of converting a C1 carbon into a multicarbon product. For example, a methanotroph can be used. Further any of the genetically modified microorganisms described throughout can be used.

In some instances, the 1,4-BDO can be isolated or purified before proceeding to the condensation process.

Once made, the polyurethanes can be isolated and/or purified. The polyurethanes can be substantially pure.

It should be appreciated that the methods of the invention may be integrated or linked with one or more methods for the production of downstream products from PBT, THF, and/or polyurethanes. For example, the methods described may feed PBT, THF, and/or polyurethanes directly or indirectly to chemical processes or reactions sufficient for the conversion or production of other useful chemical products. In some embodiments, as noted herein before, 1,4-BDO can be converted to one or more chemical products directly via the intermediate compounds PBT, THF, and/or polyurethanes without the need for recovery of PBT, THF, and/or polyurethanes from the method before subsequent use in production of the one or more chemical products. Some commercially relevant products that can be made from 1,4-BDO, PBT, THF, and/or polyurethanes include, but are not limited to, Spandex.

IV. Fermentation

In general, the microorganisms disclosed herein should be used in fermentation conditions that are appropriate to convert a C1 carbon (such as methane) to 1,4-BDO (or other desired products). Reaction conditions that should be considered include temperature, media flow rate, pH, incubation period, media redox potential, agitation rate (if using a continuous stirred tank reactor), inoculum level, maximum substrate concentrations and rates of introduction of the substrate to the bioreactor to ensure that substrate level does not become limiting, and maximum product concentrations to avoid product inhibition.

The optimum reaction conditions will depend partly on the particular microorganism of used. However, in general, it is preferred that the fermentation be performed at a pressure higher than ambient pressure. Operating at increased pressures allows a significant increase in the rate of C1 carbon transfer from the gas phase to the liquid phase where it can be taken up by the microorganism as a carbon source for the production of 1,4-BDO. This in turn means that the retention time (defined as the liquid volume in the bioreactor divided by the input gas flow rate) can be reduced when bioreactors are maintained at elevated pressure rather than atmospheric pressure.

The use of pressurized systems can greatly reduce the volume of the bioreactor required, and consequently the capital cost of the fermentation equipment. In some cases, reactor volume can be reduced in linear proportion to increases in reactor operating pressure, i.e. bioreactors operated at 10 atmospheres of pressure need only be one tenth the volume of those operated at 1 atmosphere of pressure.

It is also desirable that the rate of introduction of the C1 carbon substrate (such as methane) containing gaseous substrate is such as to ensure that the concentration of the C1 carbon substrate (such as methane) in the liquid phase does not become limiting. This is because a consequence of C1 carbon substrate (e.g., methane) limited conditions may be that the 1,4-BDO product (or other desired product) is consumed by the culture.

Fermentation Conditions pH can be optimized based on the microorganism used. For example, the pH used during the methanotroph fermentation of methane to a desired product, can from 4 to 10. In other instances, the pH can be from 5 to 9; 6 to 8; 6.1 to 7.9; 6.2 to 7.8; 6.3 to 7.7; 6.4 to 7.6; or 6.5 to 7.5. For example, the pH can be from 6.6 to 7.4. In some instances, the pH can be from 5 to 9. In some instances, the pH can be from 6 to 8. In some instances, the pH can be from 6.1 to 7.9. In some instances, the pH can be from 6.2 to 7.8. In some instances, the pH can be from 6.3 to 7.7. In some instances, the pH can be from 6.4 to 7.6. In some instances, the pH can be from 6.5 to 7.5. In some instances the pH used for the fermentation of methanotrophs can be greater than 6.

Temperature can also be adjusted based on the microorganism used. For example, the temperature used during the methanotroph fermentation of methane to a desired product, can from 30 C° to 45 C°. In other instances, the temperature of the fermentation can be from 30 C° to 45 C°; 31 C° to 44 C°; 32 C° to 43 C°; 33 C° to 42 C°; 34 C° to 41 C°; 35 C° to 40 C°. For example, the temperature can be from 36 C° to 39 C° (e.g., 36 C°, 37 C°, 38 C°, or 39 C°). In some instances, the temperature can be from 30 C° to 45 C°. In some instances, the temperature can be from 31 C° to 44 C°. In some instances, the temperature can be from 32 C° to 43 C°. In some instances, the temperature can be from 33 C° to 42 C°. In some instances, the temperature can be from 34 C° to 41 C°. In some instances, the temperature can be from 35 C° to 40 C°.

Availability of oxygen and other gases such as gaseous C1 carbon substrates (such as methane) can affect yield and fermentation rate. For example, when considering oxygen availability, the percent of dissolved oxygen (DO) within the fermentation media can be from 1% to 40%. In certain instances, the DO concentration can be from 1.5% to 35%; 2% to 30%; 2.5% to 25%; 3% to 20%; 4% to 19%; 5% to 18%; 6% to 17%; 7% to 16%; 8% to 15%; 9% to 14%; 10% to 13%; or 11% to 12%. For example, in some cases the DO concentration can be from 2% to 30%. In other cases, the DO can be from 3% to 20%. In some instances, the DO can be from 4% to 10%. In some cases, the DO can be from 1.5% to 35%. In some cases, the DO can be from 2.5% to 25%. In some cases, the DO can be from 4% to 19%. In some cases, the DO can be from 5% to 18%. In some cases, the DO can be from 6% to 17%. In some cases, the DO can be from 7% to 16%. In some cases, the DO can be from 8% to 15%. In some cases, the DO can be from 9% to 14%. In some cases, the DO can be from 10% to 13%. In some cases, the DO can be from 11% to 12%. In some cases, the DO concentration can be lower than 1%. For example, the DO can be from 0% to 1%.

When using a methanotroph, the type of methane substances can have an effect on yield and fermentation rates. For example, natural gas can be used, which typically has a methane content of above 85% (e.g., above 90%) methane. Other components within natural gas can include but is not limited to ethane, propane, iso-butane, normal-butane, iso-pentane, normal pentane, hexanes plus, nitrogen, carbon dioxide, oxygen, hydrogen, and hydrogen sulfides.

"Pure" methane can be used as well. In these cases, the methane typically comes from a tank. The methane contained within these tanks can range from 90% or greater methane content and the remaining gas are other gases (such as carbon dioxide). For example, gas having a methane content of greater than 90% can be used during the fermentation process. In certain instances, the methane concentration can be greater than 90%; 91%; 92%; 93%; 94%; 95%; 96%; 97%; 98%; 99%; or 99.9%. In some instances, the methane concentration can be 90% methane and 10% are other gases (such as carbon dioxide). In other instances, the methane concentration can be 91% methane and 9% are other gases (such as carbon dioxide). In some instances, the methane concentration can be 92% methane and 8% are other gases (such as carbon dioxide). In some instances, the methane concentration can be 93% methane and 7% are other gases (such as carbon dioxide). In some instances, the methane concentration can be 94% methane and 6% are other gases (such as carbon dioxide). In some instances, the methane concentration can be 95% methane and 5% are other gases (such as carbon dioxide). In other instances, the methane concentration can be 96% methane and 4% are other gases (such as carbon dioxide). In some instances, the methane concentration can be 97% methane and 3% are other gases (such as carbon dioxide). In some instances, the methane concentration can be 98% methane and 2% are other gases (such as carbon dioxide). In some instances, the methane concentration can be 99% methane and 1% are other gases (such as carbon dioxide). In some instances, the methane concentration can be 99.9% methane and 0.1% are other gases (such as carbon dioxide).

The length of incubation can have a significant effect on 1,4-BDO (or other products) titer. For example, the microorganism (such as methanotrophs) may produce minimal or no product before 72 hours. In these cases, incubating the microorganism for longer than 72 hours may be necessary. Thus in some cases, the microorganism disclosed throughout can be fermented for at least 73 hours, 74 hours, 75 hours, 76 hours, 77 hours, 78 hours, 79 hours, 80 hours, 81 hours, 82 hours, 83 hours, 84 hours, 85 hours, 86 hours, 87 hours, 89 hours, 90 hours, 91 hours, 92 hours, 93 hours, 94 hours, 95 hours, 96 hours, 97 hours, 98 hours, 99 hours, 100 hours, 101 hours, 102 hours, 103 hours, 104 hours, 105 hours, 106 hours, 107 hours, 108 hours, 109 hours, 110 hours, 111 hours, 112 hours, 113 hours, 114 hours, 115 hours, 116 hours, 117 hours, 118 hours, 119 hours, 120 hours, 121 hours, 122 hours, 123 hours, 124 hours, 125 hours, 126 hours, 127 hours, 128 hours, 129 hours, 130 hours, 131 hours, 132 hours, 133 hours, 134 hours, 135 hours, or 136 hours. In some cases, the microorganism disclosed throughout can be fermented for at least 84 hours. In some cases, the microorganism disclosed throughout can be fermented for at least 96 hours. In some cases, the microorganism disclosed throughout can be fermented for at least 108 hours. In some cases, the microorganism disclosed throughout can be fermented for at least 120 hours. In some cases, the microorganism disclosed throughout can be fermented for at least 132 hours. In some cases, the microorganism disclosed throughout can be fermented for at least 144 hours. In some cases, the microorganism disclosed throughout can be fermented for at least 156 hours.

Bioreactor

Fermentation reactions may be carried out in any suitable bioreactor. In some embodiments of the invention, the bioreactor may comprise a first, growth reactor in which the micro-organisms are cultured, and a second, fermentation reactor, to which broth from the growth reactor is fed and in which most of the fermentation product (1,4-BDO, for example) is produced.

Product Recovery

The fermentation of the microorganisms disclosed herein can produce a fermentation broth comprising a desired product (e.g., 1,4-BDO, THF, PBT, and/or polyurethanes) and/or one or more by-products as well as the microorganisms (e.g., a genetically modified methanotroph), in a nutrient medium.

The microorganisms and the methods herein can produce 1,4-BDO at surprisingly high efficiency, more so than other known 1,4-BDO fermentation processes. For example, the microorganisms and the methods disclosed herein can convert a C1 carbon substrate (such as methane) at a yield of greater than 50%. This means that at least 50% of the C1 carbons within the systems are converted into product, such as 1,4-BDO. In some cases, the conversion of a C1 carbon substrate into 1,4-BDO can be at least 60%, 70%, 80%, 81%, 83%, 84%, 85%, 86%, 87%, 88%, 89%, 90%, 91%, 93%, 94%, 95%, 96%, 97%, 98%, or 99%. In some cases, the conversion of a C1 carbon substrate into 1,4-BDO can be at least 60%. In some cases, the conversion of a C1 carbon substrate into 1,4-BDO can be at least 70%. In some cases, the conversion of a C1 carbon substrate into 1,4-BDO can be at least 80%. In some cases, the conversion of a C1 carbon substrate into 1,4-BDO can be at least 81%. In some cases, the conversion of a C1 carbon substrate into 1,4-BDO can be at least 82%. In some cases, the conversion of a C1 carbon substrate into 1,4-BDO can be at least 83%. In some cases, the conversion of a C1 carbon substrate into 1,4-BDO can be at least 84%. In some cases, the conversion of a C1 carbon substrate into 1,4-BDO can be at least 85%. In some cases, the conversion of a C1 carbon substrate into 1,4-BDO can be at least 86%. In some cases, the conversion of a C1 carbon substrate into 1,4-BDO can be at least 87%. In some cases, the conversion of a C1 carbon substrate into 1,4-BDO can be at least 88%. In some cases, the conversion of a C1 carbon substrate into 1,4-BDO can be at least 89%. In some cases, the conversion of a C1 carbon substrate into 1,4-BDO can be at least 90%. In some cases, the conversion of a C1 carbon substrate into 1,4-BDO can be at least 91%. In some cases, the conversion of a C1 carbon substrate into 1,4-BDO can be at least 92%. In some cases, the conversion of a C1 carbon substrate into 1,4-BDO can be at least 93%. In some cases, the conversion of a C1 carbon substrate into 1,4-BDO can be at least 94%. In some cases, the conversion of a C1 carbon substrate into 1,4-BDO can be at least 95%. In some cases, the conversion of a C1 carbon substrate into 1,4-BDO can be at least 96%. In some cases, the conversion of a C1 carbon substrate into 1,4-BDO can be at least 97%. In some cases, the conversion of a C1 carbon substrate into 1,4-BDO can be at least 98%. In some cases, the conversion of a C1 carbon substrate into 1,4-BDO can be at least 99%.

In certain methods when producing 1,4-BDO, the concentration of 1,4-BDO in the fermentation broth is at least 1 g/L. For example, the concentration of 1,4-BDO produced in the fermentation broth can be from 1 g/L to 5 g/L, 2 g/L to 6 g/L, 3 g/L to 7 g/L, 4 g/L to 8 g/L, 5 g/L to 9 g/L, or 6 g/L to 10 g/L. In some cases, the concentration of 1,4-BDO can be at least 9 g/L. In some cases, the concentration of 1,4-BDO can be from 1 g/L to 5 g/L. In some cases, the concentration of 1,4-BDO can be from 2 g/L to 6 g/L. In some cases, the concentration of 1,4-BDO can be from 3 g/L to 7 g/L. In some cases, the concentration of 1,4-BDO can be from 4 g/L to 8 g/L. In some cases, the concentration of 1,4-BDO can be from 5 g/L to 9 g/L. In some cases, the concentration of 1,4-BDO can be from 6 g/L to 10 g/L.

In other cases, when microorganisms are used that normally produce at least some 1,4-BDO, after genetic modification and fermentation, the genetically modified microorganism can produce 1,4-BDO in concentrations that are at least 1.1× the amount that is normally produced (e.g., without using any genetically modified microorganisms). In some cases, the genetically modified microorganism can produce at least 2×, 3×, 4×, 5×, 10×, 25×, 50×, and or 100× the amount that is normally produced. In some cases, the genetically modified microorganism can produce at least 2× the amount that is normally produced. In some cases, the genetically modified microorganism can produce at least 3× the amount that is normally produced. In some cases, the genetically modified microorganism can produce at least 4× the amount that is normally produced. In some cases, the genetically modified microorganism can produce at least 5× the amount that is normally produced. In some cases, the genetically modified microorganism can produce at least 10× the amount that is normally produced. In some cases, the genetically modified microorganism can produce at least 25× the amount that is normally produced. In some cases, the genetically modified microorganism can produce at least 50× the amount that is normally produced. In some cases, the genetically modified microorganism can produce at least 100× the amount that is normally produced.

As discussed above, in certain embodiments the 1,4-BDO produced in the fermentation reaction is converted to PBT, THF, and/or polyurethane (or other products) directly from the fermentation broth. In other embodiments, the 1,4-BDO is first recovered from the fermentation broth before conversion to PBT, THF, and/or polyurethane.

In some cases, 1,4-BDO can be continuously removed from a portion of broth and recovered as purified 1,4-BDO. In particular embodiments, the recovery of 1,4-BDO includes passing the removed portion of the broth containing 1,4-BDO through a separation unit to separate the microorganisms (e.g., genetically modified methanotroph) from the broth, to produce a cell-free 1,4-BDO containing permeate, and returning the microorganisms to the bioreactor. The cell-free 1,4-BDO-containing permeate may then can be stored or be used for subsequent conversion to PBT, THF, and/or polyurethane (or other desired product).

The recovering of 1,4-BDO and/or one or more other products or by-products produced in the fermentation reaction can comprise continuously removing a portion of the broth and recovering separately 1,4-BDO and one or more other products from the removed portion of the broth. In some embodiments the recovery of 1,4-BDO and/or one or more other products includes passing the removed portion of the broth containing 1,4-BDO and/or one or more other products through a separation unit to separate microorganisms from the 1,4-BDO and/or one or more other products, to produce a cell-free 1,4-BDO and one or more other product-containing permeate, and returning the microorganisms to the bioreactor.

In the above embodiments, the recovery of 1,4-BDO and one or more other products can include first removing 1,4-BDO from the cell-free permeate followed by removing the one or more other products from the cell-free permeate. The cell-free permeate can be then returned to the bioreactor.

1,4-BDO, or a mixed product stream containing 1,4-BDO, can be recovered from the fermentation broth. For example, methods that can be used can include but are not limited to, fractional distillation or evaporation, pervaporation, and extractive fermentation. Further examples include: recovery using steam from whole fermentation broths (Wheat et al. 1948); reverse osmosis combined with distillation (Sridhar 1989); Liquid-liquid extraction techniques involving solvent extraction of 1,4-BDO (Othmer et al. 1945; Tsao 1978; Eiteman and Gainer 1989); aqueous two-phase extraction of 1,4-BDO in PEG/dextran system (Ghosh and Swaminathan 2003; solvent extraction using alcohols or esters, e.g., ethyl acetate, tributylphosphate, diethyl ether, n-butanol, dodecanol, oleyl alcohol, and an ethanol/phosphate system (Bo Jianga 2009); aqueous two-phase systems composed of hydrophilic solvents and inorganic salts (Zhigang et. al. 2010).

Pervaporation or vacuum membrane distillation, used previously in ethanol and butanol fermentations, can be used to concentrate 1,4-BDO (Qureshi et al. 1994) in water as an extract from the fermentation broth. A microporous polytetrafluoroethylene (PTFE) membrane is used in the integrated process, while a silicone membrane is usually used in pervaporative ethanol or butanol fermentations.

By-products such as acids including acetate and butyrate may also be recovered from the fermentation broth using methods known in the art. For example, an adsorption system involving an activated charcoal filter or electrodialysis may be used.

In certain embodiments of the invention, 1,4-BDO and by-products are recovered from the fermentation broth by continuously removing a portion of the broth from the bioreactor, separating microbial cells from the broth (conveniently by filtration, for example), and recovering 1,4-BDO and optionally other alcohols and acids from the broth. Alcohols may conveniently be recovered for example by distillation, and acids may be recovered for example by adsorption on activated charcoal. The separated microbial cells are preferably returned to the fermentation bioreactor. The cell free permeate remaining after the alcohol(s) and acid(s) have been removed is also preferably returned to the fermentation bioreactor. Additional nutrients may be added to the cell free permeate to replenish the nutrient medium before it is returned to the bioreactor.

Also, if the pH of the broth was adjusted during recovery of 1,4-BDO and/or by-products, the pH should be re-adjusted to a similar pH to that of the broth in the fermentation bioreactor, before being returned to the bioreactor.

In certain embodiments, the 1,4-BDO is continuously recovered from the fermentation broth or bioreactor and fed directly for chemical conversion to one or more of THF, PBT, and/or polyurethanes. For example, the 1,4-BDO may be fed directly through a conduit to one or more vessel suitable for chemical synthesis of one or more of THF, PBT, polyurethanes or other downstream chemical products.

While some embodiments have been shown and described herein, such embodiments are provided by way of example only. Numerous variations, changes, and substitutions will now occur to those skilled in the art without departing from the invention. It should be understood that various alternatives to the embodiments of the invention described herein will be employed in practicing the invention.

EXAMPLES

Example 1: Genetic Engineering of a Microorganism to Produce 1,4-BDO Pathway from α-Ketoglutarate To engineer an α-ketoglutarate to 1,4-BDO pathway (see FIG. 2) in a microorganism, we started with a methanotroph (specifically *M. capsulatus*) and tested several genes from various bacteria and yeast. Table 1 below shows the genes tested and the origin of the genes.

TABLE 1

| Gene | Gene variants | Gene ID | Protein ID | Organism |
|---|---|---|---|---|
| Kgd | Mbo. Kgd | Mb1280c | Q7U0A6 | *Mycobacterium bovis* |
|  | Mtu. Kgd | Rv1248c | P9WIS5 | *Mycobacterium tuberculosis* H37Rv |
|  | Cte.kgd | A606_07515 | S4XHJ4 | *Corynebacterium terpenotabidum* Y-11 |
|  | Rjo.kgd | RHA1_ro06012 | Q0S3U7 | *Rhodococcus jostii* (strain RHA1) |
| 4hBD | Eco. Yihu | b3882 | P0A9V8 | *Escherichia coli* K-12 |
|  | Pgi 4hbd | PG0689 | Q7MWD4 | *Porphyromonas gingivalis* W38 |
|  | Ckl 4hbd | CKL_3014 | P38945 | *Clostridium kluyveri* DSM 555 |
| Cat2 | Pgi abfT-1 | PG0690 | Q7MWD3 | *Porphyromonas gingivalis* W38 |
|  | Pgi abfT-2 | PG1956 | Q7MTJ6 | *Porphyromonas gingivalis* W38 |
|  | Cam abft | abfT | Q9RM86 | *Clostridium acetobutylicum* |
| Ald/ADH | Cam. adhE2 | CA_P0035 | Q9ANR5 | *Clostridium acetobutylicum* (strain ATCC 824) |
|  | Eco. adhE | b1241 | P0A9Q7 | *Escherichia coli* K-12 |
|  | Eco.yqhD | b3011 | Q46856 | *Escherichia coli* K-12 |
|  | Eco.fucO | b2799 | P0A9S1 | *Escherichia coli* K-12 |
|  | Sce. ADH6 | YMR318C | Q04894 | *Saccharomyces cerevisiae* |
|  | Aba. ADP1 | ACIAD3612 | Q6F6R9 | *Acinetobacter baylyi* (strain ATCC 33305) |
|  | Eco. ahr (yjgB) | b4269 | P27250 | *Escherichia coli* K-12 |

Several strains were generated (as seen in Table 2 below) and cultured in cell culture media supplemented with exogenous α-ketoglutarate. Strains were cultured in microtiter plates for a total of 7 days at 37° C. Of this total 7 days, 3 days were done as a pre-induction and 4 days after induction. The strains were tested for 7-hydroxybutyrate ("GHB") and 1,4-BDO formation. Table 2 below shows the various production amounts of the different strains. Strain XZ79 produced both the highest amounts of GHB and 1,4-BDO. This strain expressed a *Mycobacterium bovis* Kgd, *Clostridium kluyveri* 4hbD, *Porphyromonas gingivalis* Cat2, *Clostridium acetobutylicum* Ald and an *Acinetobacter baylyi* Adh.

TABLE 2

| | GHB | 1,4 BDO | Genotype | | | | |
|---|---|---|---|---|---|---|---|
| Sample | (μg/L) | (μg/L) | kgd | 4hbD | Cat2 | Ald | Adh |
| XZ76 | 209 | 118 | g.Mbo.SucA | g.Eco.yihu | g.Pgi.Cat2.abfT-1 | g.Cac.adhe2 | g.Aba.ADP1 |
| XZ79 | 875 | 261 | g.Mbo.SucA | g.Ckl.4hbD | g.Pgi.Cat2.abfT-1 | g.Cac.adhe2 | g.Aba.ADP1 |
| XZ84 | 461 | | g.Mbo.SucA | g.Eco.yihu | g.Cam.abft | g.Cac.adhe2 | g.Aba.ADP1 |

TABLE 2-continued

| Sample | GHB (µg/L) | 1,4 BDO (µg/L) | kgd | 4hbD | Cat2 | Ald | Adh |
|---|---|---|---|---|---|---|---|
| XZ276 | 535 | | g.Mbo.SucA | g.Eco.yihu | g.Pgi.Cat2.abfT-1 | g.Eco.adhe | g.Aba.ADP1 |
| XZ88 | 530 | | g.Mbo.SucA | g.Eco.yihu | g.Pgi.Cat2.abfT-1 | g.Eco.fucO | g.Aba.ADP1 |
| XZ278 | 163 | 52 | g.Mbo.SucA | g.Eco.yihu | g.Pgi.Cat2.abfT-1 | g.Cac.adhe2 | g.Sce.adh6 |
| XZ95 | 305 | | g.Mbo.SucA | g.Eco.yihu | g.Pgi.Cat2.abfT-1 | g.Eco.yqhD | g.Sce.adh6 |

Figure 4:
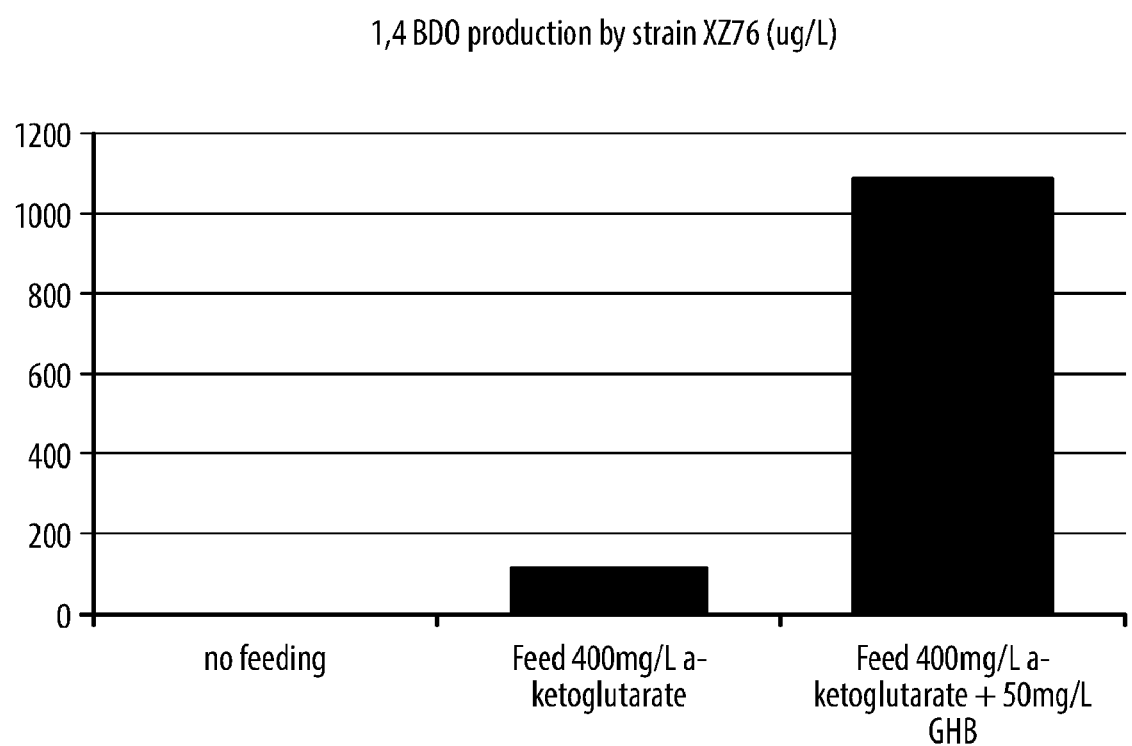
FIG. 4 shows the production of 1,4-BDO by strain XZ76. StainXZ76 produces over 1000 μg/L of 1,4-BDO when supplemented with 400 mg/L of α-ketoglutarate and 50 mg/L GHB. Supplementing the media with only 400 mg/L of α-ketoglutarate produced approximately 100 μg/L of 1,4-BDO, whereas no supplementation did not produce any 1,4-BDO.

Strain XZ76 was further tested. This strain was cultured in the same media and time frame as above however supplemented with exogenous α-ketoglutarate (400 mg/L) and exogenous GHB (50 mg/L). 1,4-BDO production by these strains were tested. As shown in FIG. 4, the production of 1,4-BDO was seen with α-ketoglutarate alone to a level greater than 100 µg/L. Surprisingly, however, when the culture media was supplemented with exogenous GHB, 1,4-BDO production spiked approximately 11-fold over α-ketoglutarate alone.

Example 2: Genetic Engineering of a Microorganism to Produce 1,4-BDO from Succinate Methanotrophs were further genetically engineered to express enzymes of the succinate to 1,4-BDO pathway. Methanotrophs were transformed with various genes from various bacteria and yeast. Table 3 below shows the genes tested and the origin of the genes.

TABLE 3

| Gene | Gene variants | Gene ID | Protein ID | Organism |
|---|---|---|---|---|
| SucC/SucD | Eco.SucC | b0728 | P0A836 | *Escherichia coli* K-12 |
| | Eco.SucD | b0729 | P0AGE9 | *Escherichia coli* K-12 |
| | Ckl.SucD | CKL_3015 | P38947 | *Clostridium kluyveri* DSM 555 |
| | Pgi.SucD | PG0687 | Q7MWD5 | *Porphyromonas gingivalis* W38 |
| 4hBD | Eco. Yihu | b3882 | P0A9V8 | *Escherichia coli* K-12 |
| | Pgi 4hbd | PG0689 | Q7MWD4 | *Porphyromonas gingivalis* W38 |
| | Ckl 4hbd | CKL_3014 | P38945 | *Clostridium kluyveri* DSM 555 |
| Cat2 | Pgi abfT-1 | PG0690 | Q7MWD3 | *Porphyromonas gingivalis* W38 |
| | Pgi abfT-2 | PG1956 | Q7MTJ6 | *Porphyromonas gingivalis* W38 |
| | Cam abft | abfT | Q9RM86 | *Clostridium acetobutylicum* |
| Ald/ADH | Cam. adhE2 | CA_P0035 | Q9ANR5 | *Clostridium acetobutylicum* (strain ATCC 824) |
| | Eco. adhE | b1241 | P0A9Q7 | *Escherichia coli* K-12 |
| | Eco.yqhD | b3011 | Q46856 | *Escherichia coli* K-12 |
| | Eco.fucO | b2799 | P0A9S1 | *Escherichia coli* K-12 |
| | Sce. ADH6 | YMR318C | Q04894 | *Saccharomyces cerevisiae* |
| | Aba. ADP1 | ACIAD3612 | Q6F6R9 | *Acinetobacter baylyi* (strain ATCC 33305) |
| | Eco. ahr (yjgB) | b4269 | P27250 | *Escherichia coli* K-12 |

Several strains were generated (as seen in Table 4 below) and cultured in IM5 media supplemented with exogenous succinic acid. Strains were cultured in microtiter plates and for the same period of time (7 days: 3 days pre-induction and 4 days of induction at 37C) and tested for GHB and 1,4-BDO formation. Table 4 below shows the various production amounts of the different strains. Strain XZ440 produced the highest amounts of GHB. Strain XZ440 expressed an *Escherichia coli* SucD; *Porphyromonas gingivalis* SucD; *Porphyromonas gingivalis* 4hbD; *Porphyromonas gingivalis* Cat2.abfT-2, *Clostridium acetobutylicum* adhe2; and *Acinetobacter baylyi* ADP1. Strain XZ438 produced the highest amounts of 1,4-BDO. This strain expressed an *Escherichia coli* SucD; *Porphyromonas gingivalis* SucD; *Porphyromonas gingivalis* 4hbD; *Porphyromonas gingivalis* Cat2.abfT-1, *Clostridium acetobutylicum* adhe2; and *Acinetobacter baylyi* ADP1.

TABLE 4

| Strains | GHB (µg/L) | 1,4-BDO (µg/L) | Genotype | | | | | |
|---|---|---|---|---|---|---|---|---|
| XZ344 | 33.608 | | g.Eco.SucD | g.Pgi.SucD | g.Pgi.4hbD | g.Pgi.Cat2.abfT-1 | g.Cac.adhe2 | g.Aba.ADP1 |
| XZ345 | 13455.08 | | g.Eco.SucD | g.Pgi.SucD | g.Pgi.4hbD | g.Pgi.Cat2.abfT-1 | g.Cac.adhe2 | g.Aba.ADP1 |
| XZ347 | 3434.5 | | g.Eco.SucD | g.Pgi.SucD | g.Pgi.4hbD | g.Pgi.Cat2.abfT-2 | g.Cac.adhe2 | g.Aba.ADP1 |
| XZ350 | 201.916 | | g.Eco.SucC | g.Ckl.SucD | g.Eco.yihu | g.Pgi.Cat2.abfT-2 | g.Eco.adhe | g.Eco.ahr |
| XZ437 | 16029.96 | | g.Eco.SucC | g.Pgi.SucD | g.Pgi.4hbD | g.Pgi.Cat2.abfT-2 | g.Cac.adhe2 | g.Aba.ADP1 |

TABLE 4-continued

| Strains | GHB (μg/L) | 1,4-BDO (μg/L) | Genotype | | | | |
|---|---|---|---|---|---|---|---|
| XZ438 | 3236.62 | 73.018 | g.Eco.SucD | g.Pgi.SucD | g.Pgi.4hbD | g.Pgi.Cat2.abfT-1 | g.Cac.adhe2 g.Aba.ADP1 |
| XZ439 | 58.593 | | g.Eco.SucD | g.Pgi.SucD | g.Pgi.4hbD | g.Pgi.Cat2.abfT-1 | g.Cac.adhe2 g.Aba.ADP1 |
| XZ440 | 16707.54 | | g.Eco.SucD | g.Pgi.SucD | g.Pgi.4hbD | g.Pgi.Cat2.abfT-2 | g.Cac.adhe2 g.Aba.ADP1 |
| XZ441 | 1190.559 | | g.Eco.SucD | g.Pgi.SucD | g.Pgi.4hbD | g.Pgi.Cat2.abfT-2 | g.Cac.adhe2 g.Aba.ADP1 |
| XZ442 | 5355.94 | | g.Eco.SucD | g.Pgi.SucD | g.Pgi.4hbD | g.Pgi.Cat2.abfT-1 | g.Eco.adhe g.Eco.ahr |
| XZ443 | 3442.24 | | g.Eco.SucD | g.Pgi.SucD | g.Pgi.4hbD | g.Pgi.Cat2.abfT-1 | g.Eco.adhe g.Eco.ahr |

Example 3: Genetic Engineering to Produce Higher Levels of α-Ketoglutarate

Figure 5:
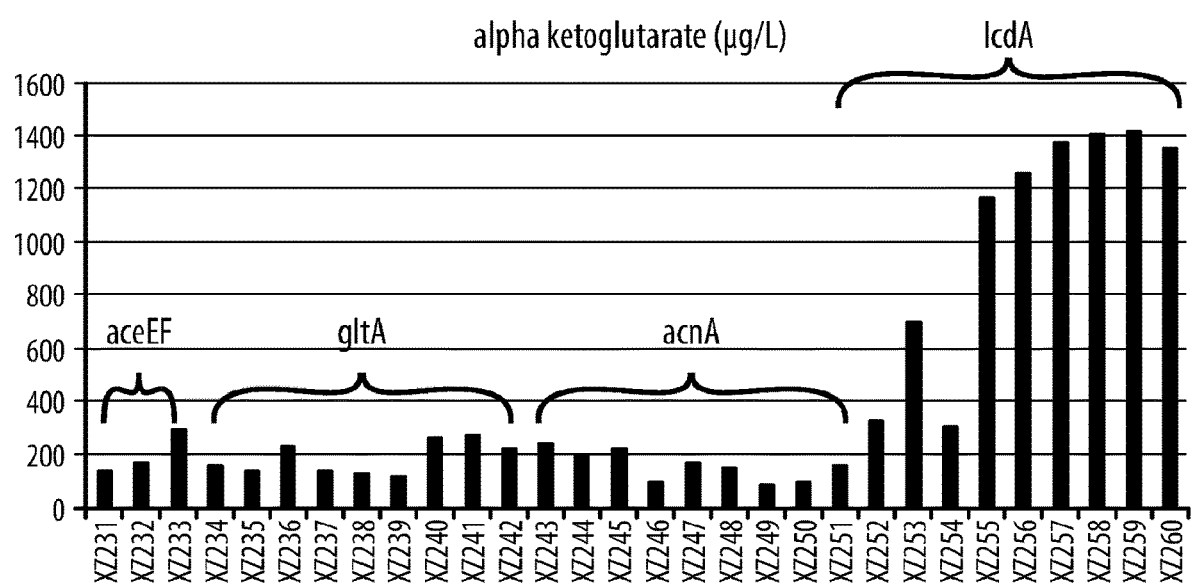
FIG. 5 shows the production of α-ketoglutarate from various strains overexpression pyruvate dehydrogenase (aceEF), citrate synthase (gltA), aconitate hydratase 1 (acnA), or isocitrate dehydrogenase (icdA). Overexpression of icdA lead to a large increase α-ketoglutarate production.

After finding that 1,4-BDO could be produced in surprisingly high quantities and very efficiently, we focused our attention to the pyruvate to the α-ketoglutarate part of the pathway. FIG. 1 (with the circle) shows the pathway from pyruvate to the α-ketoglutarate. We attempted to increase the overall amount of α-ketoglutarate produced in our system. To do this, we overexpressed four genes in the pathway: aceEF, gltA, acnA, or IcdA. FIG. 5 shows the results of this study.

Overexpression of aceEF, gltA, and acnA lead to only minor production of α-ketoglutarate. However, overexpression of IcdA (isocitrate dehydrogenase) significantly increased the overall α-ketoglutarate levels. The highest producer of α-ketoglutarate was Strain XZ259 with α-ketoglutarate at levels of over 1400 μg/L.

Example 4: 1,4-BDO Production Directly from Methane in Microtiter Plates

We generated 78 and 48 different broad host plasmids containing variations in the 5-gene 1,4 BDO pathway, from the α-ketoglutarate and succinate pathway respectively, and transformed the aforementioned plasmids into a transformation competent methanotroph strain, RL83A, and evaluated 112 and 60 resulting strains (including biological replicate strains) for 1,4 BDO production in small scale microtiter plate fermentation using methane as the carbon source. For these experiments, starter cultures were inoculated into microtiter plates containing 500 μl of media. The microtiter plates were fed a source of methane, arabinose, ketoglutarate or succinate, and incubated in a shaker at 37° C. for 96 hours. Samples were tested after 96 hours.

The genotypes for each of the strains are provided in Table 5 (α-ketoglutarate pathway) and Table 6 (succinate pathway) below.

TABLE 5

Genotypes of Microorganisms tested for the a-ketoglutarate pathway

| Plasmid | Strain | Heterologous genes | | | |
|---|---|---|---|---|---|
| p172asn1 | XZ75 | g.Mbo.SucA | g.Eco.yihu | g.Pgi.Cat2.abfT-1 | g.Cac.adhe2 g.Aba.ADP1 |
| p172asn1 | XZ76 | g.Mbo.SucA | g.Eco.yihu | g.Pgi.Cat2.abfT-1 | g.Cac.adhe2 g.Aba.ADP1 |
| p172asn2 | XZ77 | g.Mbo.SucA | g.Pgi.4hbD | g.Pgi.Cat2.abfT-1 | g.Cac.adhe2 g.Aba.ADP1 |
| p172asn2 | XZ78 | g.Mbo.SucA | g.Pgi.4hbD | g.Pgi.Cat2.abfT-1 | g.Cac.adhe2 g.Aba.ADP1 |
| p172asn3 | XZ79 | g.Mbo.SucA | g.Ckl.4hbD | g.Pgi.Cat2.abfT-1 | g.Cac.adhe2 g.Aba.ADP1 |
| p172asn3 | XZ80 | g.Mbo.SucA | g.Ckl.4hbD | g.Pgi.Cat2.abfT-1 | g.Cac.adhe2 g.Aba.ADP1 |
| p172asn4 | XZ81 | g.Mbo.SucA | g.Eco.yihu | g.Pgi.Cat2.abfT-2 | g.Cac.adhe2 g.Aba.ADP1 |
| p172asn4 | XZ82 | g.Mbo.SucA | g.Eco.yihu | g.Pgi.Cat2.abfT-2 | g.Cac.adhe2 g.Aba.ADP1 |
| p172asn5 | XZ83 | g.Mbo.SucA | g.Eco.yihu | g.Cam.abft | g.Cac.adhe2 g.Aba.ADP1 |
| p172asn5 | XZ84 | g.Mbo.SucA | g.Eco.yihu | g.Cam.abft | g.Cac.adhe2 g.Aba.ADP1 |
| p172asn6 | XZ276 | g.Mbo.SucA | g.Eco.yihu | g.Pgi.Cat2.abfT-1 | g.Eco.adhe g.Aba.ADP1 |
| p172asn6 | XZ277 | g.Mbo.SucA | g.Eco.yihu | g.Pgi.Cat2.abfT-1 | g.Eco.adhe g.Aba.ADP1 |
| p172asn7 | XZ85 | g.Mbo.SucA | g.Eco.yihu | g.Pgi.Cat2.abfT-1 | g.Eco.yqhD g.Aba.ADP1 |
| p172asn7 | XZ86 | g.Mbo.SucA | g.Eco.yihu | g.Pgi.Cat2.abfT-1 | g.Eco.yqhD g.Aba.ADP1 |
| p172asn8 | XZ87 | g.Mbo.SucA | g.Eco.yihu | g.Pgi.Cat2.abfT-1 | g.Eco.fucO g.Aba.ADP1 |
| p172asn8 | XZ88 | g.Mbo.SucA | g.Eco.yihu | g.Pgi.Cat2.abfT-1 | g.Eco.fucO g.Aba.ADP1 |
| p172asn9 | XZ278 | g.Mbo.SucA | g.Eco.yihu | g.Pgi.Cat2.abfT-1 | g.Cac.adhe2 g.Sce.adh6 |
| p172asn9 | XZ279 | g.Mbo.SucA | g.Eco.yihu | g.Pgi.Cat2.abfT-1 | g.Cac.adhe2 g.Sce.adh6 |
| p172asn10 | XZ280 | g.Mbo.SucA | g.Eco.yihu | g.Pgi.Cat2.abfT-1 | g.Cac.adhe2 g.Eco.ahr |
| p172asn10 | XZ281 | g.Mbo.SucA | g.Eco.yihu | g.Pgi.Cat2.abfT-1 | g.Cac.adhe2 g.Eco.ahr |
| p172asn11 | XZ89 | g.Mtu.kgd | g.Eco.yihu | g.Pgi.Cat2.abfT-1 | g.Cac.adhe2 g.Aba.ADP1 |
| p172asn12 | XZ90 | g.Cte.kgd | g.Eco.yihu | g.Pgi.Cat2.abfT-1 | g.Cac.adhe2 g.Aba.ADP1 |
| p172asn12 | XZ91 | g.Cte.kgd | g.Eco.yihu | g.Pgi.Cat2.abfT-1 | g.Cac.adhe2 g.Aba.ADP1 |
| p172asn13 | XZ92 | g.Rjo.odhA | g.Eco.yihu | g.Pgi.Cat2.abfT-1 | g.Cbe.Ald g.Aba.ADP1 |
| p172asn13 | XZ93 | g.Rjo.odhA | g.Eco.yihu | g.Pgi.Cat2.abfT-1 | g.Cbe.Ald g.Aba.ADP1 |
| p172asn14 | XZ94 | g.Mbo.SucA | g.Eco.yihu | g.Pgi.Cat2.abfT-1 | g.Eco.yqhD g.Sce.adh6 |
| p172asn14 | XZ95 | g.Mbo.SucA | g.Eco.yihu | g.Pgi.Cat2.abfT-1 | g.Eco.yqhD g.Sce.adh6 |
| p172asn15 | XZ96 | g.Mbo.SucA | g.Eco.yihu | g.Pgi.Cat2.abfT-1 | g.Eco.fucO g.Sce.adh6 |
| p172asn16 | XZ97 | g.Mbo.SucA | g.Eco.yihu | g.Pgi.Cat2.abfT-1 | g.Eco.adhe g.Sce.adh6 |
| p172asn16 | XZ98 | g.Mbo.SucA | g.Eco.yihu | g.Pgi.Cat2.abfT-1 | g.Eco.adhe g.Sce.adh6 |
| p172asn17 | XZ99 | g.Mbo.SucA | g.Eco.yihu | g.Pgi.Cat2.abfT-2 | g.Eco.adhe g.Eco.ahr |
| p172asn17 | XZ100 | g.Mbo.SucA | g.Eco.yihu | g.Pgi.Cat2.abfT-2 | g.Eco.adhe g.Eco.ahr |
| p172asn18 | XZ216 | g.Mbo.SucA | g.Pgi.4hbD | g.Pgi.Cat2.abfT-2 | g.Eco.adhe g.Sce.adh6 |
| p172asn18 | XZ217 | g.Mbo.SucA | g.Pgi.4hbD | g.Pgi.Cat2.abfT-2 | g.Eco.adhe g.Sce.adh6 |
| p172asn20 | XZ101 | g.Mbo.SucA | g.Pgi.4hbD | g.Pgi.Cat2.abfT-1 | g.Cac.adhe2 g.Aba.ADP1 |
| p172asn20 | XZ102 | g.Mbo.SucA | g.Pgi.4hbD | g.Pgi.Cat2.abfT-1 | g.Cac.adhe2 g.Aba.ADP1 |
| p172asn21 | XZ282 | g.Mbo.SucA | g.Ckl.4hbD | g.Pgi.Cat2.abfT-1 | g.Cac.adhe2 g.Aba.ADP1 |
| p172asn24 | XZ283 | g.Mbo.SucA | g.Eco.yihu | g.Pgi.Cat2.abfT-1 | g.Eco.adhe g.Aba.ADP1 |

TABLE 5-continued

Genotypes of Microorganisms tested for the a-ketoglutarate pathway

| Plasmid | Strain | Heterologous genes | | | |
|---|---|---|---|---|---|
| p172asn24 | XZ284 | g.Mbo.SucA | g.Eco.yihu | g.Pgi.Cat2.abfT-1 | g.Eco.adhe | g.Aba.ADP1 |
| p172asn25 | XZ285 | g.Mbo.SucA | g.Eco.yihu | g.Pgi.Cat2.abfT-1 | g.Eco.yqhD | g.Aba.ADP1 |
| p172asn25 | XZ286 | g.Mbo.SucA | g.Eco.yihu | g.Pgi.Cat2.abfT-1 | g.Eco.yqhD | g.Aba.ADP1 |
| p172asn26 | XZ103 | g.Mbo.SucA | g.Eco.yihu | g.Pgi.Cat2.abfT-1 | g.Eco.fucO | g.Aba.ADP1 |
| p172asn26 | XZ104 | g.Mbo.SucA | g.Eco.yihu | g.Pgi.Cat2.abfT-1 | g.Eco.fucO | g.Aba.ADP1 |
| p172asn28 | XZ287 | g.Mbo.SucA | g.Eco.yihu | g.Pgi.Cat2.abfT-1 | g.Cac.adhe2 | g.Eco.ahr |
| p172asn28 | XZ288 | g.Mbo.SucA | g.Eco.yihu | g.Pgi.Cat2.abfT-1 | g.Cac.adhe2 | g.Eco.ahr |
| p172asn29 | XZ289 | g.Mtu.kgd | g.Eco.yihu | g.Pgi.Cat2.abfT-1 | g.Cac.adhe2 | g.Aba.ADP1 |
| p172asn29 | XZ290 | g.Mtu.kgd | g.Eco.yihu | g.Pgi.Cat2.abfT-1 | g.Cac.adhe2 | g.Aba.ADP1 |
| p172asn30 | XZ291 | g.Cte.kgd | g.Eco.yihu | g.Pgi.Cat2.abfT-1 | g.Cac.adhe2 | g.Aba.ADP1 |
| p172asn31 | XZ105 | g.Rjo.odhA | g.Eco.yihu | g.Pgi.Cat2.abfT-1 | g.Cbe.Ald | g.Aba.ADP1 |
| p172asn31 | XZ106 | g.Rjo.odhA | g.Eco.yihu | g.Pgi.Cat2.abfT-1 | g.Cbe.Ald | g.Aba.ADP1 |
| p172asn32 | XZ107 | g.Mbo.SucA | g.Eco.yihu | g.Pgi.Cat2.abfT-1 | g.Eco.yqhD | g.Sce.adh6 |
| p172asn32 | XZ108 | g.Mbo.SucA | g.Eco.yihu | g.Pgi.Cat2.abfT-1 | g.Eco.yqhD | g.Sce.adh6 |
| p172asn33 | XZ292 | g.Mbo.SucA | g.Eco.yihu | g.Pgi.Cat2.abfT-1 | g.Eco.fucO | g.Sce.adh6 |
| p172asn33 | XZ293 | g.Mbo.SucA | g.Eco.yihu | g.Pgi.Cat2.abfT-1 | g.Eco.fucO | g.Sce.adh6 |
| p172asn34 | XZ294 | g.Mbo.SucA | g.Eco.yihu | g.Pgi.Cat2.abfT-1 | g.Eco.adhe | g.Sce.adh6 |
| p172asn34 | XZ295 | g.Mbo.SucA | g.Eco.yihu | g.Pgi.Cat2.abfT-1 | g.Eco.adhe | g.Sce.adh6 |
| p172asn35 | XZ109 | g.Mbo.SucA | g.Eco.yihu | g.Pgi.Cat2.abfT-2 | g.Eco.adhe | g.Eco.ahr |
| p172asn36 | XZ110 | g.Mbo.SucA | g.Pgi.4hbD | g.Pgi.Cat2.abfT-2 | g.Eco.adhe | g.Sce.adh6 |
| p172asn36 | XZ296 | g.Mbo.SucA | g.Pgi.4hbD | g.Pgi.Cat2.abfT-2 | g.Eco.adhe | g.Sce.adh6 |
| p172asn36 | XZ297 | g.Mbo.SucA | g.Pgi.4hbD | g.Pgi.Cat2.abfT-2 | g.Eco.adhe | g.Sce.adh6 |
| p172asn37 | XZ111 | g.Eco.yihu | g.Mbo.SucA | g.Pgi.Cat2.abfT-1 | g.Cac.adhe2 | g.Aba.ADP1 |
| p172asn37 | XZ112 | g.Eco.yihu | g.Mbo.SucA | g.Pgi.Cat2.abfT-1 | g.Cac.adhe2 | g.Aba.ADP1 |
| p172asn37 | XZ298 | g.Eco.yihu | g.Mbo.SucA | g.Pgi.Cat2.abfT-1 | g.Cac.adhe2 | g.Aba.ADP1 |
| p172asn37 | XZ299 | g.Eco.yihu | g.Mbo.SucA | g.Pgi.Cat2.abfT-1 | g.Cac.adhe2 | g.Aba.ADP1 |
| p172asn37 | XZ300 | g.Eco.yihu | g.Mbo.SucA | g.Pgi.Cat2.abfT-1 | g.Cac.adhe2 | g.Aba.ADP1 |
| p172asn37 | XZ301 | g.Eco.yihu | g.Mbo.SucA | g.Pgi.Cat2.abfT-1 | g.Cac.adhe2 | g.Aba.ADP1 |
| p172asn38 | XZ302 | g.Pgi.4hbD | g.Mbo.SucA | g.Pgi.Cat2.abfT-1 | g.Cac.adhe2 | g.Aba.ADP1 |
| p172asn40 | XZ303 | g.Pgi.4hbD | g.Mbo.SucA | g.Pgi.Cat2.abfT-2 | g.Cac.adhe2 | g.Aba.ADP1 |
| p172asn40 | XZ304 | g.Pgi.4hbD | g.Mbo.SucA | g.Pgi.Cat2.abfT-2 | g.Cac.adhe2 | g.Aba.ADP1 |
| p172asn41 | XZ218 | g.Eco.yihu | g.Mbo.SucA | g.Cam.abft | g.Cac.adhe2 | g.Aba.ADP1 |
| p172asn41 | XZ219 | g.Eco.yihu | g.Mbo.SucA | g.Cam.abft | g.Cac.adhe2 | g.Aba.ADP1 |
| p172asn45 | XZ305 | g.Eco.yihu | g.Mbo.SucA | g.Pgi.Cat2.abfT-2 | g.Cac.adhe2 | g.Sce.adh6 |
| p172asn45 | XZ306 | g.Eco.yihu | g.Mbo.SucA | g.Pgi.Cat2.abfT-2 | g.Cac.adhe2 | g.Sce.adh6 |
| p172asn46 | XZ220 | g.Pgi.4hbD | g.Mbo.SucA | g.Pgi.Cat2.abfT-2 | g.Cac.adhe2 | g.Sce.adh6 |
| p172asn46 | XZ221 | g.Pgi.4hbD | g.Mbo.SucA | g.Pgi.Cat2.abfT-2 | g.Cac.adhe2 | g.Sce.adh6 |
| p172asn47 | XZ307 | g.Eco.yihu | g.Mbo.SucA | g.Cam.abft | g.Cac.adhe2 | g.Sce.adh6 |
| p172asn47 | XZ308 | g.Eco.yihu | g.Mbo.SucA | g.Cam.abft | g.Cac.adhe2 | g.Sce.adh6 |
| p172asn48 | XZ222 | g.Pgi.4hbD | g.Mbo.SucA | g.Cam.abft | g.Cac.adhe2 | g.Sce.adh6 |
| p172asn48 | XZ223 | g.Pgi.4hbD | g.Mbo.SucA | g.Cam.abft | g.Cac.adhe2 | g.Sce.adh6 |
| p172asn49 | XZ309 | g.Eco.yihu | g.Mtu.kgd | g.Pgi.Cat2.abfT-1 | g.Cac.adhe2 | g.Aba.ADP1 |
| p172asn49 | XZ310 | g.Eco.yihu | g.Mtu.kgd | g.Pgi.Cat2.abfT-1 | g.Cac.adhe2 | g.Aba.ADP1 |
| p172asn50 | XZ311 | g.Eco.yihu | g.Cte.kgd | g.Pgi.Cat2.abfT-1 | g.Cac.adhe2 | g.Aba.ADP1 |
| p172asn50 | XZ312 | g.Eco.yihu | g.Cte.kgd | g.Pgi.Cat2.abfT-1 | g.Cac.adhe2 | g.Aba.ADP1 |
| p172asn52 | XZ224 | g.Eco.yihu | g.Mbo.SucA | g.Pgi.Cat2.abfT-1 | g.Eco.adhe | g.Aba.ADP1 |
| p172asn54 | XZ313 | g.Eco.yihu | g.Mbo.SucA | g.Pgi.Cat2.abfT-1 | g.Eco.adhe | g.Eco.ahr |
| p172asn57 | XZ314 | g.Ckl.4hbD | g.Mbo.SucA | g.Pgi.Cat2.abfT-2 | g.Eco.adhe | g.Aba.ADP1 |
| p172asn58 | XZ113 | g.Eco.yihu | g.Mtu.kgd | g.Pgi.Cat2.abfT-2 | g.Eco.adhe | g.Aba.ADP1 |
| p172asn59 | XZ315 | g.Eco.yihu | g.Mbo.SucA | g.Pgi.Cat2.abfT-2 | g.Eco.adhe | g.Sce.adh6 |
| p172asn59 | XZ316 | g.Eco.yihu | g.Mbo.SucA | g.Pgi.Cat2.abfT-2 | g.Eco.adhe | g.Sce.adh6 |
| p172asn60 | XZ225 | g.Eco.yihu | g.Mbo.SucA | g.Pgi.Cat2.abfT-2 | g.Eco.adhe | g.Eco.ahr |
| p172asn60 | XZ226 | g.Eco.yihu | g.Mbo.SucA | g.Pgi.Cat2.abfT-2 | g.Eco.adhe | g.Eco.ahr |
| p172asn61 | XZ114 | g.Mbo.SucA | g.Eco.yihu | g.Pgi.Cat2.abfT-1 | g.Cac.adhe2 | g.Aba.ADP1 |
| p172asn61 | XZ317 | g.Mbo.SucA | g.Eco.yihu | g.Pgi.Cat2.abfT-1 | g.Cac.adhe2 | g.Aba.ADP1 |
| p172asn61 | XZ318 | g.Mbo.SucA | g.Eco.yihu | g.Pgi.Cat2.abfT-1 | g.Cac.adhe2 | g.Aba.ADP1 |
| p172asn62 | XZ319 | g.Mbo.SucA | g.Pgi.4hbD | g.Pgi.Cat2.abfT-1 | g.Cac.adhe2 | g.Aba.ADP1 |
| p172asn62 | XZ320 | g.Mbo.SucA | g.Pgi.4hbD | g.Pgi.Cat2.abfT-1 | g.Cac.adhe2 | g.Aba.ADP1 |
| p172asn64 | XZ321 | g.Mbo.SucA | g.Eco.yihu | g.Pgi.Cat2.abfT-2 | g.Cac.adhe2 | g.Aba.ADP1 |
| p172asn64 | XZ322 | g.Mbo.SucA | g.Eco.yihu | g.Pgi.Cat2.abfT-2 | g.Cac.adhe2 | g.Aba.ADP1 |
| p172asn65 | XZ323 | g.Mbo.SucA | g.Eco.yihu | g.Cam.abft | g.Cac.adhe2 | g.Aba.ADP1 |
| p172asn65 | XZ324 | g.Mbo.SucA | g.Eco.yihu | g.Cam.abft | g.Cac.adhe2 | g.Aba.ADP1 |
| p172asn66 | XZ115 | g.Mbo.SucA | g.Eco.yihu | g.Pgi.Cat2.abfT-1 | g.Eco.adhe | g.Aba.ADP1 |
| p172asn69 | XZ325 | g.Mbo.SucA | g.Eco.yihu | g.Pgi.Cat2.abfT-1 | g.Cac.adhe2 | g.Sce.adh6 |
| p172asn69 | XZ326 | g.Mbo.SucA | g.Eco.yihu | g.Pgi.Cat2.abfT-1 | g.Cac.adhe2 | g.Sce.adh6 |
| p172asn70 | XZ116 | g.Mbo.SucA | g.Eco.yihu | g.Pgi.Cat2.abfT-1 | g.Cac.adhe2 | g.Eco.ahr |
| p172asn70 | XZ117 | g.Mbo.SucA | g.Eco.yihu | g.Pgi.Cat2.abfT-1 | g.Cac.adhe2 | g.Eco.ahr |
| p172asn71 | XZ327 | g.Mtu.kgd | g.Eco.yihu | g.Pgi.Cat2.abfT-1 | g.Cac.adhe2 | g.Aba.ADP1 |
| p172asn71 | XZ328 | g.Mtu.kgd | g.Eco.yihu | g.Pgi.Cat2.abfT-1 | g.Cac.adhe2 | g.Aba.ADP1 |
| p172asn72 | XZ329 | g.Cte.kgd | g.Eco.yihu | g.Pgi.Cat2.abfT-1 | g.Cac.adhe2 | g.Aba.ADP1 |
| p172asn75 | XZ227 | g.Mbo.SucA | g.Eco.yihu | g.Pgi.Cat2.abfT-1 | g.Eco.fucO | g.Sce.adh6 |
| p172asn75 | XZ228 | g.Mbo.SucA | g.Eco.yihu | g.Pgi.Cat2.abfT-1 | g.Eco.fucO | g.Sce.adh6 |
| p172asn77 | XZ229 | g.Mbo.SucA | g.Eco.yihu | g.Pgi.Cat2.abfT-2 | g.Eco.adhe | g.Eco.ahr |
| p172asn77 | XZ230 | g.Mbo.SucA | g.Eco.yihu | g.Pgi.Cat2.abfT-2 | g.Eco.adhe | g.Eco.ahr |
| p172asn77 | XZ330 | g.Mbo.SucA | g.Eco.yihu | g.Pgi.Cat2.abfT-2 | g.Eco.adhe | g.Eco.ahr |
| p172asn77 | XZ331 | g.Mbo.SucA | g.Eco.yihu | g.Pgi.Cat2.abfT-2 | g.Eco.adhe | g.Eco.ahr |

TABLE 5-continued

Genotypes of Microorganisms tested for the a-ketoglutarate pathway

| Plasmid | Strain | Heterologous genes | | | | |
|---|---|---|---|---|---|---|
| p172asn78 | XZ332 | g.Mbo.SucA | g.Pgi.4hbD | g.Pgi.Cat2.abfT-2 | g.Eco.adhe | g.Sce.adh6 |
| p172asn78 | XZ333 | g.Mbo.SucA | g.Pgi.4hbD | g.Pgi.Cat2.abfT-2 | g.Eco.adhe | g.Sce.adh6 |

TABLE 6

Genotypes of Microorganisms tested for the Succinate pathway

| Plasmid | Strain | Heterologous genes | | | | |
|---|---|---|---|---|---|---|
| P176-Asn1 | XZ334 | g.Eco.SucC | g.Ckl.SucD | g.Eco.yihu | g.Pgi.Cat2.abfT-1 | g.Eco.adhe | g.Eco.ahr |
| P176-Asn2 | XZ335 | g.Eco.SucC | g.Ckl.SucD | g.Eco.yihu | g.Pgi.Cat2.abfT-2 | g.Eco.adhe | g.Eco.ahr |
| P176-Asn2 | XZ430 | g.Eco.SucC | g.Ckl.SucD | g.Eco.yihu | g.Pgi.Cat2.abfT-2 | g.Eco.adhe | g.Eco.ahr |
| P176-Asn2 | XZ431 | g.Eco.SucC | g.Ckl.SucD | g.Eco.yihu | g.Pgi.Cat2.abfT-2 | g.Eco.adhe | g.Eco.ahr |
| P176-Asn3 | XZ336 | g.Eco.SucD | g.Ckl.SucD | g.Eco.yihu | g.Pgi.Cat2.abfT-1 | g.Eco.adhe | g.Eco.ahr |
| P176-Asn3 | XZ337 | g.Eco.SucD | g.Ckl.SucD | g.Eco.yihu | g.Pgi.Cat2.abfT-1 | g.Eco.adhe | g.Eco.ahr |
| P176-Asn4 | XZ338 | g.Eco.SucD | g.Ckl.SucD | g.Eco.yihu | g.Pgi.Cat2.abfT-2 | g.Eco.adhe | g.Eco.ahr |
| P176-Asn4 | XZ339 | g.Eco.SucD | g.Ckl.SucD | g.Eco.yihu | g.Pgi.Cat2.abfT-2 | g.Eco.adhe | g.Eco.ahr |
| P176-Asn4 | XZ432 | g.Eco.SucD | g.Ckl.SucD | g.Eco.yihu | g.Pgi.Cat2.abfT-2 | g.Eco.adhe | g.Eco.ahr |
| P176-Asn4 | XZ433 | g.Eco.SucD | g.Ckl.SucD | g.Eco.yihu | g.Pgi.Cat2.abfT-2 | g.Eco.adhe | g.Eco.ahr |
| P176-Asn5 | XZ340 | g.Eco.SucC | g.Pgi.SucD | g.Pgi.4hbD | g.Pgi.Cat2.abfT-1 | g.Cac.adhe2 | g.Aba.ADP1 |
| P176-Asn5 | XZ341 | g.Eco.SucC | g.Pgi.SucD | g.Pgi.4hbD | g.Pgi.Cat2.abfT-1 | g.Cac.adhe2 | g.Aba.ADP1 |
| P176-Asn5 | XZ434 | g.Eco.SucC | g.Pgi.SucD | g.Pgi.4hbD | g.Pgi.Cat2.abfT-1 | g.Cac.adhe2 | g.Aba.ADP1 |
| P176-Asn5 | XZ435 | g.Eco.SucC | g.Pgi.SucD | g.Pgi.4hbD | g.Pgi.Cat2.abfT-1 | g.Cac.adhe2 | g.Aba.ADP1 |
| P176-Asn6 | XZ342 | g.Eco.SucC | g.Pgi.SucD | g.Pgi.4hbD | g.Pgi.Cat2.abfT-2 | g.Cac.adhe2 | g.Aba.ADP1 |
| P176-Asn6 | XZ343 | g.Eco.SucC | g.Pgi.SucD | g.Pgi.4hbD | g.Pgi.Cat2.abfT-2 | g.Cac.adhe2 | g.Aba.ADP1 |
| P176-Asn6 | XZ436 | g.Eco.SucC | g.Pgi.SucD | g.Pgi.4hbD | g.Pgi.Cat2.abfT-2 | g.Cac.adhe2 | g.Aba.ADP1 |
| P176-Asn6 | XZ437 | g.Eco.SucC | g.Pgi.SucD | g.Pgi.4hbD | g.Pgi.Cat2.abfT-2 | g.Cac.adhe2 | g.Aba.ADP1 |
| P176-Asn7 | XZ344 | g.Eco.SucD | g.Pgi.SucD | g.Pgi.4hbD | g.Pgi.Cat2.abfT-1 | g.Cac.adhe2 | g.Aba.ADP1 |
| P176-Asn7 | XZ345 | g.Eco.SucD | g.Pgi.SucD | g.Pgi.4hbD | g.Pgi.Cat2.abfT-1 | g.Cac.adhe2 | g.Aba.ADP1 |
| P176-Asn7 | XZ438 | g.Eco.SucD | g.Pgi.SucD | g.Pgi.4hbD | g.Pgi.Cat2.abfT-1 | g.Cac.adhe2 | g.Aba.ADP1 |
| P176-Asn7 | XZ439 | g.Eco.SucD | g.Pgi.SucD | g.Pgi.4hbD | g.Pgi.Cat2.abfT-1 | g.Cac.adhe2 | g.Aba.ADP1 |
| P176-Asn8 | XZ346 | g.Eco.SucD | g.Pgi.SucD | g.Pgi.4hbD | g.Pgi.Cat2.abfT-2 | g.Cac.adhe2 | g.Aba.ADP1 |
| P176-Asn8 | XZ347 | g.Eco.SucD | g.Pgi.SucD | g.Pgi.4hbD | g.Pgi.Cat2.abfT-2 | g.Cac.adhe2 | g.Aba.ADP1 |
| P176-Asn8 | XZ440 | g.Eco.SucD | g.Pgi.SucD | g.Pgi.4hbD | g.Pgi.Cat2.abfT-2 | g.Cac.adhe2 | g.Aba.ADP1 |
| P176-Asn8 | XZ441 | g.Eco.SucD | g.Pgi.SucD | g.Pgi.4hbD | g.Pgi.Cat2.abfT-2 | g.Cac.adhe2 | g.Aba.ADP1 |
| P176-Asn9 | XZ442 | g.Eco.SucD | g.Pgi.SucD | g.Pgi.4hbD | g.Pgi.Cat2.abfT-1 | g.Eco.adhe | g.Eco.ahr |
| P176-Asn9 | XZ443 | g.Eco.SucD | g.Pgi.SucD | g.Pgi.4hbD | g.Pgi.Cat2.abfT-1 | g.Eco.adhe | g.Eco.ahr |
| P176-Asn10 | XZ444 | g.Eco.SucD | g.Pgi.SucD | g.Pgi.4hbD | g.Pgi.Cat2.abfT-2 | g.Eco.adhe | g.Eco.ahr |
| P176-Asn11 | XZ445 | g.Eco.SucD | g.Pgi.SucD | g.Eco.yihu | g.Pgi.Cat2.abfT-1 | g.Eco.adhe | g.Eco.ahr |
| P176-Asn12 | XZ446 | g.Eco.SucD | g.Pgi.SucD | g.Eco.yihu | g.Pgi.Cat2.abfT-2 | g.Eco.adhe | g.Eco.ahr |
| P176-Asn12 | XZ447 | g.Eco.SucD | g.Pgi.SucD | g.Eco.yihu | g.Pgi.Cat2.abfT-2 | g.Eco.adhe | g.Eco.ahr |
| P176-Asn15 | XZ448 | g.Eco.SucD | g.Ckl.SucD | g.Eco.yihu | g.Pgi.Cat2.abfT-1 | g.Eco.adhe | g.Eco.ahr |
| P176-Asn15 | XZ449 | g.Eco.SucD | g.Ckl.SucD | g.Eco.yihu | g.Pgi.Cat2.abfT-1 | g.Eco.adhe | g.Eco.ahr |
| P176-Asn18 | XZ348 | g.Eco.SucC | g.Pgi.SucD | g.Pgi.4hbD | g.Pgi.Cat2.abfT-2 | g.Cac.adhe2 | g.Aba.ADP1 |
| P176-Asn18 | XZ450 | g.Eco.SucC | g.Pgi.SucD | g.Pgi.4hbD | g.Pgi.Cat2.abfT-2 | g.Cac.adhe2 | g.Aba.ADP1 |
| P176-Asn18 | XZ451 | g.Eco.SucC | g.Pgi.SucD | g.Pgi.4hbD | g.Pgi.Cat2.abfT-2 | g.Cac.adhe2 | g.Aba.ADP1 |
| P176-Asn25 | XZ452 | g.Eco.SucC | g.Ckl.SucD | g.Eco.yihu | g.Pgi.Cat2.abfT-1 | g.Eco.adhe | g.Eco.ahr |
| P176-Asn25 | XZ453 | g.Eco.SucC | g.Ckl.SucD | g.Eco.yihu | g.Pgi.Cat2.abfT-1 | g.Eco.adhe | g.Eco.ahr |
| P176-Asn26 | XZ454 | g.Eco.SucC | g.Ckl.SucD | g.Eco.yihu | g.Pgi.Cat2.abfT-2 | g.Eco.adhe | g.Eco.ahr |
| P176-Asn34 | XZ460 | g.Eco.SucD | g.Pgi.SucD | g.Pgi.4hbD | g.Pgi.Cat2.abfT-2 | g.Eco.adhe | g.Eco.ahr |
| P176-Asn34 | XZ461 | g.Eco.SucD | g.Pgi.SucD | g.Pgi.4hbD | g.Pgi.Cat2.abfT-2 | g.Eco.adhe | g.Eco.ahr |
| P176-Asn35 | XZ462 | g.Eco.SucD | g.Pgi.SucD | g.Eco.yihu | g.Pgi.Cat2.abfT-1 | g.Eco.adhe | g.Eco.ahr |
| P176-Asn36 | XZ463 | g.Eco.SucD | g.Pgi.SucD | g.Eco.yihu | g.Pgi.Cat2.abfT-2 | g.Eco.adhe | g.Eco.ahr |
| P176-Asn36 | XZ464 | g.Eco.SucD | g.Pgi.SucD | g.Eco.yihu | g.Pgi.Cat2.abfT-2 | g.Eco.adhe | g.Eco.ahr |
| P176-Asn38 | XZ349 | g.Eco.SucC | g.Ckl.SucD | g.Eco.yihu | g.Pgi.Cat2.abfT-2 | g.Eco.adhe | g.Eco.ahr |
| P176-Asn38 | XZ350 | g.Eco.SucC | g.Ckl.SucD | g.Eco.yihu | g.Pgi.Cat2.abfT-2 | g.Eco.adhe | g.Eco.ahr |
| P176-Asn38 | XZ465 | g.Eco.SucC | g.Ckl.SucD | g.Eco.yihu | g.Pgi.Cat2.abfT-2 | g.Eco.adhe | g.Eco.ahr |
| P176-Asn38 | XZ466 | g.Eco.SucC | g.Ckl.SucD | g.Eco.yihu | g.Pgi.Cat2.abfT-2 | g.Eco.adhe | g.Eco.ahr |
| P176-Asn40 | XZ467 | g.Eco.SucD | g.Ckl.SucD | g.Eco.yihu | g.Pgi.Cat2.abfT-2 | g.Eco.adhe | g.Eco.ahr |
| P176-Asn40 | XZ468 | g.Eco.SucD | g.Ckl.SucD | g.Eco.yihu | g.Pgi.Cat2.abfT-2 | g.Eco.adhe | g.Eco.ahr |
| P176-Asn41 | XZ351 | g.Eco.SucC | g.Pgi.SucD | g.Pgi.4hbD | g.Pgi.Cat2.abfT-1 | g.Cac.adhe2 | g.Aba.ADP1 |
| P176-Asn41 | XZ352 | g.Eco.SucC | g.Pgi.SucD | g.Pgi.4hbD | g.Pgi.Cat2.abfT-1 | g.Cac.adhe2 | g.Aba.ADP1 |
| P176-Asn46 | XZ469 | g.Eco.SucD | g.Pgi.SucD | g.Pgi.4hbD | g.Pgi.Cat2.abfT-2 | g.Eco.adhe | g.Eco.ahr |
| P176-Asn46 | XZ470 | g.Eco.SucD | g.Pgi.SucD | g.Pgi.4hbD | g.Pgi.Cat2.abfT-2 | g.Eco.adhe | g.Eco.ahr |

Figure 6:
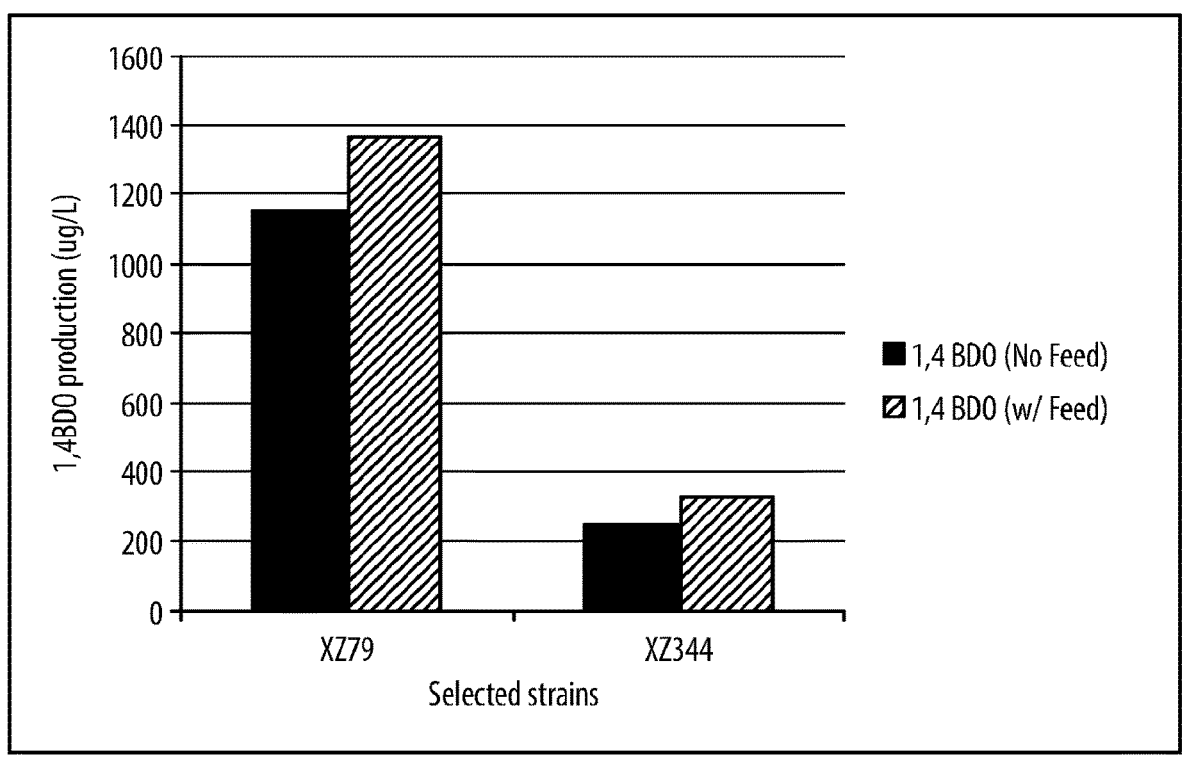
FIG. 6 shows 1,4-BDO production from two top strains XZ79 and XZ344 with or without the presence α-ketoglutarate or succinic acid (collectively "feed"). XZ79 and XZ344 were able both able to produce detectable 1,4 BDO directly from methane in a shake bottle experiment. XZ79 and XZ344 both produced detectable amount of 1,4 BDO directly from methane whereas supplementing the media with feed increased the 1,4 BDO productivity.
Figure 7:
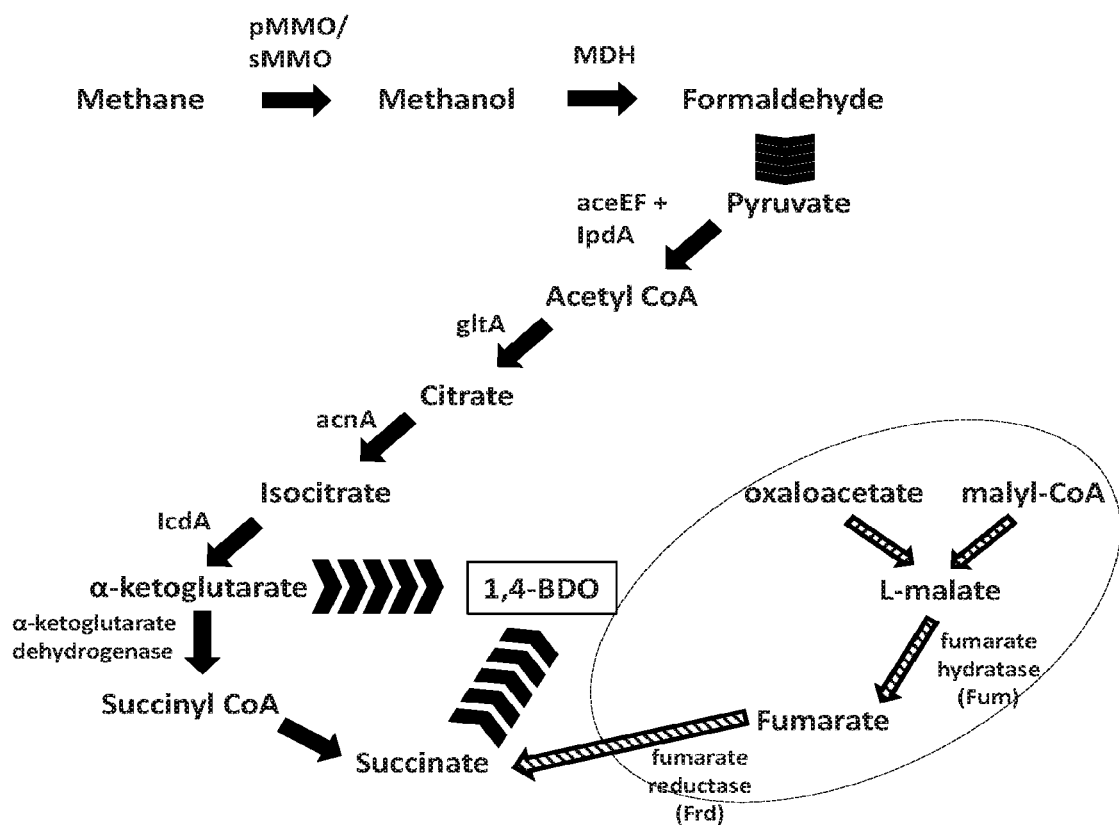
FIG. 7 shows a metabolic pathway from methane ($CH_4$) to 1,4-BDO. The circled part shows the pathway from oxaloacetate and malyl-CoA to succinate, the conversions which are facilitated in part by fumarate hydratase (fum) and fumarate reductase (frd).

Several of the top engineered strains XZ79 (p.BAD>Mbo.SucA>Ckl.4hbD>Pgi.abfT-1>Cac.adhe2>Aba.ADP1) and XZ344 (p.BAD>Eco.SucD>Pgi.SucD>Pgi.4hbD>Pgi.abfT-1>Cac.adhe2>Aba.ADP 1) were selected based on the results from small scale microtiter plate analysis. These strains were able to produce detectable 1,4 BDO without feeding intermediates α-ketoglutarate or succinic acid. To determine if XZ79 and XZ344 were able to produce detectable 1,4 BDO directly from methane in a shake bottle experiment, we tested XZ79 and XZ344 in media with and without supplementation of the intermediates. As shown in FIG. 6, XZ79 and XZ344 both produced detectable amount of 1,4 BDO directly from methane. Feeding α-ketoglutarate or succinic acid increased the 1,4 BDO productivity.

Example 5: 1,4-BDO Production Directly from Methane in Shake Bottles

We tested 35 and 15 different broad host plasmids containing variations in the 5-gene 1,4 BDO pathway, from the α-ketoglutarate and succinate pathway respectively, and transformed the aforementioned plasmids into a transformation competent methanotroph strain, RL83A, and evaluated the strains for 1,4 BDO production in shake bottles using methane as the carbon source. For these experiments, starter cultures were inoculated into 125 ml shake bottles containing 10 ml of media. The bottles were fed a source of methane and incubated in a shaker at 37° C. for 72 hours. After 72h, the cultures were fed 1% of arabinose and α-ketoglutarate or succinate. Samples were collected after 96 hours and tested.

The genotypes and relevant production titers for each of the strains are provided in Table 7 (α-ketoglutarate pathway) and Table 8 (succinate pathway) below. For the fermentation of the strains utilizing the α-ketoglutarate pathway, the media contained in the bottles were supplemented with 400 mg/L of α-ketoglutarate. For the fermentation of the strains utilizing the succinate pathway, the media contained in the bottles were supplemented with 200 mg/L of succinate.

TABLE 7

Genotypes of Microorganisms tested for the a-ketoglutarate pathway

| Strain | Productivity GHB (μg/L) | 1,4 BDO (μg/L) | kgd | 4hbD | Cat2 | Ald | Adh |
|---|---|---|---|---|---|---|---|
| XZ75 | 211.724 | 69.536 | g.Mbo.SucA | g.Eco.yihu | g.Pgi.Cat2.abfT-1 | g.Cac.adhe2 | g.Aba.ADP1 |
| XZ76 | 208.769 | 118.376 | g.Mbo.SucA | g.Eco.yihu | g.Pgi.Cat2.abfT-1 | g.Cac.adhe2 | g.Aba.ADP1 |
| XZ77 | | | g.Mbo.SucA | g.Pgi.4hbD | g.Pgi.Cat2.abfT-1 | g.Cac.adhe2 | g.Aba.ADP1 |
| XZ78 | | | g.Mbo.SucA | g.Pgi.4hbD | g.Pgi.Cat2.abfT-1 | g.Cac.adhe2 | g.Aba.ADP1 |
| XZ79 | 875.47 | 260.966 | g.Mbo.SucA | g.Ckl.4hbD | g.Pgi.Cat2.abfT-1 | g.Cac.adhe2 | g.Aba.ADP1 |
| XZ80 | 562.381 | 174.142 | g.Mbo.SucA | g.Ckl.4hbD | g.Pgi.Cat2.abfT-1 | g.Cac.adhe2 | g.Aba.ADP1 |
| XZ81 | | | g.Mbo.SucA | g.Eco.yihu | g.Pgi.Cat2.abfT-2 | g.Cac.adhe2 | g.Aba.ADP1 |
| XZ82 | | | g.Mbo.SucA | g.Eco.yihu | g.Pgi.Cat2.abfT-2 | g.Cac.adhe2 | g.Aba.ADP1 |
| XZ83 | | | g.Mbo.SucA | g.Eco.yihu | g.Cam.abft | g.Cac.adhe2 | g.Aba.ADP1 |
| XZ84 | 461.119 | | g.Mbo.SucA | g.Eco.yihu | g.Cam.abft | g.Cac.adhe2 | g.Aba.ADP1 |
| XZ85 | | | g.Mbo.SucA | g.Eco.yihu | g.Pgi.Cat2.abfT-1 | g.Eco.yqhD | g.Aba.ADP1 |
| XZ86 | | | g.Mbo.SucA | g.Eco.yihu | g.Pgi.Cat2.abfT-1 | g.Eco.yqhD | g.Aba.ADP1 |
| XZ87 | | | g.Mbo.SucA | g.Eco.yihu | g.Pgi.Cat2.abfT-1 | g.Eco.fucO | g.Aba.ADP1 |
| XZ88 | 530.438 | | g.Mbo.SucA | g.Eco.yihu | g.Pgi.Cat2.abfT-1 | g.Eco.fucO | g.Aba.ADP1 |
| XZ89 | | | g.Mtu.kgd | g.Eco.yihu | g.Pgi.Cat2.abfT-1 | g.Cac.adhe2 | g.Aba.ADP1 |
| XZ90 | 109.323 | 30.634 | g.Cte.kgd | g.Eco.yihu | g.Pgi.Cat2.abfT-1 | g.Cac.adhe2 | g.Aba.ADP1 |
| XZ91 | | | g.Cte.kgd | g.Eco.yihu | g.Pgi.Cat2.abfT-1 | g.Cac.adhe2 | g.Aba.ADP1 |
| XZ92 | | | g.Rjo.odhA | g.Eco.yihu | g.Pgi.Cat2.abfT-1 | g.Cbe.Ald | g.Aba.ADP1 |
| XZ93 | | | g.Rjo.odhA | g.Eco.yihu | g.Pgi.Cat2.abfT-1 | g.Cbe.Ald | g.Aba.ADP1 |
| XZ94 | 410.306 | | g.Mbo.SucA | g.Eco.yihu | g.Pgi.Cat2.abfT-1 | g.Eco.yqhD | g.Sce.adh6 |
| XZ95 | 354.687 | | g.Mbo.SucA | g.Eco.yihu | g.Pgi.Cat2.abfT-1 | g.Eco.yqhD | g.Sce.adh6 |
| XZ96 | | | g.Mbo.SucA | g.Eco.yihu | g.Pgi.Cat2.abfT-1 | g.Eco.fucO | g.Sce.adh6 |
| XZ97 | | | g.Mbo.SucA | g.Eco.yihu | g.Pgi.Cat2.abfT-1 | g.Eco.adhe | g.Sce.adh6 |
| XZ98 | | | g.Mbo.SucA | g.Eco.yihu | g.Pgi.Cat2.abfT-1 | g.Eco.adhe | g.Sce.adh6 |
| XZ99 | | | g.Mbo.SucA | g.Eco.yihu | g.Pgi.Cat2.abfT-2 | g.Eco.adhe | g.Eco.ahr |
| XZ100 | | | g.Mbo.SucA | g.Eco.yihu | g.Pgi.Cat2.abfT-2 | g.Eco.adhe | g.Eco.ahr |
| XZ216 | 2067.802 | | g.Mbo.SucA | g.Pgi.4hbD | g.Pgi.Cat2.abfT-2 | g.Eco.adhe | g.Sce.adh6 |
| XZ217 | | | g.Mbo.SucA | g.Pgi.4hbD | g.Pgi.Cat2.abfT-2 | g.Eco.adhe | g.Sce.adh6 |
| XZ276 | 535.295 | | g.Mbo.SucA | g.Eco.yihu | g.Pgi.Cat2.abfT-1 | g.Eco.adhe | g.Aba.ADP1 |
| XZ277 | | | g.Mbo.SucA | g.Eco.yihu | g.Pgi.Cat2.abfT-1 | g.Eco.adhe | g.Aba.ADP1 |
| XZ278 | 163.658 | 52.054 | g.Mbo.SucA | g.Eco.yihu | g.Pgi.Cat2.abfT-1 | g.Cac.adhe2 | g.Sce.adh6 |
| XZ279 | | | g.Mbo.SucA | g.Eco.yihu | g.Pgi.Cat2.abfT-1 | g.Cac.adhe2 | g.Sce.adh6 |
| XZ280 | | | g.Mbo.SucA | g.Eco.yihu | g.Pgi.Cat2.abfT-1 | g.Cac.adhe2 | g.Eco.ahr |
| XZ281 | | | g.Mbo.SucA | g.Eco.yihu | g.Pgi.Cat2.abfT-1 | g.Cac.adhe2 | g.Eco.ahr |
| RL83 | | | Parental strain control | | | | |

Example 6: Increased Succinate Production

TABLE 8

| Genotypes of Microorganisms tested for the Succinate pathway | | | | | | | | | |
|---|---|---|---|---|---|---|---|---|---|
| Strain | GHB (μg/l) | 1,4 BDO (μg/l) | Genotype | | | | | | |
| XZ340 | 133.3 | | g.Eco.SucC | g.Pgi.SucD | g.Pgi.4hbD | g.Pgi.Cat2.abfT-1 | g.Cac.adhe2 | g.Aba.ADP1 |
| XZ341 | 101.9 | | g.Eco.SucC | g.Pgi.SucD | g.Pgi.4hbD | g.Pgi.Cat2.abfT-1 | g.Cac.adhe2 | g.Aba.ADP1 |
| XZ343 | 1711.4 | 31.6 | g.Eco.SucC | g.Pgi.SucD | g.Pgi.4hbD | g.Pgi.Cat2.abfT-2 | g.Cac.adhe2 | g.Aba.ADP1 |
| XZ344 | 1789.8 | 344.4 | g.Eco.SucD | g.Pgi.SucD | g.Pgi.4hbD | g.Pgi.Cat2.abfT-1 | g.Cac.adhe2 | g.Aba.ADP1 |
| XZ345 | 1926.9 | 579.4 | g.Eco.SucD | g.Pgi.SucD | g.Pgi.4hbD | g.Pgi.Cat2.abfT-1 | g.Cac.adhe2 | g.Aba.ADP1 |
| XZ346 | 5512.5 | 268.2 | g.Eco.SucD | g.Pgi.SucD | g.Pgi.4hbD | g.Pgi.Cat2.abfT-2 | g.Cac.adhe2 | g.Aba.ADP1 |
| XZ347 | 5131.2 | 244.6 | g.Eco.SucD | g.Pgi.SucD | g.Pgi.4hbD | g.Pgi.Cat2.abfT-2 | g.Cac.adhe2 | g.Aba.ADP1 |
| XZ434 | 112.3 | | g.Eco.SucC | g.Pgi.SucD | g.Pgi.4hbD | g.Pgi.Cat2.abfT-1 | g.Cac.adhe2 | g.Aba.ADP1 |
| XZ435 | 165.2 | | g.Eco.SucC | g.Pgi.SucD | g.Pgi.4hbD | g.Pgi.Cat2.abfT-1 | g.Cac.adhe2 | g.Aba.ADP1 |
| XZ436 | 3983.5 | 225.3 | g.Eco.SucC | g.Pgi.SucD | g.Pgi.4hbD | g.Pgi.Cat2.abfT-2 | g.Cac.adhe2 | g.Aba.ADP1 |
| XZ437 | 1362.9 | 106.5 | g.Eco.SucC | g.Pgi.SucD | g.Pgi.4hbD | g.Pgi.Cat2.abfT-2 | g.Cac.adhe2 | g.Aba.ADP1 |
| XZ438 | 3200.1 | 524.8 | g.Eco.SucD | g.Pgi.SucD | g.Pgi.4hbD | g.Pgi.Cat2.abfT-1 | g.Cac.adhe2 | g.Aba.ADP1 |
| XZ439 | 3387.2 | 313 | g.Eco.SucD | g.Pgi.SucD | g.Pgi.4hbD | g.Pgi.Cat2.abfT-1 | g.Cac.adhe2 | g.Aba.ADP1 |
| XZ440 | 7580.2 | 365.8 | g.Eco.SucD | g.Pgi.SucD | g.Pgi.4hbD | g.Pgi.Cat2.abfT-2 | g.Cac.adhe2 | g.Aba.ADP1 |
| XZ441 | 6103.7 | 245.2 | g.Eco.SucD | g.Pgi.SucD | g.Pgi.4hbD | g.Pgi.Cat2.abfT-2 | g.Cac.adhe2 | g.Aba.ADP1 |

In order to increase 1,4-BDO titers, the production of the upstream product succinate was measured in the presence or absence of fumarate reductase (frd) genes. See FIG. 7. 58 *Methylococcus capsulatus* methanotroph strains were generated comprising *E. coli* FrdA, *E. coli* FrdB, *E. coli* FrdC, *E. coli* FrdD with varying promoters. Each strain was inoculated into 125 ml shake bottles containing 10 ml of media to create a start culture. The starter cultures were then used to inoculate a shake bottle at an initial GD of 0.1. The shake bottles were incubated for 96 hours at 37° C. in the presence of excess methane. Succinate titers were then measured.

Figure 8:
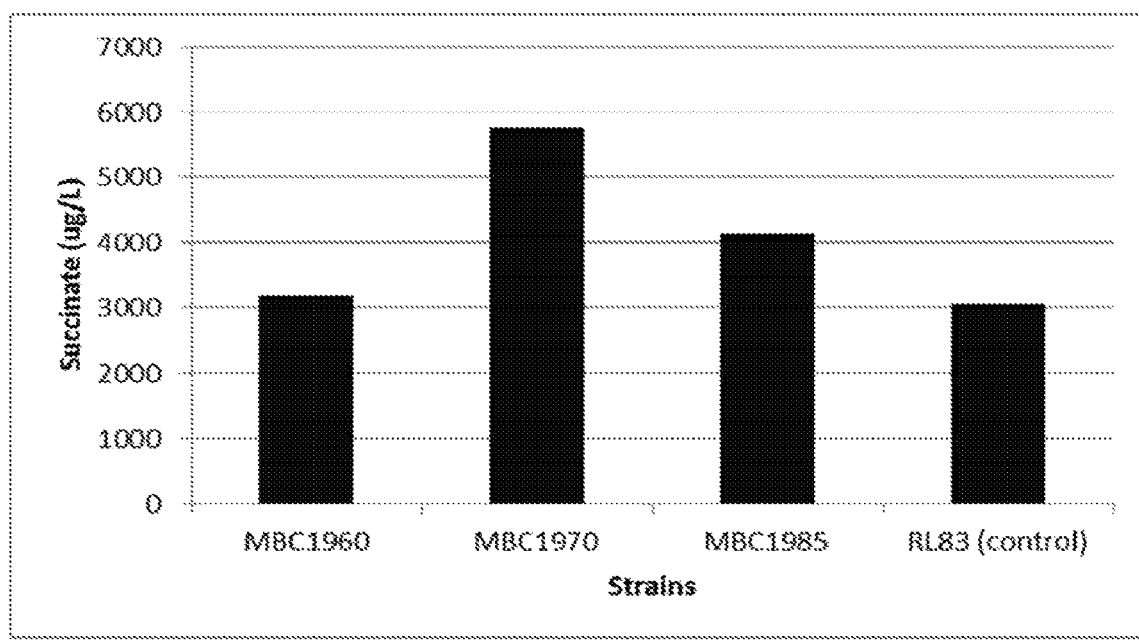
FIG. 8 shows methanotrophs expressing Frd genes under the control of different promoters. The MBC1960 strain expressed a heterologous *E. coli* FrdA, FrdB, FrdC, and FrdD under the control of a pmxaF promoter. The MBC1970 strain expresses the same genes except they are under the control of a J23111 promoter whereas MBC1985 expresses the genes under the control of a J23100 promoter. The MBC1970 and MBC1985 strains produced significantly more succinate than its parent control strain.

All the strains MBC1960, MBC1970, and MBC1985 expressed a heterologous *E. coli* FrdA, FrdB, FrdC, and FrdD but were under the control of different promoters (pmxaF, J23111, and J23100, respectively). See FIG. 8. As seen in FIG. 8, the MBC1970 and MBC1985 strains produced significantly more succinate than its parent control strain (RL83).

What is claimed is:

1. A genetically modified methanotroph capable of converting a single carbon-containing hydrocarbon molecule to 1,4-butanediol, the genetically modified methanotroph comprising heterologous genes encoding:
   (a) an α-ketoglutarate decarboxylase comprising an amino acid sequence that is at least 90% identical to any one of SEQ ID NOs: 1, 3, 5, and 7;
   (b) a 4-hydroxybutyrate dehydrogenase comprising an amino acid sequence that is at least 90% identical to SEQ ID NO: 11 or 13;
   (c) a 4-hydroxybutyrate CoA transferase comprising an amino acid sequence that is at least 90% identical to any one of SEQ ID NOs: 15, 17, and 19;
   (d) an aldehyde dehydrogenase comprising an amino acid sequence that is at least 90% identical to any one of SEQ ID NOs: 21, 23, 25, 27, 29, 31, 33, and 35; and
   (e) an alcohol dehydrogenase comprising an amino acid sequence that is at least 90% identical to any one of SEQ ID NOs: 21, 23, 25, 27, 29, 31, 33, and 35.

2. The genetically modified methanotroph of claim 1, further comprising a gene encoding fumarate hydratase or fumarate reductase.

3. The genetically modified methanotroph of claim 1, wherein the genetically modified methanotroph is a *Methylococcus*.

4. The genetically modified methanotroph of claim 1, wherein at least one heterologous gene is overexpressed.

5. A vector encoding:
   (a) an α-ketoglutarate decarboxylase comprising an amino acid sequence that is at least 90% identical to any one of SEQ ID NOs: 1, 3, 5, and 7;
   (b) a 4-hydroxybutyrate dehydrogenase comprising an amino acid sequence that is at least 90% identical to SEQ ID NO: 11 or 13;
   (c) a 4-hydroxybutyrate CoA transferase comprising an amino acid sequence that is at least 90% identical to any one of SEQ ID NOs: 15, 17, and 19;
   (d) an aldehyde dehydrogenase comprising an amino acid sequence that is at least 90% identical to any one of SEQ ID NOs: 21, 23, 25, 27, 29, 31, 33, and 35; and
   (e) an alcohol dehydrogenase comprising an amino acid sequence that is at least 90% identical to any one of SEQ ID NOs: 21, 23, 25, 27, 29, 31, 33, and 35.

6. A method of making the genetically modified methanotroph of claim 1, the method comprising contacting a methanotroph with a nucleic acid encoding:
   (a) an α-ketoglutarate decarboxylase comprising an amino acid sequence that is at least 90% identical to any one of SEQ ID NOs: 1, 3, 5, and 7;
   (b) a 4-hydroxybutyrate dehydrogenase comprising an amino acid sequence that is at least 90% identical to SEQ ID NO: 11 and 13;
   (c) a 4-hydroxybutyrate CoA transferase comprising an amino acid sequence that is at least 90% identical to any one of SEQ ID NOs: 15, 17, and 19;
   (d) an aldehyde dehydrogenase comprising an amino acid sequence that is at least 90% identical to any one of SEQ ID NOs: 21, 23, 25, 27, 29, 31, 33, and 35; and (e) an alcohol dehydrogenase comprising an amino acid sequence that is at least 90% identical to any one of SEQ ID NOs: 21, 23, 25, 27, 29, 31, 33, and 35.

7. A method of making 1,4-butanediol, the method comprising:
 (a) contacting a single carbon-containing hydrocarbon molecule with the genetically modified methanotroph of claim 1; and
 (b) growing the methanotroph to produce the 1,4-butanediol.

8. The method of claim 7, wherein the single carbon-containing hydrocarbon molecule is methane.

9. The method of claim 7, wherein the methanotroph is grown in the presence of exogenous gamma-hydroxybutyrate (GHB), exogenous α-ketoglutarate, and/or exogenous succinate.

10. The method of claim 7, further comprising contacting the 1,4-butanediol with a catalyst.

11. The method of claim 10, wherein tetrahydrofuran is formed after 1,4-butanediol is contacted with the catalyst.

12. The method of claim 7, further comprising contacting the 1,4-butanediol with a dicarboxylic acid/anhydride.

13. The method of claim 12, wherein a polyurethane is formed after the 1,4-butanediol is contacted with the dicarboxylic acid/anhydride.

14. The method of claim 10, further comprising transesterifying the 1,4-butanediol.

15. The method of claim 14, wherein polybutylene terephthalate is formed after the 1,4-butanediol is transesterified.

16. The genetically modified methanotroph of claim 1, wherein: (a) the α-ketoglutarate decarboxylase comprises an amino acid sequence that is at least 95% identical to any one of SEQ ID NOs: 1, 3, 5, and 7; (b) the 4-hydroxybutyrate comprises an amino acid sequence that is at least 95% identical to SEQ ID NO: 11 or 13; (c) the 4-hydroxybutyrate CoA transferase comprises an amino acid sequence that is at least 95% identical to any one of SEQ ID NOs: 15, 17, and 19; (d) the aldehyde dehydrogenase comprises an amino acid sequence that is at least 95% identical to any one of SEQ ID NOs: 21, 23, 25, 27, 29, 31, 33, and 35; and (e) the alcohol dehydrogenase comprises an amino acid sequence that is at least 95% identical to any one of SEQ ID NOs: 21, 23, 25, 27, 29, 31, 33, and 35.

17. The genetically modified methanotroph of claim 1, wherein: (a) the α-ketoglutarate decarboxylase comprises the amino acid sequence of any one of SEQ ID NOs: 1, 3, 5, and 7; (b) the 4-hydroxybutyrate comprises the amino acid sequence of SEQ ID NO: 11 or 13; (c) the 4-hydroxybutyrate CoA transferase comprises the amino acid sequence of any one of SEQ ID NOs: 15, 17, and 19; (d) the aldehyde dehydrogenase comprises the amino acid sequence of any one of SEQ ID NOs: 21, 23, 25, 27, 29, 31, 33, and 35; and (e) the alcohol dehydrogenase comprises the amino acid sequence of any one of SEQ ID NOs: 21, 23, 25, 27, 29, 31, 33, and 35.

18. The genetically modified methanotroph of claim 1, wherein: (a) the α-ketoglutarate decarboxylase comprises an amino acid sequence that is at least 90% identical to SEQ ID NO: 1; (b) the 4-hydroxybutyrate comprises an amino acid sequence that is at least 90% identical to SEQ ID NO: 13; (c) the 4-hydroxybutyrate CoA transferase comprises an amino acid sequence that is at least 90% identical to SEQ ID NO: 15; (d) the aldehyde dehydrogenase comprises an amino acid sequence that is at least 90% identical to SEQ ID NO: 21; and (e) the alcohol dehydrogenase comprises an amino acid sequence that is at least 90% identical to SEQ ID NO: 33.

19. The genetically modified methanotroph of claim 1, wherein: (a) the α-ketoglutarate decarboxylase comprises an amino acid sequence that is at least 95% identical to SEQ ID NO: 1; (b) the 4-hydroxybutyrate comprises an amino acid sequence that is at least 95% identical to SEQ ID NO: 13; (c) the 4-hydroxybutyrate CoA transferase comprises an amino acid sequence that is at least 95% identical to SEQ ID NO: 15; (d) the aldehyde dehydrogenase comprises an amino acid sequence that is at least 95% identical to SEQ ID NO: 21; and (e) the alcohol dehydrogenase comprises an amino acid sequence that is at least 95% identical to SEQ ID NO: 33.

20. The genetically modified methanotroph of claim 1, wherein: (a) the α-ketoglutarate decarboxylase comprises the amino acid sequence of SEQ ID NO: 1; (b) the 4-hydroxybutyrate comprises the amino acid sequence of SEQ ID NO: 13; (c) the 4-hydroxybutyrate CoA transferase comprises the amino acid sequence of SEQ ID NO: 15; (d) the aldehyde dehydrogenase comprises the amino acid sequence of SEQ ID NO: 21; and (e) the alcohol dehydrogenase comprises the amino acid sequence of SEQ ID NO: 33.

* * * * *

SEQUENCE LISTING

```
<160> NUMBER OF SEQ ID NOS: 58

<210> SEQ ID NO 1
<211> LENGTH: 1231
<212> TYPE: PRT
<213> ORGANISM: Mycobacterium bovis

<400> SEQUENCE: 1

Met Ala Asn Ile Ser Ser Pro Phe Gly Gln Asn Glu Trp Leu Val Glu
1               5                   10                  15

Ala Met Tyr Arg Lys Phe Arg Asp Asp Pro Ser Ser Val Asp Pro Ser
            20                  25                  30

Trp His Glu Phe Leu Val Asp Tyr Ser Pro Glu Pro Thr Ser Gln Pro
        35                  40                  45

Ala Ala Glu Pro Thr Arg Val Thr Ser Pro Leu Val Ala Glu Arg Ala
    50                  55                  60

Ala Ala Ala Ala Pro Gln Ala Pro Pro Lys Pro Ala Asp Thr Ala Ala
65                  70                  75                  80

Ala Gly Asn Gly Val Val Ala Ala Leu Ala Ala Lys Thr Ala Val Pro
                85                  90                  95

Pro Pro Ala Glu Gly Asp Glu Val Ala Val Leu Arg Gly Ala Ala Ala
            100                 105                 110

Ala Val Val Lys Asn Met Ser Ala Ser Leu Glu Val Pro Thr Ala Thr
        115                 120                 125

Ser Val Arg Ala Val Pro Ala Lys Leu Leu Ile Asp Asn Arg Ile Val
```

```
              130             135             140
Ile Asn Asn Gln Leu Lys Arg Thr Arg Gly Lys Ile Ser Phe Thr
145                 150                 155                 160

His Leu Leu Gly Tyr Ala Leu Val Gln Ala Val Lys Lys Phe Pro Asn
                165                 170                 175

Met Asn Arg His Tyr Thr Glu Val Asp Gly Lys Pro Thr Ala Val Thr
                180                 185                 190

Pro Ala His Thr Asn Leu Gly Leu Ala Ile Asp Leu Gln Gly Lys Asp
                195                 200                 205

Gly Lys Arg Ser Leu Val Val Ala Gly Ile Lys Arg Cys Glu Thr Met
                210                 215                 220

Arg Phe Ala Gln Phe Val Thr Ala Tyr Glu Asp Ile Val Arg Arg Ala
225                 230                 235                 240

Arg Asp Gly Lys Leu Thr Thr Glu Asp Phe Ala Gly Val Thr Ile Ser
                245                 250                 255

Leu Thr Asn Pro Gly Thr Ile Gly Thr Val His Ser Val Pro Arg Leu
                260                 265                 270

Met Pro Gly Gln Gly Ala Ile Ile Gly Val Gly Ala Met Glu Tyr Pro
                275                 280                 285

Ala Glu Phe Gln Gly Ala Ser Glu Glu Arg Ile Ala Glu Leu Gly Ile
290                 295                 300

Gly Lys Leu Ile Thr Leu Thr Ser Thr Tyr Asp His Arg Ile Ile Gln
305                 310                 315                 320

Gly Ala Glu Ser Gly Asp Phe Leu Arg Thr Ile His Glu Leu Leu Leu
                325                 330                 335

Ser Asp Gly Phe Trp Asp Glu Val Phe Arg Glu Leu Ser Ile Pro Tyr
                340                 345                 350

Leu Pro Val Arg Trp Ser Thr Asp Asn Pro Asp Ser Ile Val Asp Lys
                355                 360                 365

Asn Ala Arg Val Met Asn Leu Ile Ala Ala Tyr Arg Asn Arg Gly His
370                 375                 380

Leu Met Ala Asp Thr Asp Pro Leu Arg Leu Asp Lys Ala Arg Phe Arg
385                 390                 395                 400

Ser His Pro Asp Leu Glu Val Leu Thr His Gly Leu Thr Leu Trp Asp
                405                 410                 415

Leu Asp Arg Val Phe Lys Val Asp Gly Phe Ala Gly Ala Gln Tyr Lys
                420                 425                 430

Lys Leu Arg Asp Val Leu Gly Leu Leu Arg Asp Ala Tyr Cys Arg His
                435                 440                 445

Ile Gly Val Glu Tyr Ala His Ile Leu Asp Pro Glu Gln Lys Glu Trp
                450                 455                 460

Leu Glu Gln Arg Val Glu Thr Lys His Val Lys Pro Thr Val Ala Gln
465                 470                 475                 480

Gln Lys Tyr Ile Leu Ser Lys Leu Asn Ala Ala Glu Ala Phe Glu Thr
                485                 490                 495

Phe Leu Gln Thr Lys Tyr Val Gly Gln Lys Arg Phe Ser Leu Glu Gly
                500                 505                 510

Ala Glu Ser Val Ile Pro Met Met Asp Ala Ala Ile Asp Gln Cys Ala
                515                 520                 525

Glu His Gly Leu Asp Glu Val Val Ile Gly Met Pro His Arg Gly Arg
                530                 535                 540

Leu Asn Val Leu Ala Asn Ile Val Gly Lys Pro Tyr Ser Gln Ile Phe
545                 550                 555                 560
```

```
Thr Glu Phe Glu Gly Asn Leu Asn Pro Ser Gln Ala His Gly Ser Gly
                565                 570                 575

Asp Val Lys Tyr His Leu Gly Ala Thr Gly Leu Tyr Leu Gln Met Phe
            580                 585                 590

Gly Asp Asn Asp Ile Gln Val Ser Leu Thr Ala Asn Pro Ser His Leu
        595                 600                 605

Glu Ala Val Asp Pro Val Leu Glu Gly Leu Val Arg Ala Lys Gln Asp
    610                 615                 620

Leu Leu Asp His Gly Ser Ile Asp Ser Asp Gly Gln Arg Ala Phe Ser
625                 630                 635                 640

Val Val Pro Leu Met Leu His Gly Asp Ala Ala Phe Ala Gly Gln Gly
                645                 650                 655

Val Val Ala Glu Thr Leu Asn Leu Ala Asn Leu Pro Gly Tyr Arg Val
            660                 665                 670

Gly Gly Thr Ile His Ile Ile Val Asn Asn Gln Ile Gly Phe Thr Thr
        675                 680                 685

Ala Pro Glu Tyr Ser Arg Ser Ser Glu Tyr Cys Thr Asp Val Ala Lys
    690                 695                 700

Met Ile Gly Ala Pro Ile Phe His Val Asn Gly Asp Asp Pro Glu Ala
705                 710                 715                 720

Cys Val Trp Val Ala Arg Leu Ala Val Asp Phe Arg Gln Arg Phe Lys
                725                 730                 735

Lys Asp Val Val Ile Asp Met Leu Cys Tyr Arg Arg Arg Gly His Asn
            740                 745                 750

Glu Gly Asp Asp Pro Ser Met Thr Asn Pro Tyr Met Tyr Asp Val Val
        755                 760                 765

Asp Thr Lys Arg Gly Ala Arg Lys Ser Tyr Thr Glu Ala Leu Ile Gly
    770                 775                 780

Arg Gly Asp Ile Ser Met Lys Glu Ala Glu Asp Ala Leu Arg Asp Tyr
785                 790                 795                 800

Gln Gly Gln Leu Glu Arg Val Phe Asn Glu Val Arg Glu Leu Glu Lys
                805                 810                 815

His Gly Val Gln Pro Ser Glu Ser Val Glu Ser Asp Gln Met Ile Pro
            820                 825                 830

Ala Gly Leu Ala Thr Ala Val Asp Lys Ser Leu Leu Ala Arg Ile Gly
        835                 840                 845

Asp Ala Phe Leu Ala Leu Pro Asn Gly Phe Thr Ala His Pro Arg Val
    850                 855                 860

Gln Pro Val Leu Glu Lys Arg Arg Glu Met Ala Tyr Glu Gly Lys Ile
865                 870                 875                 880

Asp Trp Ala Phe Gly Glu Leu Leu Ala Leu Gly Ser Leu Val Ala Glu
                885                 890                 895

Gly Lys Leu Val Arg Leu Ser Gly Gln Asp Ser Arg Arg Gly Thr Phe
            900                 905                 910

Ser Gln Arg His Ser Val Leu Ile Asp Arg His Thr Gly Glu Glu Phe
        915                 920                 925

Thr Pro Leu Gln Leu Leu Ala Thr Asn Ser Asp Gly Ser Pro Thr Gly
    930                 935                 940

Gly Lys Phe Leu Val Tyr Asp Ser Pro Leu Ser Glu Tyr Ala Ala Val
945                 950                 955                 960

Gly Phe Glu Tyr Gly Tyr Thr Val Gly Asn Pro Asp Ala Val Val Leu
                965                 970                 975
```

Trp Glu Ala Gln Phe Gly Asp Phe Val Asn Gly Ala Gln Ser Ile Ile
           980                 985                 990

Asp Glu Phe Ile Ser Ser Gly Glu Ala Lys Trp Gly Gln Leu Ser Asn
           995                1000                1005

Val Val Leu Leu Leu Pro His Gly His Glu Gly Gln Gly Pro Asp
       1010                1015                1020

His Thr Ser Ala Arg Ile Glu Arg Phe Leu Gln Leu Trp Ala Glu
       1025                1030                1035

Gly Ser Met Thr Ile Ala Met Pro Ser Thr Pro Ser Asn Tyr Phe
       1040                1045                1050

His Leu Leu Arg Arg His Ala Leu Asp Gly Ile Gln Arg Pro Leu
       1055                1060                1065

Ile Val Phe Thr Pro Lys Ser Met Leu Arg His Lys Ala Ala Val
       1070                1075                1080

Ser Glu Ile Lys Asp Phe Thr Glu Ile Lys Phe Arg Ser Val Leu
       1085                1090                1095

Glu Glu Pro Thr Tyr Glu Asp Gly Ile Gly Asp Arg Asn Lys Val
       1100                1105                1110

Ser Arg Ile Leu Leu Thr Ser Gly Lys Leu Tyr Tyr Glu Leu Ala
       1115                1120                1125

Ala Arg Lys Ala Lys Asp Asn Arg Asn Asp Leu Ala Ile Val Arg
       1130                1135                1140

Leu Glu Gln Leu Ala Pro Leu Pro Arg Arg Arg Leu Arg Glu Thr
       1145                1150                1155

Leu Asp Arg Tyr Glu Asn Val Lys Glu Phe Phe Trp Val Gln Glu
       1160                1165                1170

Glu Pro Ala Asn Gln Gly Ala Trp Pro Arg Phe Gly Leu Glu Leu
       1175                1180                1185

Pro Glu Leu Leu Pro Asp Lys Leu Ala Gly Ile Lys Arg Ile Ser
       1190                1195                1200

Arg Arg Ala Met Ser Ala Pro Ser Ser Gly Ser Ser Lys Val His
       1205                1210                1215

Ala Val Glu Gln Gln Glu Ile Leu Asp Glu Ala Phe Gly
       1220                1225                1230

<210> SEQ ID NO 2
<211> LENGTH: 3696
<212> TYPE: DNA
<213> ORGANISM: Mycobacterium bovis

<400> SEQUENCE: 2
atggccaata tctcgtcccc gttcggccag aacgagtggc tcgtggaggc catgtatcgg     60
aagttccggg acgacccgtc cagcgtcgac ccgtcctggc acgagttcct cgtggactac    120
tcccccgagc cgaccagcca gccggcggcc gagccgaccc gggtcacgtc gccgctcgtc    180
gccgaacggg ccgccgccgc cgccccccag gcgcccccca gccggccgga cacggccgcc    240
gccggcaacg gcgtggtggc ggccctggcc gccaagaccg ccgtgccgcc cccggccgaa    300
ggcgacgaag tcgccgtcct ccggggcgcg cggcggcggg tcgtgaagaa catgagcgcg    360
tccctggagg tgccgaccgc cacgtcggtc cgggccgtcc ccgcgaaact cctcatcgac    420
aaccgcatcg tcatcaataa ccagctgaag cggacgcggg cggcaagat ctcgttcacg    480 cacctcctcg gctacgcgct cgtgcaggcc gtcaagaagt cccgaacat gaacggcac    540 tacacggaag tggacggcaa acccacggcc gtcacccccg cccatacgaa cctcggcctg    600

-continued

```
gccatcgacc tgcagggcaa ggacggcaag cggtcgctgg tggtcgccgg catcaagcgc    660
tgcgagacga tgcgcttcgc gcagttcgtc acggcctatg aagacatcgt ccgccgggcc    720
cgggacggca agctcaccac ggaagatttc gcgggcgtca ccatctcgct caccaatccc    780
ggcacgatcg gcaccgtcca tagcgtgccg cgcctgatgc ccggccaggg cgcgatcatc    840
ggcgtcggcg cgatggaata ccccgccgag ttccagggcg cgtccgagga gcggatcgcg    900
gaactgggca tcggcaagct catcaccctc accagcacgt atgaccaccg catcatccag    960
ggcgccgagt cgggcgactt cctccggacg atccatgagc tgctgctgag cgacggcttc   1020
tgggatgagg tgttccggga actgtccatc ccgtatctgc cggtccggtg gagcacggac   1080
aaccccgata gcatcgtgga caaaaacgcc cgcgtgatga acctcatcgc cgcctaccgc   1140
aaccgcggcc acctgatggc cgacaccgat ccgctgcggc tcgacaaagc ccgcttccgg   1200
agccatcccg acctggaagt cctgacccac ggcctcaccc tgtgggatct ggatcgggtc   1260
ttcaaggtcg acggcttcgc cggcgcccag tacaagaagc tgcgcgatgt gctcggcctg   1320
ctgcgggacg cctattgccg ccacatcggc gtggagtacg cgcacatcct cgacccggaa   1380
cagaaagaat ggctggaaca gcgcgtcgaa accaagcatg tgaagcccac ggtggcgcag   1440
cagaagtaca tcctgtcgaa gctgaatgcg gccgaagcct tcgaaacctt cctgcagacc   1500
aagtacgtcg gccagaagcg cttctccctg gaaggcgccg agtccgtcat cccgatgatg   1560
gatgccgcga tcgaccagtg cgccaacac ggcctggacg aagtcgtgat cggcatgccc   1620
catcgcggcc ggctcaacgt cctcgcgaac atcgtcggca agccgtactc gcagatcttc   1680
acggagttcg aaggcaacct gaaccccctcc caggcccacg gcagcggcga cgtgaaatat   1740
cacctgggcg ccaccggcct gtatctgcag atgttcggcg acaacgacat ccaggtcagc   1800
ctgaccgcca ccccctcgca tctggaagcc gtcgaccccg tcctggaagg cctggtccgc   1860
gcgaagcagg acctcctgga ccacggcagc atcgatagcg acggccagcg ggccttctcc   1920
gtggtgcccc tcatgctgca cggcgacgcc gccttcgccg ccagggcgt ggtcgccgag   1980 acgctcaacc tggcgaacct gcccggctac cgcgtcggcg gcacgatcca catcatcgtc   2040
aacaatcaga tcggcttcac caccgccccc gagtactccc gcagctcgga atactgcacc   2100
gatgtggcga aaatgatcgg cgccccgatc ttccatgtca atggcgatga tccggaagcg   2160
tgcgtgtggg tggcccgcct ggcggtggat ttccgccagc ggttcaagaa ggatgtggtg   2220
atcgacatgc tgtgctaccg ccgccggggc cataatgaag gcgacgatcc ctccatgacc   2280 aaccccctaca tgtacgatgt cgtggacacg aagcgcggcg cccgcaagtc ctataccgag   2340
gccctcatcg gccggggcga tatcagcatg aaagaagccg aggatgcgct ccgcgactat   2400
cagggccagc tggaacgggt gttcaacgag gtgcgggaac tcgaaaaaca cggcgtccag   2460
ccgtccgaga gcgtggagtc cgatcagatg atcccggcgg gcctcgccac ggcggtcgat   2520
aagtccctgc tggcccggat cggcgatgcc ttcctggccc tccccaatgg cttcacggcg   2580
cacccgcggg tgcagccggt gctcgaaaaa cgccggaaa tggcctacga aggcaagatc   2640
gactgggcct tcggcgagct gctggcgctg ggctccctgg tggccgaagg caaactggtg   2700
cgcctgtccg gccaggactc gcgcgcggc accttctccc agcgccactc ggtcctgatc   2760
gatcgccata ccggcgagga gttcaccccg ctccagctcc tggccacgaa ctccgacggc   2820
tcgcccaccg gcggcaagtt cctggtgtat gacagcccc tgagcgagta tgcggcggtc   2880
ggcttcgagt acgctacac cgtcggcaat cccgacgccc tcgtcctgtg ggaagcgcag   2940
ttcggcgact tcgtcaatgg cgcccagtcg atcatcgacg agttcatctc gtcgggcgag   3000
```

```
gccaaatggg gccagctctc gaacgtcgtg ctgctgctcc cgcacggcca cgaaggccag    3060
ggcccggatc acacctccgc ccggatcgaa cggttcctgc agctctgggc cgagggctcc    3120
atgacgatcg ccatgcccag caccccgtcc aactatttcc acctcctgcg gcgccatgcg    3180
ctcgacggca tccagcggcc cctgatcgtc ttcacgccga gagcatgct gcgccataag    3240 gccgccgtct cggagatcaa ggacttcacc gagatcaaat ccggtcggt gctggaagaa    3300 ccgacctatg aagatggcat cggcgaccgc aataaggtgt cgcgcatcct gctgacctcg    3360
ggcaagctgt actacgagct ggccgcccgc aaggccaaag acaaccggaa cgacctggcc    3420
atcgtccggc tggagcagct ggcgcccctc ccgcgccggc gcctgcgcga accctggat    3480 cgctatgaga acgtcaagga gttcttctgg gtgcaggagg aacccgcgaa tcagggcgcc    3540
tggccccgct tcggcctgga gctgccggag ctgctccccg acaagctggc cggcatcaag    3600
cggatcagcc gccgcgcgat gtcggccccg agctcgggct ccagcaaggt ccatgcggtc    3660
gagcagcagg agatcctgga tgaagcgttc ggctga                              3696

<210> SEQ ID NO 3
<211> LENGTH: 1231
<212> TYPE: PRT
<213> ORGANISM: Mycobacterium tuberculosis

<400> SEQUENCE: 3

Met Ala Asn Ile Ser Ser Pro Phe Gly Gln Asn Glu Trp Leu Val Glu
1               5                   10                  15

Glu Met Tyr Arg Lys Phe Arg Asp Asp Pro Ser Ser Val Asp Pro Ser
            20                  25                  30

Trp His Glu Phe Leu Val Asp Tyr Ser Pro Glu Pro Thr Ser Gln Pro
        35                  40                  45

Ala Ala Glu Pro Thr Arg Val Thr Ser Pro Leu Val Ala Glu Arg Ala
    50                  55                  60

Ala Ala Ala Ala Pro Gln Ala Pro Lys Pro Ala Asp Thr Ala Ala
65                  70                  75                  80

Ala Gly Asn Gly Val Val Ala Ala Leu Ala Ala Lys Thr Ala Val Pro
                85                  90                  95

Pro Pro Ala Glu Gly Asp Glu Val Ala Val Leu Arg Gly Ala Ala Ala
            100                 105                 110

Ala Val Val Lys Asn Met Ser Ala Ser Leu Glu Val Pro Thr Ala Thr
        115                 120                 125

Ser Val Arg Ala Val Pro Ala Lys Leu Leu Ile Asp Asn Arg Ile Val
    130                 135                 140

Ile Asn Asn Gln Leu Lys Arg Thr Arg Gly Gly Lys Ile Ser Phe Thr
145                 150                 155                 160

His Leu Leu Gly Tyr Ala Leu Val Gln Ala Val Lys Lys Phe Pro Asn
                165                 170                 175

Met Asn Arg His Tyr Thr Glu Val Asp Gly Lys Pro Thr Ala Val Thr
            180                 185                 190

Pro Ala His Thr Asn Leu Gly Leu Ala Ile Asp Leu Gln Gly Lys Asp
        195                 200                 205

Gly Lys Arg Ser Leu Val Val Ala Gly Ile Lys Arg Cys Glu Thr Met
    210                 215                 220

Arg Phe Ala Gln Phe Val Thr Ala Tyr Glu Asp Ile Val Arg Arg Ala
225                 230                 235                 240

Arg Asp Gly Lys Leu Thr Thr Glu Asp Phe Ala Gly Val Thr Ile Ser
```

```
                    245                 250                 255
Leu Thr Asn Pro Gly Thr Ile Gly Thr Val His Ser Val Pro Arg Leu
                260                 265                 270
Met Pro Gly Gln Gly Ala Ile Ile Gly Val Gly Ala Met Glu Tyr Pro
                275                 280                 285
Ala Glu Phe Gln Gly Ala Ser Glu Glu Arg Ile Ala Glu Leu Gly Ile
            290                 295                 300
Gly Lys Leu Ile Thr Leu Thr Ser Thr Tyr Asp His Arg Ile Ile Gln
305                 310                 315                 320
Gly Ala Glu Ser Gly Asp Phe Leu Arg Thr Ile His Glu Leu Leu Leu
                325                 330                 335
Ser Asp Gly Phe Trp Asp Glu Val Phe Arg Glu Leu Ser Ile Pro Tyr
                340                 345                 350
Leu Pro Val Arg Trp Ser Thr Asp Asn Pro Asp Ser Ile Val Asp Lys
                355                 360                 365
Asn Ala Arg Val Met Asn Leu Ile Ala Ala Tyr Arg Asn Arg Gly His
                370                 375                 380
Leu Met Ala Asp Thr Asp Pro Leu Arg Leu Asp Lys Ala Arg Phe Arg
385                 390                 395                 400
Ser His Pro Asp Leu Glu Val Leu Thr His Gly Leu Thr Leu Trp Asp
                405                 410                 415
Leu Asp Arg Val Phe Lys Val Asp Gly Phe Ala Gly Ala Gln Tyr Lys
                420                 425                 430
Lys Leu Arg Asp Val Leu Gly Leu Leu Arg Asp Ala Tyr Cys Arg His
                435                 440                 445
Ile Gly Val Glu Tyr Ala His Ile Leu Asp Pro Glu Gln Lys Glu Trp
            450                 455                 460
Leu Glu Gln Arg Val Glu Thr Lys His Val Lys Pro Thr Val Ala Gln
465                 470                 475                 480
Gln Lys Tyr Ile Leu Ser Lys Leu Asn Ala Ala Glu Ala Phe Glu Thr
                485                 490                 495
Phe Leu Gln Thr Lys Tyr Val Gly Gln Lys Arg Phe Ser Leu Glu Gly
                500                 505                 510
Ala Glu Ser Val Ile Pro Met Met Asp Ala Ala Ile Asp Gln Cys Ala
            515                 520                 525
Glu His Gly Leu Asp Glu Val Val Ile Gly Met Pro His Arg Gly Arg
            530                 535                 540
Leu Asn Val Leu Ala Asn Ile Val Gly Lys Pro Tyr Ser Gln Ile Phe
545                 550                 555                 560
Thr Glu Phe Glu Gly Asn Leu Asn Pro Ser Gln Ala His Gly Ser Gly
                565                 570                 575
Asp Val Lys Tyr His Leu Gly Ala Thr Gly Leu Tyr Leu Gln Met Phe
                580                 585                 590
Gly Asp Asn Asp Ile Gln Val Ser Leu Thr Ala Asn Pro Ser His Leu
                595                 600                 605
Glu Ala Val Asp Pro Val Leu Glu Gly Leu Val Arg Ala Lys Gln Asp
                610                 615                 620
Leu Leu Asp His Gly Ser Ile Asp Ser Asp Gly Gln Arg Ala Phe Ser
625                 630                 635                 640
Val Val Pro Leu Met Leu His Gly Asp Ala Ala Phe Ala Gly Gln Gly
                645                 650                 655
Val Val Ala Glu Thr Leu Asn Leu Ala Asn Leu Pro Gly Tyr Arg Val
                660                 665                 670
```

-continued

Gly Gly Thr Ile His Ile Ile Val Asn Asn Gln Ile Gly Phe Thr Thr
            675                 680                 685

Ala Pro Glu Tyr Ser Arg Ser Ser Glu Tyr Cys Thr Asp Val Ala Lys
690                 695                 700

Met Ile Gly Ala Pro Ile Phe His Val Asn Gly Asp Asp Pro Glu Ala
705                 710                 715                 720

Cys Val Trp Val Ala Arg Leu Ala Val Asp Phe Arg Gln Arg Phe Lys
                725                 730                 735

Lys Asp Val Val Ile Asp Met Leu Cys Tyr Arg Arg Arg Gly His Asn
                740                 745                 750

Glu Gly Asp Asp Pro Ser Met Thr Asn Pro Tyr Val Tyr Asp Val Val
                755                 760                 765

Asp Thr Lys Arg Gly Ala Arg Lys Ser Tyr Thr Glu Ala Leu Ile Gly
770                 775                 780

Arg Gly Asp Ile Ser Met Lys Glu Ala Glu Asp Ala Leu Arg Asp Tyr
785                 790                 795                 800

Gln Gly Gln Leu Glu Arg Val Phe Asn Glu Val Arg Glu Leu Glu Lys
                805                 810                 815

His Gly Val Gln Pro Ser Glu Ser Val Glu Ser Asp Gln Met Ile Pro
                820                 825                 830

Ala Gly Leu Ala Thr Ala Val Asp Lys Ser Leu Leu Ala Arg Ile Gly
                835                 840                 845

Asp Ala Phe Leu Ala Leu Pro Asn Gly Phe Thr Ala His Pro Arg Val
850                 855                 860

Gln Pro Val Leu Glu Lys Arg Arg Glu Met Ala Tyr Glu Gly Lys Ile
865                 870                 875                 880

Asp Trp Ala Phe Gly Glu Leu Leu Ala Leu Gly Ser Leu Val Ala Glu
                885                 890                 895

Gly Lys Leu Val Arg Leu Ser Gly Gln Asp Ser Arg Arg Gly Thr Phe
                900                 905                 910

Ser Gln Arg His Ser Val Leu Ile Asp Arg His Thr Gly Glu Glu Phe
                915                 920                 925

Thr Pro Leu Gln Leu Leu Ala Thr Asn Ser Asp Gly Ser Pro Thr Gly
                930                 935                 940

Gly Lys Phe Leu Val Tyr Asp Ser Pro Leu Ser Glu Tyr Ala Ala Val
945                 950                 955                 960

Gly Phe Glu Tyr Gly Tyr Thr Val Gly Asn Pro Asp Ala Val Val Leu
                965                 970                 975

Trp Glu Ala Gln Phe Gly Asp Phe Val Asn Gly Ala Gln Ser Ile Ile
                980                 985                 990

Asp Glu Phe Ile Ser Ser Gly Glu Ala Lys Trp Gly Gln Leu Ser Asn
                995                 1000                1005

Val Val Leu Leu Leu Pro His Gly His Glu Gly Gln Gly Pro Asp
    1010                1015                1020

His Thr Ser Ala Arg Ile Glu Arg Phe Leu Gln Leu Trp Ala Glu
    1025                1030                1035

Gly Ser Met Thr Ile Ala Met Pro Ser Thr Pro Ser Asn Tyr Phe
    1040                1045                1050

His Leu Leu Arg Arg His Ala Leu Asp Gly Ile Gln Arg Pro Leu
    1055                1060                1065

Ile Val Phe Thr Pro Lys Ser Met Leu Arg His Lys Ala Ala Val
    1070                1075                1080

Ser Glu Ile Lys Asp Phe Thr Glu Ile Lys Phe Arg Ser Val Leu
    1085                1090                1095

Glu Glu Pro Thr Tyr Glu Asp Gly Ile Gly Asp Arg Asn Lys Val
    1100                1105                1110

Ser Arg Ile Leu Leu Thr Ser Gly Lys Leu Tyr Tyr Glu Leu Ala
    1115                1120                1125

Ala Arg Lys Ala Lys Asp Asn Arg Asn Asp Leu Ala Ile Val Arg
    1130                1135                1140

Leu Glu Gln Leu Ala Pro Leu Pro Arg Arg Leu Arg Glu Thr
    1145                1150                1155

Leu Asp Arg Tyr Glu Asn Val Lys Glu Phe Phe Trp Val Gln Glu
    1160                1165                1170

Glu Pro Ala Asn Gln Gly Ala Trp Pro Arg Phe Gly Leu Glu Leu
    1175                1180                1185

Pro Glu Leu Leu Pro Asp Lys Leu Ala Gly Ile Lys Arg Ile Ser
    1190                1195                1200

Arg Arg Ala Met Ser Ala Pro Ser Ser Gly Ser Ser Lys Val His
    1205                1210                1215

Ala Val Glu Gln Gln Glu Ile Leu Asp Glu Ala Phe Gly
    1220                1225                1230

<210> SEQ ID NO 4
<211> LENGTH: 3696
<212> TYPE: DNA
<213> ORGANISM: Mycobacterium tuberculosis

<400> SEQUENCE: 4
atggccaaca tcagcagccc cttcggccag aatgaatggc tcgtggagga gatgtaccgg      60
aagttccggg atgatcccag ctcggtcgat ccgtcgtggc acgagttcct ggtcgactat     120
agccccgaac ccacctccca gccggcggcc gagcccacgc gggtgacctc cccgctggtc     180
gcggaacgcg ccgcggcggc ggccccccag gccccgccga acccgccga tacgccgcc      240 gcgggcaacg cgtcgtcgc ggccctggcc gcgaagaccg ccgtgccccc cccgccgag      300 ggcgacgagg tggcggtgct ccgggcgcc ccgcggcc tggtcaagaa catgagcgcc        360
tccctcgaag tgccgaccgc caccagcgtc cgggcggtgc cggccaagct gctgatcgat    420
aatcggatcg tcatcaacaa tcagctgaaa cggacccgcg cggcaagat cagcttcacc    480 catctgctcg gctatgcgct ggtccaggcc gtgaagaagt cccccaacat gaatcgccac    540
tataccgaag tcgacggcaa acccaccgcc gtgaccccgg cgcacacgaa cctcggcctg    600
gcgatcgacc tgcagggcaa ggacggcaag cggagcctcg tggtggccgg catcaaacgg    660
tgcgagacga tgcggttcgc gcagttcgtg acgccctatg aggatatcgt gcgccgcgcc    720
cgggacggca aactgaccac cgaagacttc gccggcgtca cgatctcgct gaccaacccg    780
ggcaccatcg gcacggtcca ttcggtcccg cgcctcatgc cgggccaggg cgccatcatc    840
ggcgtgggcg cgatggaata tcccgccgag ttccagggcg cctccgagga gcggatcgcc    900
gagctgggca tcgcaaaact catcacgctg acctccacgt atgaccaccg catcatccag    960
ggcgcggaaa cggcgacttt cctccggacg atccatgagc tgctgctctc cgacggcttc   1020
tgggatgaag tgttccgcga gctgtcgatc ccctatctcc cggtgcgctg gagcaccgac   1080
aacccggact cgatcgtgga caaaaacgcc cgcgtcatga atctgatcgc cgcgtaccgc   1140
aatcggggcc acctcatggc ggacacggac cccctgcgc tcgataaggc ccggttccgc    1200
tcccacccca cctcgaagt cctgacccac ggcctgaccc tgtgggacct ggatcgcgtc    1260

```
ttcaaggtcg atggcttcgc cggcgcccag tataagaagc tgcgcgatgt gctgggcctg    1320
ctccgcgatg cctattgccg gcatatcggc gtggagtacg cccacatcct ggaccccgag    1380
cagaaagaat ggctggaaca gcgcgtcgaa acgaagcacg tcaagcccac cgtcgcgcag    1440
cagaaataca tcctcagcaa actcaacgcc gccgaagcgt tcgaaacgtt cctccagacg    1500
aagtacgtgg ccagaaacg cttcagcctg gaaggcgcgg agagcgtcat ccccatgatg    1560
gacgccgcca tcgaccagtg cgccgaacac ggcctggatg aagtggtcat cggcatgccg    1620
caccgcggcc ggctcaacgt cctggccaat atcgtgggca agccctacag ccagatcttc    1680
accgagttcg aaggcaacct gaacccgtcg caggcgcacg gctcgggcga tgtcaagtac    1740
catctcggcg ccacgggcct gtatctgcag atgttcggcg acaacgacat ccaggtgtcc    1800
ctgacggcga accccagcca cctggaggcg gtcgatcccg tcctggaagg cctggtgcgg    1860
gccaagcagg atctcctcga ccacggctcg atcgactccg atggccagcg ggcgttcagc    1920
gtggtgcccc tcatgctgca tggcgacgcg gcgttcgcgg gccagggcgt ggtggcggaa    1980
accctcaacc tcgcgaacct cccgggctat cgggtgggcg gcaccatcca tatcatcgtg    2040
aacaaccaga tcggcttcac cacgcgcgcg gaatattccc ggagctcgga atattgcacg    2100
gacgtggcca agatgatcgg cgccccgatc ttccacgtca atggcgatga cccggaggcc    2160
tgtgtgtggg tcgcccggct ggccgtcgat ttccgccagc gcttcaaaaa agatgtggtc    2220
atcgacatgc tctgctaccg ccgccggggc cataatgagg gcgacgaccc ctccatgacg    2280
aacccgtacg tctacgacgt ggtcgacacc aagcgcggcg cccgcaagtc ctatacggag    2340
gcgctcatcg gccgcggcga catctcgatg aaggaagcgg aagacgcgct ccgcgactac    2400
cagggccagc tggagcgcgt cttcaacgaa gtgcgggaac tcgaaaagca tggcgtgcag    2460
ccctccgaat cggtggagag cgatcagatg atcccggccg gctggccac cgccgtcgat    2520 aaaagcctgc tcgcccgcat cggcgacgcc ttcctggccc tgccgaacgg cttcacggcc    2580
catccccgcg tccagccggt gctggagaaa cgccgcgaaa tggcctacga gggcaagatc    2640
gattgggcct tcggcgagct gctggcgctc ggcagcctgg tggccgaagg caagctcgtg    2700
cggctctccg gccaggactc gcggcgcggc acgttctcgc agcgccattc cgtgctgatc    2760
gaccggcaca ccggcgaaga gttcaccccc ctccagctgc tggccaccaa ttcggacggc    2820
agcccgacgg gcgcaagtt cctggtctat gactccccgc tgagcgagta tgccgccgtc    2880
ggcttcgagt atggctacac cgtcggcaat ccggacgcgg tcgtgctgtg ggaagcgcag    2940
ttcggcgact cgtgaacgg cgcccagtcg atcatcgatg agttcatctc gtcgggcgaa    3000
gccaagtggg gccagctcag caacgtggtg ctcctgctcc gcacggcca cgagggccag    3060 ggcccggatc atacgagcgc ccgcatcgag cggttcctgc agctgtgggc cgagggctcc    3120
atgacgatcg cgatgccctc gacgccgtcc aactacttcc acctgctgcg ccggcacgcg    3180
ctggacggca tccagcgccc gctgatcgtc ttcaccccca agagcatgct ccggcacaaa    3240
gccgccgtgt ccgagatcaa ggacttcacg gagatcaaat tccggagcgt gctggaggag    3300
cccacgtacg aggacggcat cggcgaccgc aacaaggtgt cccgcatcct cctgacgagc    3360
ggcaagctgt actacgagct cgccgcccgc aaggccaagg ataaccggaa cgacctggcc    3420
atcgtgcgcc tcgaacagct ggccccgctg ccgcgccgcc ggctgcggga aaccctggac    3480
cgctacgaga acgtcaaaga gttcttctgg gtccaggaag aaccggccaa ccagggcgcg    3540
tggccgcgct tcggcctgga actgcccgag ctcctgccgg acaagctggc cggcatcaag    3600
```

```
cgcatctcgc ggcgggcgat gagcgccccg tcgagcggct cctccaaggt gcatgccgtg    3660
gagcagcagg aaatcctgga cgaggcgttc ggctga                              3696
```

<210> SEQ ID NO 5
<211> LENGTH: 1245
<212> TYPE: PRT
<213> ORGANISM: Corynebacterium terpenotabidum

<400> SEQUENCE: 5

| | | | | | | | | | | | | | | |
|---|---|---|---|---|---|---|---|---|---|---|---|---|---|---|
| Met | Asn | Ser | Thr | Asn | Phe | Gly | Ser | Asn | Gly | Trp | Leu | Val | Asp | Gln | Met |
| 1 | | | | 5 | | | | | 10 | | | | | 15 | |
| His | Gln | Gln | Phe | Lys | Glu | Asp | Pro | Gln | Ser | Val | Asp | Lys | Glu | Trp | Arg |
| | | | 20 | | | | | 25 | | | | | 30 | | |
| Asp | Phe | Phe | Thr | Ala | Gly | Ser | Ala | Ser | Gly | Pro | Asp | Ala | Pro | Glu | Thr |
| | | 35 | | | | | 40 | | | | | 45 | | | |
| Thr | Ala | Pro | Thr | Thr | Thr | Ala | Ala | Thr | Thr | Thr | Ala | Thr | Thr | Ser | |
| 50 | | | | | 55 | | | | | 60 | | | | | |
| Ala | Ala | Pro | Ala | Thr | Ala | Gln | Thr | Ser | Gly | Val | Ala | Val | Pro | Ser | Thr |
| 65 | | | | | 70 | | | | | 75 | | | | | 80 |
| Ala | Gly | Thr | Thr | His | Arg | Ala | Ser | Ala | Ala | Thr | Val | Ala | Ser | Asn | |
| | | | | 85 | | | | | 90 | | | | | 95 | |
| Val | Ala | Leu | Ser | Ala | Asn | Pro | Ile | Pro | Glu | Arg | Val | Ala | Pro | Pro | Ala |
| | | | 100 | | | | | 105 | | | | | 110 | | |
| Pro | Lys | Asp | Ala | Ala | Glu | Pro | Leu | Thr | Pro | Gly | Glu | Ala | Ala | Leu | Lys |
| | | | 115 | | | | | 120 | | | | | 125 | | |
| Gly | Ala | Gln | Arg | Ala | Ile | Ala | Lys | Asn | Met | Asp | Ala | Ser | Leu | Asp | Ile |
| 130 | | | | | 135 | | | | | 140 | | | | | |
| Pro | Thr | Ala | Thr | Thr | Val | Arg | Asp | Met | Pro | Ala | Lys | Leu | Met | Phe | Glu |
| 145 | | | | | 150 | | | | | 155 | | | | | 160 |
| Asn | Arg | Ala | Met | Ile | Asn | Asn | His | Leu | Arg | Ser | Gln | Gly | Arg | Gly | Lys |
| | | | | 165 | | | | | 170 | | | | | 175 | |
| Ile | Ser | Phe | Thr | His | Ile | Leu | Gly | Trp | Ala | Met | Val | Asn | Ala | Val | Lys |
| | | | 180 | | | | | 185 | | | | | 190 | | |
| Ala | His | Pro | Thr | Met | Asn | Asn | Asn | Tyr | Lys | Val | Ile | Asp | Gly | Lys | Pro |
| | | | 195 | | | | | 200 | | | | | 205 | | |
| Ser | Val | Val | Thr | Pro | Glu | His | Ile | Asn | Leu | Gly | Leu | Ala | Ile | Asp | Leu |
| | | 210 | | | | | 215 | | | | | 220 | | | |
| Val | Ser | Lys | Asn | Gly | Ser | Arg | Asn | Leu | Val | Val | Ala | Ala | Ile | Arg | Ala |
| 225 | | | | | 230 | | | | | 235 | | | | | 240 |
| Cys | Glu | Thr | Phe | Asp | Phe | Glu | Gly | Phe | Val | Asp | Ala | Tyr | Glu | Asp | Ile |
| | | | | 245 | | | | | 250 | | | | | 255 | |
| Val | Val | Arg | Ala | Arg | Lys | Gly | Lys | Leu | Thr | Met | Asp | Asp | Phe | Ser | Gly |
| | | | 260 | | | | | 265 | | | | | 270 | | |
| Val | Thr | Ile | Gln | Leu | Thr | Asn | Pro | Gly | Gly | Ile | Gly | Thr | Arg | His | Ser |
| | | 275 | | | | | 280 | | | | | 285 | | | |
| Val | Pro | Arg | Leu | Thr | His | Gly | Gln | Gly | Ala | Ile | Ile | Gly | Val | Gly | Ala |
| | | 290 | | | | | 295 | | | | | 300 | | | |
| Met | Asp | Tyr | Pro | Ala | Glu | Phe | Ala | Gly | Ala | Ser | Glu | Asp | Arg | Leu | Ala |
| 305 | | | | | 310 | | | | | 315 | | | | | 320 |
| Asp | Leu | Gly | Val | Gly | Lys | Leu | Val | Thr | Ile | Thr | Ser | Thr | Tyr | Asp | His |
| | | | | 325 | | | | | 330 | | | | | 335 | |
| Arg | Ile | Ile | Gln | Gly | Ala | Glu | Ser | Gly | Glu | Phe | Leu | Arg | Asp | Met | Ser |
| | | | 340 | | | | | 345 | | | | | 350 | | |
| Arg | Gln | Leu | Ile | Asp | Asp | Gly | Phe | Trp | Asp | Gly | Ile | Tyr | Ala | Ser | Leu |

355                 360                 365
Lys Val Pro Tyr Ala Pro Val Arg Trp Ser Gln Asp Val Pro Asn Thr
    370                 375                 380
Gly Val Asp Lys Ser Thr Arg Val Met Gln Leu Ile Glu Ala Tyr Arg
385                 390                 395                 400
Ser Arg Gly His Leu Ile Ala Asp Ile Asp Pro Leu His Trp Thr Gln
                405                 410                 415
Pro Gly Leu Pro Val Pro Asp His Ser Asp Leu Asp Ile Glu Ser His
                420                 425                 430
Gly Leu Thr Leu Trp Asp Phe Asp Arg Arg Phe His Val Gly Gly Phe
                435                 440                 445
Ala Gly Arg Glu Ser Met Thr Leu Arg Glu Val Leu Ala Thr Leu Arg
            450                 455                 460
Lys Ala Tyr Thr Leu Lys Val Gly Ser Glu Tyr Thr His Ile Leu Asp
465                 470                 475                 480
Lys Asp Glu Arg Leu Trp Leu Gln Glu His Ile Glu Ala Gly Gln Gln
                485                 490                 495
Lys Leu Ser Asn Pro Glu Gln Lys Tyr Leu Leu Gln Thr Leu Asn Ser
                500                 505                 510
Ala Glu Ala Phe Glu Asn Phe Leu Gln Thr Lys Tyr Ile Gly Gln Lys
            515                 520                 525
Arg Phe Ser Leu Glu Gly Ala Glu Ala Leu Ile Pro Leu Leu Asp Ala
        530                 535                 540
Ala Ala Asp Gln Ala Ala Glu Gln Gly Leu Glu Glu Val Val Ile Gly
545                 550                 555                 560
Met Pro His Arg Gly Arg Leu Asn Val Leu Ala Asn Ile Val Gly Lys
                565                 570                 575
Pro Tyr Ser Thr Ile Phe Gly Glu Phe Glu Gly Asn Ile Glu Pro Ala
                580                 585                 590
Ala Ala Gly Gly Ser Gly Asp Val Lys Tyr His Leu Gly Ala Glu Gly
                595                 600                 605
Val Tyr Thr Gln Met Phe Gly Asp Asn Asp Ile Lys Val Thr Leu Thr
        610                 615                 620
Ala Asn Pro Ser His Leu Glu Ala Val Asn Pro Val Met Glu Gly Leu
625                 630                 635                 640
Ala Arg Ala His Gln Asp Ile Ser Pro Arg Ala Glu Asp Arg Pro Ile
                645                 650                 655
Met Pro Ile Leu Met His Gly Asp Ala Ala Phe Thr Gly Leu Gly Ile
                660                 665                 670
Val Pro Glu Thr Ile Asn Met Ala Gln Leu Arg Gly Tyr Ser Val Gly
            675                 680                 685
Gly Thr Val His Val Val Asn Asn Gln Ile Gly Phe Thr Thr Thr
        690                 695                 700
Pro Asp Arg Gly Arg Ser Thr His Tyr Ala Thr Asp Ile Ala Lys Gly
705                 710                 715                 720
Phe Asp Cys Pro Val Phe His Val Asn Gly Asp Asp Pro Glu Ala Val
                725                 730                 735
Val Trp Val Ala Arg Leu Ala Val Glu Tyr Arg Arg Phe Gly Lys
            740                 745                 750
Asp Val Phe Ile Asp Leu Val Cys Tyr Arg Arg Gly His Asn Glu
            755                 760                 765
Ala Asp Asp Pro Ser Met Thr Gln Pro Glu Leu Tyr Ser Ile Ile Glu
        770                 775                 780

-continued

Ser Arg Pro Thr Val Arg Ser Leu Tyr His Asp Thr Leu Val Gly Arg
785                 790                 795                 800

Gly Asp Ile Thr Ala Glu Asp Ala Gln Arg Ala Ala Asp Phe His
            805                 810                 815

Gly Gln Leu Glu Ser Val Phe Asn Gln Val Lys Glu Gly Val Lys Gly
                820                 825                 830

Val Thr Pro Ala Ala Gln Thr Gly Ile Ala Gly Gln Asp Leu Ser
            835                 840                 845

Thr Gly Leu Asp Thr Ser Ile Thr Ala Asp Val Ile Ala Glu Ile Gly
850                 855                 860

Asp Ser Tyr Thr Val Asp Ala Pro Glu Asp Phe Asn Val His Gln Arg
865                 870                 875                 880

Val Lys Pro Val Val Lys Arg Arg His Gln Met Ser Arg Gln Gly Lys
                885                 890                 895

Ile Asp Trp Ala Phe Gly Glu Leu Leu Ala Phe Gly Ser Leu Ala Arg
            900                 905                 910

Glu Gly Arg Leu Val Arg Leu Ala Gly Glu Asp Ser Gln Arg Gly Thr
            915                 920                 925

Phe Thr Gln Arg His Ala Ile Leu Phe Asp Ser Thr Thr Asn Lys Pro
930                 935                 940

Phe Ser Pro Leu Glu Met Val Ala Arg Asn Ser Gly Asn Gly Ser
945                 950                 955                 960

Phe Arg Ala Phe Asn Ser Pro Leu Thr Glu Tyr Ala Gly Met Gly Phe
            965                 970                 975

Glu Tyr Gly Tyr Ser Val Gly Asn Leu Asp Ala Val Val Ala Trp Glu
            980                 985                 990

Ala Gln Phe Gly Asp Phe Ala Asp Gly Ala Gln Thr Ile Ile Asp Glu
            995                 1000                1005

Tyr Ile Ser Ser Gly Glu Ala Lys Trp Gly Gln Leu Ser Ser Val
    1010                1015                1020

Ile Leu Leu Pro His Gly Tyr Glu Gly Gln Gly Pro Asp His
    1025                1030                1035

Ser Ser Ala Arg Ile Glu Arg Tyr Leu Gln Met Ala Ala Glu Gly
    1040                1045                1050

Ser Met Thr Ile Ala Gln Pro Ser Thr Pro Ala Asn His Phe His
    1055                1060                1065

Leu Leu Arg Arg His Ala Leu Gly Thr Met Arg Pro Leu Val
    1070                1075                1080

Val Phe Thr Pro Lys Ser Met Leu Arg Asn Lys Ala Ala Val Ser
    1085                1090                1095

Ser Val Glu Asp Phe Thr Glu Val Thr Lys Phe Arg Ser Val Leu
    1100                1105                1110

Asp Asp Pro Arg Phe Ala Gly Thr Ala Asp Arg Ser Gly Val
    1115                1120                1125

Lys Thr Val Leu Met Cys Ser Gly Lys Ile Tyr Tyr Asp Leu Glu
    1130                1135                1140

Lys Lys Arg Ala Glu Asp Gly Arg Asp Asp Ile Ala Ile Val Arg
    1145                1150                1155

Val Glu Met Leu His Pro Ile Pro His Asn Arg Ile Arg Glu Thr
    1160                1165                1170

Val Val Glu Gly Tyr Pro Gly Ala Glu Val Arg Trp Val Gln Asp
    1175                1180                1185

-continued

```
Glu Pro Ala Asn Gln Gly Ala Trp Pro Phe Leu Ala Leu Asn Leu
    1190            1195                1200

Pro Glu Arg Ile Pro Gly Phe Thr Met Lys Arg Val Ser Arg Arg
    1205            1210                1215

Ala Gln Ser Ser Thr Ala Thr Gly Val Ala Lys Val His His Leu
    1220            1225                1230

Glu Gln Glu Thr Leu Leu Thr Glu Ala Phe Ala Thr
    1235            1240                1245

<210> SEQ ID NO 6
<211> LENGTH: 3738
<212> TYPE: DNA
<213> ORGANISM: Corynebacterium terpenotabidum

<400> SEQUENCE: 6
```

| | | | | | |
|---|---|---|---|---|---|
| atgaactcga | ccaacttcgg | cagcaatggc | tggctggtcg | accagatgca | ccagcagttc | 60 |
| aaggaagatc | cgcagtcggt | cgacaaggaa | tggcgcgact | tcttcaccgc | cggctcggcg | 120 |
| tccggcccgg | atgccccgga | aacgaccgcc | ccgacgacca | ccgccgccac | gaccacgacc | 180 |
| gcgaccacga | gcgcggcccc | cgccaccgcg | cagaccagcg | gcgtggccgt | cccgtccacc | 240 |
| gcgggcacca | cccaccgggc | ctcggccgcc | gcgaccgtgg | cctcgaacgt | ggccctgagc | 300 |
| gcgaacccga | tccccgaacg | ggtcgccccc | ccggccccga | aggacgcggc | cgagccgctg | 360 |
| accccgggcg | aggccgccct | gaaaggcgcc | cagcgggcga | tcgccaaaaa | catggacgcc | 420 |
| agcctggata | tccccaccgc | gacgacggtc | gcgacatgc | cggccaaact | catgttcgaa | 480 |
| aaccgggcca | tgatcaacaa | ccatctgcgc | agccagggcc | ggggcaagat | ctcgttcacc | 540 |
| cacatcctgg | gctgggcgat | ggtcaacgcc | gtgaaagccc | accccaccat | gaataacaat | 600 |
| tacaaggtca | tcgacggcaa | gccgtcggtc | gtgaccccg | aacatatcaa | tctcggcctc | 660 |
| gccatcgatc | tggtcagcaa | aaacggctcg | cggaacctgg | tcgtggccgc | catccgcgcg | 720 |
| tgcgaaacct | tcgacttcga | gggcttcgtg | gacgcctacg | aggacatcgt | ggtccgcgcc | 780 |
| cggaagggca | aactgacgat | ggacgacttc | agcggcgtca | ccatccagct | gaccaacccg | 840 |
| ggcggcatcg | gcacccgcca | ctccgtcccg | gcctgacgc | acggccaggg | cgcgatcatc | 900 |
| ggcgtgggcg | cgatggacta | cccggcggag | ttcgccggcg | cctcggaaga | ccgcctcgcg | 960 |
| gacctgggcg | tgggcaaact | ggtgaccatc | acgagcacgt | atgaccaccg | gatcatccag | 1020 |
| ggcgccgagt | cgggcgagtt | cctgcgcgac | atgagccgcc | agctcatcga | cgatggcttc | 1080 |
| tgggacggca | tctacgccag | cctgaaagtc | ccgtatgcgc | ccgtgcggtg | gtcgcaggac | 1140 |
| gtgcccaaca | ccggcgtcga | caagagcacc | cgcgtcatgc | agctcatcga | ggcgtaccgc | 1200 |
| tcccgcggcc | acctgatcgc | cgacatcgac | ccgctgcatt | ggacccagcc | cggcctgccg | 1260 |
| gtgccggacc | atagcgacct | ggacatcgaa | tcccacggcc | tgaccctgtg | ggacttcgac | 1320 |
| cggcgcttcc | acgtcggcgg | cttcgccggc | cgcgaatcga | tgaccctgcg | ggaagtgctg | 1380 |
| gccacgctgc | ggaaggcgta | tacgctgaag | gtcggctccg | aatatacca | tatcctcgac | 1440 |
| aaggacgaac | gcctctggct | ccaggagcac | atcgaggccg | ccagcagaa | gctcagcaac | 1500 |
| cccgaacaga | gtatctgct | gcagacgctg | aactccgccg | aggcgttcga | aaacttcctg | 1560 |
| cagaccaaat | atatcggcca | gaagcgcttc | agcctggaag | gcgccgaagc | cctgatcccg | 1620 |
| ctgctcgatg | ccgccgcgga | tcaggccgcc | gaacagggcc | tcgaagaggt | ggtgatcggc | 1680 |
| atgccgcatc | gcgccggct | gaatgtcctc | gcgaacatcg | tcgcaaacc | gtacagcacc | 1740 |
| atcttcggcg | agttcgaggg | caacatcgag | ccggccgccg | cggcggctc | cggcgatgtc | 1800 |

```
aaataccatc tgggcgccga gggcgtgtat acgcagatgt tcggcgacaa cgacatcaag    1860
gtgacgctga ccgccaaccc ctcccacctg gaagcggtca atcccgtcat ggagggcctc    1920
gcgcgggcgc atcaggatat ctcgccccgg gcggaggatc ggccgatcat gccgatcctg    1980
atgcacggcg acgccgcctt caccggcctg gcatcgtcc cggaaacgat caacatggcc     2040
cagctgcggg gctactccgt gggcggcacg gtgcatgtgg tggtcaacaa ccagatcggc    2100
ttcaccacga cgccggatcg cggccggtcc acgcactacg cgacggacat cgcgaagggc    2160
ttcgattgcc ccgtcttcca cgtcaacggc gacgatccgg aggccgtcgt ctgggtcgcc    2220
cggctcgccg tggaataccg cgccgcttc ggcaaagacg tgttcatcga cctggtgtgt    2280
tatcggcgcc gcggccataa tgaagccgat gaccccagca tgacccagcc gaactgtac     2340 agcatcatcg agagccggcc gacggtccgg agcctgtatc atgacacgct ggtcggccgg    2400
ggcgacatca cggcggaaga cgcccagcgg gccgccgacg acttccacgg ccagctggaa    2460
agcgtcttca accaggtcaa ggaaggcgtg aagggcgtga ccccggcggc ccagaccggc    2520
atcgccggcg ccaggacct gtccaccggc ctcgacacca gcatcaccgc ggatgtgatc    2580
gccgagatcg gcgattccta taccgtggat gcccccgaag acttcaatgt ccaccagcgc    2640
gtgaagcccg tggtcaaacg gcggcaccag atgtcgcgcc agggcaagat cgattgggcg    2700
ttcggcgaac tcctcgcgtt cggctcgctg gcccgggaag gccggctggt ccggctcgcc    2760
ggcgaggact cgcagcgggg caccttcacc cagcggcacg ccatcctgtt cgacagcacc    2820
accaacaagc ccttcagccc cctggaaatg gtcgcgcgga actccggcaa cggcggctcg    2880
ttccgggcct tcaattcccc gctgacggaa tatgcgggca tgggcttcga gtatggctac    2940
tcggtgggca acctggatgc cgtggtggcc tgggaggcgc agttcggcga cttcgcggac    3000
ggcgcccaga cgatcatcga cgagtacatc tcctccggcg aggccaaatg gggccagctg    3060
tcgagcgtga tcctgctgct cccgcacggc tacgagggcc agggcccgga ccactcctcc    3120
gcccgcatcg aacgctacct gcagatggcc gccgaaggct cgatgaccat cgcgcagccg    3180
tcgacgcccg ccaaccactt ccacctgctc cgccgccacg ccctgggcac catgcggcgc    3240
ccgctggtcg tcttcacccc gaagtccatg ctgcgcaaca aggcggccgt ctcctcggtc    3300
gaagacttca cggaagtcac caagttccgg agcgtcctgg atgaccccg gttcgcggat    3360 ggcaccgcca ccggagcgg cgtcaagacg gtgctgatgt gttccggcaa gatctactat    3420
gatctggaga agaagcgggc ggaagacggc cgcgacgata tcgccatcgt ccgcgtcgaa    3480
atgctgcatc ccatcccgca taaccgcatc cgcgaaacgg tcgtggaggg ctaccccggc    3540
gcggaggtgc gctgggtgca ggacgagccc gccaaccagg gcgcctggcc gttcctggcc    3600
ctcaacctcc ccgagcgcat ccccggcttc accatgaagc gcgtcagccg ccgggcccag    3660
agcagcaccg ccacgggcgt ggccaaggtc caccatctgg agcaggagac gctgctgacc    3720
gaagccttcg ccacctga                                                  3738
```

<210> SEQ ID NO 7
<211> LENGTH: 1258
<212> TYPE: PRT
<213> ORGANISM: Rhodococcus jostii

<400> SEQUENCE: 7

```
Met Ser Ser Ser Thr Ser Gln Phe Gly Gln Asn Gln Trp Leu Val
1               5                   10                  15

Asp Glu Met Tyr Gln Arg Phe Gln Asp Asp Pro Ser Ser Val Asp Ala
```

-continued

```
               20                  25                  30
Ser Trp His Glu Phe Leu Thr Asp Tyr Ser Pro Asp Ala Ala Lys
             35                  40                  45
Ala Gly Ala Ala Asn Gly His Gly Thr Asn Gly Thr Thr Ala Ala
 50                  55                  60
Pro Ala Ala Ala Pro Ser Ala Lys Ala Ala Thr Pro Pro Val Pro Glu
 65                  70                  75                  80
Ser Glu Thr Ala Pro Lys Pro Gln Thr Lys Thr Ala Asn Gly Ala Ala
                 85                  90                  95
Pro Lys Ala Ala Pro Asn Gly Ala Ala Pro Lys Ala Ala Pro Lys
                100                 105                 110
Thr Glu Ala Pro Lys Lys Ala Ala Pro Ala Lys Glu Thr Ala Ala Thr
             115                 120                 125
Asp Ala Lys Ala Ser Ala Pro Ala Pro Ala Val Glu Glu Ser Lys Val
         130                 135                 140
Leu Arg Gly Ala Ala Ala Val Ala Lys Asn Met Ser Ala Ser Leu
145                 150                 155                 160
Ala Ile Pro Thr Ala Thr Ser Val Arg Ala Ile Pro Ala Lys Leu Met
                 165                 170                 175
Phe Asp Asn Arg Ile Val Ile Asn Asn His Leu Ala Arg Thr Arg Gly
                 180                 185                 190
Gly Lys Ile Ser Phe Thr His Leu Leu Gly Tyr Ala Ile Val Gln Ala
             195                 200                 205
Val Lys Ala Phe Pro Asn Met Asn Arg His Phe Ala Glu Ile Asp Gly
         210                 215                 220
Lys Pro Asn Ala Val Thr Pro Ala His Thr Asn Leu Gly Leu Ala Ile
225                 230                 235                 240
Asp Leu Pro Gly Lys Asp Gly Ser Arg Ser Leu Val Val Ala Ala Ile
                 245                 250                 255
Lys Asn Thr Asp Thr His Asn Phe Thr Gln Phe Tyr Ser Ala Tyr Glu
                 260                 265                 270
Asp Ile Val Arg Arg Ala Arg Asp Gly Lys Leu Thr Ala Glu Asp Phe
             275                 280                 285
Ser Gly Val Thr Ile Ser Leu Thr Asn Pro Gly Gly Ile Gly Thr Val
         290                 295                 300
His Ser Val Pro Arg Leu Met Asn Gly Gln Gly Ala Ile Ile Gly Ala
305                 310                 315                 320
Gly Ala Met Glu Tyr Pro Ala Glu Phe Gln Gly Ala Ser Asp Glu Arg
                 325                 330                 335
Leu Ala Glu Ile Gly Val Gly Lys Leu Met Thr Leu Thr Ser Thr Tyr
             340                 345                 350
Asp His Arg Ile Ile Gln Gly Ala Glu Ser Gly Asp Phe Leu Arg Thr
         355                 360                 365
Ile His Asn Leu Leu Ile Ser Asp Glu Phe Tyr Asp Glu Ile Phe His
370                 375                 380
Ala Leu His Ile Pro Tyr Glu Pro Val Arg Trp Arg Lys Asp Val Pro
385                 390                 395                 400
Glu Gly Ala Val Asp Lys Asn Thr Arg Val Leu Glu Leu Ile Ala Ala
                 405                 410                 415
Tyr Arg Asn Arg Gly His Leu Met Ala Asp Thr Asp Pro Leu Gln Phe
             420                 425                 430
Val Lys Asp Lys Phe Arg Ser His Pro Asp Leu Asp Val Arg Thr His
         435                 440                 445
```

```
Asp Leu Thr Leu Trp Asp Leu Asp Arg Glu Phe Lys Val Gly Gly Phe
    450                 455                 460

His Gly Gln Glu Lys Met Lys Leu Arg Asp Val Leu Ser Val Leu Arg
465                 470                 475                 480

Asp Ala Tyr Cys Arg His Val Gly Val Glu Tyr Thr His Ile Leu Glu
                485                 490                 495

Pro Glu Gln Gln Gln Trp Leu Gln Asp Arg Val Glu Ala His His Val
                500                 505                 510

Lys Pro Thr Val Ala Gln Gln Lys Tyr Ile Leu Ser Lys Leu Asn Ala
            515                 520                 525

Ala Glu Ala Phe Glu Thr Phe Leu Gln Thr Lys Tyr Val Gly Gln Lys
    530                 535                 540

Arg Phe Ser Leu Glu Gly Ala Glu Ser Val Ile Pro Met Met Asp Ala
545                 550                 555                 560

Val Ile Asp Gln Ala Ala Glu His Gln Leu Asp Glu Val Val Ile Gly
                565                 570                 575

Met Pro His Arg Gly Arg Leu Asn Val Leu Ala Asn Ile Val Gly Lys
                580                 585                 590

Pro Tyr Ser Lys Ile Phe Thr Glu Phe Glu Gly Asn Met Asn Pro Ala
            595                 600                 605

Ala Ala His Gly Ser Gly Asp Val Lys Tyr His Leu Gly Ala Glu Gly
    610                 615                 620

Thr Tyr Ile Gln Met Phe Gly Asp Asn Asp Ile Thr Val Ser Leu Thr
625                 630                 635                 640

Ala Asn Pro Ser His Leu Glu Ala Val Asp Pro Val Leu Glu Gly Leu
                645                 650                 655

Val Arg Ala Lys Gln Asp Ile Leu Asp Lys Gly Glu Asp Gly Phe Thr
                660                 665                 670

Val Leu Pro Leu Met Leu His Gly Asp Ala Ala Phe Ala Gly Gln Gly
            675                 680                 685

Val Val Ala Glu Thr Leu Asn Leu Ala Leu Leu Arg Gly Tyr Arg Thr
    690                 695                 700

Gly Gly Thr Val His Ile Val Val Asn Asn Gln Val Gly Phe Thr Thr
705                 710                 715                 720

Ala Pro Glu Tyr Ser Arg Ser Ser Glu Tyr Cys Thr Asp Val Ala Lys
                725                 730                 735

Met Ile Gly Ala Pro Ile Phe His Val Asn Gly Asp Asp Pro Glu Ala
                740                 745                 750

Cys Val Trp Val Ala Gln Leu Ala Val Asp Phe Arg Glu Lys Phe Gln
            755                 760                 765

Lys Asp Val Val Ile Asp Met Ile Cys Tyr Arg Arg Gly His Asn
    770                 775                 780

Glu Gly Asp Asp Pro Ser Met Thr Gln Pro Ala Met Tyr Asp Val Ile
785                 790                 795                 800

Asp Thr Lys Arg Ser Val Arg Lys Ser Tyr Thr Glu Ser Leu Ile Gly
                805                 810                 815

Arg Gly Asp Ile Ser Leu Lys Glu Ala Glu Asp Ala Leu Arg Asp Tyr
                820                 825                 830

Gln Gly Gln Leu Glu Arg Val Phe Asn Glu Val Arg Glu Leu Glu Lys
            835                 840                 845

Tyr Thr Pro Glu Pro Ser Glu Ser Val Glu Leu Asp Gln Val Leu Pro
    850                 855                 860
```

-continued

```
Thr Lys Leu Lys Thr Ser Val Asp Glu Ser Val Leu Glu Arg Ile Gly
865                 870                 875                 880

Asp Ala Phe Val Asn Val Pro Glu Gly Phe Thr Val His Pro Arg Val
                885                 890                 895

Lys Pro Val Ile Glu Lys Arg Arg Glu Met Ser Arg Glu Gly Lys Ile
            900                 905                 910

Asp Trp Ala Phe Ala Glu Leu Leu Ala Phe Gly Ser Leu Val Asp Gln
        915                 920                 925

Gly Lys Met Val Arg Leu Ser Gly Gln Asp Ser Lys Arg Gly Thr Phe
    930                 935                 940

Thr Gln Arg His Ser Val Leu Ile Asp Arg Lys Thr Gly Ala Glu Tyr
945                 950                 955                 960

Thr Pro Leu Gln Asn Leu Gly Ser Glu Asn Pro Gly Lys Phe Leu Val
                965                 970                 975

Tyr Asp Ser Ala Leu Ser Glu Phe Ala Ala Val Gly Phe Glu Tyr Gly
            980                 985                 990

Tyr Ser Val Gly Asn Pro Asp Ala Leu Val Leu Trp Glu Ala Gln Phe
        995                 1000                1005

Gly Asp Phe Val Asn Gly Ala Gln Ser Ile Ile Asp Glu Phe Ile
    1010                1015                1020

Ser Ser Gly Glu Ala Lys Trp Gly Gln Leu Ser Asp Val Val Leu
    1025                1030                1035

Leu Leu Pro His Gly His Glu Gly Gln Gly Pro Asp His Thr Ser
    1040                1045                1050

Gly Arg Ile Glu Arg Phe Leu Gln Leu Cys Ala Glu Gly Ser Met
    1055                1060                1065

Thr Val Ala Val Pro Ser Thr Pro Ala Ser Tyr Phe His Leu Leu
    1070                1075                1080

Arg Arg His Ser Leu Asp Gly Ile Arg Arg Pro Leu Val Val Phe
    1085                1090                1095

Thr Pro Lys Ser Met Leu Arg Asn Lys Ala Ala Val Ser Asp Val
    1100                1105                1110

Glu Asp Phe Thr Thr Gly Lys Phe Arg Ser Val Phe Glu Glu Pro
    1115                1120                1125

Thr Tyr Glu Thr Gly Asp Ala Glu Arg Asp Lys Val Arg Arg Val
    1130                1135                1140

Leu Leu Val Ser Gly Lys Leu Tyr Trp Glu Leu Leu Ala Lys Lys
    1145                1150                1155

Gln Lys Asp Asn Arg Glu Asp Ile Ala Ile Val Arg Ile Glu Gln
    1160                1165                1170

Leu Tyr Pro Val Pro Ser Arg Arg Leu Arg Glu Thr Leu Asp Arg
    1175                1180                1185

Tyr Pro Asn Ala Thr Glu Phe Arg Trp Val Gln Glu Glu Pro Ala
    1190                1195                1200

Asn Gln Gly Ala Trp Pro Phe Phe Gly Leu Ala Leu Pro Glu Leu
    1205                1210                1215

Leu Pro Asp Lys Leu Ser Gly Ile Lys Arg Ile Ser Arg Arg Ser
    1220                1225                1230

Met Ser Ala Pro Ser Ser Gly Ser Ser Lys Val His Ala Val Glu
    1235                1240                1245

Gln Gln Glu Ile Ile Asp Glu Ala Phe Gly
    1250                1255
```

```
<210> SEQ ID NO 8
<211> LENGTH: 3777
<212> TYPE: DNA
<213> ORGANISM: Rhodococcus jostii

<400> SEQUENCE: 8
atgagctcgt cctcgacctc ccagttcggc cagaaccagt ggctcgtgga tgaaatgtac      60
cagcgcttcc aggatgatcc gtcgtccgtg gacgcctcct ggcatgagtt cctgacggac     120
tatagccccg acgccgccgc caaggcgggc gcggcgaacg ccacggcac caacggcacc     180 accacggcgg cgccggcggc ggcgccgtcc gccaaagccg cgaccccccc ggtccccgag     240
agcgagacgg ccccgaaacc ccagaccaag acggcgaacg gcgcggcgcc gaaagccgcg     300
cccaacggcg cggcgccgaa ggccgcggcc cccaagaccg aggcccccaa gaaggccgcc     360
cccgcgaagg aaacggccgc gacggacgcg aaagcctcgg ccccggcccc cgccgtggag     420
gaatccaagg tgctgcgggg cgccgccgcc gccgtcgcca gaatatgtc cgcgtcgctc     480 gccatcccga ccgccacctc cgtccggggcc atcccggcga agctgatgtt cgacaaccgc     540
atcgtcatca acaaccacct ggcgcggacc cggggcggca agatctcgtt cacccatctg     600
ctgggctacg cgatcgtgca ggccgtgaaa gcgttcccca acatgaaccg ccacttcgcg     660
gagatcgatg gcaagcccaa tgcggtgacc cccgcccata ccaatctggg cctcgcgatc     720
gatctgccgg gcaaagatgg cagccgctcg ctggtcgtcg cggccatcaa gaacaccgat     780
acgcacaatt tcacccagtt ctatagcgcc tacgaggata tcgtgcgccg ggcgcgggac     840
ggcaaactga ccgccgaaga cttcagcggc gtcacgatct cgctgaccaa cccgggcggc     900
atcggcaccg tccattccgt cccgcgcctg atgaacggcc agggcgccat catcggcgcg     960
ggcgcgatgg agtacccggc cgagttccag gcgcctcgg acgagcggct ggccgaaatc    1020
ggcgtcggca agctgatgac cctcacgagc acctacgatc atcggatcat ccagggcgcc    1080
gaatccggcg acttcctccg gacgatccat aatctgctca tcagcgacga gttctacgac    1140
gaaatcttcc atgccctgca tatcccctat gaacccgtcc ggtggcgcaa agacgtgccc    1200
gaaggcgccg tggataagaa cacccgggtc ctggagctca tcgccgccta ccggaaccgc    1260
ggccacctga tggcggacac cgaccgctg cagttcgtga aggacaagtt ccggtcgcac    1320
ccggacctcg acgtgcgcac ccatgatctg acgctctggg acctggatcg ggagttcaaa    1380
gtgggcggct ccacggccca ggagaagatg aagctgcgcg atgtcctgtc ggtgctgcgc    1440
gatgcgtatt gtcgccatgt cggcgtggag tacccccaca tcctggagcc ggagcagcag    1500
cagtggctgc aggatcgcgt cgaggccac cacgtcaaac cgacggtcgc ccagcagaag    1560
tatatcctgt ccaaactgaa cgccgccgag gccttcgaga cgttcctgca gacgaagtat    1620
gtcggccaga aacgcttctc gctggagggc cggagagcg tgatccccat gatgacgcc    1680 gtcatcgacc aggccgccga gcatcagctg gacgaggtgg tgatcggcat gccgcatcgg    1740
ggccgcctga atgtcctggc gaacatcgtg gcaagccgt attccaagat cttcaccgag    1800
ttcgagggca acatgaaccc ggcggcggcc cacgcagcg cgacgtgaa gtatcacctg    1860 ggcgccgaag gcacgtatat ccagatgttc ggcgataacg acatcaccgt ctcgctcacc    1920
gcgaacccga ccatctgga agccgtggac ccggtgctgg agggcctggt ccgggccaag    1980
caggacatcc tcgacaaggg cgaagacggc ttcacggtgc tcccctcat gctccacggc    2040 gacgcggcct tcgccggcca gggcgtggtc gccgagacgc tcaacctcgc cctgctgcgc    2100
ggctaccgga ccggcggcac cgtgcacatc gtggtgaaca accaggtcgg cttcacgacc    2160
```

-continued

```
gccccccgagt atagccgctc cagcgagtac tgcacggatg tggcgaagat gatcggcgcc   2220
cccatcttcc acgtcaacgg cgatgacccc gaggcgtgcg tgtgggtggc ccagctggcg   2280
gtggacttcc gcgagaagtt ccagaaggac gtggtcatcg acatgatctg ttatcggcgg   2340
cggggccata tgagggcga cgatccgagc atgacccagc ccgcgatgta cgacgtgatc   2400
gacacgaaac gctccgtccg caaatcctat accgagtcgc tgatcggccg cggcgacatc   2460
tcgctgaagg aagcggagga cgccctgcgc gactatcagg ccagctgga acgggtcttc   2520
aatgaggtgc gcgagctgga gaagtacacg cccgaaccga gcgagagcgt cgagctggac   2580
caggtcctgc ccacgaagct gaaaacctcc gtcgatgaat cggtgctgga gcgcatcggc   2640
gatgccttcg tgaacgtccc ggagggcttc acggtccatc cgcgggtgaa gccggtgatc   2700
gaaaagcgcc gcgagatgag ccgcgaaggc aagatcgact gggccttcgc cgagctgctg   2760
gccttcggct ccctggtgga tcagggcaag atggtgcgcc tctccggcca ggacagcaag   2820
cgcggcacgt tcacccagcg ccactcggtc ctcatcgacc gcaaaaccgg cgccgaatat   2880
accccccctcc agaacctggg cagcgaaaac ccgggcaagt tcctggtcta cgattccgcg   2940
ctgagcgagt tcgcggcggt cggcttcgag tacggctata gcgtcggcaa ccccgacgcg   3000
ctggtgctgt gggaagccca gttcggcgat ttcgtgaatg gcgcccagag catcatcgac   3060
gagttcatct cgtcgggcga agccaaatgg ggccagctga gcgacgtggt cctgctgctg   3120
ccccacggcc acgaaggcca gggcccggac atacgtccg ccgcatcga acggttcctc   3180
cagctgtgtg ccgaaggctc catgaccgtg gcggtcccca gcacgccggc ctcgtacttc   3240
cacctgctgc gccggcatag cctcgacggc atccgccggc cgctcgtcgt gttcacccc   3300
aaaagcatgc tgcgcaacaa agccgccgtg agcgacgtgg aagacttcac gaccggcaag   3360
ttccggagcg tcttcgagga gcccacctac gagacgggcg atgccgagcg ggacaaggtg   3420
cgccgggtcc tcctggtgtc gggcaagctg tactgggagc tgctggccaa gaagcagaag   3480
gataaccgcg aggacatcgc catcgtgcgc atcgaacagc tgtacccgt ccctcgcgg   3540
cggctccgcg agacgctgga ccgctacccc aacgccaccg agttccgctg ggtgcaggag   3600
gagcccgcca accagggcgc ctggcccttc ttcggcctcg cgctgcccga actgctgccc   3660
gacaaactgt cgggcatcaa gcgcatcagc cgccggtcca tgtcggcccc gtcctccggc   3720
tcgtccaagg tgcacgcggt cgaacagcag gaaatcatcg acgaggcctt cggctga     3777
```

<210> SEQ ID NO 9  
<211> LENGTH: 298  
<212> TYPE: PRT  
<213> ORGANISM: Escherichia coli

<400> SEQUENCE: 9

```
Met Ala Ala Ile Ala Phe Ile Gly Leu Gly Gln Met Gly Ser Pro Met
 1               5                  10                  15

Ala Ser Asn Leu Leu Gln Gln Gly His Gln Leu Arg Val Phe Asp Val
            20                  25                  30

Asn Ala Glu Ala Val Arg His Leu Val Asp Lys Gly Ala Thr Pro Ala
        35                  40                  45

Ala Asn Pro Ala Gln Ala Ala Lys Asp Ala Glu Phe Ile Ile Thr Met
    50                  55                  60

Leu Pro Asn Gly Asp Leu Val Arg Asn Val Leu Phe Gly Glu Asn Gly
65                  70                  75                  80

Val Cys Glu Gly Leu Ser Thr Asp Ala Leu Val Ile Asp Met Ser Thr
                85                  90                  95
```

```
Ile His Pro Leu Gln Thr Asp Lys Leu Ile Ala Asp Met Gln Ala Lys
            100                 105                 110

Gly Phe Ser Met Met Asp Val Pro Val Gly Arg Thr Ser Ala Asn Ala
        115                 120                 125

Ile Thr Gly Thr Leu Leu Leu Ala Gly Gly Thr Ala Glu Gln Val
    130                 135                 140

Glu Arg Ala Thr Pro Ile Leu Met Ala Met Gly Ser Glu Leu Ile Asn
145                 150                 155                 160

Ala Gly Gly Pro Gly Met Gly Ile Arg Val Lys Leu Ile Asn Asn Tyr
                165                 170                 175

Met Ser Ile Ala Leu Asn Ala Leu Ser Ala Glu Ala Ala Val Leu Cys
            180                 185                 190

Glu Ala Leu Asn Leu Pro Phe Asp Val Ala Val Lys Val Met Ser Gly
        195                 200                 205

Thr Ala Ala Gly Lys Gly His Phe Thr Thr Ser Trp Pro Asn Lys Val
    210                 215                 220

Leu Ser Gly Asp Leu Ser Pro Ala Phe Met Ile Asp Leu Ala His Lys
225                 230                 235                 240

Asp Leu Gly Ile Ala Leu Asp Val Ala Asn Gln Leu His Val Pro Met
                245                 250                 255

Pro Leu Gly Ala Ala Ser Arg Glu Val Tyr Ser Gln Ala Arg Ala Ala
            260                 265                 270

Gly Arg Gly Arg Gln Asp Trp Ser Ala Ile Leu Glu Gln Val Arg Val
        275                 280                 285

Ser Ala Gly Met Thr Ala Lys Val Lys Met
    290                 295

<210> SEQ ID NO 10
<211> LENGTH: 897
<212> TYPE: DNA
<213> ORGANISM: Escherichia coli

<400> SEQUENCE: 10
atggcggcga tcgcgttcat cggcctcggc cagatgggct ccccgatggc cagcaacctc    60
ctgcagcagg ccatcagct ccgggtgttc gacgtgaacg cggaggcggt ccggcatctg   120
gtggacaaag cgcgacccc ggccgccaac cccgcccagg cggccaagga cgcggagttc   180
atcatcacca tgctccccaa cggcgacctc gtccgcaatg tgctgttcgg cgagaacggc   240
gtgtgtgagg cctgtcgac cgacgccctc gtcatcgaca tgagcaccat ccacccgctg   300
cagacggata agctcatcgc cgacatgcag gcgaagggct tcagcatgat ggatgtcccc   360
gtcggccgca cctccgcgaa cgcgatcacc ggcaccctgc tgctcctggc cggcggcacc   420
gccgagcagg tggagcgggc cacgcccatc ctgatggcga tgggctccga actcatcaac   480
gcgggcggcc ccggcatggg catccgcgtc aagctcatca acaactacat gtcgatcgcg   540
ctgaatgccc tctccgcgga agcggcggtg ctgtgcgaag cgctgaatct gccgttcgat   600
gtggcggtga agtcatgag cggcaccgcg gcgggcaagg gccacttcac cacctcctgg   660
ccgaacaagg tgctgtccgg cgacctgagc ccggcgttca tgatcgatct ggcccacaag   720
gatctgggca tcgcgctcga cgtggccaac cagctgcacg tcccgatgcc gctcggcgcc   780
gcctcccggg aagtgtattc ccaggcccgc gccgccggcc gcggccggca ggattggtcc   840
gccatcctgg agcaggtgcg cgtcagcgcc ggcatgaccg cgaaggtgaa gatgtga      897
```

<210> SEQ ID NO 11
<211> LENGTH: 371
<212> TYPE: PRT
<213> ORGANISM: Porphyromonas gingivalis

<400> SEQUENCE: 11

Met Gln Leu Phe Lys Leu Lys Ser Val Thr His His Phe Asp Thr Phe
1               5                   10                  15

Ala Glu Phe Ala Lys Glu Phe Cys Leu Gly Glu Arg Asp Leu Val Ile
            20                  25                  30

Thr Asn Glu Phe Ile Tyr Glu Pro Tyr Met Lys Ala Cys Gln Leu Pro
        35                  40                  45

Cys His Phe Val Met Gln Glu Lys Tyr Gly Gln Gly Glu Pro Ser Asp
    50                  55                  60

Glu Met Met Asn Asn Ile Leu Ala Asp Ile Arg Asn Ile Gln Phe Asp
65                  70                  75                  80

Arg Val Ile Gly Ile Gly Gly Thr Val Ile Asp Ile Ser Lys Leu
            85                  90                  95

Phe Val Leu Lys Gly Leu Asn Asp Val Leu Asp Ala Phe Asp Arg Lys
            100                 105                 110

Ile Pro Leu Ile Lys Glu Lys Glu Leu Ile Ile Val Pro Thr Thr Cys
            115                 120                 125

Gly Thr Gly Ser Glu Val Thr Asn Ile Ser Ile Ala Glu Ile Lys Ser
    130                 135                 140

Arg His Thr Lys Met Gly Leu Ala Asp Asp Ala Ile Val Ala Asp His
145                 150                 155                 160

Ala Ile Ile Ile Pro Glu Leu Leu Lys Ser Leu Pro Phe His Phe Tyr
                165                 170                 175

Ala Cys Ser Ala Ile Asp Ala Leu Ile His Ala Ile Glu Ser Tyr Val
            180                 185                 190

Ser Pro Lys Ala Ser Pro Tyr Ser Arg Leu Phe Ser Glu Ala Ala Trp
        195                 200                 205

Asp Ile Ile Leu Glu Val Phe Lys Lys Ile Ala Glu His Gly Pro Glu
210                 215                 220

Tyr Arg Phe Glu Lys Leu Gly Glu Met Ile Met Ala Ser Asn Tyr Ala
225                 230                 235                 240

Gly Ile Ala Phe Gly Asn Ala Gly Val Gly Ala Val His Ala Leu Ser
                245                 250                 255

Tyr Pro Leu Gly Gly Asn Tyr His Val Pro His Gly Glu Ala Asn Tyr
            260                 265                 270

Gln Phe Phe Thr Glu Val Phe Lys Val Tyr Gln Lys Lys Asn Pro Phe
        275                 280                 285

Gly Tyr Ile Val Glu Leu Asn Trp Lys Leu Ser Lys Ile Leu Asn Cys
290                 295                 300

Gln Pro Glu Tyr Val Tyr Pro Lys Leu Asp Glu Leu Leu Gly Cys Leu
305                 310                 315                 320

Leu Thr Lys Lys Pro Leu His Glu Tyr Gly Met Lys Asp Glu Val
                325                 330                 335

Arg Gly Phe Ala Glu Ser Val Leu Lys Thr Gln Gln Arg Leu Leu Ala
            340                 345                 350

Asn Asn Tyr Val Glu Leu Thr Val Asp Glu Ile Glu Gly Ile Tyr Arg
        355                 360                 365

Arg Leu Tyr
    370

<210> SEQ ID NO 12
<211> LENGTH: 1116
<212> TYPE: DNA
<213> ORGANISM: Porphyromonas gingivalis

<400> SEQUENCE: 12

| | |
|---|---:|
| atgcagctgt tcaaactcaa agcgtgacg caccacttcg atacgttcgc ggagttcgcc | 60 |
| aaggagttct gcctcggcga gcgggacctg gtcatcacca atgagttcat ctacgagccc | 120 |
| tatatgaagg cgtgccagct cccgtgccac ttcgtcatgc aggaaaagta cggccagggc | 180 |
| gaaccgtcgg atgagatgat gaacaacatc ctggcggata tccggaacat ccagttcgac | 240 |
| cgggtcatcg gcatcggcgg cggcaccgtc atcgacatct ccaaactgtt cgtcctgaaa | 300 |
| ggcctcaacg acgtgctgga cgccttcgac cgcaaaatcc cgctcatcaa ggagaaggag | 360 |
| ctcatcatcg tgcccacgac ctgcggcacc ggctcggaag tgaccaacat ctcgatcgcc | 420 |
| gagatcaagt cgcgccacac caagatgggc ctggcggatg acgcgatcgt ggccgaccat | 480 |
| gccatcatca tccccgagct gctgaagagc ctgccgttcc acttctatgc cgtgctccgcc | 540 |
| atcgatgccc tgatccacgc catcgagagc tacgtctcgc cgaaggcctc cccgtacagc | 600 |
| cggctgttca gcgaggcggc ctgggacatc atcctgaagt cttcaagaa gatcgccgag | 660 |
| cacggccccg aatatcggtt cgaaaagctc ggcgagatga tcatggccag caattacgcc | 720 |
| ggcatcgcct cggcaacgc cggcgtcggc gccgtccacg ccctgtcgta cccgctgggc | 780 |
| ggcaattatc atgtgccgca tggcgaagcg aattaccagt cttcaccga ggtgttcaag | 840 |
| gtctatcaga gaaaaaaccc gttcggctac atcgtcgagc tgaactggaa gctgtcgaag | 900 |
| atcctgaact gccagccgga gtatgtgtat cccaagctgg atgaactcct gggctgcctg | 960 |
| ctgaccaaaa agccgctgca tgaatatggc atgaaggacg aagaggtgcg gggcttcgcc | 1020 |
| gaatcggtgc tgaagaccca gcagcgcctg ctcgccaaca actacgtgga gctgaccgtc | 1080 |
| gacgaaatcg aaggcatcta ccgccggctg tactga | 1116 |

<210> SEQ ID NO 13
<211> LENGTH: 371
<212> TYPE: PRT
<213> ORGANISM: Clostridium kluyveri

<400> SEQUENCE: 13

Met Lys Leu Leu Lys Leu Ala Pro Asp Val Tyr Lys Phe Asp Thr Ala
1               5                   10                  15

Glu Glu Phe Met Lys Tyr Phe Lys Val Gly Lys Gly Asp Phe Ile Leu
            20                  25                  30

Thr Asn Glu Phe Leu Tyr Lys Pro Phe Leu Glu Lys Phe Asn Asp Gly
        35                  40                  45

Ala Asp Ala Val Phe Gln Glu Lys Tyr Gly Leu Gly Glu Pro Ser Asp
    50                  55                  60

Glu Met Ile Asn Asn Ile Ile Lys Asp Ile Gly Asp Lys Gln Tyr Asn
65                  70                  75                  80

Arg Ile Ile Ala Val Gly Gly Gly Ser Val Ile Asp Ile Ala Lys Ile
                85                  90                  95

Leu Ser Leu Lys Tyr Thr Asp Asp Ser Leu Asp Leu Phe Glu Gly Lys
            100                 105                 110

Val Pro Leu Val Lys Asn Lys Glu Leu Ile Ile Val Pro Thr Thr Cys
        115                 120                 125

Gly Thr Gly Ser Glu Val Thr Asn Val Ser Val Ala Glu Leu Lys Arg

```
                    130                 135                 140
Arg His Thr Lys Lys Gly Ile Ala Ser Asp Glu Leu Tyr Ala Thr Tyr
145                 150                 155                 160

Ala Val Leu Val Pro Glu Phe Ile Lys Gly Leu Pro Tyr Lys Phe Phe
                165                 170                 175

Val Thr Ser Ser Val Asp Ala Leu Ile His Ala Thr Glu Ala Tyr Val
            180                 185                 190

Ser Pro Asn Ala Asn Pro Tyr Thr Asp Met Phe Ser Val Lys Ala Met
        195                 200                 205

Glu Leu Ile Leu Asn Gly Tyr Met Gln Met Val Glu Lys Gly Asn Asp
    210                 215                 220

Tyr Arg Val Glu Ile Ile Glu Asp Phe Val Ile Gly Ser Asn Tyr Ala
225                 230                 235                 240

Gly Ile Ala Phe Gly Asn Ala Gly Val Gly Ala Val His Ala Leu Ser
                245                 250                 255

Tyr Pro Ile Gly Gly Asn Tyr His Val Pro His Gly Glu Ala Asn Tyr
            260                 265                 270

Leu Phe Phe Thr Glu Ile Phe Lys Thr Tyr Tyr Glu Lys Asn Pro Asn
        275                 280                 285

Gly Lys Ile Lys Asp Val Asn Lys Leu Leu Ala Gly Ile Leu Lys Cys
    290                 295                 300

Asp Glu Ser Glu Ala Tyr Asp Ser Leu Ser Gln Leu Leu Asp Lys Leu
305                 310                 315                 320

Leu Ser Arg Lys Pro Leu Arg Glu Tyr Gly Met Lys Glu Glu Ile
                325                 330                 335

Glu Thr Phe Ala Asp Ser Val Ile Glu Gly Gln Gln Arg Leu Leu Val
                340                 345                 350

Asn Asn Tyr Glu Pro Phe Ser Arg Glu Asp Ile Val Asn Thr Tyr Lys
            355                 360                 365

Lys Leu Tyr
    370

<210> SEQ ID NO 14
<211> LENGTH: 1116
<212> TYPE: DNA
<213> ORGANISM: Clostridium kluyveri

<400> SEQUENCE: 14
atgaagctcc tgaagctggc cccggatgtg tacaaattcg ataccgccga ggagttcatg    60
aagtatttca aggtcggcaa gggcgacttc atcctgacga cgagttcct ctataaaccc   120 ttcctggaaa agttcaatga tggcgccgac gccgtgttcc aggaaaagta cggcctgggc   180
gagccgtccg acgaaatgat caacaacatc atcaaggata tcggcgacaa acagtacaat   240
cggatcatcg cggtgggcgg cggcagcgtc atcgatatcg ccaaaatcct gtcgctgaaa   300
tacacggacg attccctgga cctgttcgaa ggcaaggtcc cgctggtgaa gaataaagag   360
ctcatcatcg tcccgaccac ctgcggcacc ggctcggaag tgacgaatgt ctcggtcgcc   420
gaactgaagc ggcgccatac gaagaaaggc atcgcctccg acgaactcta tgcgacgtac   480
gcggtcctgg tgcccgagtt catcaaaggc ctgccctata gttcttcgt gacgagctcc   540 gtcgacgccc tcatccatgc gaccgaggcc tacgtgtcgc cgaacgccaa ccctacacc    600 gacatgttct cggtcaaggc gatggaactg atcctgaacg gctacatgca gatggtggag   660
aagggcaacg attatcgcgt ggaaatcatc gaggatttcg tgatcggctc caactacgcg   720
```

-continued

```
ggcatcgcgt tcggcaacgc gggcgtcggc gcggtccatg ccctcagcta ccccatcggc      780
ggcaactacc atgtcccgca tggcgaagcc aactacctct tcttcacgga gatcttcaag      840
acctactacg agaagaaccc gaatggcaag atcaaggacg tgaataagct cctggcgggc      900
atcctcaagt gcgatgagtc cgaggcgtac gattcgctct cgcagctgct ggacaaactg      960
ctctcgcgca agccgctgcg cgagtacggc atgaaggagg aagagatcga aaccttcgcc     1020
gacagcgtga tcgaaggcca gcagcggctg ctggtcaaca actacgagcc cttcagccgc     1080
gaggatatcg tcaacaccta caaaaagctc tactga                               1116
```

<210> SEQ ID NO 15
<211> LENGTH: 431
<212> TYPE: PRT
<213> ORGANISM: Porphyromonas gingivalis

<400> SEQUENCE: 15

```
Met Lys Asp Val Leu Ala Glu Tyr Ala Ser Arg Ile Val Ser Ala Glu
1               5                   10                  15

Glu Ala Val Lys His Ile Lys Asn Gly Glu Arg Val Ala Leu Ser His
            20                  25                  30

Ala Ala Gly Val Pro Gln Ser Cys Val Asp Ala Leu Val Gln Gln Ala
        35                  40                  45

Asp Leu Phe Gln Asn Val Glu Ile Tyr His Met Leu Cys Leu Gly Glu
    50                  55                  60

Gly Lys Tyr Met Ala Pro Glu Met Ala Pro His Phe Arg His Ile Thr
65                  70                  75                  80

Asn Phe Val Gly Gly Asn Ser Arg Lys Ala Val Glu Glu Asn Arg Ala
                85                  90                  95

Asp Phe Ile Pro Val Phe Phe Tyr Glu Val Pro Ser Met Ile Arg Lys
            100                 105                 110

Asp Ile Leu His Ile Asp Val Ala Ile Val Gln Leu Ser Met Pro Asp
        115                 120                 125

Glu Asn Gly Tyr Cys Ser Phe Gly Val Ser Cys Asp Tyr Ser Lys Pro
    130                 135                 140

Ala Ala Glu Ser Ala His Leu Val Ile Gly Glu Ile Asn Arg Gln Met
145                 150                 155                 160

Pro Tyr Val His Gly Asp Asn Leu Ile His Ile Ser Lys Leu Asp Tyr
                165                 170                 175

Ile Val Met Ala Asp Tyr Pro Ile Tyr Ser Leu Ala Lys Pro Lys Ile
            180                 185                 190

Gly Glu Val Glu Glu Ala Ile Gly Arg Asn Cys Ala Glu Leu Ile Glu
        195                 200                 205

Asp Gly Ala Thr Leu Gln Leu Gly Ile Gly Ala Ile Pro Asp Ala Ala
    210                 215                 220

Leu Leu Phe Leu Lys Asp Lys Asp Leu Gly Ile His Thr Glu Met
225                 230                 235                 240

Phe Ser Asp Gly Val Val Glu Leu Val Arg Ser Gly Val Ile Thr Gly
                245                 250                 255

Lys Lys Lys Thr Leu His Pro Gly Lys Met Val Ala Thr Phe Leu Met
            260                 265                 270

Gly Ser Glu Asp Val Tyr His Phe Ile Asp Lys Asn Pro Asp Val Glu
        275                 280                 285

Leu Tyr Pro Val Asp Tyr Val Asn Asp Pro Arg Val Ile Ala Gln Asn
    290                 295                 300
```

```
Asp Asn Met Val Ser Ile Asn Ser Cys Ile Glu Ile Asp Leu Met Gly
305                 310                 315                 320

Gln Val Val Ser Glu Cys Ile Gly Ser Lys Gln Phe Ser Gly Thr Gly
            325                 330                 335

Gly Gln Val Asp Tyr Val Arg Gly Ala Ala Trp Ser Lys Asn Gly Lys
        340                 345                 350

Ser Ile Met Ala Ile Pro Ser Thr Ala Lys Asn Gly Thr Ala Ser Arg
    355                 360                 365

Ile Val Pro Ile Ile Ala Glu Gly Ala Ala Val Thr Thr Leu Arg Asn
370                 375                 380

Glu Val Asp Tyr Val Val Thr Glu Tyr Gly Ile Ala Gln Leu Lys Gly
385                 390                 395                 400

Lys Ser Leu Arg Gln Arg Ala Glu Ala Leu Ile Ala Ile Ala His Pro
                405                 410                 415

Asp Phe Arg Glu Glu Leu Thr Lys His Leu Arg Lys Arg Phe Gly
        420                 425                 430
```

<210> SEQ ID NO 16
<211> LENGTH: 1296
<212> TYPE: DNA
<213> ORGANISM: Porphyromonas gingivalis

<400> SEQUENCE: 16

| | |
|---|---:|
| atgaaggacg tgctggccga gtacgcctcg cgcatcgtct cggcggaaga agcggtcaag | 60 |
| cacatcaaga acggcgagcg cgtcgcgctc tcgcatgccg ccggcgtccc gcagtcctgc | 120 |
| gtcgatgccc tggtccagca ggccgatctc ttccagaatg tcgaaatcta ccatatgctc | 180 |
| tgcctgggcg agggcaagta catggccccc gagatggcgc cgcatttccg ccatatcacg | 240 |
| aatttcgtcg cggcaactc gcggaaagcc gtggaggaga accgggccga cttcatcccc | 300 |
| gtgttcttct acgaggtccc cagcatgatc cgcaaagata tcctccacat cgacgtggcg | 360 |
| atcgtgcagc tgagcatgcc ggatgagaac ggctactgca gcttcggcgt gagctgtgac | 420 |
| tacagcaagc cggccgccga atccgcccac ctcgtcatcg gcgagatcaa ccggcagatg | 480 |
| ccgtacgtcc acgcgacaa cctgatccac atcagcaagc tggactacat cgtcatggcc | 540 |
| gactatccga tctatagcct ggcgaaaccc aagatcggcg aggtcgagga ggccatcggc | 600 |
| cggaactgcg ccgagctgat cgaagacggc gccacccctcc agctgggcat cggcgccatc | 660 |
| ccggacgccg ccctgctctt cctgaaagac aagaaagacc tgggcatcca caccgaaatg | 720 |
| ttcagcgacg gcgtcgtcga actggtccgg agcggcgtca tcaccggcaa gaaaaaaacc | 780 |
| ctgcacccgg gcaaaatggt cgcgacgttc ctgatgggct ccgaagatgt ctatcatttc | 840 |
| atcgacaaga ccccgacgt ggagctctac ccggtggact atgtgaacga cccgcgcgtc | 900 |
| atcgcccaga cgacaacat ggtcagcatc aactcctgta tcgagatcga cctcatgggc | 960 |
| caggtcgtga cgaatgtat cggctccaag cagttctcgg gcacgggcgg ccaggtggac | 1020 |
| tacgtccgcg gcgcggcgtg gtcgaagaac ggcaagtcga tcatggccat ccctccacc | 1080 |
| gccaagaacg gcaccgcctc gcgcatcgtg ccgatcatcg cggagggcgc cgcggtgacg | 1140 |
| accctgcgga cgaagtgga ttacgtggtc acggagtatg catcgcccca gctgaagggc | 1200 |
| aagtcgctcc gccagcgggc ggaagcgctg atcgcgatcg cgcacccgga cttccgggag | 1260 |
| gagctgacca acaccctgcg gaaacggttc ggctga | 1296 |

<210> SEQ ID NO 17
<211> LENGTH: 431

```
<212> TYPE: PRT
<213> ORGANISM: Porphyromonas gingivalis

<400> SEQUENCE: 17
```

| | | | | | | | | | | | | | | |
|---|---|---|---|---|---|---|---|---|---|---|---|---|---|---|
| Met | Gln | Trp | Gln | Glu | Leu | Tyr | Arg | Gln | Arg | Val | Cys | Ser | Ala | Asp | Glu |
| 1 | | | | 5 | | | | | 10 | | | | | 15 |
| Ala | Val | Val | Asp | Ser | Leu | Lys | Pro | Gly | Thr | Lys | Val | Val | Phe | Gly | His |
| | | | 20 | | | | | 25 | | | | | 30 | |
| Ala | Ala | Ala | Ala | Pro | Val | Arg | Phe | Ser | Gln | Ala | Met | Tyr | Arg | Gln | Arg |
| | | 35 | | | | | 40 | | | | | 45 | | |
| Glu | Lys | Leu | Glu | Asn | Ile | Thr | Val | Phe | His | Met | Leu | Tyr | Phe | Gly | Asp |
| | 50 | | | | | 55 | | | | | 60 | | | |
| Ala | Pro | His | Leu | Ala | Pro | Glu | Met | Arg | Ser | His | Val | His | Pro | Thr | Leu |
| 65 | | | | | 70 | | | | | 75 | | | | | 80 |
| Asn | Phe | Leu | Glu | Gly | Asn | Ser | Arg | Pro | Ala | Ser | Arg | Asp | Arg | Arg | Val |
| | | | | 85 | | | | | 90 | | | | | 95 | |
| Asp | Phe | Ile | Pro | Cys | His | Phe | His | Glu | Val | Pro | Glu | Leu | Phe | Arg | Gln |
| | | | 100 | | | | | 105 | | | | | 110 | | |
| Gly | Phe | Phe | Pro | Leu | Asp | Val | Ala | Val | Val | Gln | Val | Ser | Thr | Pro | Asn |
| | | 115 | | | | | 120 | | | | | 125 | | | |
| Glu | Glu | Gly | Tyr | Cys | Ser | Phe | Gly | Val | Ser | Cys | Asp | Tyr | Thr | Lys | Ala |
| | 130 | | | | | 135 | | | | | 140 | | | | |
| Ala | Ala | Glu | Cys | Ala | Pro | Val | Val | Ala | Glu | Val | Asn | Lys | Gln | Met |
| 145 | | | | | 150 | | | | | 155 | | | | | 160 |
| Pro | Phe | Ile | Gly | Gly | Glu | Asn | Leu | Ile | His | Ile | Ser | Lys | Leu | Thr | His |
| | | | | 165 | | | | | 170 | | | | | 175 | |
| Ile | Ile | Glu | Val | Asp | Glu | Pro | Ile | Ala | Glu | Val | Leu | Pro | Pro | Ala | Ile |
| | | | 180 | | | | | 185 | | | | | 190 | | |
| Ser | Asp | Leu | Glu | Leu | Arg | Ile | Gly | Gln | Asn | Cys | Ala | Ser | Leu | Ile | Lys |
| | | 195 | | | | | 200 | | | | | 205 | | | |
| Asp | Gly | Asp | Thr | Leu | Gln | Leu | Gly | Ile | Gly | Ile | Pro | Asp | Ala | Val |
| | 210 | | | | | 215 | | | | | 220 | | | | |
| Leu | Arg | Ala | Leu | Glu | Gly | His | Lys | Asp | Leu | Gly | Ile | His | Thr | Glu | Met |
| 225 | | | | | 230 | | | | | 235 | | | | | 240 |
| Phe | Thr | Asp | Gly | Val | Met | Arg | Met | Ile | Arg | Lys | Gly | Ile | Ile | Asn | Gly |
| | | | | 245 | | | | | 250 | | | | | 255 | |
| Lys | Lys | Lys | Thr | Leu | His | Pro | Glu | Lys | Val | Val | Thr | Ser | Leu | Ile | Phe |
| | | | 260 | | | | | 265 | | | | | 270 | | |
| Gly | Ser | Lys | Glu | Leu | Tyr | Asp | Phe | Val | Asn | Asn | Pro | Val | Ile | Glu |
| | | 275 | | | | | 280 | | | | | 285 | | | |
| Cys | Tyr | Pro | Val | Asp | Tyr | Ile | Asn | Asn | Pro | Asp | Val | Ile | Gly | Lys | Asn |
| | 290 | | | | | 295 | | | | | 300 | | | | |
| Asp | Arg | Met | Val | Ser | Ile | Asn | Ser | Cys | Leu | Glu | Met | Asp | Leu | Met | Gly |
| 305 | | | | | 310 | | | | | 315 | | | | | 320 |
| Gln | Ala | Ala | Ser | Glu | Ser | Ile | Gly | Tyr | Glu | Gln | Phe | Ser | Gly | Ser | Gly |
| | | | | 325 | | | | | 330 | | | | | 335 | |
| Gly | Gln | Val | Asp | Phe | Leu | Arg | Gly | Ala | Lys | Arg | Ser | Lys | Gly | Gly | Ile |
| | | | 340 | | | | | 345 | | | | | 350 | | |
| Ser | Ile | Met | Ala | Phe | Pro | Ser | Thr | Ala | Lys | Lys | Gly | Thr | Glu | Ser | Arg |
| | | 355 | | | | | 360 | | | | | 365 | | | |
| Ile | Val | Pro | Ile | Leu | Lys | Glu | Gly | Ala | Cys | Val | Thr | Thr | Gly | Arg | Asn |
| | 370 | | | | | 375 | | | | | 380 | | | | |
| Glu | Val | Asp | Tyr | Val | Val | Thr | Glu | Tyr | Gly | Val | Ala | Arg | Leu | Arg | Gly |
| 385 | | | | | 390 | | | | | 395 | | | | | 400 |

Ala Thr Leu Arg Gln Arg Ala Glu Ala Leu Thr Ala Ile Ala His Pro
            405                 410                 415

Asp Phe Arg Pro Ala Leu Glu Glu Glu Ile Arg Arg Phe Glu
        420                 425                 430

<210> SEQ ID NO 18
<211> LENGTH: 1296
<212> TYPE: DNA
<213> ORGANISM: Porphyromonas gingivalis

<400> SEQUENCE: 18

```
atgcagtggc aggaactcta ccggcagcgc gtgtgctccg cggatgaagc cgtcgtggat      60
agcctgaagc ccggcaccaa ggtggtcttc ggccatgccg ccgccgcgcc cgtgcggttc     120
tcgcaggcca tgtatcgcca gcgcgaaaag ctcgaaaaca tcaccgtgtt ccatatgctc     180
tatttcggcg atgcccccca cctggccccc gaaatgcgct cccatgtcca cccgacgctc     240
aacttcctgg aaggcaatag ccgccccgcg tcgcgggatc ggcgcgtgga tttcatcccc     300
tgccacttcc acgaagtgcc cgagctgttc cgccagggct tcttccccct cgacgtggcg     360
gtggtgcagt gtcgaccccc gaacgaggag ggctattgta gcttcggcgt ctcgtgtgac     420
tatacgaagg ccgcggccga atgtgccccg gtcgtggtgg ccgaggtgaa caagcagatg     480
ccgttcatcg gcgcgagaa cctgatccat atctccaagc tgacccatat catcgaagtg     540
gatgagccga tcgccgaggt gctgcccccc gcgatcagcg acctggagct gcgcatcggc     600
cagaactgcg cgtccctcat caaggacggc gatacgctcc agctgggcat cggcggcatc     660
ccggacgcgg tgctgcgggc cctggaaggc cataaagacc tcggcatcca cacggagatg     720
ttcaccgacg cgtgtgatgcg gatgatccgg aagggcatca tcaacggcaa gaaaaagacc     780
ctgcacccgg aaaaagtggt gaccagcctg atcttcggca gcaaagaact gtacgacttc     840
gtcaacaaca acccggtgat cgagtgctat ccggtcgatt atatcaacaa tccggatgtc     900
atcggcaaga acgaccgcat ggtgagcatc aactcctgcc tggaaatgga cctgatgggc     960
caggccgcga cgaaagcat cggctacgaa cagttctccg gctcgggcgg ccaggtggat    1020
ttcctgcggg gcgcgaagcg gtccaaaggc ggcatcagca tcatggcctt ccctccacg    1080
gccaagaagg cacggagtc ccgcatcgtg cccatcctga aggagggcgc gtgcgtcacg    1140
accgccgca atgaggtgga ttacgtcgtc accgagtacg gcgtcgcccg cctccggggc    1200
gccaccctcc ggcagcgggc cgaggccctg acggccatcg cccatcccga cttccgcccc    1260
gccctggagg aagagatccg ccggcgcttc gagtga                              1296
```

<210> SEQ ID NO 19
<211> LENGTH: 438
<212> TYPE: PRT
<213> ORGANISM: Clostridium aminobutyricum

<400> SEQUENCE: 19

Met Asp Trp Lys Lys Ile Tyr Glu Asp Arg Thr Cys Thr Ala Asp Glu
1               5                   10                  15

Ala Val Lys Ser Ile Lys Ser Gly Asp Arg Val Leu Phe Ala His Cys
20 25 30

Val Ala Glu Pro Pro Val Leu Val Glu Ala Met Val Ala Asn Ala Ala
35 40 45

Ala Tyr Lys Asn Val Thr Val Ser His Met Val Thr Leu Gly Lys Gly
50 55 60

Glu Tyr Ser Lys Pro Glu Tyr Lys Glu Asn Phe Thr Phe Glu Gly Trp
 65                  70                  75                  80

Phe Thr Ser Pro Ser Thr Arg Gly Ser Ile Ala Glu Gly His Gly Gln
                 85                  90                  95

Phe Val Pro Val Phe His Glu Val Pro Ser Leu Ile Arg Lys Asp
            100                 105                 110

Ile Phe His Val Asp Val Phe Met Val Met Val Ser Pro Pro Asp His
        115                 120                 125

Asn Gly Phe Cys Cys Val Gly Val Ser Ser Asp Tyr Thr Met Gln Ala
    130                 135                 140

Ile Lys Ser Ala Lys Ile Val Leu Ala Glu Val Asn Asp Gln Val Pro
145                 150                 155                 160

Val Val Tyr Gly Asp Thr Phe Val His Val Ser Asn Ile Asp Lys Phe
                165                 170                 175

Val Glu Thr Ser His Pro Leu Pro Glu Ile Gly Leu Pro Lys Ile Gly
            180                 185                 190

Glu Val Glu Ala Ala Ile Gly Lys His Cys Ala Ser Leu Ile Glu Asp
        195                 200                 205

Gly Ser Thr Leu Gln Leu Gly Ile Gly Ala Ile Pro Asp Ala Val Leu
    210                 215                 220

Ser Gln Leu Lys Asp Lys Lys His Leu Gly Ile His Ser Glu Met Ile
225                 230                 235                 240

Ser Asp Gly Val Val Asp Leu Tyr Glu Ala Gly Val Ile Asp Cys Ser
                245                 250                 255

Gln Lys Ser Ile Asp Lys Gly Lys Met Ala Ile Thr Phe Leu Met Gly
            260                 265                 270

Thr Lys Arg Leu Tyr Asp Phe Ala Ala Asn Asn Pro Lys Val Glu Leu
        275                 280                 285

Lys Thr Val Asp Tyr Ile Asn His Pro Ser Val Val Ala Gln Cys Ser
    290                 295                 300

Lys Met Val Cys Ile Asn Ala Cys Leu Gln Val Asp Phe Met Gly Gln
305                 310                 315                 320

Ile Val Ser Asp Ser Ile Gly Thr Lys Arg Phe Ser Gly Val Gly Gly
                325                 330                 335

Gln Val Asp Phe Val Arg Gly Ala Ser Met Ser Ile Asp Gly Lys Gly
            340                 345                 350

Lys Ala Ile Ile Ala Met Pro Ser Val Ala Lys Lys Lys Asp Gly Ser
        355                 360                 365

Met Ile Ser Lys Ile Val Pro Phe Ile Asp His Gly Ala Ala Val Thr
    370                 375                 380

Thr Ser Arg Asn Asp Ala Asp Tyr Val Val Thr Glu Tyr Gly Ile Ala
385                 390                 395                 400

Glu Met Lys Gly Lys Ser Leu Gln Asp Arg Ala Arg Ala Leu Ile Asn
                405                 410                 415

Ile Ala His Pro Asp Phe Lys Asp Glu Leu Lys Ala Glu Phe Glu Lys
            420                 425                 430

Arg Phe Asn Ala Ala Phe
        435

<210> SEQ ID NO 20
<211> LENGTH: 1317
<212> TYPE: DNA
<213> ORGANISM: Clostridium aminobutyricum

<400> SEQUENCE: 20

```
atggattgga aaaagatcta cgaagatcgc acctgcaccg ccgatgaagc cgtcaagtcc    60
atcaagtccg gcgaccgcgt cctgttcgcc cactgtgtcg ccgaaccccc ggtgctggtc   120
gaagcgatgg tggccaacgc cgcggcgtac aagaacgtca ccgtgagcca tatggtgacc   180
ctgggcaagg gcgaatatag caagcccgag tacaaggaga acttcacgtt cgagggctgg   240
ttcacctccc cgtcgacgcg gggctcgatc gcggagggcc acggccagtt cgtgcccgtg   300
ttcttccatg aggtgccgtc cctgatccgc aaggatatct tccacgtcga cgtgttcatg   360
gtcatggtgt ccccgcccga tcataacggc ttctgctgtg tcggcgtcag cagcgactac   420
acgatgcagg ccatcaagtc ggccaagatc gtgctggcgg aagtcaacga ccaggtgccc   480
gtggtgtatg cgatacgtt cgtgcatgtc tcgaacatcg ataagttcgt ggaaacctcg   540
catccgctcc cggaaatcgg cctgccgaaa atcggcgagg tggaagcggc catcggcaaa   600
cactgtgcct ccctgatcga agacggctcg acgctgcagc tgggcatcgg cgccatcccc   660
gacgccgtgc tcagccagct gaaagacaag aagcacctgg gcatccactc ggagatgatc   720
tccgacggcg tcgtggacct gtatgaggcg ggcgtgatcg actgctccca gaagtcgatc   780
gacaagggca aaatggcgat caccttcctg atgggcacca gcgcctgta cgacttcgcg   840
gcgaacaatc cgaaggtgga gctgaaaacg gtggactaca tcaaccatcc gtcggtggtg   900
gcccagtgct ccaagatggt gtgcatcaac gcctgcctgc aggtggattt catgggccag   960
atcgtgagcg acagcatcgg caccaagcgc ttctcgggcg tgggcggcca ggtcgacttc  1020
gtgcggggcg cctccatgag catcgacggc aagggcaagg cgatcatcgc catgccgtcg  1080
gtcgccaaga agaaggacgg cagcatgatc tcgaaaatcg tccccttcat cgatcacggc  1140
gccgccgtga ccacctcgcg gaacgacgcc gattatgtgg tcacggagta cggcatcgcc  1200
gagatgaaag gcaagtccct ccaggaccgg gcccgggcgc tcatcaacat cgcgcacccg  1260
gatttcaagg atgagctgaa ggcggagttc gagaagcggt tcaacgcggc gttctga     1317
```

<210> SEQ ID NO 21
<211> LENGTH: 858
<212> TYPE: PRT
<213> ORGANISM: Clostridium acetobutylicum

<400> SEQUENCE: 21

```
Met Lys Val Thr Asn Gln Lys Glu Leu Lys Gln Lys Leu Asn Glu Leu
1               5                   10                  15

Arg Glu Ala Gln Lys Lys Phe Ala Thr Tyr Thr Gln Glu Gln Val Asp
            20                  25                  30

Lys Ile Phe Lys Gln Cys Ala Ile Ala Ala Lys Glu Arg Ile Asn
        35                  40                  45

Leu Ala Lys Leu Ala Val Glu Glu Thr Gly Ile Gly Leu Val Glu Asp
    50                  55                  60

Lys Ile Ile Lys Asn His Phe Ala Ala Glu Tyr Ile Tyr Asn Lys Tyr
65                  70                  75                  80

Lys Asn Glu Lys Thr Cys Gly Ile Ile Asp His Asp Asp Ser Leu Gly
                85                  90                  95

Ile Thr Lys Val Ala Glu Pro Ile Gly Ile Val Ala Ala Ile Val Pro
            100                 105                 110

Thr Thr Asn Pro Thr Ser Thr Ala Ile Phe Lys Ser Leu Ile Ser Leu
        115                 120                 125

Lys Thr Arg Asn Ala Ile Phe Phe Ser Pro His Pro Arg Ala Lys Lys
    130                 135                 140
```

```
Ser Thr Ile Ala Ala Ala Lys Leu Ile Leu Asp Ala Ala Val Lys Ala
145                 150                 155                 160

Gly Ala Pro Lys Asn Ile Ile Gly Trp Ile Asp Glu Pro Ser Ile Glu
            165                 170                 175

Leu Ser Gln Asp Leu Met Ser Glu Ala Asp Ile Ile Leu Ala Thr Gly
        180                 185                 190

Gly Pro Ser Met Val Lys Ala Ala Tyr Ser Ser Gly Lys Pro Ala Ile
    195                 200                 205

Gly Val Gly Ala Gly Asn Thr Pro Ala Ile Ile Asp Glu Ser Ala Asp
210                 215                 220

Ile Asp Met Ala Val Ser Ser Ile Ile Leu Ser Lys Thr Tyr Asp Asn
225                 230                 235                 240

Gly Val Ile Cys Ala Ser Glu Gln Ser Ile Leu Val Met Asn Ser Ile
                245                 250                 255

Tyr Glu Lys Val Lys Glu Glu Phe Val Lys Arg Gly Ser Tyr Ile Leu
            260                 265                 270

Asn Gln Asn Glu Ile Ala Lys Ile Lys Glu Thr Met Phe Lys Asn Gly
        275                 280                 285

Ala Ile Asn Ala Asp Ile Val Gly Lys Ser Ala Tyr Ile Ile Ala Lys
    290                 295                 300

Met Ala Gly Ile Glu Val Pro Gln Thr Thr Lys Ile Leu Ile Gly Glu
305                 310                 315                 320

Val Gln Ser Val Glu Lys Ser Glu Leu Phe Ser His Glu Lys Leu Ser
                325                 330                 335

Pro Val Leu Ala Met Tyr Lys Val Lys Asp Phe Asp Glu Ala Leu Lys
            340                 345                 350

Lys Ala Gln Arg Leu Ile Glu Leu Gly Gly Ser Gly His Thr Ser Ser
        355                 360                 365

Leu Tyr Ile Asp Ser Gln Asn Asn Lys Asp Lys Val Lys Glu Phe Gly
    370                 375                 380

Leu Ala Met Lys Thr Ser Arg Thr Phe Ile Asn Met Pro Ser Ser Gln
385                 390                 395                 400

Gly Ala Ser Gly Asp Leu Tyr Asn Phe Ala Ile Ala Pro Ser Phe Thr
                405                 410                 415

Leu Gly Cys Gly Thr Trp Gly Gly Asn Ser Val Ser Gln Asn Val Glu
            420                 425                 430

Pro Lys His Leu Leu Asn Ile Lys Ser Val Ala Glu Arg Arg Glu Asn
        435                 440                 445

Met Leu Trp Phe Lys Val Pro Gln Lys Ile Tyr Phe Lys Tyr Gly Cys
    450                 455                 460

Leu Arg Phe Ala Leu Lys Glu Leu Lys Asp Met Asn Lys Lys Arg Ala
465                 470                 475                 480

Phe Ile Val Thr Asp Lys Asp Leu Phe Lys Leu Gly Tyr Val Asn Lys
                485                 490                 495

Ile Thr Lys Val Leu Asp Glu Ile Asp Ile Lys Tyr Ser Ile Phe Thr
            500                 505                 510

Asp Ile Lys Ser Asp Pro Thr Ile Asp Ser Val Lys Lys Gly Ala Lys
        515                 520                 525

Glu Met Leu Asn Phe Glu Pro Asp Thr Ile Ile Ser Ile Gly Gly Gly
    530                 535                 540

Ser Pro Met Asp Ala Ala Lys Val Met His Leu Leu Tyr Glu Tyr Pro
545                 550                 555                 560
```

```
Glu Ala Glu Ile Glu Asn Leu Ala Ile Asn Phe Met Asp Ile Arg Lys
                565                 570                 575

Arg Ile Cys Asn Phe Pro Lys Leu Gly Thr Lys Ala Ile Ser Val Ala
            580                 585                 590

Ile Pro Thr Thr Ala Gly Thr Gly Ser Glu Ala Thr Pro Phe Ala Val
        595                 600                 605

Ile Thr Asn Asp Glu Thr Gly Met Lys Tyr Pro Leu Thr Ser Tyr Glu
    610                 615                 620

Leu Thr Pro Asn Met Ala Ile Ile Asp Thr Glu Leu Met Leu Asn Met
625                 630                 635                 640

Pro Arg Lys Leu Thr Ala Ala Thr Gly Ile Asp Ala Leu Val His Ala
                645                 650                 655

Ile Glu Ala Tyr Val Ser Val Met Ala Thr Asp Tyr Thr Asp Glu Leu
            660                 665                 670

Ala Leu Arg Ala Ile Lys Met Ile Phe Lys Tyr Leu Pro Arg Ala Tyr
        675                 680                 685

Lys Asn Gly Thr Asn Asp Ile Glu Ala Arg Glu Lys Met Ala His Ala
    690                 695                 700

Ser Asn Ile Ala Gly Met Ala Phe Ala Asn Ala Phe Leu Gly Val Cys
705                 710                 715                 720

His Ser Met Ala His Lys Leu Gly Ala Met His His Val Pro His Gly
                725                 730                 735

Ile Ala Cys Ala Val Leu Ile Glu Glu Val Ile Lys Tyr Asn Ala Thr
            740                 745                 750

Asp Cys Pro Thr Lys Gln Thr Ala Phe Pro Gln Tyr Lys Ser Pro Asn
        755                 760                 765

Ala Lys Arg Lys Tyr Ala Glu Ile Ala Glu Tyr Leu Asn Leu Lys Gly
    770                 775                 780

Thr Ser Asp Thr Glu Lys Val Thr Ala Leu Ile Glu Ala Ile Ser Lys
785                 790                 795                 800

Leu Lys Ile Asp Leu Ser Ile Pro Gln Asn Ile Ser Ala Ala Gly Ile
                805                 810                 815

Asn Lys Lys Asp Phe Tyr Asn Thr Leu Asp Lys Met Ser Glu Leu Ala
            820                 825                 830

Phe Asp Asp Gln Cys Thr Thr Ala Asn Pro Arg Tyr Pro Leu Ile Ser
        835                 840                 845

Glu Leu Lys Asp Ile Tyr Ile Lys Ser Phe
    850                 855

<210> SEQ ID NO 22
<211> LENGTH: 2577
<212> TYPE: DNA
<213> ORGANISM: Clostridium acetobutylicum

<400> SEQUENCE: 22
atgaaggtga ccaaccagaa agaactgaag cagaaactga cgaactgcg ggaggcgcag      60 aaaaagttcg ccacctatac ccaggagcag gtggacaaaa tcttcaagca gtgtgcgatc    120
gccgccgcca agaacggat caacctggcg aaactcgccg tcgaagaaac cggcatcggc     180
ctcgtggagg acagatcat caaaaatcac ttcgccgccg aatatatcta taacaaatac    240
aagaacgaga agacctgcgg catcatcgac catgacgact cgctgggcat caccaaagtc    300
gccgagccca tcggcatcgt ggccgcgatc gtgcccacca ccaacccgac gagcaccgcc    360
atcttcaagt cgctgatctc cctgaagacg cgcaatgcga tcttcttcag ccccatccg    420
```

```
cgggccaaaa agtcgacgat cgcggcggcc aaactgatcc tggacgccgc ggtcaaggcc      480
ggcgccccga aaatatcat cggctggatc gacgaaccgt ccatcgagct gtcccaggac       540
ctcatgtccg aagccgacat catcctggcg accggcggcc cgagcatggt gaaggccgcc      600
tattccagcg gcaaaccggc catcggcgtc ggcgccggca acaccccgc gatcatcgac       660 gagtccgccg acatcgacat ggccgtctcc tcgatcatcc tgagcaagac ctacgataac     720
ggcgtcatct gcgcgtcgga acagagcatc ctggtcatga actccatcta tgaaaaggtc     780
aaggaagagt tcgtgaagcg cggctcgtat atcctgaacc agaatgaaat cgcgaagatc     840
aaggagacga tgttcaagaa cggcgccatc aacgccgaca tcgtcggcaa gagcgcctat    900
atcatcgcga agatggccgg catcgaagtg ccgcagacca ccaagatcct gatcggcgaa    960
gtccagtccg tcgaaaagtc cgaactgttc tcccacgaaa agctgagccc ggtgctcgcc    1020
atgtacaaag tcaaagactt cgacgaggcc ctcaaaaagg cgcagcggct catcgaactg    1080
ggcggcagcg gccataccct cgtcgctgtac atcgatagcc agaacaacaa ggacaaagtc    1140
aaagagttcg gcctggcgat gaagacgagc cgcaccttca tcaacatgcc gagcagccag    1200
ggcgcgtccg gcgacctgta caacttcgcc atcgccccga gcttcacgct cggctgcggc    1260
acctggggcg gcaattcggt gtcgcagaac gtggaaccga acatctgct gaacatcaaa     1320 tccgtcgcgg agcgccgcga aaatatgctc tggttcaagg tcccgcagaa gatctatttc    1380
aaatatggct gcctgcgctt cgccctcaaa gaactgaaag acatgaataa gaacgcgcc     1440 ttcatcgtca ccgataaaga tctgttcaag ctgggctacg tgaacaaaat cacgaaggtc    1500
ctggatgaga tcgatatcaa gtacagcatc ttcaccgaca tcaagtccga tcccaccatc   1560
gactccgtca agaagggcgc caaagagatg ctcaacttcg aaccggacac catcatcagc    1620
atcggcggcg gctcgccgat ggacgcggcc aaggtcatgc atctgctcta tgaatatccg    1680
gaggccgaga tcgaaaacct ggccatcaac ttcatggaca tccggaaacg catctgcaac    1740
ttcccgaagc tcggcacgaa agccatcagc gtggccatcc ccacgaccgc gggcaccggc    1800
tcggaagcca cgccgttcgc ggtcatcacg aatgacgaaa ccggcatgaa ataccccctg    1860
acctcctacg agctcacccc caatatggcc atcatcgaca cggagctcat gctcaacatg    1920
ccgcggaagc tcaccgccgc caccggcatc gatgccctgg tgcacgccat cgaagcctac    1980
gtgagcgtga tggcgaccga ctataccgat gagctggccc tccgggccat caagatgatc    2040
ttcaagtatc tgccgcgggc ctacaaaaac ggcacgaatg acatcgaggc ccgcgaaaag    2100
atggcgcatg cgagcaacat cgcgggcatg gccttcgcga acgccttcct gggcgtgtgc    2160
catagcatgg cgcacaaact gggcgcgatg catcacgtcc cgcatggcat cgcctgtgcc    2220
gtcctgatcg aggaggtcat caagtacaac gccacggatt gtccgaccaa acagaccgcc    2280
ttcccgcagt acaagtcccc gaacgcgaag cggaaatacg cggagatcgc ggagtacctg    2340
aatctgaaag gcaccagcga caccgaaaaa gtcacggccc tcatcgaagc catctcgaaa    2400
ctgaaaatcg atctgagcat cccccagaac atctccgcgg ccggcatcaa taagaaggat    2460
ttctataaca cgctggacaa gatgagcgag ctggcgttcg atgaccagtg cacgaccgcc    2520 aaccccggt atccgctgat ctccgaactc aaggacatct acatcaagtc cttctga       2577
```

<210> SEQ ID NO 23
<211> LENGTH: 891
<212> TYPE: PRT
<213> ORGANISM: Escherichia coli

<400> SEQUENCE: 23

-continued

```
Met Ala Val Thr Asn Val Ala Glu Leu Asn Ala Leu Val Glu Arg Val
1               5                   10                  15

Lys Lys Ala Gln Arg Glu Tyr Ala Ser Phe Thr Gln Glu Gln Val Asp
            20                  25                  30

Lys Ile Phe Arg Ala Ala Leu Ala Ala Asp Ala Arg Ile Pro
        35                  40                  45

Leu Ala Lys Met Ala Val Ala Glu Ser Gly Met Gly Ile Val Glu Asp
50                  55                  60

Lys Val Ile Lys Asn His Phe Ala Ser Glu Tyr Ile Tyr Asn Ala Tyr
65                  70                  75                  80

Lys Asp Glu Lys Thr Cys Gly Val Leu Ser Asp Asp Thr Phe Gly
                85                  90                  95

Thr Ile Thr Ile Ala Glu Pro Ile Gly Ile Ile Cys Gly Ile Val Pro
                100                 105                 110

Thr Thr Asn Pro Thr Ser Thr Ala Ile Phe Lys Ser Leu Ile Ser Leu
            115                 120                 125

Lys Thr Arg Asn Ala Ile Ile Phe Ser Pro His Pro Arg Ala Lys Asp
130                 135                 140

Ala Thr Asn Lys Ala Ala Asp Ile Val Leu Gln Ala Ala Ile Ala Ala
145                 150                 155                 160

Gly Ala Pro Lys Asp Leu Ile Gly Trp Ile Asp Gln Pro Ser Val Glu
                165                 170                 175

Leu Ser Asn Ala Leu Met His His Pro Asp Ile Asn Leu Ile Leu Ala
                180                 185                 190

Thr Gly Gly Pro Gly Met Val Lys Ala Ala Tyr Ser Ser Gly Lys Pro
            195                 200                 205

Ala Ile Gly Val Gly Ala Gly Asn Thr Pro Val Val Ile Asp Glu Thr
210                 215                 220

Ala Asp Ile Lys Arg Ala Val Ala Ser Val Leu Met Ser Lys Thr Phe
225                 230                 235                 240

Asp Asn Gly Val Ile Cys Ala Ser Glu Gln Ser Val Val Val Asp
                245                 250                 255

Ser Val Tyr Asp Ala Val Arg Glu Arg Phe Ala Thr His Gly Gly Tyr
            260                 265                 270

Leu Leu Gln Gly Lys Glu Leu Lys Ala Val Gln Asp Val Ile Leu Lys
            275                 280                 285

Asn Gly Ala Leu Asn Ala Ala Ile Val Gly Gln Pro Ala Tyr Lys Ile
290                 295                 300

Ala Glu Leu Ala Gly Phe Ser Val Pro Glu Asn Thr Lys Ile Leu Ile
305                 310                 315                 320

Gly Glu Val Thr Val Val Asp Glu Ser Glu Pro Phe Ala His Glu Lys
                325                 330                 335

Leu Ser Pro Thr Leu Ala Met Tyr Arg Ala Lys Asp Phe Glu Asp Ala
            340                 345                 350

Val Glu Lys Ala Glu Lys Leu Val Ala Met Gly Gly Ile Gly His Thr
            355                 360                 365

Ser Cys Leu Tyr Thr Asp Gln Asp Asn Gln Pro Ala Arg Val Ser Tyr
370                 375                 380

Phe Gly Gln Lys Met Lys Thr Ala Arg Ile Leu Ile Asn Thr Pro Ala
385                 390                 395                 400

Ser Gln Gly Gly Ile Gly Asp Leu Tyr Asn Phe Lys Leu Ala Pro Ser
                405                 410                 415
```

```
Leu Thr Leu Gly Cys Gly Ser Trp Gly Asn Ser Ile Ser Glu Asn
            420                 425                 430

Val Gly Pro Lys His Leu Ile Asn Lys Lys Thr Val Ala Lys Arg Ala
        435                 440                 445

Glu Asn Met Leu Trp His Lys Leu Pro Lys Ser Ile Tyr Phe Arg Arg
    450                 455                 460

Gly Ser Leu Pro Ile Ala Leu Asp Glu Val Ile Thr Asp Gly His Lys
465                 470                 475                 480

Arg Ala Leu Ile Val Thr Asp Arg Phe Leu Phe Asn Asn Gly Tyr Ala
                485                 490                 495

Asp Gln Ile Thr Ser Val Leu Lys Ala Ala Gly Val Glu Thr Glu Val
            500                 505                 510

Phe Phe Glu Val Glu Ala Asp Pro Thr Leu Ser Ile Val Arg Lys Gly
        515                 520                 525

Ala Glu Leu Ala Asn Ser Phe Lys Pro Asp Val Ile Ala Leu Gly
    530                 535                 540

Gly Gly Ser Pro Met Asp Ala Ala Lys Ile Met Trp Val Met Tyr Glu
545                 550                 555                 560

His Pro Glu Thr His Phe Glu Glu Leu Ala Leu Arg Phe Met Asp Ile
                565                 570                 575

Arg Lys Arg Ile Tyr Lys Phe Pro Lys Met Gly Val Lys Ala Lys Met
            580                 585                 590

Ile Ala Val Thr Thr Thr Ser Gly Thr Gly Ser Glu Val Thr Pro Phe
        595                 600                 605

Ala Val Val Thr Asp Asp Ala Thr Gly Gln Lys Tyr Pro Leu Ala Asp
    610                 615                 620

Tyr Ala Leu Thr Pro Asp Met Ala Ile Val Asp Ala Asn Leu Val Met
625                 630                 635                 640

Asp Met Pro Lys Ser Leu Cys Ala Phe Gly Gly Leu Asp Ala Val Thr
                645                 650                 655

His Ala Met Glu Ala Tyr Val Ser Val Leu Ala Ser Glu Phe Ser Asp
            660                 665                 670

Gly Gln Ala Leu Gln Ala Leu Lys Leu Leu Lys Glu Tyr Leu Pro Ala
        675                 680                 685

Ser Tyr His Glu Gly Ser Lys Asn Pro Val Ala Arg Glu Arg Val His
    690                 695                 700

Ser Ala Ala Thr Ile Ala Gly Ile Ala Phe Ala Asn Ala Phe Leu Gly
705                 710                 715                 720

Val Cys His Ser Met Ala His Lys Leu Gly Ser Gln Phe His Ile Pro
                725                 730                 735

His Gly Leu Ala Asn Ala Leu Leu Ile Cys Asn Val Ile Arg Tyr Asn
            740                 745                 750

Ala Asn Asp Asn Pro Thr Lys Gln Thr Ala Phe Ser Gln Tyr Asp Arg
        755                 760                 765

Pro Gln Ala Arg Arg Arg Tyr Ala Glu Ile Ala Asp His Leu Gly Leu
    770                 775                 780

Ser Ala Pro Gly Asp Arg Thr Ala Ala Lys Ile Glu Lys Leu Leu Ala
785                 790                 795                 800

Trp Leu Glu Thr Leu Lys Ala Glu Leu Gly Ile Pro Lys Ser Ile Arg
                805                 810                 815

Glu Ala Gly Val Gln Glu Ala Asp Phe Leu Ala Asn Val Asp Lys Leu
            820                 825                 830

Ser Glu Asp Ala Phe Asp Asp Gln Cys Thr Gly Ala Asn Pro Arg Tyr
```

```
                835               840               845
Pro Leu Ile Ser Glu Leu Lys Gln Ile Leu Leu Asp Thr Tyr Tyr Gly
            850               855               860

Arg Asp Tyr Val Glu Gly Glu Thr Ala Ala Lys Glu Ala Ala Pro
865               870               875               880

Ala Lys Ala Glu Lys Lys Ala Lys Lys Ser Ala
                885               890
```

<210> SEQ ID NO 24
<211> LENGTH: 2676
<212> TYPE: DNA
<213> ORGANISM: Escherichia coli

<400> SEQUENCE: 24

| | | | | |
|---|---|---|---|---|
| atggcggtga | cgaacgtcgc | cgaactgaac | gccctcgtcg | aacgggtgaa | aaaggcgcag | 60 |
| cgggagtacg | cctcgttcac | gcaggagcag | gtggataaaa | tcttccgcgc | cgccgccctg | 120 |
| gccgcggccg | acgcccgcat | cccgctcgcc | aaaatggcgg | tggccgagtc | cggcatgggc | 180 |
| atcgtggagg | acaaggtcat | caagaaccat | ttcgcctccg | agtacatcta | caacgcctac | 240 |
| aaggacgaga | gacctgcgg | cgtcctgtcg | gaggacgata | ccttcggcac | catcacgatc | 300 |
| gccgagccca | tcggcatcat | ctgcggcatc | gtcccgacca | ccaatcccac | ctccaccgcc | 360 |
| atcttcaaaa | gcctcatctc | cctgaaaacc | cgcaatgcga | tcatcttcag | ccccatccc | 420 |
| cgcgccaaag | acgccacgaa | caaggcggcc | gacatcgtcc | tccaggccgc | catcgcggcc | 480 |
| ggcgccccca | agacctgat | cggctggatc | gaccagccgt | cggtggagct | gtccaacgcc | 540 |
| ctcatgcatc | acccggacat | caatctcatc | ctggccacgg | gcggcccggg | catggtgaag | 600 |
| gccgcctact | ccagcggcaa | gccggcgatc | ggcgtgggcg | cgggcaacac | gcccgtggtc | 660 |
| atcgacgaaa | cggccgatat | caaacgcgcc | gtcgcctccg | tgctcatgag | caagaccttc | 720 |
| gacaacggcg | tgatctgcgc | gtcggaacag | tcggtcgtgg | tcgtcgactc | cgtgtacgac | 780 |
| gcggtgcgcg | agcgcttcgc | cacgcatggc | ggctacctgc | tgcagggcaa | ggagctgaaa | 840 |
| gccgtgcagg | acgtgatcct | caaaaacggc | gccctgaacg | ccgccatcgt | cggccagccc | 900 |
| gcgtataaga | tcgcggagct | ggccggcttc | tcggtcccgg | agaacacgaa | gatcctgatc | 960 |
| ggcgaggtca | cggtcgtcga | cgagagcgaa | cccttcgccc | acgagaagct | gtccccgacc | 1020 |
| ctggcgatgt | accgggcgaa | agacttcgaa | gacgcggtcg | agaaggccga | gaaactggtg | 1080 |
| gcgatgggcg | gcatcggcca | tacgagctgt | ctgtacaccg | accaggacaa | tcagcccgcc | 1140 |
| cgcgtgtcct | acttcggcca | gaaaatgaag | accgcccgca | tcctcatcaa | tacgcccgcg | 1200 |
| agccagggcg | gcatcggcga | tctctacaat | ttcaagctcg | cgccgtcgct | gaccctcggc | 1260 |
| tgcggctcct | gggcggcaa | ctccatctcc | gagaacgtgg | gccgaaaca | cctcatcaac | 1320 |
| aagaagaccg | tggccaagcg | ggcggagaac | atgctgtggc | ataagctgcc | caagtcgatc | 1380 |
| tacttccgcc | ggggctcgct | gcccatcgcg | ctggacgaag | tcatcacgga | cggccacaag | 1440 |
| cgggcgctga | tcgtgacgga | ccgcttcctg | ttcaataacg | gctacgccga | ccagatcacc | 1500 |
| tccgtcctga | aggccgcggg | cgtcgaaacg | gaagtcttct | tcgaagtcga | agccgacccg | 1560 |
| accctctcca | tcgtccggaa | gggcgccgag | ctggccaatt | ccttcaagcc | ggatgtcatc | 1620 |
| atcgcgctgg | gcggcggctc | gccgatggac | gccgccaaaa | tcatgtgggt | gatgtacgag | 1680 |
| caccccgaaa | cgcacttcga | agaactggcc | ctgcgcttca | tggatatccg | caagcggatc | 1740 |
| tacaaattcc | cgaaaatggg | cgtgaaagcg | aagatgatcg | cggtgacgac | caccagcggc | 1800 |

```
acgggctccg aggtgacgcc gttcgcggtc gtcaccgatg atgccaccgg ccagaaatac   1860
cccctggccg actacgccct gaccccgac atggccatcg tggacgccaa tctcgtgatg    1920
gacatgccga agagcctctg cgccttcggc ggcctggatg ccgtgacgca tgcgatggag   1980
gcgtatgtca gcgtgctggc gtccgagttc tcggacggcc aggcgctgca ggccctgaag   2040
ctgctgaagg agtacctgcc ggcctcctac cacgagggct ccaaaaaccc ggtggcccgg   2100
gagcgggtcc actcggcggc caccatcgcg ggcatcgcct tcgcgaacgc cttcctcggc   2160
gtgtgccatt cgatggccca aagctgggc tcccagttcc atatccccca cggcctggcg    2220
aacgcgctgc tgatctgtaa cgtcatccgg tacaacgcga acgataaccc gaccaaacag   2280
accgccttct cccagtatga ccgcccccag gcccggcgcc gctatgcgga aatcgccgac   2340
catctcggcc tgtcggcccc gggcgaccgc accgccgcca agatcgagaa gctgctggcc   2400
tggctcgaaa cgctgaaggc cgaactgggc atcccgaagt cgatccgcga agccggcgtc   2460
caggaagcgg acttcctggc gaatgtggat aaactgagcg aggacgcctt cgatgaccag   2520
tgcacgggcg ccaacccgcg ctaccgctc atcagcgagc tgaaacagat cctgctcgac    2580
acctattatg ccgcgattta cgtcgagggc gaaaccgccg cgaagaagga ggccgccccg   2640
gccaaagccg aaagaaggc caagaaaagc gcctga                              2676
```

<210> SEQ ID NO 25
<211> LENGTH: 387
<212> TYPE: PRT
<213> ORGANISM: Escherichia coli

<400> SEQUENCE: 25

```
Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Ala Asn Tyr Pro Glu
            100                 105                 110

Asn Ile Asp Pro Trp His Ile Leu Gln Thr Gly Gly Lys Glu Ile Lys
        115                 120                 125

Ser Ala Ile Pro Met Gly Cys Val Leu Thr Leu Pro Ala Thr Gly Ser
    130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
    210                 215                 220
```

Ile Glu Asp Gly Pro Lys Ala Leu Lys Glu Pro Glu Asn Tyr Asp Val
225                 230                 235                 240

Arg Ala Asn Val Met Trp Gly Ala Thr Gln Ala Leu Asn Gly Leu Ile
            245                 250                 255

Gly Ala Gly Val Pro Gln Asp Trp Ala Thr His Met Leu Gly His Glu
        260                 265                 270

Leu Thr Ala Met His Gly Leu Asp His Ala Gln Thr Leu Ala Ile Val
    275                 280                 285

Leu Pro Ala Leu Trp Asn Glu Lys Arg Glu Thr Lys Arg Ala Lys Leu
290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
        355                 360                 365

Gly Glu Asn His Asp Ile Thr Leu Asp Val Ser Arg Arg Ile Tyr Glu
    370                 375                 380

Ala Ala Arg
385

<210> SEQ ID NO 26
<211> LENGTH: 1164
<212> TYPE: DNA
<213> ORGANISM: Escherichia coli

<400> SEQUENCE: 26
atgaacaact taatctgca caccccaacc cgcattctgt ttggtaaagg cgcaatcgct      60
ggtttacgcg aacaaattcc tcacgatgct cgcgtattga ttacctacgg cggcggcagc    120
gtgaaaaaaa ccggcgttct cgatcaagtt ctggatgccc tgaaaggcat ggacgtgctg    180
gaatttggcg gtattgagcc aaaccccggct atgaaaacgc tgatgaacgc cgtgaaactg    240
gttcgcgaac agaaagtgac tttcctgctg gcggttggcg gcggttctgt actggacggc    300
accaaattta tcgccgcagc ggctaactat ccggaaaata tcgatccgtg gcacattctg    360
caaacgggcg gtaaagagat taaagcgcc atcccgatgg gctgtgtgct gacgctgcca    420
gcaaccggtt cagaatccaa cgcaggcgcg gtgatctccc gtaaaaccac aggcgacaag    480
caggcgttcc attctgccca tgttcagccg gtatttgccg tgctcgatcc ggtttatacc    540
tacaccctgc cgccgcgtca ggtggctaac ggcgtagtgg acgcctttgt acacaccgtg    600
gaacagtatg ttaccaaacc ggttgatgcc aaaattcagg accgtttcgc agaaggcatt    660
ttgctgacgc taatcgaaga tggtccgaaa gccctgaaag agccagaaaa ctacgatgtg    720
cgcgccaacg tcatgtgggc ggcgactcag gcgctgaacg gtttgattgg cgctggcgta    780
ccgcaggact gggcaacgca tatgctgggc cacgaactga ctgcgatgca cggtctggat    840
cacgcgcaaa cactggctat cgtcctgcct gcactgtgga tgaaaaaacg cgataccaag    900
cgcgctaagc tgctgcaata tgctgaacgc gtctggaaca tcactgaagg ttccgatgat    960
gagcgtattg acgccgcgat tgccgcaacc cgcaatttct ttgagcaatt aggcgtgccg   1020
acccacctct ccgactacgg tctgacggc agctccatcc cggctttgct gaaaaaactg   1080
gaagagcacg gcatgaccca actgggcgaa aatcatgaca ttacgttgga tgtcagccgc   1140
cgtatatacg aagccgcccg ctaa    1164

<210> SEQ ID NO 27
<211> LENGTH: 383
<212> TYPE: PRT
<213> ORGANISM: Escherichia coli

<400> SEQUENCE: 27

Met Met Ala Asn Arg Met Ile Leu Asn Glu Thr Ala Trp Phe Gly Arg
1               5                   10                  15

Gly Ala Val Gly Ala Leu Thr Asp Glu Val Lys Arg Arg Gly Tyr Gln
            20                  25                  30

Lys Ala Leu Ile Val Thr Asp Lys Thr Leu Val Gln Cys Gly Val Val
        35                  40                  45

Ala Lys Val Thr Asp Lys Met Asp Ala Ala Gly Leu Ala Trp Ala Ile
    50                  55                  60

Tyr Asp Gly Val Val Pro Asn Pro Thr Ile Thr Val Val Lys Glu Gly
65                  70                  75                  80

Leu Asp Val Phe Gln Asn Ser Gly Ala Asp Tyr Leu Ile Ala Ile Gly
                85                  90                  95

Gly Gly Ser Pro Gln Asp Thr Cys Lys Ala Ile Gly Ile Ile Ser Asn
            100                 105                 110

Asn Pro Glu Phe Ala Asp Val Arg Ser Leu Glu Gly Leu Ser Pro Thr
        115                 120                 125

Asn Lys Pro Ser Val Pro Ile Leu Ala Ile Pro Thr Thr Ala Gly Thr
    130                 135                 140

Ala Ala Glu Val Thr Ile Asn Tyr Val Ile Thr Asp Glu Glu Lys Arg
145                 150                 155                 160

Arg Lys Phe Val Cys Val Asp Pro His Asp Ile Pro Gln Val Ala Phe
                165                 170                 175

Ile Asp Ala Asp Met Met Asp Gly Met Pro Pro Ala Leu Lys Ala Ala
            180                 185                 190

Thr Gly Val Asp Ala Leu Thr His Ala Ile Glu Gly Tyr Ile Thr Arg
        195                 200                 205

Gly Ala Trp Ala Leu Thr Asp Ala Leu His Ile Lys Ala Ile Glu Ile
    210                 215                 220

Ile Ala Gly Ala Leu Arg Gly Ser Val Ala Gly Asp Lys Asp Ala Gly
225                 230                 235                 240

Glu Glu Met Ala Leu Gly Gln Tyr Val Ala Gly Met Gly Phe Ser Asn
                245                 250                 255

Val Gly Leu Gly Leu Val His Gly Met Ala His Pro Leu Gly Ala Phe
            260                 265                 270

Tyr Asn Thr Pro His Gly Val Ala Asn Ala Ile Leu Leu Pro His Val
        275                 280                 285

Met Arg Tyr Asn Ala Asp Phe Thr Asp Glu Lys Tyr Arg Asp Ile Ala
    290                 295                 300

Arg Val Met Gly Val Lys Val Glu Gly Met Ser Leu Glu Glu Ala Arg
305                 310                 315                 320

Asn Ala Ala Val Glu Ala Val Phe Ala Leu Asn Arg Asp Val Gly Ile
                325                 330                 335

Pro Pro His Leu Arg Asp Val Gly Val Arg Lys Glu Asp Ile Pro Ala
            340                 345                 350

Leu Ala Gln Ala Ala Leu Asp Asp Val Cys Thr Gly Gly Asn Pro Arg
        355                 360                 365

Glu Ala Thr Leu Glu Asp Ile Val Glu Leu Tyr His Thr Ala Trp
        370                 375                 380

<210> SEQ ID NO 28
<211> LENGTH: 1149
<212> TYPE: DNA
<213> ORGANISM: Escherichia coli

<400> SEQUENCE: 28

| | | |
|---|---|---|
| atggcgaatc ggatgatcct caatgaaacg gcctggttcg ccgcggcgc ggtcggcgcc | 60 |
| ctcaccgatg aggtcaagcg gcggggctac cagaaggccc tgatcgtcac ggataaaacc | 120 |
| ctggtgcagt gcggcgtcgt cgccaaggtg accgacaaga tggatgcggc cggcctggcc | 180 |
| tgggcgatct acgacggcgt ggtgcccaac cccaccatca ccgtggtgaa ggaaggcctg | 240 |
| ggcgtgttcc agaactcggg cgcggattat ctcatcgcga tcggcggcgg cagcccccag | 300 |
| gacacctgca aggccatcgg catcatctcg aacaaccccg agttcgcgga cgtgcgctcc | 360 |
| ctggagggcc tgtcgccgac gaacaagccc tccgtcccga cctcgccat cccgacgacg | 420 |
| gccggcaccg cggccgaggt gaccatcaat tacgtcatca ccgacgagga aaagcggcgc | 480 |
| aagttcgtgt gtgtggaccc ccatgacatc ccccaggtcg ccttcatcga cgccgacatg | 540 |
| atggatggca tgccccccgc cctcaaggcc gcgacgggcg tggacgcgct gacgcatgcc | 600 |
| atcgaaggct acatcacccg gggcgcctgg gccctgacgg atgccctgca tatcaaggcc | 660 |
| atcgaaatca tcgccggcgc cctgcgcggc tccgtggccg cgacaagga tgcgggcgag | 720 |
| gagatggcgc tgggccagta cgtggccggc atgggcttct ccaatgtggg cctgggcctg | 780 |
| gtgcatggca tggcccatcc gctcggcgcc ttctacaaca cgccgcatgg cgtcgcgaac | 840 |
| gcgatcctcc tgccgcatgt catgcgctac aatgcggact tcacgggcga gaaataccgc | 900 |
| gatatcgccc gggtcatggg cgtgaaggtc gagggcatgt cgctggaaga ggcgcggaac | 960 |
| gccgcggtcg aagccgtctt cgccctgaac cgggatgtgg cgatcccgcc gcacctgcgc | 1020 |
| gatgtcggcg tccgcaagga agacatcccc gcgctggcgc aggccgccct ggacgatgtg | 1080 |
| tgcaccggcg caaccccccg cgaggcgacg ctggaagaca tcgtcgaact ctaccatacc | 1140 |
| gcgtggtga | 1149 |

<210> SEQ ID NO 29
<211> LENGTH: 860
<212> TYPE: PRT
<213> ORGANISM: Clostridium beijerinckii

<400> SEQUENCE: 29

Met Arg Val Thr Asn Pro Glu Glu Leu Thr Lys Arg Ile Glu Gln Ile
1               5                   10                  15

Arg Glu Ala Gln Arg Glu Phe Ala Lys Phe Ser Gln Glu Glu Val Asp
            20                  25                  30

Glu Ile Phe Arg Gln Ala Ala Met Ala Ala Asn Asp Ala Arg Ile Thr
        35                  40                  45

Leu Ala Lys Met Ala Val Glu Glu Ser Gly Met Gly Ile Val Glu Asp
    50                  55                  60

Lys Val Ile Lys Asn His Phe Ala Ala Glu Tyr Ile Tyr Asn Gln Tyr
65                  70                  75                  80

Lys Asp Thr Lys Thr Cys Gly Val Ile Glu Arg Asp Glu Met Phe Gly
                85                  90                  95

Ile Thr His Ile Ala Glu Pro Ile Gly Val Ile Ala Ala Ile Val Pro

```
            100                 105                 110
Thr Thr Asn Pro Thr Ser Thr Ala Ile Phe Lys Thr Leu Ile Ala Leu
            115                 120                 125

Lys Thr Arg Asn Gly Ile Ile Ile Ser Pro His Pro Arg Ala Lys Asn
            130                 135                 140

Ser Thr Ile Ala Ala Lys Ile Val Leu Glu Ala Ala Glu Arg Ala
145                 150                 155                 160

Gly Ala Pro Lys Gly Ile Ile Gly Trp Ile Asp Glu Pro Ser Ile Glu
                    165                 170                 175

Leu Ser Arg Asn Val Met Ser Glu Ser Asp Ile Ile Leu Ala Thr Gly
                    180                 185                 190

Gly Pro Gly Met Val Arg Ala Ala Tyr Ser Ser Gly Lys Pro Ala Ile
            195                 200                 205

Gly Val Gly Ala Gly Asn Thr Pro Ala Ile Ile Asp Asp Thr Ala His
            210                 215                 220

Ile Lys Met Ala Val Asn Ser Ile Leu Leu Ser Lys Thr Phe Asp Asn
225                 230                 235                 240

Gly Val Val Cys Ala Ser Glu Gln Ser Ile Ile Ala Met Glu Ser Val
                    245                 250                 255

Tyr Asp Glu Val Arg Lys Glu Leu Asp Glu Arg Gly Ala Tyr Ile Leu
                    260                 265                 270

Lys Gly Asp Glu Val Asp Lys Val Arg Ser Ile Ile Leu Asp Pro Lys
                    275                 280                 285

Gly Ser Leu Asn Ser Glu Ile Val Gly Gln Ser Ala Tyr Lys Ile Ala
            290                 295                 300

Lys Met Ala Gly Val Glu Val Ser Glu Ala Val Lys Val Leu Ile Gly
305                 310                 315                 320

Glu Val Glu Ser Pro Glu Leu Glu Glu Pro Phe Ser His Glu Lys Leu
                    325                 330                 335

Ser Pro Ile Leu Gly Met Tyr Lys Ala Lys Thr Phe Asp Asp Ala Leu
            340                 345                 350

Arg Leu Ala Ser Arg Met Ile Glu Leu Gly Gly Phe Gly His Thr Ser
            355                 360                 365

Ile Leu Tyr Thr Asn Gln Val Glu Ser Val Asp Arg Ile Glu Lys Phe
            370                 375                 380

Gly Val Ala Met Lys Thr Ala Arg Thr Leu Ile Asn Met Pro Ala Ser
385                 390                 395                 400

Gln Gly Ala Ile Gly Asp Ile Tyr Asn Phe Lys Leu Ala Pro Ser Leu
                    405                 410                 415

Thr Leu Gly Cys Gly Ser Trp Gly Gly Asn Ser Ile Ser Glu Asn Val
            420                 425                 430

Gly Pro Lys His Leu Ile Asn Val Lys Arg Ile Ala Glu Arg Arg Glu
            435                 440                 445

Asn Met Leu Trp Phe Arg Val Pro Asp Lys Ile Tyr Phe Lys Phe Gly
            450                 455                 460

Cys Leu Pro Ile Ala Leu Glu Glu Leu Asn Ala Met Lys Lys Arg
465                 470                 475                 480

Ala Phe Ile Val Thr Asp Arg Val Leu Phe Asp Leu Gly Tyr Thr His
                    485                 490                 495

Lys Ile Thr Asp Ile Leu Ser Glu Asn His Ile Glu Tyr Lys Ile Phe
                    500                 505                 510

Ser Asp Val Glu Pro Asp Pro Thr Leu Lys Ala Ala Lys Leu Gly Ala
                    515                 520                 525
```

| | | | | | | | | | | | |
|---|---|---|---|---|---|---|---|---|---|---|---|
| Asp | Ala | Met | Arg | Asp | Phe | Asn | Pro | Asp | Val | Ile | Ile | Ala | Ile | Gly | Gly |
| | 530 | | | | 535 | | | | 540 | | |

Asp Ala Met Arg Asp Phe Asn Pro Asp Val Ile Ile Ala Ile Gly Gly
          530                 535                 540

Gly Ser Pro Met Asp Ala Ala Lys Ile Met Trp Val Met Tyr Glu His
545                 550                 555                 560

Pro Asp Val Arg Phe Glu Asp Leu Ala Met Arg Phe Met Asp Ile Arg
                565                 570                 575

Lys Arg Val Tyr Glu Phe Pro Pro Met Gly Glu Arg Ala Ile Leu Val
            580                 585                 590

Ala Ile Pro Thr Ser Ala Gly Thr Gly Ser Glu Val Thr Pro Phe Ala
        595                 600                 605

Val Ile Thr Asp Gln Gln Thr Gly Val Lys Tyr Pro Leu Ala Asp Tyr
    610                 615                 620

Ala Leu Thr Pro Asn Met Ala Ile Ile Asp Ala Glu Leu Met Met Ser
625                 630                 635                 640

Met Pro Lys Gly Leu Thr Ala Ala Ser Gly Ile Asp Ala Leu Val His
                645                 650                 655

Ala Ile Glu Ala Tyr Val Ser Val Leu Ala Ser Glu Tyr Thr Asn Gly
            660                 665                 670

Leu Ala Leu Glu Ala Ile Arg Leu Thr Phe Lys Tyr Leu Pro Asp Ala
        675                 680                 685

Tyr Asn Gly Gly Thr Thr Asn Ile Lys Ala Arg Glu Lys Met Ala His
    690                 695                 700

Ala Ser Ser Val Ala Gly Met Ala Phe Ala Asn Ala Phe Leu Gly Ile
705                 710                 715                 720

Cys His Ser Met Ala His Lys Leu Gly Ala Phe His His Val Pro His
                725                 730                 735

Gly Ile Ala Asn Ala Leu Leu Ile Asp Glu Val Ile Arg Phe Asn Ala
            740                 745                 750

Thr Asp Ala Pro Arg Lys Gln Ala Ala Phe Pro Gln Tyr Lys Tyr Pro
        755                 760                 765

Asn Ala Gly Trp Arg Tyr Ala Arg Ile Ala Asp Tyr Leu Asn Leu Gly
    770                 775                 780

Gly Asn Thr Glu Glu Lys Val Glu Leu Leu Ile Lys Ala Ile Asp
785                 790                 795                 800

Asp Leu Lys Val Lys Val Arg Ile Pro Lys Ser Ile Lys Glu Phe Gly
                805                 810                 815

Val Ser Glu Glu Lys Phe Tyr Asp Ser Met Asp Glu Met Val Glu Gln
            820                 825                 830

Ala Phe Asp Asp Gln Cys Thr Gly Ala Asn Pro Arg Tyr Pro Leu Met
        835                 840                 845

Ser Glu Ile Lys Glu Met Tyr Ile Lys Ser Tyr Asn
850                 855                 860

<210> SEQ ID NO 30
<211> LENGTH: 1407
<212> TYPE: DNA
<213> ORGANISM: Clostridium beijerinckii

<400> SEQUENCE: 30

```
atgaacaagg acacgctgat ccccaccacg aaagacctca aggtgaagac caacggcgag    60
aacatcaacc tgaaaaacta caaggacaac agcagctgct tcggcgtgtt cgaaaacgtc   120
gaaacgccca tcagctcggc ggtgcatgcc cagaaaatcc tcagcctgca ctatacgaag   180
gaacagcgcg aaaagatcat caccgaaatc cgcaaggccg cgctccagaa caaagaggtg   240
```

```
ctggccacga tgatcctgga ggaaacccat atgggccgct acgaagataa aatcctgaag    300
cacgagctgg tggcgaaata cacgcccggc accgaagacc tgacgaccac cgcctggagc    360
ggcgataacg gcctgacggt ggtggagatg tcgccgtatg gcgtgatcgg cgcgatcacc    420
ccgtccacca acccgaccga acggtcatc tgtaactcga tcggcatgat cgcggccggc    480
aacgcggtcg tgttcaatgg ccacccgtgc gccaagaagt gcgtcgcctt cgccgtcgag    540
atgatcaaca aggccatcat ctcctgcggc ggcccggaga acctcgtgac gacgatcaaa    600
aacccgacga tggagtccct ggatgccatc atcaagcacc cgtccatcaa gctgctctgc    660
ggcaccggcg cccgggcat ggtcaaaacg ctgctgaact ccggcaaaaa agccatcggc    720
gcgggcgcgg gcaacccccc cgtcatcgtg gatgacaccg ccgacatcga aaagccggc    780 cggtcgatca tcgaaggctg ctccttcgac aataacctcc cgtgcatcgc cgagaaagag    840
gtcttcgtct tcgagaacgt cgcggacgat ctgatctcca acatgctgaa gaacaacgcc    900
gtcatcatca cgaagacca ggtgtccaag ctgatcgacc tcgtgctgca gaagaacaat    960
gaaacccagg agtacttcat caacaagaag tgggtcggca aggacgcgaa gctgttcctg   1020
gacgaaatcg atgtggagtc cccgagcaat gtgaagtgca tcatctgcga ggtcaacgcg   1080
aaccacccct tcgtcatgac cgagctcatg atgccgatcc tgccgatcgt gcgggtgaag   1140
gatatcgacg aagccatcaa gtacgcgaaa atcgcggaac agaatcggaa gcattcggcc   1200
tatatctaca gcaagaacat cgataacctc aaccgcttcg aacgggagat cgacaccacc   1260
atcttcgtca agaacgccaa atccttcgcc ggcgtgggct atgaggcgga aggcttcacc   1320
accttcacga tcgccggctc caccggcgag ggcatcacct ccgcccggaa cttcacccgc   1380
cagcgccgct gcgtgctggc gggctga                                       1407
```

<210> SEQ ID NO 31
<211> LENGTH: 360
<212> TYPE: PRT
<213> ORGANISM: Saccharomyces cerevisiae

<400> SEQUENCE: 31

```
Met Ser Tyr Pro Glu Lys Phe Glu Gly Ile Ala Ile Gln Ser His Glu
1               5                   10                  15

Asp Trp Lys Asn Pro Lys Lys Thr Lys Tyr Asp Pro Lys Pro Phe Tyr
            20                  25                  30

Asp His Asp Ile Asp Ile Lys Ile Glu Ala Cys Gly Val Cys Gly Ser
        35                  40                  45

Asp Ile His Cys Ala Ala Gly His Trp Gly Asn Met Lys Met Pro Leu
    50                  55                  60

Val Val Gly His Glu Ile Val Gly Lys Val Val Lys Leu Gly Pro Lys
65                  70                  75                  80

Ser Asn Ser Gly Leu Lys Val Gly Gln Arg Val Gly Val Gly Ala Gln
                85                  90                  95

Val Phe Ser Cys Leu Glu Cys Asp Arg Cys Lys Asn Asp Asn Glu Pro
            100                 105                 110

Tyr Cys Thr Lys Phe Val Thr Thr Tyr Ser Gln Pro Tyr Glu Asp Gly
        115                 120                 125

Tyr Val Ser Gln Gly Gly Tyr Ala Asn Tyr Val Arg Val His Glu His
    130                 135                 140

Phe Val Val Pro Ile Pro Glu Asn Ile Pro Ser His Leu Ala Ala Pro
145                 150                 155                 160
```

| | | | | | | | | | | | |
|---|---|---|---|---|---|---|---|---|---|---|---|
|Leu|Leu|Cys|Gly|Gly|Leu|Thr|Val|Tyr|Ser|Pro|Leu|Val|Arg|Asn|Gly|
| | | | |165| | | | |170| | | | |175| |

Cys Gly Pro Gly Lys Lys Val Gly Ile Val Gly Leu Gly Gly Ile Gly
            180                  185                  190

Ser Met Gly Thr Leu Ile Ser Lys Ala Met Gly Ala Glu Thr Tyr Val
            195                  200                  205

Ile Ser Arg Ser Ser Arg Lys Arg Glu Asp Ala Met Lys Met Gly Ala
            210                  215                  220

Asp His Tyr Ile Ala Thr Leu Glu Glu Gly Asp Trp Gly Glu Lys Tyr
225                  230                  235                  240

Phe Asp Thr Phe Asp Leu Ile Val Val Cys Ala Ser Ser Leu Thr Asp
            245                  250                  255

Ile Asp Phe Asn Ile Met Pro Lys Ala Met Lys Val Gly Gly Arg Ile
            260                  265                  270

Val Ser Ile Ser Ile Pro Glu Gln His Glu Met Leu Ser Leu Lys Pro
            275                  280                  285

Tyr Gly Leu Lys Ala Val Ser Ile Ser Tyr Ser Ala Leu Gly Ser Ile
            290                  295                  300

Lys Glu Leu Asn Gln Leu Leu Lys Leu Val Ser Glu Lys Asp Ile Lys
305                  310                  315                  320

Ile Trp Val Glu Thr Leu Pro Val Gly Glu Ala Gly Val His Glu Ala
            325                  330                  335

Phe Glu Arg Met Glu Lys Gly Asp Val Arg Tyr Arg Phe Thr Leu Val
            340                  345                  350

Gly Tyr Asp Lys Glu Phe Ser Asp
            355                  360

<210> SEQ ID NO 32
<211> LENGTH: 1083
<212> TYPE: DNA
<213> ORGANISM: Saccharomyces cerevisiae

<400> SEQUENCE: 32

```
atgagctatc ccgagaagtt cgaggggatc gccatccaga gccacgagga ctggaagaac    60
ccgaaaaaga ccaagtatga tccgaagccc ttctacgatc acgacatcga catcaagatc   120
gaggcctgcg gcgtctgcgg cagcgatatc cattgtgcgg ctggccactg gggcaacatg   180
aagatgccgt tggtcgtcgg ccacgagatc gtgggcaagg tcgtgaagtt aggcccgaaa   240
agcaacagcg gcttgaaggt gggccagcgc gtgggtgtgg gtgcgcaggt cttcagctgt   300
ctggagtgcg accgttgcaa gaacgacaac gaaccgtact gcaccaagtt cgtcaccacc   360
tactcgcagc cctacgagga cggctacgtc tcgcagggcg gttacgccaa ctatgtccga   420
gtccacgaac acttcgtggt gcccatcccg gaaaatatcc ccagccatct ggcggctccc   480
ctgctgtgcg gtggcttgac cgtctacagc cccctcgtcc gcaatggctg cggtcccggc   540
aagaaggtgg gtatcgtggg cctcggcggt ataggctcta tgggcacgct gatctcgaaa   600
gcgatgggcg cagaaacgta cgtgatctcg cgttcctcgc gcaagcgcga ggatgcgatg   660
aagatgggtg cggaccacta catcgccacg ctggaggagg gtgactgggg tgagaagtac   720
ttcgacacgt tcgacctcat cgtggtgtgc gcgagttccc tgacggacat cgacttcaat   780
atcatgccca aggcgatgaa ggtcggaggg cgcatcgtct ccatctcgat cccggagcag   840
cacgaaatgc tgtcgctgaa gccctacggc ctgaaagccg tctccattag ctactcggcg   900
ctcggtagta tcaaggagct caaccagctg ttgaagttgg tttccgaaaa ggacatcaag   960
```

```
atctgggtgg aaacgctccc ggtgggcgaa gccggtgtgc acgaggcctt tgagcggatg    1020
gagaaggggg atgtccgtta tcggtttaca ctcgtcggct acgataaaga gttctcggat    1080
taa                                                                  1083
```

<210> SEQ ID NO 33
<211> LENGTH: 340
<212> TYPE: PRT
<213> ORGANISM: Acinetobacter baylyi

<400> SEQUENCE: 33

```
Met Thr Thr Asn Val Ile His Ala Tyr Ala Ala Met Gln Ala Gly Glu
1               5                  10                  15

Ala Leu Val Pro Tyr Ser Phe Asp Ala Gly Glu Leu Gln Pro His Gln
            20                  25                  30

Val Glu Val Lys Val Glu Tyr Cys Gly Leu Cys His Ser Asp Val Ser
        35                  40                  45

Val Leu Asn Asn Glu Trp His Ser Ser Val Tyr Pro Val Val Ala Gly
    50                  55                  60

His Glu Val Ile Gly Thr Ile Thr Gln Leu Gly Ser Glu Ala Lys Gly
65                  70                  75                  80

Leu Lys Ile Gly Gln Arg Val Gly Ile Gly Trp Thr Ala Glu Ser Cys
                85                  90                  95

Gln Ala Cys Asp Gln Cys Ile Ser Gly Gln Gln Val Leu Cys Thr Gly
            100                 105                 110

Glu Asn Thr Ala Thr Ile Ile Gly His Ala Gly Gly Phe Ala Asp Lys
        115                 120                 125

Val Arg Ala Gly Trp Gln Trp Val Ile Pro Leu Pro Asp Glu Leu Asp
    130                 135                 140

Pro Thr Ser Ala Gly Pro Leu Leu Cys Gly Gly Ile Thr Val Phe Asp
145                 150                 155                 160

Pro Ile Leu Lys His Gln Ile Gln Ala Ile His His Val Ala Val Ile
                165                 170                 175

Gly Ile Gly Gly Leu Gly His Met Ala Ile Lys Leu Leu Lys Ala Trp
            180                 185                 190

Gly Cys Glu Ile Thr Ala Phe Ser Ser Asn Pro Asn Lys Thr Asp Glu
        195                 200                 205

Leu Lys Ala Met Gly Ala Asp His Val Val Asn Ser Arg Asp Asp Ala
    210                 215                 220

Glu Ile Lys Ser Gln Gln Gly Lys Phe Asp Leu Leu Leu Ser Thr Val
225                 230                 235                 240

Asn Val Pro Leu Asn Trp Asn Ala Tyr Leu Asn Thr Leu Ala Pro Asn
                245                 250                 255

Gly Thr Phe His Phe Leu Gly Val Val Met Glu Pro Ile Pro Val Pro
            260                 265                 270

Val Gly Ala Leu Leu Gly Gly Ala Lys Ser Leu Thr Ala Ser Pro Thr
        275                 280                 285

Gly Ser Pro Ala Ala Leu Arg Lys Leu Leu Glu Phe Ala Ala Arg Lys
    290                 295                 300

Asn Ile Ala Pro Gln Ile Glu Met Tyr Pro Met Ser Glu Leu Asn Glu
305                 310                 315                 320

Ala Ile Glu Arg Leu His Ser Gly Gln Ala Arg Tyr Arg Ile Val Leu
                325                 330                 335

Lys Ala Asp Phe
            340
```

<210> SEQ ID NO 34
<211> LENGTH: 1023
<212> TYPE: DNA
<213> ORGANISM: Acinetobacter baylyi

<400> SEQUENCE: 34

| | | | | | |
|---|---|---|---|---|---|
| atgacgacca | acgtcatcca | tgcctatgcg | gccatgcagg | ccggcgaggc | gctggtgccg | 60 |
| tatagcttcg | acgcgggcga | gctccagccg | catcaggtcg | aggtgaaggt | ggaatactgc | 120 |
| ggcctgtgtc | attccgatgt | gtcggtcctg | aataacgaat | ggcactcctc | cgtctatccg | 180 |
| gtggtcgccg | gccacgaggt | catcggcacg | atcacccagc | tgggcagcga | agccaagggc | 240 |
| ctgaagatcg | gccagcgcgt | cggcatcggc | tggacggccg | agagctgcca | ggcctgcgat | 300 |
| cagtgcatct | ccggccagca | ggtgctgtgc | accggcgaga | caccgccac | catcatcggc | 360 |
| catgccggcg | gcttcgcgga | taaagtgcgg | gccggctggc | agtgggtgat | cccgctcccg | 420 |
| gatgagctcg | atcccacgag | cgccggcccg | ctgctgtgtg | gcggcatcac | cgtgttcgac | 480 |
| ccgatcctga | agcaccagat | ccaggccatc | caccatgtcg | ccgtgatcgg | catcggcggc | 540 |
| ctgggccaca | tggcgatcaa | gctgctcaag | gcctggggct | gtgaaatcac | cgccttcagc | 600 |
| agcaatccca | acaagaccga | cgaactgaag | gcgatgggcg | ccgaccatgt | ggtcaactcc | 660 |
| cgcgatgacg | cggaaatcaa | gagccagcag | ggcaagttcg | acctgctgct | gtcgacggtg | 720 |
| aatgtccccc | tcaactggaa | cgcctacctg | aatacctgg | ccccgaacgg | cacgttccac | 780 |
| ttcctgggcg | tcgtcatgga | gccgatcccg | gtgccggtgg | gcgccctcct | gggcggcgcg | 840 |
| aaaagcctga | ccgcctcgcc | cacgggcagc | cccgccgccc | tccgcaagct | gctggagttc | 900 |
| gccgcccgca | gaacatcgc | gccccagatc | gaaatgtatc | ccatgagcga | gctgaacgaa | 960 |
| gccatcgagc | gcctgcatag | cggccaggcc | cgctatcgga | tcgtgctcaa | agcggacttc | 1020 |
| tga | | | | | | 1023 |

<210> SEQ ID NO 35
<211> LENGTH: 339
<212> TYPE: PRT
<213> ORGANISM: Escherichia coli

<400> SEQUENCE: 35

Met Ser Met Ile Lys Ser Tyr Ala Ala Lys Glu Ala Gly Gly Glu Leu
1               5                   10                  15

Glu Val Tyr Glu Tyr Asp Pro Gly Glu Leu Arg Pro Gln Asp Val Glu
            20                  25                  30

Val Gln Val Asp Tyr Cys Gly Ile Cys His Ser Asp Leu Ser Met Ile
        35                  40                  45

Asp Asn Glu Trp Gly Phe Ser Gln Tyr Pro Leu Val Ala Gly His Glu
    50                  55                  60

Val Ile Gly Arg Val Val Ala Leu Gly Ser Ala Ala Gln Asp Lys Gly
65                  70                  75                  80

Leu Gln Val Gly Gln Arg Val Gly Ile Gly Trp Thr Ala Arg Ser Cys
                85                  90                  95

Gly His Cys Asp Ala Cys Ile Ser Gly Asn Gln Ile Asn Cys Glu Gln
            100                 105                 110

Gly Ala Val Pro Thr Ile Met Asn Arg Gly Gly Phe Ala Glu Lys Leu
        115                 120                 125

Arg Ala Asp Trp Gln Trp Val Ile Pro Leu Pro Glu Asn Ile Asp Ile
    130                 135                 140

```
Glu Ser Ala Gly Pro Leu Leu Cys Gly Gly Ile Thr Val Phe Lys Pro
145                 150                 155                 160

Leu Leu Met His His Ile Thr Ala Thr Ser Arg Val Gly Val Ile Gly
                165                 170                 175

Ile Gly Gly Leu Gly His Ile Ala Ile Lys Leu Leu His Ala Met Gly
            180                 185                 190

Cys Glu Val Thr Ala Phe Ser Ser Asn Pro Ala Lys Glu Gln Glu Val
        195                 200                 205

Leu Ala Met Gly Ala Asp Lys Val Val Asn Ser Arg Asp Pro Gln Ala
    210                 215                 220

Leu Lys Ala Leu Ala Gly Gln Phe Asp Leu Ile Ile Asn Thr Val Asn
225                 230                 235                 240

Val Ser Leu Asp Trp Gln Pro Tyr Phe Glu Ala Leu Thr Tyr Gly Gly
                245                 250                 255

Asn Phe His Thr Val Gly Ala Val Leu Thr Pro Leu Ser Val Pro Ala
            260                 265                 270

Phe Thr Leu Ile Ala Gly Asp Arg Ser Val Ser Gly Ser Ala Thr Gly
        275                 280                 285

Thr Pro Tyr Glu Leu Arg Lys Leu Met Arg Phe Ala Ala Arg Ser Lys
    290                 295                 300

Val Ala Pro Thr Thr Glu Leu Phe Pro Met Ser Lys Ile Asn Asp Ala
305                 310                 315                 320

Ile Gln His Val Arg Asp Gly Lys Ala Arg Tyr Arg Val Val Leu Lys
                325                 330                 335

Ala Asp Phe

<210> SEQ ID NO 36
<211> LENGTH: 1020
<212> TYPE: DNA
<213> ORGANISM: Escherichia coli

<400> SEQUENCE: 36
atgtccatga tcaaaagcta cgccgcgaaa gaggcgggcg gcgagctgga ggtgtatgag      60
tatgacccgg gcgagctgcg gccccaggac gtggaagtgc aggtcgacta ctgcggcatc     120
tgccattcgg acctctcgat gatcgataac gagtggggct tcagccagta cccctggtg     180
gccggccacg aggtgatcgg ccgcgtggtc gccctgggct cggccgcgca ggataaaggc     240
ctgcaggtcg ccagcgcgt cggcatcggc tggacggccc gcagctgcgg ccattgcgat     300
gcctgcatca gcggcaatca gatcaattgc gaacaggggcg cggtcccgac catcatgaac     360
cggggcggct cgccgaaaa gctgcgggcc gattggcagt gggtgatccc gctgccggag     420
aacatcgata tcgagtcggc cggccccctg ctgtgcggcg catcaccgt cttcaagccg     480
ctcctgatgc atcatatcac ggcgaccagc cgggtcggcg tgatcggcat cggcggcctc     540
ggccacatcg cgatcaaact gctgcacgcg atgggctgcg aggtcaccgc gttctcctcg     600
aaccccgcca aggagcagga agtgctggcg atgggcgccg ataaagtcgt gaactcgcgc     660
gaccccagg ccctcaaagc cctggccggc cagttcgatc tcatcatcaa cacggtgaac     720
gtgtcgctgg actggcagcc ctacttcgaa gccctgacct atggcggcaa cttccatacc     780
gtcggcgccg tgctgacccc gctgtccgtc ccggccttca ccctgatcgc cggcgaccgc     840
agcgtgtccg gcagcgccac cggcacgccc tatgagctgc gcaagctgat gcgcttcgcc     900
gcccgcagca aggtcgcccc gaccaccgag ctgttcccca tgtccaagat caatgacgcg     960
```
atccagcatg tccgggacgg caaggcccgc tatcgcgtcg tcctcaaggc ggacttctga    1020

<210> SEQ ID NO 37
<211> LENGTH: 388
<212> TYPE: PRT
<213> ORGANISM: Escherichia coli

<400> SEQUENCE: 37

Met Asn Leu His Glu Tyr Gln Ala Lys Gln Leu Phe Ala Arg Tyr Gly
1               5                   10                  15

Leu Pro Ala Pro Val Gly Tyr Ala Cys Thr Thr Pro Arg Glu Ala Glu
            20                  25                  30

Glu Ala Ala Ser Lys Ile Gly Ala Gly Pro Trp Val Val Lys Cys Gln
        35                  40                  45

Val His Ala Gly Gly Arg Gly Lys Ala Gly Gly Val Lys Val Val Asn
    50                  55                  60

Ser Lys Glu Asp Ile Arg Ala Phe Ala Glu Asn Trp Leu Gly Lys Arg
65                  70                  75                  80

Leu Val Thr Tyr Gln Thr Asp Ala Asn Gly Gln Pro Val Asn Gln Ile
                85                  90                  95

Leu Val Glu Ala Ala Thr Asp Ile Ala Lys Glu Leu Tyr Leu Gly Ala
            100                 105                 110

Val Val Asp Arg Ser Ser Arg Arg Val Val Phe Met Ala Ser Thr Glu
        115                 120                 125

Gly Gly Val Glu Ile Glu Lys Val Ala Glu Glu Thr Pro His Leu Ile
    130                 135                 140

His Lys Val Ala Leu Asp Pro Leu Thr Gly Pro Met Pro Tyr Gln Gly
145                 150                 155                 160

Arg Glu Leu Ala Phe Lys Leu Gly Leu Glu Gly Lys Leu Val Gln Gln
                165                 170                 175

Phe Thr Lys Ile Phe Met Gly Leu Ala Thr Ile Phe Leu Glu Arg Asp
            180                 185                 190

Leu Ala Leu Ile Glu Ile Asn Pro Leu Val Ile Thr Lys Gln Gly Asp
        195                 200                 205

Leu Ile Cys Leu Asp Gly Lys Leu Gly Ala Asp Gly Asn Ala Leu Phe
    210                 215                 220

Arg Gln Pro Asp Leu Arg Glu Met Arg Asp Gln Ser Gln Glu Asp Pro
225                 230                 235                 240

Arg Glu Ala Gln Ala Ala Gln Trp Glu Leu Asn Tyr Val Ala Leu Asp
                245                 250                 255

Gly Asn Ile Gly Cys Met Val Asn Gly Ala Gly Leu Ala Met Gly Thr
            260                 265                 270

Met Asp Ile Val Lys Leu His Gly Gly Glu Pro Ala Asn Phe Leu Asp
        275                 280                 285

Val Gly Gly Gly Ala Thr Lys Glu Arg Val Thr Glu Ala Phe Lys Ile
    290                 295                 300

Ile Leu Ser Asp Asp Lys Val Lys Ala Val Leu Val Asn Ile Phe Gly
305                 310                 315                 320

Gly Ile Val Arg Cys Asp Leu Ile Ala Asp Gly Ile Ile Gly Ala Val
                325                 330                 335

Ala Glu Val Gly Val Asn Val Pro Val Val Arg Leu Glu Gly Asn
            340                 345                 350

Asn Ala Glu Leu Gly Ala Lys Lys Leu Ala Asp Ser Gly Leu Asn Ile
        355                 360                 365

Ile Ala Ala Lys Gly Leu Thr Asp Ala Ala Gln Gln Val Val Ala Ala
        370                 375                 380

Val Glu Gly Lys
385

<210> SEQ ID NO 38
<211> LENGTH: 1167
<212> TYPE: DNA
<213> ORGANISM: Escherichia coli

<400> SEQUENCE: 38

| | | | | | |
|---|---|---|---|---|---|
| atgaacctgc | atgaatatca | ggccaagcag | ctgttcgcgc | ggtatggcct | cccggcgccg | 60 |
| gtcggctacg | cctgtacgac | cccgcgggaa | gcggaggagg | ccgcctccaa | gatcggcgcc | 120 |
| ggcccgtggg | tggtcaaatg | ccaggtgcat | gcgggcggcc | ggggcaaggc | gggcggcgtg | 180 |
| aaggtcgtca | actccaagga | ggacatccgc | gccttcgccg | agaactggct | gggcaagcgg | 240 |
| ctggtgacct | atcagacgga | cgccaatggc | cagcccgtca | atcagatcct | ggtcgaggcg | 300 |
| gccacggaca | tcgcgaaaga | actgtacctc | ggcgccgtct | ggaccggag | cagcggcgg | 360 |
| gtggtgttca | tggcgtccac | cgagggcggc | gtggaaatcg | aaaaagtggc | cgaggaaacc | 420 |
| ccgcacctga | tccataaagt | cgcgctggac | ccgctgaccg | gccccatgcc | gtatcagggc | 480 |
| cgggaactcg | cgttcaagct | cggcctggag | ggcaagctgg | tgcagcagtt | cacgaaaatc | 540 |
| ttcatgggcc | tggcgaccat | cttcctggag | cgcgacctgg | ccctgatcga | atcaacccg | 600 |
| ctggtcatca | cgaagcaggg | cgacctgatc | tgcctggacg | gcaagctcgg | cgccgacggc | 660 |
| aacgccctgt | ccgccagcc | ggacctgcgg | gaaatgcgcg | atcagtcgca | ggaggacccc | 720 |
| cgggaggccc | aggcggccca | gtgggagctg | aattatgtgg | cgctcgatgg | caatatcggc | 780 |
| tgcatggtca | atggcgcggg | cctggcgatg | ggcacgatgg | acatcgtgaa | gctgcatggc | 840 |
| ggcgagcccg | ccaacttcct | ggacgtgggc | ggcggcgcga | ccaaagagcg | ggtgacggaa | 900 |
| gcgttcaaga | tcatcctgag | cgacgataaa | gtcaaggccg | tgctggtcaa | catcttcggc | 960 |
| ggcatcgtcc | gctgcgacct | gatcgccgac | ggcatcatcg | gcgcggtggc | ggaggtcggc | 1020 |
| gtcaatgtgc | cggtcgtggt | ccgcctggag | ggcaacaacg | ccgaactggg | cgccaagaag | 1080 |
| ctggccgatt | ccggcctgaa | catcatcgcg | gcgaagggcc | tgaccgatgc | cgcgcagcag | 1140 |
| gtcgtggccg | ccgtcgaggg | caagtga | | | | 1167 |

<210> SEQ ID NO 39
<211> LENGTH: 289
<212> TYPE: PRT
<213> ORGANISM: Escherichia coli

<400> SEQUENCE: 39

Met Ser Ile Leu Ile Asp Lys Asn Thr Lys Val Ile Cys Gln Gly Phe
1               5                   10                  15

Thr Gly Ser Gln Gly Thr Phe His Ser Glu Gln Ala Ile Ala Tyr Gly
            20                  25                  30

Thr Lys Met Val Gly Gly Val Thr Pro Gly Lys Gly Gly Thr Thr His
        35                  40                  45

Leu Gly Leu Pro Val Phe Asn Thr Val Arg Glu Ala Val Ala Ala Thr
    50                  55                  60

Gly Ala Thr Ala Ser Val Ile Tyr Val Pro Ala Pro Phe Cys Lys Asp
65                  70                  75                  80

Ser Ile Leu Glu Ala Ile Asp Ala Gly Ile Lys Leu Ile Ile Thr Ile
                85                  90                  95

```
Thr Glu Gly Ile Pro Thr Leu Asp Met Leu Thr Val Lys Val Lys Leu
            100                 105                 110

Asp Glu Ala Gly Val Arg Met Ile Gly Pro Asn Cys Pro Gly Val Ile
            115                 120                 125

Thr Pro Gly Glu Cys Lys Ile Gly Ile Gln Pro Gly His Ile His Lys
            130                 135                 140

Pro Gly Lys Val Gly Ile Val Ser Arg Ser Gly Thr Leu Thr Tyr Glu
145                 150                 155                 160

Ala Val Lys Gln Thr Thr Asp Tyr Gly Phe Gly Gln Ser Thr Cys Val
                165                 170                 175

Gly Ile Gly Gly Asp Pro Ile Pro Gly Ser Asn Phe Ile Asp Ile Leu
            180                 185                 190

Glu Met Phe Glu Lys Asp Pro Gln Thr Glu Ala Ile Val Met Ile Gly
            195                 200                 205

Glu Ile Gly Gly Ser Ala Glu Glu Ala Ala Ala Tyr Ile Lys Glu
            210                 215                 220

His Val Thr Lys Pro Val Val Gly Tyr Ile Ala Gly Val Thr Ala Pro
225                 230                 235                 240

Lys Gly Lys Arg Met Gly His Ala Gly Ala Ile Ile Ala Gly Gly Lys
                245                 250                 255

Gly Thr Ala Asp Glu Lys Phe Ala Ala Leu Glu Ala Ala Gly Val Lys
            260                 265                 270

Thr Val Arg Ser Leu Ala Asp Ile Gly Glu Ala Leu Lys Thr Val Leu
            275                 280                 285

Lys

<210> SEQ ID NO 40
<211> LENGTH: 870
<212> TYPE: DNA
<213> ORGANISM: Escherichia coli

<400> SEQUENCE: 40
atgtccatcc tcatcgacaa gaacaccaag gtgatctgcc agggcttcac cggctcccag      60
ggcaccttcc acagcgagca ggcgatcgcc tacggcacca gatggtgggc ggcgtcacc     120
cccggcaagg gcggcaccac ccatctcggc ctcccggtgt caatacggt gcgggaagcc     180
gtggcggcca ccgcgcgac cgccagcgtc atctatgtgc ccgcgccgtt ctgcaaggac     240
tccatcctgg aagccatcga cgccggcatc aagctcatca tcaccatcac cgagggcatc     300
cccacctcg acatgctgac ggtgaaagtc aagctggacg aggcgggcgt ccggatgatc     360
ggccccaact gcccgggcgt catcaccccc ggcgagtgca aaatcggcat ccagccgggc     420
cacatccaca aaccgggcaa ggtgggcatc gtctcgcgct ccggcaccct cacctatgaa     480
gccgtcaagc agaccaccga ctatggcttc ggccagtcga cctgcgtcgg catcggcggc     540
gaccccatcc cgggctcgaa cttcatcgac atcctggaga tgttcgagaa agaccccag     600
accgaggcca tcgtgatgat cggcgagatc ggcggctcgg cggaggagga ggcggcggcg     660
tacatcaaag agcatgtgac caagccggtc gtgggctata tcgcgggcgt gacggcgccc     720
aagggcaagc gcatgggcca tgcgggcgcc atcatcgcgg gcggcaaagg caccgcggat     780
gagaagttcg ccgccctgga ggccgccggc gtcaagaccg tccgcagcct cgccgatatc     840
ggcgaagccc tgaagaccgt gctcaagtga                                     870

<210> SEQ ID NO 41
```

```
<211> LENGTH: 453
<212> TYPE: PRT
<213> ORGANISM: Clostridium kluyveri

<400> SEQUENCE: 41
```

| | | | | | | | | | | | | | | | |
|---|---|---|---|---|---|---|---|---|---|---|---|---|---|---|---|
| Met | Ser | Asn | Glu | Val | Ser | Ile | Lys | Glu | Leu | Ile | Glu | Lys | Ala | Lys | Val |
| 1 | | | | 5 | | | | | 10 | | | | | 15 | |
| Ala | Gln | Lys | Lys | Leu | Glu | Ala | Tyr | Ser | Gln | Glu | Gln | Val | Asp | Val | Leu |
| | | | 20 | | | | | 25 | | | | | 30 | | |
| Val | Lys | Ala | Leu | Gly | Lys | Val | Tyr | Asp | Asn | Ala | Glu | Met | Phe | Ala | |
| | | 35 | | | | | 40 | | | | | 45 | | | |
| Lys | Glu | Ala | Val | Glu | Glu | Thr | Glu | Met | Gly | Val | Tyr | Glu | Asp | Lys | Val |
| | 50 | | | | | 55 | | | | | 60 | | | | |
| Ala | Lys | Cys | His | Leu | Lys | Ser | Gly | Ala | Ile | Trp | Asn | His | Ile | Lys | Asp |
| 65 | | | | | 70 | | | | | 75 | | | | | 80 |
| Lys | Lys | Thr | Val | Gly | Ile | Ile | Lys | Glu | Glu | Pro | Glu | Arg | Ala | Leu | Val |
| | | | | 85 | | | | | 90 | | | | | 95 | |
| Tyr | Val | Ala | Lys | Pro | Lys | Gly | Val | Val | Ala | Ala | Thr | Thr | Pro | Ile | Thr |
| | | | 100 | | | | | 105 | | | | | 110 | | |
| Asn | Pro | Val | Val | Thr | Pro | Met | Cys | Asn | Ala | Met | Ala | Ala | Ile | Lys | Gly |
| | | 115 | | | | | 120 | | | | | 125 | | | |
| Arg | Asn | Thr | Ile | Ile | Val | Ala | Pro | His | Pro | Lys | Ala | Lys | Lys | Val | Ser |
| | 130 | | | | | 135 | | | | | 140 | | | | |
| Ala | His | Thr | Val | Glu | Leu | Met | Asn | Ala | Glu | Leu | Lys | Lys | Leu | Gly | Ala |
| 145 | | | | | 150 | | | | | 155 | | | | | 160 |
| Pro | Glu | Asn | Ile | Ile | Gln | Ile | Val | Glu | Ala | Pro | Ser | Arg | Glu | Ala | Ala |
| | | | | 165 | | | | | 170 | | | | | 175 | |
| Lys | Glu | Leu | Met | Glu | Ser | Ala | Asp | Val | Val | Ile | Ala | Thr | Gly | Gly | Ala |
| | | | 180 | | | | | 185 | | | | | 190 | | |
| Gly | Arg | Val | Lys | Ala | Ala | Tyr | Ser | Ser | Gly | Arg | Pro | Ala | Tyr | Gly | Val |
| | | 195 | | | | | 200 | | | | | 205 | | | |
| Gly | Pro | Gly | Asn | Ser | Gln | Val | Ile | Val | Asp | Lys | Gly | Tyr | Asp | Tyr | Asn |
| | 210 | | | | | 215 | | | | | 220 | | | | |
| Lys | Ala | Ala | Gln | Asp | Ile | Ile | Thr | Gly | Arg | Lys | Tyr | Asp | Asn | Gly | Ile |
| 225 | | | | | 230 | | | | | 235 | | | | | 240 |
| Ile | Cys | Ser | Ser | Glu | Gln | Ser | Val | Ile | Ala | Pro | Ala | Glu | Asp | Tyr | Asp |
| | | | | 245 | | | | | 250 | | | | | 255 | |
| Lys | Val | Ile | Ala | Ala | Phe | Val | Glu | Asn | Gly | Ala | Phe | Tyr | Val | Glu | Asp |
| | | | 260 | | | | | 265 | | | | | 270 | | |
| Glu | Glu | Thr | Val | Glu | Lys | Phe | Arg | Ser | Thr | Leu | Phe | Lys | Asp | Gly | Lys |
| | | 275 | | | | | 280 | | | | | 285 | | | |
| Ile | Asn | Ser | Lys | Ile | Ile | Gly | Lys | Ser | Val | Gln | Ile | Ile | Ala | Asp | Leu |
| | 290 | | | | | 295 | | | | | 300 | | | | |
| Ala | Gly | Val | Lys | Val | Pro | Glu | Gly | Thr | Lys | Val | Ile | Val | Leu | Lys | Gly |
| 305 | | | | | 310 | | | | | 315 | | | | | 320 |
| Lys | Gly | Ala | Gly | Glu | Lys | Asp | Val | Leu | Cys | Lys | Glu | Lys | Met | Cys | Pro |
| | | | | 325 | | | | | 330 | | | | | 335 | |
| Val | Leu | Val | Ala | Leu | Lys | Tyr | Asp | Thr | Phe | Glu | Glu | Ala | Val | Glu | Ile |
| | | | 340 | | | | | 345 | | | | | 350 | | |
| Ala | Met | Ala | Asn | Tyr | Met | Tyr | Glu | Gly | Ala | Gly | His | Thr | Ala | Gly | Ile |
| | | 355 | | | | | 360 | | | | | 365 | | | |
| His | Ser | Asp | Asn | Asp | Glu | Asn | Ile | Arg | Tyr | Ala | Gly | Thr | Val | Leu | Pro |
| | 370 | | | | | 375 | | | | | 380 | | | | |
| Ile | Ser | Arg | Leu | Val | Val | Asn | Gln | Pro | Ala | Thr | Thr | Ala | Gly | Gly | Ser |

```
                385                 390                 395                 400
            Phe Asn Asn Gly Phe Asn Pro Thr Thr Thr Leu Gly Cys Gly Ser Trp
                            405                 410                 415
            Gly Arg Asn Ser Ile Ser Glu Asn Leu Thr Tyr Glu His Leu Ile Asn
                            420                 425                 430
            Val Ser Arg Ile Gly Tyr Phe Asn Lys Glu Ala Lys Val Pro Ser Tyr
                            435                 440                 445
            Glu Glu Ile Trp Gly
                450
```

<210> SEQ ID NO 42
<211> LENGTH: 1362
<212> TYPE: DNA
<213> ORGANISM: Clostridium kluyveri

<400> SEQUENCE: 42

```
atgtcgaatg aagtctcgat caaggaactg atcgaaaagg cgaaggtggc ccagaagaaa     60
ctggaagcct actcgcagga gcaggtggat gtcctggtca aggccctggg caaggtcgtg    120
tatgataacg cggagatgtt cgccaaagaa gcggtggaag aaacggaaat gggcgtgtac    180
gaggacaagg tggcgaagtg ccacctgaaa tccggcgcca tctggaacca tatcaaggac    240
aagaaaaccg tgggcatcat caaggaagag ccggagcggg ccctggtcta cgtcgccaag    300
cccaagggcg tggtggccgc caccacgccc atcaccaacc ccgtcgtcac gccgatgtgt    360
aatgcgatgg ccgcgatcaa gggccgcaat acgatcatcg tggccccgca ccccaaagcg    420
aaaaaggtgt ccgcccacac cgtcgagctg atgaacgccg agctgaagaa gctgggcgcc    480
ccggagaaca tcatccagat cgtggaagcg ccctcgcggg aggcggcgaa ggaactcatg    540
gagagcgccg acgtggtcat cgccaccggc ggcgcgggcc gggtgaaggc cgcctactcg    600
tccggccgcc ccgcgtacgg cgtcggcccg ggcaactcgc aggtcatcgt cgacaagggc    660
tatgactaca caaggccgc gcaggacatc atcaccggcc gcaagtatga caacggcatc    720
atctgctcct ccgagcagag cgtgatcgcg cccgccgaag actatgacaa ggtgatcgcc    780
gccttcgtcg agaatggcgc gttctacgtg gaggatgaag aaaccgtgga aaagttccgc    840
tccaccctgt tcaaagacgg caagatcaat tccaagatca tcggcaagag cgtccagatc    900
atcgccgacc tggcgggcgt caaggtcccc gagggcacga aggtcatcgt gctgaagggc    960
aagggcgcgg gcgagaagga tgtcctgtgc aaggaaaaga tgtgcccggt gctggtggcc   1020
ctgaagtacg acaccttcga agaggccgtc gaaatcgcga tggccaacta tatgtatgaa   1080
ggcgccggcc acaccgccgg catccattcg gacaacgacg agaacatccg ctacgcgggc   1140
accgtgctcc ccatcagccg cctcgtggtg aaccagccgg ccaccaccgc cggcggcagc   1200
ttcaataacg gcttcaaccc caccaccacc ctgggctgcg gcagctgggg ccgcaacagc   1260
atctcggaaa acctcacgta cgaacatctc atcaacgtct cccgcatcgg ctatttcaac   1320
aaggaagcga aggtgccctc ctatgaagag atctggggct ga                      1362
```

<210> SEQ ID NO 43
<211> LENGTH: 451
<212> TYPE: PRT
<213> ORGANISM: Porphyromonas gingivalis

<400> SEQUENCE: 43

```
            Met Glu Ile Lys Glu Met Val Ser Leu Ala Arg Lys Ala Gln Lys Glu
            1               5                   10                  15
```

-continued

```
Tyr Gln Ala Thr His Asn Gln Glu Ala Val Asp Asn Ile Cys Arg Ala
             20                  25                  30
Ala Ala Lys Val Ile Tyr Glu Asn Ala Ala Ile Leu Ala Arg Glu Ala
         35                  40                  45
Val Asp Glu Thr Gly Met Gly Val Tyr Glu His Lys Val Ala Lys Asn
     50                  55                  60
Gln Gly Lys Ser Lys Gly Val Trp Tyr Asn Leu His Asn Lys Lys Ser
65                  70                  75                  80
Ile Gly Ile Leu Asn Ile Asp Glu Arg Thr Gly Met Ile Glu Ile Ala
                 85                  90                  95
Lys Pro Ile Gly Val Val Gly Ala Val Thr Pro Thr Thr Asn Pro Ile
            100                 105                 110
Val Thr Pro Met Ser Asn Ile Ile Phe Ala Leu Lys Thr Cys Asn Ala
        115                 120                 125
Ile Ile Ile Ala Pro His Pro Arg Ser Lys Lys Cys Ser Ala His Ala
    130                 135                 140
Val Arg Leu Ile Lys Glu Ala Ile Ala Pro Phe Asn Val Pro Glu Gly
145                 150                 155                 160
Met Val Gln Ile Ile Glu Glu Pro Ser Ile Glu Lys Thr Gln Glu Leu
                165                 170                 175
Met Gly Ala Val Asp Val Val Ala Thr Gly Gly Met Gly Met Val
            180                 185                 190
Lys Ser Ala Tyr Ser Ser Gly Lys Pro Ser Phe Gly Val Gly Ala Gly
        195                 200                 205
Asn Val Gln Val Ile Val Asp Ser Asn Ile Asp Phe Glu Ala Ala Ala
    210                 215                 220
Glu Lys Ile Ile Thr Gly Arg Ala Phe Asp Asn Gly Ile Ile Cys Ser
225                 230                 235                 240
Gly Glu Gln Ser Ile Ile Tyr Asn Glu Ala Asp Lys Glu Ala Val Phe
                245                 250                 255
Thr Ala Phe Arg Asn His Gly Ala Tyr Phe Cys Asp Glu Ala Glu Gly
            260                 265                 270
Asp Arg Ala Arg Ala Ala Ile Phe Glu Asn Gly Ala Ile Ala Lys Asp
        275                 280                 285
Val Val Gly Gln Ser Val Ala Phe Ile Ala Lys Lys Ala Asn Ile Asn
    290                 295                 300
Ile Pro Glu Gly Thr Arg Ile Leu Val Val Glu Ala Arg Gly Val Gly
305                 310                 315                 320
Ala Glu Asp Val Ile Cys Lys Glu Lys Met Cys Pro Val Met Cys Ala
                325                 330                 335
Leu Ser Tyr Lys His Phe Glu Glu Gly Val Glu Ile Ala Arg Thr Asn
            340                 345                 350
Leu Ala Asn Glu Gly Asn Gly His Thr Cys Ala Ile His Ser Asn Asn
        355                 360                 365
Gln Ala His Ile Ile Leu Ala Gly Ser Glu Leu Thr Val Ser Arg Ile
    370                 375                 380
Val Val Asn Ala Pro Ser Ala Thr Thr Ala Gly Gly His Ile Gln Asn
385                 390                 395                 400
Gly Leu Ala Val Thr Asn Thr Leu Gly Cys Gly Ser Trp Gly Asn Asn
                405                 410                 415
Ser Ile Ser Glu Asn Phe Thr Tyr Lys His Leu Leu Asn Ile Ser Arg
            420                 425                 430
Ile Ala Pro Leu Asn Ser Ser Ile His Ile Pro Asp Asp Lys Glu Ile
```

```
                 435                 440                 445

Trp Glu Leu
    450

<210> SEQ ID NO 44
<211> LENGTH: 1356
<212> TYPE: DNA
<213> ORGANISM: Porphyromonas gingivalis

<400> SEQUENCE: 44
atggagatca aggaaatggt gtccctggcc cgcaaggccc agaaggagta ccaggccacc     60
cataatcagg aagccgtgga caacatctgc cgcgccgcgg cgaaagtcat ctacgaaaat    120
gccgccatcc tcgcccgcga ggcggtcgat gaaaccggca tgggcgtgta cgaacacaag    180
gtggccaaga tcagggcaa aagcaagggc gtgtggtaca acctgcataa caagaaaagc    240
atcggcatcc tgaacatcga cgagcgcacc ggcatgatcg agatcgccaa gcccatcggc    300
gtcgtcggcg cggtcacgcc gaccaccaat cccatcgtca ccccgatgtc caacatcatc    360
ttcgcgctga aacctgcaa cgcgatcatc atcgccccc acccgcgcag caaaaaatgc    420
tcggcccacg ccgtgcggct catcaaggaa gccatcgcgc cgttcaacgt gccggagggc    480
atggtgcaga tcatcgaaga gccgtcgatc gagaagaccc aggaactgat gggcgccgtc    540
gacgtggtgg tggccaccgg cggcatgggc atggtgaagt cggcgtatag ctcgggcaag    600
ccgagcttcg gcgtgggcgc cggcaacgtg caggtcatcg tcgattcgaa catcgatttc    660
gaagccgccg cggaaaagat catcacgggc cgcgcgttcg ataacggcat catctgctcc    720
ggcgaacaga gcatcatcta caacgaggcg gataaggagg ccgtcttcac ggccttccgg    780
aaccacggcg cgtacttctg cgatgaagcc gaaggcgatc gcgcccgggc ggcgatcttc    840
gaaaacggcg ccatcgccaa agacgtggtg ggccagagcg tggcgttcat cgccaagaaa    900
gcgaacatca atatccccga aggcacgcgc atcctggtgg tggaagcccg cggcgtcggc    960
gcggaagatg tgatctgcaa ggaaaagatg tgccccgtga tgtgcgccct gtcctacaaa   1020
cacttcgaag agggcgtcga gatcgcccgc accaacctcg cgaacgaggg caacggccac   1080
acctgcgcca tccattcgaa taatcaggcc cacatcatcc tggccggcag cgagctcacc   1140
gtcagccgca tcgtggtcaa cgcgccctcc gccaccaccg ccggcggcca tatccagaac   1200
ggcctggccg tgacgaacac cctgggctgc ggctcgtggg gcaacaacag catctcggaa   1260
aacttcacct ataagcatct gctcaatatc agccgcatcg ccccgctgaa cagcagcatc   1320 catatccgg acgacaaaga gatctgggaa ctctga                             1356

<210> SEQ ID NO 45
<211> LENGTH: 469
<212> TYPE: PRT
<213> ORGANISM: Methylococcus capsulatus

<400> SEQUENCE: 45

Met Ser Gln Asp Asp Tyr Arg Ile Glu Lys Asp Ser Met Gly Glu Leu
1               5                   10                  15

Arg Val Pro Val Ser Ala Leu Tyr Ala Ala Gln Thr Gln Arg Ala Ile
            20                  25                  30

Asp Asn Phe Pro Val Ser Gly Leu Ala Leu Pro Pro Ala Phe Ile Arg
        35                  40                  45

Ala Ile Ala Arg Ile Lys Gln Cys Ala Ala Arg Val Asn Val Ala Leu
    50                  55                  60
```

```
Gly His Leu Asp Ala Gly Lys Gly Glu Ala Ile Met Ala Ala Ala Glu
 65                  70                  75                  80

Glu Ile Ile Gly Gly Ala Tyr Ala Asp Gln Phe Pro Val Asp Val Phe
                 85                  90                  95

Gln Thr Gly Ser Gly Thr Ser Thr Asn Met Asn Val Asn Glu Val Leu
            100                 105                 110

Ala Thr Leu Ala Ser Arg Arg Ala Gly Thr Pro Val Ser Ala Asn Asp
        115                 120                 125

Asp Val Asn Met Gly Gln Ser Ser Asn Asp Val Ile Pro Thr Ala Ile
130                 135                 140

His Val Ser Ala Ala Leu Ala Val Asn Glu His Leu Ile Pro Ala Leu
145                 150                 155                 160

Glu His Leu Ala Ala Thr Ile Arg Tyr Lys Gly Leu Ala His Pro Lys
                165                 170                 175

Ala Val Lys Thr Gly Arg Thr His Leu Met Asp Ala Met Pro Val Arg
            180                 185                 190

Leu Glu Gln Glu Leu Ser Gly Trp Ala Leu Gln Val Ala Asn Gly Val
        195                 200                 205

Asp Arg Leu Arg Ala Ser Leu Pro Arg Leu Tyr Lys Leu Gly Gln Gly
210                 215                 220

Gly Thr Ala Val Gly Thr Gly Ile Asn Ala Asp Pro Ala Phe Ala Ser
225                 230                 235                 240

Ser Phe Ala Glu Ala Leu Ala Asp Ala Thr Gly Leu Pro Phe Arg Pro
                245                 250                 255

Asn Asp Ser Phe Phe Glu Ser Leu Ser Cys Gln Asp Ala Ala Val Glu
            260                 265                 270

Leu Ser Gly Gln Leu Lys Thr Ile Ala Val Gly Ile Met Lys Ile Ala
        275                 280                 285

Asn Asp Leu Arg Trp Met Asn Ser Gly Pro Leu Ala Gly Leu Gly Glu
290                 295                 300

Ile Glu Leu Pro Ala Leu Gln Pro Gly Ser Ser Ile Met Pro Gly Lys
305                 310                 315                 320

Val Asn Pro Val Ile Pro Glu Ala Ala Cys Met Val Ala Ala Gln Val
                325                 330                 335

Ile Gly Asn Asp Ala Ala Ile Thr Val Ala Gly Gln Ser Gly Ser Phe
            340                 345                 350

Gln Leu Asn Val Met Leu Pro Val Ile Ala Tyr Asn Leu Leu Gln Ser
        355                 360                 365

Ile Glu Leu Leu Ala Asn Ile Ala Arg Leu Leu Ala Asp Lys Ala Ile
370                 375                 380

Ala Asp Phe Arg Val Arg Glu Asp Asn Leu Arg Arg Ala Leu Ala Thr
385                 390                 395                 400

Asn Pro Ile Leu Val Thr Ala Leu Asn Pro Val Ile Gly Tyr Leu Lys
                405                 410                 415

Ala Ala Glu Ile Ala Lys Thr Ala Tyr Arg Thr Gly Arg Pro Ile Leu
            420                 425                 430

Glu Val Ala Ile Glu Met Ser Gly Leu Asp Arg Ala Glu Leu Glu Arg
        435                 440                 445

Leu Leu Asp Pro Ala Ala Leu Thr Thr Gly Gly Ile His Gly Val Pro
450                 455                 460

Ala Gly Ala Ala Gly
465
```

<210> SEQ ID NO 46
<211> LENGTH: 1410
<212> TYPE: DNA
<213> ORGANISM: Methylococcus capsulatus

<400> SEQUENCE: 46

```
atgagccaag acgactatcg catcgaaaaa gacagcatgg gtgagctgcg ggttccggtt      60
tccgcgctct acgcggctca gacccagcgt gccatcgaca attttccggt gagcgggctg     120
gctttgccgc cggcgttcat ccgcgcgatc gcccggatca agcagtgcgc ggcccgggtc     180
aatgtggcgc tggggcatct ggatgcaggc aagggcgagg cgatcatggc ggcggccgag     240
gagatcatcg gcgggcata cgccgaccag tttcctgtcg acgtgttcca gaccggttcc     300
ggcaccagca ccaacatgaa cgtcaacgaa gtgctggcga ctttggcttc ccggcgcgcg     360
ggaacgcccg tgagcgccaa cgacgacgtc aacatggggc agagcagcaa tgacgtcatc     420
cccacggcga ttcacgtcag tgccgcgctg gcagtcaacg aacatctgat cccggcgctg     480
gaacacctgg cggcgacgat acgctacaag ggcttggcgc atccgaaggc ggtcaagacc     540
ggcggacccc atctgatgga cgccatgcca gtgcggctgg agcaagaact ctcgggctgg     600
gcgctgcagt cgccaacggc gtcgaccgc ctgcgggcga gtctgccgcg gctttacaaa     660
ttggggcagg gcggcacggc cgtgggcact ggcatcaacg ccgatccggc cttcgcttcc     720
tccttcgccg aagctctggc cgatgccacg gcctgccctt tcgccccaa cgattcgttc     780
ttcgagagcc tgagttgcca ggacgcggca gtcgaactgt cgggccagct caagaccatc     840
gccgtcggca tcatgaagat cgccaacgac ctgcgctgga tgaattcggg tcccctggct     900
ggcctggggg agatcgagct gccgcgctc cagcccggca gctccatcat gcccggcaag     960
gtgaatccgg tgattcccga agccgcctgc atggtcgcgg cgcaggtcat cggcaacgac    1020
gccgccatca cggtggctgg tcagtcgggt tctttccaac tcaacgtgat gctgccggtg    1080
atcgcctaca acttgctgca gagcatcgag ttgctggcca acattgctcg tctgctggcc    1140
gacaaggcca tcgccgactt ccgggtgcgt gaggacaatc tgcgccgggc tctggcaacg    1200
aatccgatcc tggtcaccgc actcaacccg gtgatcggct acctgaaggc ggcggaaatc    1260
gccaagaccg cctaccggac ggggcggccg attctggagg tggccatcga atgagcggt     1320
ctggaccgcg ccgaactgga gcgactgctc gatccggcgg ccctgaccac cggcggcatc    1380
cacggtgtac cgccggcgc ggcgggctga                                      1410
```

<210> SEQ ID NO 47
<211> LENGTH: 467
<212> TYPE: PRT
<213> ORGANISM: Escherichia coli

<400> SEQUENCE: 47

```
Met Asn Thr Val Arg Ser Glu Lys Asp Ser Met Gly Ala Ile Asp Val
1               5                   10                  15

Pro Ala Asp Lys Leu Trp Gly Ala Gln Thr Gln Arg Ser Leu Glu His
            20                  25                  30

Phe Arg Ile Ser Thr Glu Lys Met Pro Thr Ser Leu Ile His Ala Leu
        35                  40                  45

Ala Leu Thr Lys Arg Ala Ala Ala Lys Val Asn Glu Asp Leu Gly Leu
    50                  55                  60

Leu Ser Glu Glu Lys Ala Ser Ala Ile Arg Gln Ala Ala Asp Glu Val
65                  70                  75                  80

Leu Ala Gly Gln His Asp Asp Glu Phe Pro Leu Ala Ile Trp Gln Thr
```

```
                      85                  90                  95
Gly Ser Gly Thr Gln Ser Asn Met Asn Met Asn Glu Val Leu Ala Asn
                100                 105                 110
Arg Ala Ser Glu Leu Leu Gly Val Arg Gly Met Glu Arg Lys Val
                115                 120                 125
His Pro Asn Asp Asp Val Asn Lys Ser Gln Ser Ser Asn Asp Val Phe
            130                 135                 140
Pro Thr Ala Met His Val Ala Ala Leu Leu Ala Leu Arg Lys Gln Leu
145                 150                 155                 160
Ile Pro Gln Leu Lys Thr Leu Thr Gln Thr Leu Asn Glu Lys Ser Arg
                165                 170                 175
Ala Phe Ala Asp Ile Val Lys Ile Gly Arg Thr His Leu Gln Asp Ala
                180                 185                 190
Thr Pro Leu Thr Leu Gly Gln Glu Ile Ser Gly Trp Val Ala Met Leu
                195                 200                 205
Glu His Asn Leu Lys His Ile Glu Tyr Ser Leu Pro His Val Ala Glu
210                 215                 220
Leu Ala Leu Gly Gly Thr Ala Val Gly Thr Gly Leu Asn Thr His Pro
225                 230                 235                 240
Glu Tyr Ala Arg Arg Val Ala Asp Glu Leu Ala Val Ile Thr Cys Ala
                245                 250                 255
Pro Phe Val Thr Ala Pro Asn Lys Phe Glu Ala Leu Ala Thr Cys Asp
                260                 265                 270
Ala Leu Val Gln Ala His Gly Ala Leu Lys Gly Leu Ala Ala Ser Leu
                275                 280                 285
Met Lys Ile Ala Asn Asp Val Arg Trp Leu Ala Ser Gly Pro Arg Cys
290                 295                 300
Gly Ile Gly Glu Ile Ser Ile Pro Glu Asn Glu Pro Gly Ser Ser Ile
305                 310                 315                 320
Met Pro Gly Lys Val Asn Pro Thr Gln Cys Glu Ala Leu Thr Met Leu
                325                 330                 335
Cys Cys Gln Val Met Gly Asn Asp Val Ala Ile Asn Met Gly Gly Ala
                340                 345                 350
Ser Gly Asn Phe Glu Leu Asn Val Phe Arg Pro Met Val Ile His Asn
                355                 360                 365
Phe Leu Gln Ser Val Arg Leu Leu Ala Asp Gly Met Glu Ser Phe Asn
370                 375                 380
Lys His Cys Ala Val Gly Ile Glu Pro Asn Arg Glu Arg Ile Asn Gln
385                 390                 395                 400
Leu Leu Asn Glu Ser Leu Met Leu Val Thr Ala Leu Asn Thr His Ile
                405                 410                 415
Gly Tyr Asp Lys Ala Ala Glu Ile Ala Lys Lys Ala His Lys Glu Gly
                420                 425                 430
Leu Thr Leu Lys Ala Ala Ala Leu Ala Leu Gly Tyr Leu Ser Glu Ala
                435                 440                 445
Glu Phe Asp Ser Trp Val Arg Pro Glu Gln Met Val Gly Ser Met Lys
450                 455                 460
Ala Gly Arg
465

<210> SEQ ID NO 48
<211> LENGTH: 1404
<212> TYPE: DNA
<213> ORGANISM: Escherichia coli
```

<400> SEQUENCE: 48

```
atgaacaccg tgcggagcga aaaggacagc atgggcgcca tcgacgtgcc cgccgataag      60
ctgtggggcg cccagaccca gcggtccctc gaacacttcc ggatctcgac cgaaaagatg     120
ccgaccagcc tgatccatgc gctcgccctg acgaaacggg ccgccgccaa ggtcaacgag     180
gacctcggcc tgctgagcga agagaaggcc tccgcgatcc gccaggccgc cgatgaagtc     240
ctcgccggcc agcacgacga cgagttcccg ctggccatct ggcagaccgg ctcgggcacc     300
cagtcgaaca tgaacatgaa cgaagtgctc gccaaccgcg cgtcggaact gctgggcggc     360
gtccggggca tggaacgcaa ggtccatccc aacgacgacg tgaacaagtc gcagagctcc     420
aatgatgtct tccccaccgc catgcatgtc gcggccctcc tggccctgcg caaacagctg     480
atccccccag ctgaaaaccct gacccagacc ctgaatgaaa atcccgcgc gttcgccgac     540
atcgtgaaga tcggccggac gcacctccag gacgcgaccc ccctgaccct cggccaggag     600
atctccggct gggtggcgat gctggaacac aacctgaaac atatcgagta cagcctgccg     660
cacgtcgcgg aactggcgct gggcggcacg gcggtcggca ccggcctgaa cacgcatccg     720
gagtatgcgc ggcgcgtggc cgacgaactg gccgtcatca cctgtgcccc gttcgtgacc     780
gccccgaata aattcgaagc cctggcgacc tgtgacgccc tggtccaggc gcatggcgcc     840
ctcaagggcc tggccgccag cctcatgaaa atcgcgaatg acgtgcgctg gctgccctcc     900
ggccccccgct gcggcatcgg cgaaatctcg atccccgaaa acgagccggg ctcgtcgatc     960
atgccgggca aggtgaaccc gacccagtgc gaggcgctca cgatgctctg ctgccaggtc    1020
atgggcaatg acgtggccat caatatgggc ggcgcgtccg gcaacttcga actgaatgtc    1080
ttccgcccga tggtcatcca caatttcctg cagtccgtgc gcctgctggc ggacggcatg    1140
gagagcttca ataagcactg cgcggtgggc atcgagccca accgcgagcg catcaaccag    1200
ctgctgaatg agagcctgat gctggtcacc gcgctgaata cccacatcgg ctacgacaag    1260
gcggccgaaa tcgccaagaa agcgcacaaa gaaggcctga cgctgaaagc cgccgccctg    1320
gccctgggct acctgtccga ggccgagttc gacagctggg tccgcccgga gcagatggtg    1380
ggctcgatga aagccggccg gtga                                           1404
```

<210> SEQ ID NO 49
<211> LENGTH: 474
<212> TYPE: PRT
<213> ORGANISM: Mycobacterium tuberculosis

<400> SEQUENCE: 49

```
Met Ala Val Asp Ala Asp Ser Ala Asn Tyr Arg Ile Glu His Asp Thr
  1               5                  10                  15

Met Gly Glu Val Arg Val Pro Ala Lys Ala Leu Trp Arg Ala Gln Thr
             20                  25                  30

Gln Arg Ala Val Glu Asn Phe Pro Ile Ser Gly Arg Gly Leu Glu Arg
         35                  40                  45

Thr Gln Ile Arg Ala Leu Gly Leu Leu Lys Gly Ala Cys Ala Gln Val
     50                  55                  60

Asn Ser Asp Leu Gly Leu Leu Ala Pro Glu Lys Ala Asp Ala Ile Ile
 65                  70                  75                  80

Ala Ala Ala Ala Glu Ile Ala Asp Gly Gln His Asp Asp Gln Phe Pro
                 85                  90                  95

Ile Asp Val Phe Gln Thr Gly Ser Gly Thr Ser Ser Asn Met Asn Thr
            100                 105                 110
```

```
Asn Glu Val Ile Ala Ser Ile Ala Ala Lys Gly Gly Val Thr Leu His
    115                 120                 125

Pro Asn Asp Asp Val Asn Met Ser Gln Ser Ser Asn Asp Thr Phe Pro
130                 135                 140

Thr Ala Thr His Ile Ala Ala Thr Glu Ala Ala Val Ala His Leu Ile
145                 150                 155                 160

Pro Ala Leu Gln Gln Leu His Asp Ala Leu Ala Ala Lys Ala Leu Asp
            165                 170                 175

Trp His Thr Val Val Lys Ser Gly Arg Thr His Leu Met Asp Ala Val
                180                 185                 190

Pro Val Thr Leu Gly Gln Glu Phe Ser Gly Tyr Ala Arg Gln Ile Glu
            195                 200                 205

Ala Gly Ile Glu Arg Val Arg Ala Cys Leu Pro Arg Leu Gly Glu Leu
    210                 215                 220

Ala Ile Gly Gly Thr Ala Val Gly Thr Gly Leu Asn Ala Pro Asp Asp
225                 230                 235                 240

Phe Gly Val Arg Val Val Ala Val Leu Val Ala Gln Thr Gly Leu Ser
                245                 250                 255

Glu Leu Arg Thr Ala Ala Asn Ser Phe Glu Ala Gln Ala Ala Arg Asp
            260                 265                 270

Gly Leu Val Glu Ala Ser Gly Ala Leu Arg Thr Ile Ala Val Ser Leu
    275                 280                 285

Thr Lys Ile Ala Asn Asp Ile Arg Trp Met Gly Ser Gly Pro Leu Thr
290                 295                 300

Gly Leu Ala Glu Ile Gln Leu Pro Asp Leu Gln Pro Gly Ser Ser Ile
305                 310                 315                 320

Met Pro Gly Lys Val Asn Pro Val Leu Pro Glu Ala Val Thr Gln Val
                325                 330                 335

Ala Ala Gln Val Ile Gly Asn Asp Ala Ala Ile Ala Trp Gly Gly Ala
            340                 345                 350

Asn Gly Ala Phe Glu Leu Asn Val Tyr Ile Pro Met Met Ala Arg Asn
    355                 360                 365

Ile Leu Glu Ser Phe Lys Leu Leu Thr Asn Val Ser Arg Leu Phe Ala
    370                 375                 380

Gln Arg Cys Ile Ala Gly Leu Thr Ala Asn Val Glu His Leu Arg Arg
385                 390                 395                 400

Leu Ala Glu Ser Ser Pro Ser Ile Val Thr Pro Leu Asn Ser Ala Ile
            405                 410                 415

Gly Tyr Glu Glu Ala Ala Val Ala Lys Gln Ala Leu Lys Glu Arg
            420                 425                 430

Lys Thr Ile Arg Gln Thr Val Ile Asp Arg Gly Leu Ile Gly Asp Arg
            435                 440                 445

Leu Ser Ile Glu Asp Leu Asp Arg Arg Leu Asp Val Leu Ala Met Ala
450                 455                 460

Lys Ala Glu Gln Leu Asp Ser Asp Arg Leu
465                 470

<210> SEQ ID NO 50
<211> LENGTH: 1425
<212> TYPE: DNA
<213> ORGANISM: Mycobacterium tuberculosis

<400> SEQUENCE: 50
atggcggtgg atgcggacag cgcgaactac cgcatcgaac acgatacgat gggcgaagtg      60
```

```
cgcgtccccg ccaaggccct ctggcgggcc cagacgcagc gggccgtcga aacttcccg      120
atcagcggcc ggggcctgga acgcacgcag atccgcgccc tgggcctcct gaagggcgcc     180
tgcgcccagg tgaactccga tctgggcctg ctcgcgccgg aaaaggcgga tgccatcatc     240
gccgccgcgg cggagatcgc cgacggccag cacgacgatc agttcccgat cgatgtcttc     300
cagaccggca gcggcacctc cagcaatatg aacaccaacg aggtcatcgc gagcatcgcg     360
gccaagggcg gcgtgaccct gcacccgaac gacgacgtga atatgagcca gtcgtccaac     420
gacaccttcc ccaccgccac ccatatcgcg gcgaccgagg cggccgtcgc gcatctgatc     480
cccgccctgc agcagctcca cgatgccctg ccgcgaaag cgctggactg cacaccgtc      540
gtgaaatccg gccggacgca tctcatggac gccgtgccgg tgaccctggg ccaggagttc    600
tccggctacg cccggcagat cgaagccggc atcgaacggg tccgcgcgtg cctcccgcgg    660
ctgggcgagc tggccatcgg cggcaccgcc gtgggcaccg gcctcaacgc gcccgacgat    720
ttcggcgtgc gggtggtggc ggtgctcgtg gcccagaccg gcctgtcgga actccggacg    780
gcggccaatt ccttcgaagc ccaggccgcc cgcgatggcc tggtggaggc gtcgggcgcc    840
ctgcgcacga tcgccgtgag cctgacgaag atcgcgaacg acatccggtg gatgggctcc    900
ggcccgctca ccggcctggc ggaaatccag ctcccggacc tgcagcccgg cagctccatc    960
atgcccggca aggtcaaccc cgtgctgccg gaagcggtca cccaggtcgc ggcccaggtg   1020
atcggcaacg acgccgccat cgcctggggc ggcgcgaacg gcgcgttcga actgaatgtc   1080
tatatcccga tgatggcccg gaacatcctg gagtcgttca agctgctcac caacgtgagc   1140
cggctgttcg cgcagcgctg catcgccggc ctcaccgcca acgtcgaaca tctgcggcgg   1200
ctcgcggaat cctcgcccag catcgtcacg ccgctcaaca gcgcgatcgg ctacgaagaa   1260
gcggcggccg tggccaagca ggcgctcaaa gagcgcaaga ccatccgcca gacggtgatc   1320
gaccggggcc tgatcggcga tcggctgtcg atcgaggacc tggatcgccg cctggatgtg   1380
ctcgcgatgg ccaaagccga acagctggac tccgaccgcc tgtga                   1425
```

<210> SEQ ID NO 51
<211> LENGTH: 602
<212> TYPE: PRT
<213> ORGANISM: Escherichia coli

<400> SEQUENCE: 51

```
Met Gln Thr Phe Gln Ala Asp Leu Ala Ile Val Gly Ala Gly Ala
1               5                   10                  15

Gly Leu Arg Ala Ala Ile Ala Ala Gln Ala Asn Pro Asn Ala Lys
                20                  25                  30

Ile Ala Leu Ile Ser Lys Val Tyr Pro Met Arg Ser His Thr Val Ala
            35                  40                  45

Ala Glu Gly Gly Ser Ala Ala Val Ala Gln Asp His Asp Ser Phe Glu
        50                  55                  60

Tyr His Phe His Asp Thr Val Ala Gly Gly Asp Trp Leu Cys Glu Gln
65                  70                  75                  80

Asp Val Val Asp Tyr Phe Val His His Cys Pro Thr Glu Met Thr Gln
                85                  90                  95

Leu Glu Leu Trp Gly Cys Pro Trp Ser Arg Arg Pro Asp Gly Ser Val
            100                 105                 110

Asn Val Arg Arg Phe Gly Gly Met Lys Ile Glu Arg Thr Trp Phe Ala
        115                 120                 125
```

```
Ala Asp Lys Thr Gly Phe His Met Leu His Thr Leu Phe Gln Thr Ser
    130                 135                 140

Leu Gln Phe Pro Gln Ile Gln Arg Phe Asp Glu His Phe Val Leu Asp
145                 150                 155                 160

Ile Leu Val Asp Asp Gly His Val Arg Gly Leu Val Ala Met Asn Met
                165                 170                 175

Met Glu Gly Thr Leu Val Gln Ile Arg Ala Asn Ala Val Val Met Ala
                180                 185                 190

Thr Gly Gly Ala Gly Arg Val Tyr Arg Tyr Asn Thr Asn Gly Gly Ile
                195                 200                 205

Val Thr Gly Asp Gly Met Gly Met Ala Leu Ser His Gly Val Pro Leu
    210                 215                 220

Arg Asp Met Glu Phe Val Gln Tyr His Pro Thr Gly Leu Pro Gly Ser
225                 230                 235                 240

Gly Ile Leu Met Thr Glu Gly Cys Arg Gly Glu Gly Gly Ile Leu Val
                245                 250                 255

Asn Lys Asn Gly Tyr Arg Tyr Leu Gln Asp Tyr Gly Met Gly Pro Glu
                260                 265                 270

Thr Pro Leu Gly Glu Pro Lys Asn Lys Tyr Met Glu Leu Gly Pro Arg
    275                 280                 285

Asp Lys Val Ser Gln Ala Phe Trp His Glu Trp Arg Lys Gly Asn Thr
290                 295                 300

Ile Ser Thr Pro Arg Gly Asp Val Val Tyr Leu Asp Leu Arg His Leu
305                 310                 315                 320

Gly Glu Lys Lys Leu His Glu Arg Leu Pro Phe Ile Cys Glu Leu Ala
                325                 330                 335

Lys Ala Tyr Val Gly Val Asp Pro Val Lys Glu Pro Ile Pro Val Arg
                340                 345                 350

Pro Thr Ala His Tyr Thr Met Gly Gly Ile Glu Thr Asp Gln Asn Cys
    355                 360                 365

Glu Thr Arg Ile Lys Gly Leu Phe Ala Val Gly Glu Cys Ser Ser Val
370                 375                 380

Gly Leu His Gly Ala Asn Arg Leu Gly Ser Asn Ser Leu Ala Glu Leu
385                 390                 395                 400

Val Val Phe Gly Arg Leu Ala Gly Glu Gln Ala Thr Glu Arg Ala Ala
                405                 410                 415

Thr Ala Gly Asn Gly Asn Glu Ala Ala Ile Glu Ala Gln Ala Ala Gly
                420                 425                 430

Val Glu Gln Arg Leu Lys Asp Leu Val Asn Gln Asp Gly Gly Glu Asn
    435                 440                 445

Trp Ala Lys Ile Arg Asp Glu Met Gly Leu Ala Met Glu Glu Gly Cys
450                 455                 460

Gly Ile Tyr Arg Thr Pro Glu Leu Met Gln Lys Thr Ile Asp Lys Leu
465                 470                 475                 480

Ala Glu Leu Gln Glu Arg Phe Lys Arg Val Arg Ile Thr Asp Thr Ser
                485                 490                 495

Ser Val Phe Asn Thr Asp Leu Leu Tyr Thr Ile Glu Leu Gly His Gly
                500                 505                 510

Leu Asn Val Ala Glu Cys Met Ala His Ser Ala Met Ala Arg Lys Glu
    515                 520                 525

Ser Arg Gly Ala His Gln Arg Leu Asp Glu Gly Cys Thr Glu Arg Asp
530                 535                 540

Asp Val Asn Phe Leu Lys His Thr Leu Ala Phe Arg Asp Ala Asp Gly
```

```
                545                 550                 555                 560
            Thr Thr Arg Leu Glu Tyr Ser Asp Val Lys Ile Thr Thr Leu Pro Pro
                            565                 570                 575

Ala Lys Arg Val Tyr Gly Gly Glu Ala Asp Ala Ala Asp Lys Ala Glu
                        580                 585                 590

Ala Ala Asn Lys Lys Glu Lys Ala Asn Gly
                        595                 600

<210> SEQ ID NO 52
<211> LENGTH: 1809
<212> TYPE: DNA
<213> ORGANISM: Escherichia coli

<400> SEQUENCE: 52
```

| | | | | | |
|---|---|---|---|---|---|
| atgcagacct | tccaggccga | tctggccatc | gtgggtgcag | gcggtgcagg | tctccgggca | 60 |
| gcaatcgctg | cagcccaggc | gaaccccaac | gccaagatcg | cgctcatctc | caaggtctac | 120 |
| ccgatgcggt | cccataccgt | ggcggcagag | ggcggttcgg | cggcagtggc | gcaggaccac | 180 |
| gattcgttcg | aataccactt | ccacgacacg | gtggccggcg | gcgactggct | gtgcgaacag | 240 |
| gatgtggtgg | actacttcgt | gcatcattgc | cccaccgaaa | tgacccagct | ggaactgtgg | 300 |
| ggctgcccgt | ggtcgcgccg | gcccgatggc | tccgtgaatg | tgcgccggtt | cggcggcatg | 360 |
| aagatcgaac | gcacctggtt | cgcggccgac | aagacgggct | tccacatgct | ccatacccctg | 420 |
| ttccagacga | gcctgcagtt | cccccagatc | cagcggttcg | acgagcactt | cgtcctggac | 480 |
| atcctggtgg | acgatggcca | tgtgcgcggc | ctcgtcgcca | tgaacatgat | ggagggcacc | 540 |
| ctcgtgcaga | tccgcgccaa | cgccgtggtc | atggcgaccg | gcggcgccgg | ccgcgtgtac | 600 |
| cgctacaata | ccaacggcgg | catcgtgacc | ggcgacggca | tgggcatggc | cctcagccac | 660 |
| ggcgtgcccc | tccgcgacat | ggagttcgtg | cagtaccacc | ccaccggcct | cccgggcagc | 720 |
| ggcatcctga | tgaccgaggg | ctgccggggc | gaaggcggca | tcctcgtcaa | caagaacggc | 780 |
| tatcgctacc | tgcaggacta | cggcatgggc | ccggaaaccc | cgctcggcga | gcccaagaat | 840 |
| aaatatatgg | agctgggccc | ccgggataag | gtcagccagg | cgttctggca | cgaatggcgg | 900 |
| aagggcaaca | ccatctccac | cccccgcggc | gatgtcgtgt | acctcgacct | gcggcatctg | 960 |
| ggcgaaaaaa | agctccacga | acgcctgccg | ttcatctgcg | agctggccaa | ggcctacgtg | 1020 |
| ggcgtcgacc | cggtgaagga | gccgatcccg | gtgcggccga | ccgcgcatta | cgatgggc | 1080 |
| ggcatcgaaa | ccgaccagaa | ctgcgaaacg | cgcatcaagg | gcctgttcgc | ggtgggcgag | 1140 |
| tgcagctccg | tcggcctcca | cggcgcgaac | cgcctgggca | gcaatagcct | cgccgaactc | 1200 |
| gtggtcttcg | gccggctggc | cggcgagcag | gccacggaac | gggcggccac | cgcgggcaac | 1260 |
| ggcaacgagg | ccgccatcga | ggcccaggcc | gcggcgtgg | aacagcggct | gaaggatctg | 1320 |
| gtcaaccagg | atggcggcga | aaactggcg | aagatccgcg | acgaaatggg | cctggcgatg | 1380 |
| gaagagggct | gcggcatcta | ccgcacgccg | gagctgatgc | agaagaccat | cgataagctg | 1440 |
| gcggaactgc | aggaacggtt | caaacgggtc | cggatcacgg | atacctcctc | ggtgttcaac | 1500 |
| accgacctcc | tgtacaccat | cgagctgggc | cacggcctca | acgtggcgga | gtgtatggcg | 1560 |
| cactccgcga | tggcgcggaa | ggaaagccgc | ggtgcccacc | agcgcctcga | cgaaggctgc | 1620 |
| accgagcgcg | acgatgtgaa | cttcctcaaa | cacacgctgg | ccttccggga | cgcggatggc | 1680 |
| acgacccgcc | tcgaatatag | cgatgtgaag | atcacgaccc | tgcctcctgc | gaagcgcgtc | 1740 |
| tacggcggtg | aagccgacgc | ggcagacaag | gccgaggcag | ccaataagaa | ggagaaagcc | 1800 | aatgget ga                                                          1809

<210> SEQ ID NO 53
<211> LENGTH: 244
<212> TYPE: PRT
<213> ORGANISM: Escherichia coli

<400> SEQUENCE: 53

Met Ala Glu Met Lys Asn Leu Lys Ile Glu Val Val Arg Tyr Asn Pro
1               5                   10                  15

Glu Val Asp Thr Ala Pro His Ser Ala Phe Tyr Glu Val Pro Tyr Asp
            20                  25                  30

Ala Thr Thr Ser Leu Leu Asp Ala Leu Gly Tyr Ile Lys Asp Asn Leu
        35                  40                  45

Ala Pro Asp Leu Ser Tyr Arg Trp Ser Cys Arg Met Ala Ile Cys Gly
    50                  55                  60

Ser Cys Gly Met Met Val Asn Asn Val Pro Lys Leu Ala Cys Lys Thr
65                  70                  75                  80

Phe Leu Arg Asp Tyr Thr Asp Gly Met Lys Val Glu Ala Leu Ala Asn
                85                  90                  95

Phe Pro Ile Glu Arg Asp Leu Val Val Asp Met Thr His Phe Ile Glu
            100                 105                 110

Ser Leu Glu Ala Ile Lys Pro Tyr Ile Ile Gly Asn Ser Arg Thr Ala
        115                 120                 125

Asp Gln Gly Thr Asn Ile Gln Thr Pro Ala Gln Met Ala Lys Tyr His
    130                 135                 140

Gln Phe Ser Gly Cys Ile Asn Cys Gly Leu Cys Tyr Ala Ala Cys Pro
145                 150                 155                 160

Gln Phe Gly Leu Asn Pro Glu Phe Ile Gly Pro Ala Ala Ile Thr Leu
                165                 170                 175

Ala His Arg Tyr Asn Glu Asp Ser Arg Asp His Gly Lys Lys Glu Arg
            180                 185                 190

Met Ala Gln Leu Asn Ser Gln Asn Gly Val Trp Ser Cys Thr Phe Val
        195                 200                 205

Gly Tyr Cys Ser Glu Val Cys Pro Lys His Val Asp Pro Ala Ala Ala
    210                 215                 220

Ile Gln Gln Gly Lys Val Glu Ser Ser Lys Asp Phe Leu Ile Ala Thr
225                 230                 235                 240

Leu Lys Pro Arg

<210> SEQ ID NO 54
<211> LENGTH: 735
<212> TYPE: DNA
<213> ORGANISM: Escherichia coli

<400> SEQUENCE: 54
atggcggaaa tgaagaacct gaagatcgag gtcgtccggt ataatccgga ggtggatacc      60 gcccccaca gcgcgttcta cgaagtcccg tacgacgcca ccaccagcct cctggatgcg      120
ctgggctaca tcaaggataa cctggccccc gatctgtcgt accgctggtc ctgtcgcatg     180
gccatctgtg gctcctgcgg catgatggtg aataacgtgc cgaagctggc ctgcaagacc     240
ttcctgcggg actataccga cggcatgaaa gtggaggccc tcgcgaactt cccgatcgag     300
cgcgacctgg tggtcgatat gacgcacttc atcgagagcc tggaagcgat caaaccctat     360
atcatcggca acagccggac cgccgaccag ggcacgaaca tccagacgcc cgcgcagatg     420

```
gcgaagtatc accagttctc cggctgtatc aattgcggcc tgtgctatgc ggcgtgcccg    480
cagttcggcc tgaaccccga gttcatcggc ccggcggcca tcacgctcgc ccaccgctac    540
aacgaggaca gccgcgatca cggcaagaag gagcgcatgg cccagctcaa ttcgcagaat    600
ggcgtgtgga gctgcacctt cgtgggctat tgctccgagg tctgcccaa gcatgtcgac     660 ccggcggcgg cgatccagca gggcaaggtc gagtcgtcga agacttcct gatcgccacg     720 ctcaagccgc ggtga                                                    735
```

```
<210> SEQ ID NO 55
<211> LENGTH: 131
<212> TYPE: PRT
<213> ORGANISM: Escherichia coli

<400> SEQUENCE: 55

Met Thr Thr Lys Arg Lys Pro Tyr Val Arg Pro Met Thr Ser Thr Trp
1               5                   10                  15

Trp Lys Lys Leu Pro Phe Tyr Arg Phe Tyr Met Leu Arg Glu Gly Thr
            20                  25                  30

Ala Val Pro Ala Val Trp Phe Ser Ile Glu Leu Ile Phe Gly Leu Phe
        35                  40                  45

Ala Leu Lys Asn Gly Pro Glu Ala Trp Ala Gly Phe Val Asp Phe Leu
    50                  55                  60

Gln Asn Pro Val Ile Val Ile Asn Leu Ile Thr Leu Ala Ala Ala
65                  70                  75                  80

Leu Leu His Thr Lys Thr Trp Phe Glu Leu Ala Pro Lys Ala Ala Asn
                85                  90                  95

Ile Ile Val Lys Asp Glu Lys Met Gly Pro Glu Pro Ile Ile Lys Ser
            100                 105                 110

Leu Trp Ala Val Thr Val Val Ala Thr Ile Val Ile Leu Phe Val Ala
        115                 120                 125

Leu Tyr Trp
    130
```

```
<210> SEQ ID NO 56
<211> LENGTH: 396
<212> TYPE: DNA
<213> ORGANISM: Escherichia coli

<400> SEQUENCE: 56
atgacgacca agcgcaagcc gtacgtccgg ccgatgacct cgacctggtg gaaaaagctc     60
cccttctacc gcttctatat gctgcgcgag ggcaccgcgg tgccggccgt ctggttctcg    120
atcgaactga tcttcggcct gttcgcgctg aagaatggcc cggaggcgtg gccggcttc    180 gtggacttcc tgcagaaccc cgtcatcgtc atcatcaatc tcatcacgct cgccgcggcc    240
ctcctgcaca ccaagacctg gttcgagctg gccccgaagg cggcgaacat catcgtgaag    300
gacgagaaga tgggcccgga gccgatcatc aaatccctgt gggcggtcac ggtggtcgcc    360
acgatcgtca tcctgttcgt ggcgctgtac tggtga                              396
```

```
<210> SEQ ID NO 57
<211> LENGTH: 119
<212> TYPE: PRT
<213> ORGANISM: Escherichia coli

<400> SEQUENCE: 57

Met Ile Asn Pro Asn Pro Lys Arg Ser Asp Glu Pro Val Phe Trp Gly
1               5                   10                  15
```

```
Leu Phe Gly Ala Gly Gly Met Trp Ser Ala Ile Ile Ala Pro Val Met
            20                  25                  30

Ile Leu Leu Val Gly Ile Leu Leu Pro Leu Gly Leu Phe Pro Gly Asp
        35                  40                  45

Ala Leu Ser Tyr Glu Arg Val Leu Ala Phe Ala Gln Ser Phe Ile Gly
        50                  55                  60

Arg Val Phe Leu Phe Leu Met Ile Val Leu Pro Leu Trp Cys Gly Leu
65                      70                  75                  80

His Arg Met His His Ala Met His Asp Leu Lys Ile His Val Pro Ala
                85                  90                  95

Gly Lys Trp Val Phe Tyr Gly Leu Ala Ala Ile Leu Thr Val Val Thr
            100                 105                 110

Leu Ile Gly Val Val Thr Ile
        115

<210> SEQ ID NO 58
<211> LENGTH: 360
<212> TYPE: DNA
<213> ORGANISM: Escherichia coli

<400> SEQUENCE: 58
atgatcaatc cgaaccccaa acggagcgac gagcccgtct tctggggcct gttcggcgcg      60
ggcggcatgt ggagcgccat catcgcgccg gtcatgatcc tcctcgtggg catcctcctc     120 ccctgggcc tgttccccgg cgacgccctg tcgtacgagc gcgtgctggc cttcgcccag     180
tccttcatcg gccgcgtgtt cctcttcctc atgatcgtgc tccccctctg gtgcggcctg     240
caccgcatgc accacgccat gcacgacctg aagatccatg tccccgccgg caagtgggtc     300
ttctacggcc tcgcggcgat cctgacggtc gtgacgctga tcggcgtggt cacgatctga     360
```